United States Patent
Zhang et al.

(10) Patent No.: US 12,178,854 B2
(45) Date of Patent: Dec. 31, 2024

(54) COMPOSITIONS AND METHODS FOR TREATING DISEASES ASSOCIATED WITH AN IMPRINTING DEFECT

(71) Applicant: CHILDREN'S MEDICAL CENTER CORPORATION, Boston, MA (US)

(72) Inventors: Yi Zhang, Boston, MA (US); Azusa Inoue, Boston, MA (US)

(73) Assignee: Children's Medical Center Corporation, Boston, MA (US)

( * ) Notice: Subject to any disclaimer, the term of this patent is extended or adjusted under 35 U.S.C. 154(b) by 643 days.

(21) Appl. No.: 16/631,762

(22) PCT Filed: Jul. 19, 2018

(86) PCT No.: PCT/US2018/042876
§ 371 (c)(1),
(2) Date: Jan. 16, 2020

(87) PCT Pub. No.: WO2019/018635
PCT Pub. Date: Jan. 24, 2019

(65) Prior Publication Data
US 2020/0179491 A1    Jun. 11, 2020

Related U.S. Application Data

(60) Provisional application No. 62/534,532, filed on Jul. 19, 2017.

(51) Int. Cl.
| | | |
|---|---|---|
| *A61K 38/44* | (2006.01) | |
| *A61K 31/4439* | (2006.01) | |
| *A61K 31/4545* | (2006.01) | |
| *A61K 31/496* | (2006.01) | |
| *A61K 31/5375* | (2006.01) | |
| *A61K 31/706* | (2006.01) | |

(52) U.S. Cl.
CPC .......... *A61K 38/44* (2013.01); *A61K 31/4439* (2013.01); *A61K 31/4545* (2013.01); *A61K 31/496* (2013.01); *A61K 31/5375* (2013.01); *A61K 31/706* (2013.01)

(58) Field of Classification Search
CPC ............ A61K 31/4439; A61K 31/4545; A61K 31/496; A61K 31/5375; A61K 31/706
See application file for complete search history.

(56) References Cited

U.S. PATENT DOCUMENTS

| | | |
|---|---|---|
| 4,664,097 A | 5/1987 | McGrath et al. |
| 4,994,384 A | 2/1991 | Prather et al. |
| 5,057,420 A | 10/1991 | Massey |
| 5,994,619 A | 11/1999 | Stice et al. |
| 6,011,197 A | 1/2000 | Strelchenko et al. |
| 6,107,543 A | 8/2000 | Sims et al. |
| 6,700,037 B2 | 3/2004 | Damiani et al. |
| 8,895,245 B2 | 11/2014 | Copeland et al. |
| 9,688,665 B2 | 6/2017 | Knutson et al. |
| 9,889,138 B2 | 2/2018 | Keilhack |
| 2016/0303135 A1 | 10/2016 | Keilhack et al. |
| 2016/0361309 A1 | 12/2016 | McCabe et al. |
| 2024/0000900 A1 | 1/2024 | Zhang et al. |

FOREIGN PATENT DOCUMENTS

| | | |
|---|---|---|
| CN | 1311330 A | 9/2001 |
| CN | 103025890 A | 4/2013 |
| CN | 103732222 A | 4/2014 |
| GB | 2318578 B | 1/2000 |
| GB | 2331751 B | 1/2000 |
| WO | 2015048577 A2 | 4/2015 |
| WO | 2015128837 A1 | 9/2015 |
| WO | 2017062495 A2 | 4/2017 |
| WO | 2017079738 A1 | 5/2017 |
| WO | 2017100362 A2 | 6/2017 |

OTHER PUBLICATIONS

Raas et al. Trends in Genetics, Jan. 2022, vol. 38, No. 1, pp. 82-96 (Year: 2022).*
Monk et al. PNAS, Apr. 25, 2006, vol. 103, No. 17, pp. 6623-6628 (Year: 2006).*
Maupetit-Mehouas et al. Nucleic Acids Research, 2016, vol. 44, No. 2, pp. 621-635 (Year: 2016).*
Pan et al. Molecular Cancer, 2016, vol. 15, No. 79, pp. 1-14 (Year: 2016).*
Qu et al. Nucleic Acids Research, 2016, vol. 44, No. 16, pp. 7659-7672 (Year: 2016).*
Sun et al. European Journal of Pharmaceutical Sciences, 2015, vol. 77, pp. 290-302 (Year: 2015).*
Tsung et al., "Expression of exogenous porcine transforming growth factor beta-1 gene in ES cells and its effect on their differentiation in vitro," Shi Yan Sheng Wu Xue Bao, Jun. 1995, vol. 28, No. 2, pp. 173-189. [Abstract only, 1 page].
Bunt et al., "OTX2 sustains a bivalent-like state of OTX2-bound promoters in medulloblastoma by maintaining their H3K27me3 levels," Acta Neuropathologica, Nov. 18, 2012, vol. 125, No. 3, pp. 385-394 (10 pages).
Inoue et al., "Genomic imprinting of Xist by maternal H3K27me3," Genes & Development, 2017, vol. 31, pp. 1927-1932 (6 pages).
Kobayashi et al., "Contribution of Intragenic DNA Methylation in Mouse Gametic DNA Methylomes to Establish Oocyte-Specific Heritable Marks," PLoS Genetics, Jan. 2012, vol. 8, Iss. 1, e1002440, pp. 1-14 (14 pages).
McCabe et al., "EZH2 inhibition as a therapeutic strategy for lymphoma with EZH2-activating mutations," Nature, Dec. 6, 2012, vol. 492, No. 7427, pp. 108-112 (7 pages).
Morera et al., "Targeting histone methyltransferases and demethylases in clinical trials for cancer therapy," Clinical Epigenetics, 2016, vol. 8, Article No. 57, pp. 1-16 (16 pages).
Piedrahita et al., "Generation of Transgenic Porcine Chimeras Using Primordial Germ Cell-Derived Colonies," Biology of Reproduction, 1998, vol. 58, pp. 1321-1329 (9 pages).

(Continued)

*Primary Examiner* — James D. Anderson
(74) *Attorney, Agent, or Firm* — Greenberg Traurig, LLP; Melissa Hunter-Ensor; Leslie Serunian

(57) ABSTRACT

The invention provides methods for activating a repressed allele within an imprinting control region, thereby treating an imprinting associated disorder.

6 Claims, 63 Drawing Sheets
Specification includes a Sequence Listing.

(56) References Cited

OTHER PUBLICATIONS

Qi et al., "Selective inhibition of Ezh2 by a small molecule inhibitor blocks tumor cells proliferation," Proceedings of the National Academy of Sciences of the United States of America, Dec. 26, 2012, vol. 109, No. 52, pp. 21360-21365 (6 pages).

Shim et al., "Isolation of Pluripotent Stem Cells from Cultured Porcine Primordial Germ Cells," Biology of Reproduction, 1997, vol. 57, pp. 1089-1095 (7 pages).

Wagoner et al., "Functional Enucleation of Bovine Oocytes: Effects of Centrifugation and Ultraviolet Light," Theriogenology, 1996, vol. 46, pp. 279-284 (6 pages).

Wheeler, Matthew B., "Development and Validation of Swine Embryonic Stem Cells: a Review," Reproduction, Fertility and Development, 1994, vol. 6, No. 5, pp. 563-568 (6 pages).

Zheng et al., "Resetting Epigenetic Memory by Reprogramming of Histone Modifications in Mammals," Molecular Cell, Sep. 15, 2016, vol. 63, pp. 1066-1079 (38 pages).

Extended European Search Report dated Mar. 26, 2021 received in corresponding European Patent Application No. 18835463.3 (13 pages).

Dreger et al., "Epigenetic Regulation of Cell Adhesion and Communication by Enhancer of Zeste Homolog 2 in Human Endothelial Cells," Hypertension, Nov. 2012; vol. 60, No. 5, pp. 1176-1183.

International Search Report and Written Opinion in corresponding PCT Patent Application No. PCT/US18/42876, mailed Dec. 4, 2018 (19 pages).

Office Action and Search Report dated Sep. 16, 2022 in corresponding Chinese Patent Application No. 201880060928.5 (7 pages).

English translation of the Office Action and Search Report dated Sep. 16, 2022 in corresponding Chinese Patent Application No. 201880060928.5 (7 pages).

Office Action dated Mar. 31, 2023 in corresponding Chinese Patent Application No. 201880060928.5 (5 pages).

English translation of the Office Action dated Mar. 31, 2023 in corresponding Chinese Patent Application No. 201880060928.5 (6 pages).

\* cited by examiner

| Genes with promoter Ps-DHSs (n=67) | | |
|---|---|---|
| 1700007B14Rik | Impact | Oaz2 |
| 2510002D24Rik | Jakmip2 | Olfr1349 |
| A330023F24Rik | Kcnq1ot1 | Pcyox1l |
| Actr1b | Ldhal6b | Peg3 |
| Adamts15 | Lmcd1 | Plagl1 |
| Agbl4 | Lmna | Prickle2 |
| AI197445 | Lrfn2 | Scg5 |
| Akap5 | Lynx1 | Scn11a |
| BC051142 | M1ap | Sertm1 |
| Bcas3 | Mapre2 | Sgip1 |
| Cep110 | Mir148a | Slc13a4 |
| Cntn1 | Mir210 | Stxbp5l |
| Col5a3 | Mir344 | Syce1 |
| Ebf1 | Mir6401 | Tekt3 |
| Extl3 | Msx2 | Tet3 |
| Gabrg1 | Mterfd3 | Tsc22d1 |
| Galnt18 | Nav2 | Ttc29 |
| Golim4 | Nfe2l1 | Ube2u |
| Gpr123 | Ngf | Wbp1 |
| Gpr139 | Nhsl1 | Zfp286 |
| Gykl1 | Nkx3-1 | Zfp869 |
| Hhat | Nr3c2 | Zfp879 |
| Hip1 | | |

| Genes with promoter Ms-DHSs (n=26) |
|---|
| 1700029J07Rik |
| Akap11 |
| Arhgap26 |
| Atad3a |
| Bid |
| Caly |
| Ccdc61 |
| Clec11a |
| Dhx34 |
| Drd4 |
| Ffar4 |
| Gm4827 |
| Lgmn |
| Mab21l2 |
| Mov10l1 |
| Mprip |
| Nkx2-3 |
| Nol6 |
| Pcna |
| Prmt10 |
| Rab10 |
| Syce3 |
| Trmt10c |
| Upf2 |
| Wdr91 |
| Zfp7 |

*FIG. 2G*

Normalize datasets using exogenous ERCC standard

Apply cutoff (FDR < 0.05, FPKM > 2 in either AG or GG embryos, FPKM in AG or GG embryos is > 2-fold as much as that of α-amanitin embryos) to identify zygotically expressed genes Subtract FPKM values of α-amanitin embryos from those of AG and GG embryos for every gene Consider FC > 10 genes as AG- or GG-specific differentially expressed genes

*FIG. 3C*

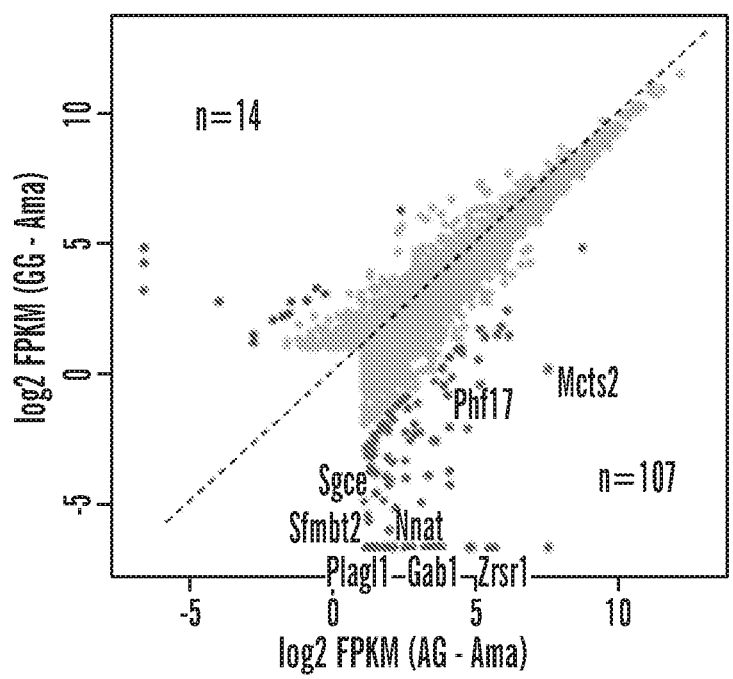

*FIG. 3D*

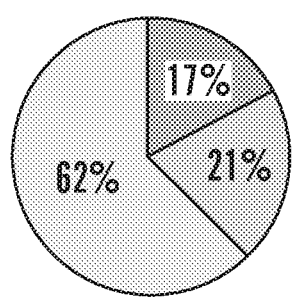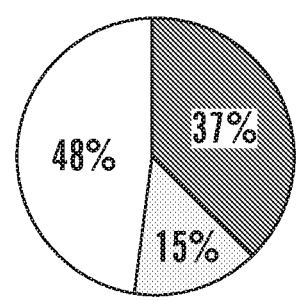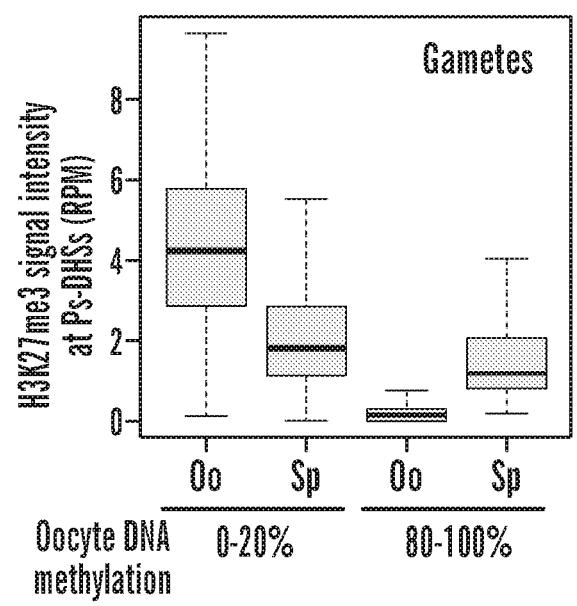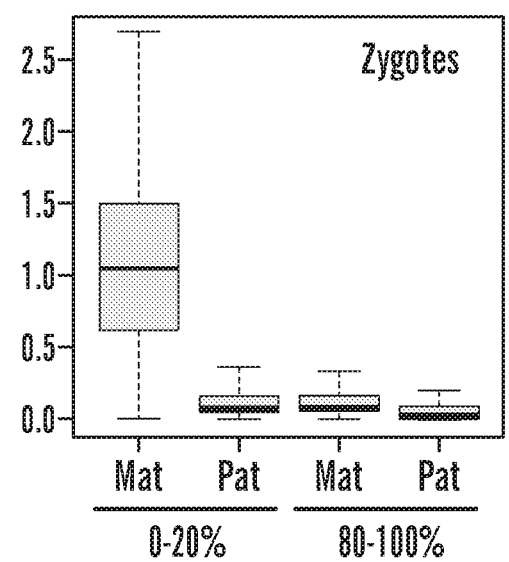
FIG. 5A   FIG. 5B   FIG. 5C

SEQUENCE LISTING

```
<160> NUMBER OF SEQ ID NOS: 17

<210> SEQ ID NO 1
<211> LENGTH: 747
<212> TYPE: PRT
<213> ORGANISM: Homo sapiens

<400> SEQUENCE: 1

Met Glu Ile Pro Asn Pro Pro Thr Ser Lys Cys Ile Thr Tyr Trp Lys
1               5                   10                  15

Arg Lys Val Lys Ser Glu Tyr Met Arg Leu Arg Gln Leu Lys Arg Leu
            20                  25                  30

Gln Ala Asn Met Gly Ala Lys Ala Leu Tyr Val Ala Asn Phe Ala Lys
        35                  40                  45

Val Gln Glu Lys Thr Gln Ile Leu Asn Glu Glu Trp Lys Lys Leu Arg
    50                  55                  60

Val Gln Pro Val Gln Ser Met Lys Pro Val Ser Gly His Pro Phe Leu
65                  70                  75                  80

Lys Lys Cys Thr Ile Glu Ser Ile Phe Pro Gly Phe Ala Ser Gln His
                85                  90                  95

Met Leu Met Arg Ser Leu Asn Thr Val Ala Leu Val Pro Ile Met Tyr
            100                 105                 110

Ser Trp Ser Pro Leu Gln Gln Asn Phe Met Val Glu Asp Glu Thr Val
        115                 120                 125

Leu Cys Asn Ile Pro Tyr Met Gly Asp Glu Val Lys Glu Glu Asp Glu
    130                 135                 140

Thr Phe Ile Glu Glu Leu Ile Asn Asn Tyr Asp Gly Lys Val His Gly
145                 150                 155                 160

Glu Glu Glu Met Ile Pro Gly Ser Val Leu Ile Ser Asp Ala Val Phe
                165                 170                 175
```

```
Leu Glu Leu Val Asp Ala Leu Asn Gln Tyr Ser Asp Glu Glu Glu
                180                 185                 190

Gly His Asn Asp Thr Ser Asp Gly Lys Gln Asp Ser Lys Glu Asp
            195                 200                 205

Leu Pro Val Thr Arg Lys Arg Lys Arg His Ala Ile Glu Gly Asn Lys
    210                 215                 220

Lys Ser Ser Lys Lys Gln Phe Pro Asn Asp Met Ile Phe Ser Ala Ile
225                 230                 235                 240

Ala Ser Met Phe Pro Glu Asn Gly Val Pro Asp Met Lys Glu Arg
                245                 250                 255

Tyr Arg Glu Leu Thr Glu Met Ser Asp Pro Asn Ala Leu Pro Pro Gln
        260                 265                 270

Cys Thr Pro Asn Ile Asp Gly Pro Asn Ala Lys Ser Val Gln Arg Glu
    275                 280                 285

Gln Ser Leu His Ser Phe His Thr Leu Phe Cys Arg Arg Cys Phe Lys
    290                 295                 300

Tyr Asp Cys Phe Leu His Pro Phe His Ala Thr Pro Asn Val Tyr Lys
305                 310                 315                 320

Arg Lys Asn Lys Glu Ile Lys Ile Glu Pro Glu Pro Cys Gly Thr Asp
                325                 330                 335

Cys Phe Leu Leu Leu Glu Gly Ala Lys Glu Tyr Ala Met Leu His Asn
                340                 345                 350

Pro Arg Ser Lys Cys Ser Gly Arg Arg Arg Arg His Ile Val
        355                 360                 365

Ser Ala Ser Cys Ser Asn Ala Ser Ala Ser Ala Val Ala Glu Thr Lys
    370                 375                 380

Glu Gly Asp Ser Asp Arg Asp Thr Gly Asn Asp Trp Ala Ser Ser Ser
385                 390                 395                 400

Ser Glu Ala Asn Ser Arg Cys Gln Thr Pro Thr Lys Gln Lys Ala Ser
                405                 410                 415

Pro Ala Pro Pro Gln Leu Cys Val Val Glu Ala Pro Ser Glu Pro Val
        420                 425                 430

Glu Trp Thr Gly Ala Glu Glu Ser Leu Phe Arg Val Phe His Gly Thr
        435                 440                 445

Tyr Phe Asn Asn Phe Cys Ser Ile Ala Arg Leu Leu Gly Thr Lys Thr
    450                 455                 460

Cys Lys Gln Val Phe Gln Phe Ala Val Lys Glu Ser Leu Ile Leu Lys
465                 470                 475                 480

Leu Pro Thr Asp Glu Leu Met Asn Pro Ser Gln Lys Lys Lys Arg Lys
                485                 490                 495

His Arg Leu Trp Ala Ala His Cys Arg Lys Ile Gln Leu Lys Lys Asp
            500                 505                 510

Asn Ser Ser Thr Gln Val Tyr Asn Tyr Gln Pro Cys Asp His Pro Asp
    515                 520                 525

Arg Pro Cys Asp Ser Thr Cys Pro Cys Ile Met Thr Gln Asn Phe Cys
    530                 535                 540

Glu Lys Phe Cys Gln Cys Asn Pro Asp Cys Gln Asn Arg Phe Pro Gly
545                 550                 555                 560

Cys Arg Cys Lys Thr Gln Cys Asn Thr Lys Gln Cys Pro Cys Tyr Leu
                565                 570                 575

Ala Val Arg Glu Cys Asp Pro Asp Leu Cys Leu Thr Cys Gly Ala Ser
        580                 585                 590

Glu His Trp Asp Cys Lys Val Val Ser Cys Lys Asn Cys Ser Ile Gln
```

```
                595                 600                 605
Arg Gly Leu Lys Lys His Leu Leu Ala Pro Ser Asp Val Ala Gly
    610                 615                 620

Trp Gly Thr Phe Ile Lys Glu Ser Val Gln Lys Asn Glu Phe Ile Ser
625                 630                 635                 640

Glu Tyr Cys Gly Glu Leu Ile Ser Gln Asp Glu Ala Asp Arg Arg Gly
                645                 650                 655

Lys Val Tyr Asp Lys Tyr Met Ser Ser Phe Leu Phe Asn Leu Asn Asn
            660                 665                 670

Asp Phe Val Val Asp Ala Thr Arg Lys Gly Asn Lys Ile Arg Phe Ala
        675                 680                 685

Asn His Ser Val Asn Pro Asn Cys Tyr Ala Lys Val Val Met Val Asn
    690                 695                 700

Gly Asp His Arg Ile Gly Ile Phe Ala Lys Arg Ala Ile Gln Ala Gly
705                 710                 715                 720

Glu Glu Leu Phe Phe Asp Tyr Arg Tyr Ser Gln Ala Asp Ala Leu Lys
                725                 730                 735

Tyr Val Gly Ile Glu Arg Glu Thr Asp Val Leu
            740                 745

<210> SEQ ID NO 2
<211> LENGTH: 4697
<212> TYPE: DNA
<213> ORGANISM: Homo sapiens

<400> SEQUENCE: 2
aggaggcgcg gggcggggca cggcgcaggg gtggggccgc ggcgcgcatg cgtcctagca    60 gcggacccg  cggctcggga tggaggctgg acacctgttc tgctgttgtg tcctgccatt   120
ctcctgaaga acagaggcac actgtaaaac ccaacacttc cccttgcatt ctataagatt   180
acagcaagat ggaaatacca aatccccta  cctccaaatg tatcacttac tggaaaagaa   240
aagtgaaatc tgaatacatg cgacttcgac aacttaaacg gcttcaggca aatatgggtg   300
caaaggcttt gtatgtggca aattttgcaa aggttcaaga aaaaacccag atcctcaatg   360
aagaatggaa gaagcttcgt gtccaacctg ttcagtcaat gaagcctgtg agtggacacc   420
cttttctcaa aaagtgtacc atagagagca ttttcccggg atttgcaagc caacatatgt   480
taatgaggtc actgaacaca gttgcattgg ttcccatcat gtattcctgg tcccctctcc   540
aacagaactt tatggtagaa gatgagacgg ttttgtgcaa tattccctac atgggagatg   600
aagtgaaaga agaagatgag acttttattg aggagctgat caataactat gatgggaaag   660
tccatggtga agaagagatg atccctggat ccgttctgat tagtgatgct gtttttctgg   720
agttggtcga tgccctgaat cagtactcag atgaggagga ggaagggcac aatgacacct   780
cagatggaaa gcaggatgac agcaaagaag atctgccagt aacaagaaag agaaagcgac   840
atgctattga aggcaacaaa aagagttcca agaaacagtt cccaaatgac atgatcttca   900
gtgcaattgc ctcaatgttc cctgagaatg tgtcccaga  tgacatgaag gagaggtatc   960
gagaactaac agagatgtca gaccccaatg cacttccccc tcagtgcaca cccaacatcg  1020
atggccccaa tgccaagtct gtgcagcggg agcaatctct gcactccttc cacacacttt  1080
tttgccggcg ctgctttaaa tacgactgct tccttcaccc ttttcatgcc accctaatg   1140 tatataaacg caagaataaa gaatcaaga  ttgaaccaga accatgtggc acagactgct  1200
tccttttgct ggaaggagca aaggagtatg ccatgctcca caacccccgc tccaagtgct  1260
```

```
ctggtcgtcg ccggagaagg caccacatag tcagtgcttc ctgctccaat gcctcagcct    1320
ctgctgtggc tgagactaaa gaaggagaca gtgacaggga cacaggcaat gactgggcct    1380
ccagttcttc agaggctaac tctcgctgtc agactcccac aaaacagaag gctagtccag    1440
ccccacctca actctgcgta gtggaagcac cctcggagcc tgtggaatgg actggggctg    1500
aagaatctct ttttcgagtc ttccatggca cctacttcaa caacttctgt tcaatagcca    1560
ggcttctggg gaccaagacg tgcaagcagg tctttcagtt tgcagtcaaa gaatcactta    1620
tcctgaagct gccaacagat gagctcatga acccctcaca gaagaagaaa agaaagcaca    1680
gattgtgggc tgcacactgc aggaagattc agctgaagaa agataactct tccacacaag    1740
tgtacaacta ccaaccctgc gaccacccag accgcccctg tgacagcacc tgcccctgca    1800
tcatgactca gaatttctgt gagaagttct gccagtgcaa cccagactgt cagaatcgtt    1860
tccctggctg tcgctgtaag acccagtgca ataccaagca atgtccttgc tatctggcag    1920
tgcgagaatg tgaccctgac ctgtgtctca cctgtggggc tcagagcac  tgggactgca    1980 aggtggtttc ctgtaaaaac tgcagcatcc agcgtggact taagaagcac ctgctgctgg    2040 cccccctctga tgtggccgga tggggcacct tcataaagga gtctgtgcag aagaacgaat    2100
tcatttctga atactgtggt gagctcatct ctcaggatga ggctgatcga cgcggaaagg    2160
tctatgacaa atacatgtcc agcttcctct tcaacctcaa taatgatttt gtagtggatg    2220
ctactcggaa aggaaacaaa attcgatttg caaatcattc agtgaatccc aactgttatg    2280
ccaaagtggt catggtgaat ggagaccatc ggattgggat cttttgccaag agggcaattc    2340 aagctggcga agagctcttc tttgattaca ggtacagcca agctgatgct ctcaagtacg    2400
tggggatcga gagggagacc gacgtccttt agccctccca ggccccacgg cagcacttat    2460
ggtagcggca ctgtcttggc tttcgtgctc acaccactgc tgctcgagtc tcctgcactg    2520
tgtctcccac actgagaaac cccccaaccc actccctctg tagtgaggcc tctgccatgt    2580
ccagagggca caaaactgtc tcaatgagag gggagacaga ggcagctagg gcttggtctc    2640
ccaggacaga gagttacaga aatgggagac tgtttctctg gcctcagaag aagcgagcac    2700
aggctggggt ggatgactta tgcgtgattt cgtgtcggct ccccaggctg tggcctcagg    2760
aatcaactta ggcagttccc aacaagcgct agcctgtaat tgtagctttc cacatcaaga    2820
gtccttatgt tattgggatg caggcaaacc tctgtggtcc taagacctgg agaggacagg    2880
ctaagtgaag tgtggtccct ggagcctaca agtggtctgg gttagaggcg agcctggcag    2940
gcagcacaga ctgaactcag aggtagacag gtcaccttac tacctcctcc ctcgtggcag    3000
ggctcaaact gaaagagtgt gggttctaag tacaggcatt caaggctggg ggaaggaaag    3060
ctacgccatc cttccttagc cagagaggga gaaccagcca gatgatagta gttaaactgc    3120
taagcttggg cccaggaggc tttgagaaag ccttctctgt gtactctgga gatagatgga    3180
gaagtgtttt cagattcctg gaacagaca ccagtgctcc agctcctcca aagttctggc    3240
ttagcagctg caggcaagca ttatgctgct attgaagaag cattagggt  atgcctggca    3300 ggtgtgagca tcctggctcg ctggatttgt gggtgttttc aggccttcca ttccccatag    3360
aggcaaggcc caatggccag tgttgcttat cgcttcaggg taggtgggca caggcttgga    3420
ctagagagga gaaagattgg tgtaatctgc tttcctgtct gtagtgcctg ctgtttggaa    3480
agggtgagtt agaatatgtt ccaaggttgg tgagggcta  aattgcacgc gtttaggctg    3540
gcaccccgtg tgcagggcac actggcagag ggtatctgaa gtgggagaag aagcaggtag    3600
accacctgtc ccaggctgtg gtgccaccct ctctggcatt catgcagagc aaagcacttt    3660
```

-continued

```
aaccatttct tttaaaaggt ctatagattg gggtagagtt tggcctaagg tctctagggt    3720
ccctgcctaa atcccactcc tgagggaggg ggaagaagag agggtgggag attctcctcc    3780
agtcctgtct catctcctgg gagaggcaga cgagtgagtt tcacacagaa gaatttcatg    3840 tgaatgggc cagcaagagc tgccctgtgt ccatggtggg tgtgccgggc tggctgggaa     3900
caaggagcag tatgttgagt agaaagggtg tgggcgggta tagattggcc tgggagtgtt    3960
acagtaggga gcaggcttct cccttctttc tgggactcag agccccgctt cttcccactc    4020
cacttgttgt cccatgaagg aagaagtggg gttcctcctg acccagctgc ctcttacggt    4080
ttggtatggg acatgcacac acactcacat gctctcactc accacactgg agggcacaca    4140 cgtacccgc acccagcaac tcctgacaga aagctcctcc cacccaaatg gccaggccc     4200 cagcatgatc ctgaaatctg catccgccgt ggtttgtatt cattgtgcat atcagggata    4260
ccctcaagct ggactgtggg ttccaaatta ctcatagagg agaaaccag agaaagatga     4320 agaggaggag ttaggtctat ttgaaatgcc aggggctcgc tgtgaggaat aggtgaaaaa    4380
aaacttttca ccagcctttg agagactaga ctgaccccac ccttccttca gtgagcagaa    4440
tcactgtggt cagtctcctg tcccagcttc agttcatgaa tactcctgtt cctccagttt    4500
cccatccttt gtccctgctg tcccccactt ttaaagatgg gtctcaaccc ctccccacca    4560
cgtcatgatg gatggggcaa ggtggtgggg actaggggag cctggtatac atgcggcttc    4620
attgccaata aatttcatgc actttaaagt cctgtggctt gtgacctctt aataaagtgt    4680
tagaatccaa aaaaaaa                                                   4697
```

```
<210> SEQ ID NO 3
<211> LENGTH: 746
<212> TYPE: PRT
<213> ORGANISM: Homo sapiens

<400> SEQUENCE: 3

Met Gly Gln Thr Gly Lys Lys Ser Glu Lys Gly Pro Val Cys Trp Arg
1               5                  10                  15

Lys Arg Val Lys Ser Glu Tyr Met Arg Leu Arg Gln Leu Lys Arg Phe
            20                  25                  30

Arg Arg Ala Asp Glu Val Lys Ser Met Phe Ser Ser Asn Arg Gln Lys
        35                  40                  45

Ile Leu Glu Arg Thr Glu Ile Leu Asn Gln Glu Trp Lys Gln Arg Arg
    50                  55                  60

Ile Gln Pro Val His Ile Leu Thr Ser Val Ser Ser Leu Arg Gly Thr
65                  70                  75                  80

Arg Glu Cys Ser Val Thr Ser Asp Leu Asp Phe Pro Thr Gln Val Ile
                85                  90                  95

Pro Leu Lys Thr Leu Asn Ala Val Ala Ser Val Pro Ile Met Tyr Ser
            100                 105                 110

Trp Ser Pro Leu Gln Gln Asn Phe Met Val Glu Asp Glu Thr Val Leu
        115                 120                 125

His Asn Ile Pro Tyr Met Gly Asp Glu Val Leu Asp Gln Asp Gly Thr
    130                 135                 140

Phe Ile Glu Glu Leu Ile Lys Asn Tyr Asp Gly Lys Val His Gly Asp
145                 150                 155                 160

Arg Glu Cys Gly Phe Ile Asn Asp Glu Ile Phe Val Glu Leu Val Asn
                165                 170                 175

Ala Leu Gly Gln Tyr Asn Asp Asp Asp Asp Asp Asp Gly Asp Asp
```

```
               180              185               190
Pro Glu Glu Arg Glu Glu Lys Gln Lys Asp Leu Glu Asp His Arg Asp
            195                 200                 205
Asp Lys Glu Ser Arg Pro Pro Arg Lys Phe Pro Ser Asp Lys Ile Phe
        210                 215                 220
Glu Ala Ile Ser Ser Met Phe Pro Asp Lys Gly Thr Ala Glu Glu Leu
225                 230                 235                 240
Lys Glu Lys Tyr Lys Glu Leu Thr Glu Gln Gln Leu Pro Gly Ala Leu
                245                 250                 255
Pro Pro Glu Cys Thr Pro Asn Ile Asp Gly Pro Asn Ala Lys Ser Val
            260                 265                 270
Gln Arg Glu Gln Ser Leu His Ser Phe His Thr Leu Phe Cys Arg Arg
        275                 280                 285
Cys Phe Lys Tyr Asp Cys Phe Leu His Pro Phe His Ala Thr Pro Asn
        290                 295                 300
Thr Tyr Lys Arg Lys Asn Thr Glu Thr Ala Leu Asp Asn Lys Pro Cys
305                 310                 315                 320
Gly Pro Gln Cys Tyr Gln His Leu Glu Gly Ala Lys Glu Phe Ala Ala
                325                 330                 335
Ala Leu Thr Ala Glu Arg Ile Lys Thr Pro Pro Lys Arg Pro Gly Gly
            340                 345                 350
Arg Arg Arg Gly Arg Leu Pro Asn Asn Ser Ser Arg Pro Ser Thr Pro
        355                 360                 365
Thr Ile Asn Val Leu Glu Ser Lys Asp Thr Asp Ser Asp Arg Glu Ala
        370                 375                 380
Gly Thr Glu Thr Gly Gly Glu Asn Asn Asp Lys Glu Glu Glu Glu Lys
385                 390                 395                 400
Lys Asp Glu Thr Ser Ser Ser Ser Glu Ala Asn Ser Arg Cys Gln Thr
                405                 410                 415
Pro Ile Lys Met Lys Pro Asn Ile Glu Pro Pro Glu Asn Val Glu Trp
            420                 425                 430
Ser Gly Ala Glu Ala Ser Met Phe Arg Val Leu Ile Gly Thr Tyr Tyr
        435                 440                 445
Asp Asn Phe Cys Ala Ile Ala Arg Leu Ile Gly Thr Lys Thr Cys Arg
        450                 455                 460
Gln Val Tyr Glu Phe Arg Val Lys Glu Ser Ser Ile Ile Ala Pro Ala
465                 470                 475                 480
Pro Ala Glu Asp Val Asp Thr Pro Pro Arg Lys Lys Lys Arg Lys His
                485                 490                 495
Arg Leu Trp Ala Ala His Cys Arg Lys Ile Gln Leu Lys Lys Asp Gly
            500                 505                 510
Ser Ser Asn His Val Tyr Asn Tyr Gln Pro Cys Asp His Pro Arg Gln
        515                 520                 525
Pro Cys Asp Ser Ser Cys Pro Cys Val Ile Ala Gln Asn Phe Cys Glu
        530                 535                 540
Lys Phe Cys Gln Cys Ser Ser Glu Cys Gln Asn Arg Phe Pro Gly Cys
545                 550                 555                 560
Arg Cys Lys Ala Gln Cys Asn Thr Lys Gln Cys Pro Cys Tyr Leu Ala
                565                 570                 575
Val Arg Glu Cys Asp Pro Asp Leu Cys Leu Thr Cys Gly Ala Ala Asp
            580                 585                 590
His Trp Asp Ser Lys Asn Val Ser Cys Lys Asn Cys Ser Ile Gln Arg
        595                 600                 605
```

```
Gly Ser Lys Lys His Leu Leu Leu Ala Pro Ser Asp Val Ala Gly Trp
        610                 615                 620
Gly Ile Phe Ile Lys Asp Pro Val Gln Lys Asn Glu Phe Ile Ser Glu
    625                 630                 635                 640
Tyr Cys Gly Glu Ile Ile Ser Gln Asp Glu Ala Asp Arg Arg Gly Lys
                645                 650                 655
Val Tyr Asp Lys Tyr Met Cys Ser Phe Leu Phe Asn Leu Asn Asn Asp
            660                 665                 670
Phe Val Val Asp Ala Thr Arg Lys Gly Asn Lys Ile Arg Phe Ala Asn
        675                 680                 685
His Ser Val Asn Pro Asn Cys Tyr Ala Lys Val Met Met Val Asn Gly
        690                 695                 700
Asp His Arg Ile Gly Ile Phe Ala Lys Arg Ala Ile Gln Thr Gly Glu
705                 710                 715                 720
Glu Leu Phe Phe Asp Tyr Arg Tyr Ser Gln Ala Asp Ala Leu Lys Tyr
                725                 730                 735
Val Gly Ile Glu Arg Glu Met Glu Ile Pro
            740                 745
```

<210> SEQ ID NO 4
<211> LENGTH: 2681
<212> TYPE: DNA
<213> ORGANISM: Homo sapiens

<400> SEQUENCE: 4

```
ggcggcgctt gattgggctg gggggggccaa ataaaagcga tggcgattgg gctgccgcgt      60
ttggcgctcg gtccggtcgc gtccgacacc cggtgggact cagaaggcag tggagccccg     120
gcggcggcgc cggcggcgcg cggggggcgac gcgcgggaac aacgcgagtc ggcgcgcggg     180
acgaagaata atcatgggcc agactgggaa gaaatctgag aagggaccag tttgttggcg     240
gaagcgtgta aaatcagagt acatgcgact gagacagctc aagaggttca gacgagctga     300
tgaagtaaag agtatgttta gttccaatcg tcagaaaatt ttggaaagaa cggaaatctt     360
aaaccaagaa tggaaacagc gaaggataca gcctgtgcac atcctgactt cttgttcggt     420
gaccagtgac ttggattttc aacacaagt catcccatta aagactctga atgcagttgc     480
ttcagtaccc ataatgtatt cttggtctcc cctacagcag aattttatgg tggaagatga     540
aactgtttta cataacattc cttatatggg agatgaagtt ttagatcagg atggtacttt     600
cattgaagaa ctaataaaaa attatgatgg gaaagtacac ggggatagag aatgtgggtt     660
tataaatgat gaaattttg tggagttggt gaatgcccct ggtcaatata atgatgatga     720
cgatgatgat gatggagacg atcctgaaga aagagaagaa aagcagaaag atctggagga     780
tcaccgagat gataagaaa gccgcccacc tcggaaattt ccttctgata aaatttttga     840
agccatttcc tcaatgtttc agataaggg cacagcagaa gaactaaagg aaaaatataa     900
agaactcacc gaacagcagc tcccaggcgc acttcctcct gaatgtaccc ccaacataga     960
tggaccaaat gctaaatctg ttcagagaga gcaaagctta cactcctttc atacgctttt    1020
ctgtaggcga tgttttaaat atgactgctt cctacatcct tttcatgcaa acccaacac     1080
ttataagcgg aagaacacag aaacagctct agacaacaaa ccttgtggac cacagtgtta    1140
ccagcatttg gagggagcaa aggagtttgc tgctgctctc accgctgagc ggataaagac    1200
cccaccaaaa cgtccaggag gccgcagaag aggacggctt cccaataaca gtagcaggcc    1260
cagcaccccc accattaatg tgctggaatc aaaggataca gacagtgata gggaagcagg    1320
```

```
gactgaaacg gggggagaga acaatgataa agaagaagaa gagaagaaag atgaaacttc    1380
gagctcctct gaagcaaatt ctcggtgtca acaccaata  aagatgaagc caaatattga    1440
acctcctgag aatgtggagt ggagtggtgc tgaagcctca atgtttagag tcctcattgg    1500
cacttactat gacaatttct gtgccattgc taggttaatt gggaccaaaa catgtagaca    1560
ggtgtatgag tttagagtca aagaatctag catcatagct ccagctcccg ctgaggatgt    1620
ggatactcct ccaaggaaaa agaagaggaa acaccggttg tgggctgcac actgcagaaa    1680
gatacagctg aaaaaggacg gctcctctaa ccatgtttac aactatcaac cctgtgatca    1740
tccacggcag ccttgtgaca gttcgtgccc ttgtgtgata gcacaaaatt tttgtgaaaa    1800
gttttgtcaa tgtagttcag agtgtcaaaa ccgctttccg ggatgccgct gcaaagcaca    1860
gtgcaacacc aagcagtgcc cgtgctacct ggctgtccga gagtgtgacc ctgacctctg    1920
tcttacttgt ggagccgctg accattggga cagtaaaaat gtgtcctgca agaactgcag    1980
tattcagcgg ggctccaaaa agcatctatt gctggcacca tctgacgtgg caggctgggg    2040
gattttatc  aaagatcctg tgcagaaaaa tgaattcatc tcagaatact gtggagagat    2100
tatttctcaa gatgaagctg acagaagagg gaaagtgtat gataaataca tgtgcagctt    2160
tctgttcaac ttgaacaatg attttgtggt ggatgcaacc cgcaagggta acaaaattcg    2220
ttttgcaaat cattcggtaa atccaaactg ctatgcaaaa gttatgatgg ttaacggtga    2280
tcacaggata ggtatttttg ccaagagagc catccagact ggcgaagagc tgttttttga    2340
ttacagatac agccaggctg atgccctgaa gtatgtcggc atcgaaagag aaatggaaat    2400
cccttgacat ctgctacctc ctcccccctc ctctgaaaca gctgccttag cttcaggaac    2460
ctcgagtact gtgggcaatt tagaaaaaga acatgcagtt tgaaattctg aatttgcaaa    2520
gtactgtaag aataatttat agtaatgagt ttaaaaatca actttttatt gccttctcac    2580
cagctgcaaa gtgttttgta ccagtgaatt tttgcaataa tgcagtatgg tacatttttc    2640
aactttgaat aaagaatact tgaacttgtc cttgttgaat c                        2681
```

<210> SEQ ID NO 5
<211> LENGTH: 1401
<212> TYPE: PRT
<213> ORGANISM: Homo sapiens

<400> SEQUENCE: 5

Met Lys Ser Cys Gly Val Ser Leu Ala Thr Ala Ala Ala Ala Ala
1               5                   10                  15

Ala Phe Gly Asp Glu Lys Lys Met Ala Ala Gly Lys Ala Ser Gly
            20                  25                  30

Glu Ser Glu Glu Ala Ser Pro Ser Leu Thr Ala Glu Glu Arg Glu Ala
        35                  40                  45

Leu Gly Gly Leu Asp Ser Arg Leu Phe Gly Phe Val Arg Phe His Glu
    50                  55                  60

Asp Gly Ala Arg Thr Lys Ala Leu Leu Gly Lys Ala Val Arg Cys Tyr
65                  70                  75                  80

Glu Ser Leu Ile Leu Lys Ala Glu Gly Lys Val Glu Ser Asp Phe Phe
                85                  90                  95

Cys Gln Leu Gly His Phe Asn Leu Leu Leu Glu Asp Tyr Pro Lys Ala
            100                 105                 110

Leu Ser Ala Tyr Gln Arg Tyr Tyr Ser Leu Gln Ser Asp Tyr Trp Lys
        115                 120                 125

```
Asn Ala Ala Phe Leu Tyr Gly Leu Gly Leu Val Tyr Phe His Tyr Asn
    130                 135                 140

Ala Phe Gln Trp Ala Ile Lys Ala Phe Gln Glu Val Leu Tyr Val Asp
145                 150                 155                 160

Pro Ser Phe Cys Arg Ala Lys Glu Ile His Leu Arg Leu Gly Leu Met
                165                 170                 175

Phe Lys Val Asn Thr Asp Tyr Glu Ser Ser Leu Lys His Phe Gln Leu
            180                 185                 190

Ala Leu Val Asp Cys Asn Pro Cys Thr Leu Ser Asn Ala Glu Ile Gln
        195                 200                 205

Phe His Ile Ala His Leu Tyr Glu Thr Gln Arg Lys Tyr His Ser Ala
    210                 215                 220

Lys Glu Ala Tyr Glu Gln Leu Leu Gln Thr Glu Asn Leu Ser Ala Gln
225                 230                 235                 240

Val Lys Ala Thr Val Leu Gln Gln Leu Gly Trp Met His His Thr Val
                245                 250                 255

Asp Leu Leu Gly Asp Lys Ala Thr Lys Glu Ser Tyr Ala Ile Gln Tyr
            260                 265                 270

Leu Gln Lys Ser Leu Glu Ala Asp Pro Asn Ser Gly Gln Ser Trp Tyr
        275                 280                 285

Phe Leu Gly Arg Cys Tyr Ser Ser Ile Gly Lys Val Gln Asp Ala Phe
    290                 295                 300

Ile Ser Tyr Arg Gln Ser Ile Asp Lys Ser Glu Ala Ser Ala Asp Thr
305                 310                 315                 320

Trp Cys Ser Ile Gly Val Leu Tyr Gln Gln Gln Asn Gln Pro Met Asp
                325                 330                 335

Ala Leu Gln Ala Tyr Ile Cys Ala Val Gln Leu Asp His Gly His Ala
            340                 345                 350

Ala Ala Trp Met Asp Leu Gly Thr Leu Tyr Glu Ser Cys Asn Gln Pro
        355                 360                 365

Gln Asp Ala Ile Lys Cys Tyr Leu Asn Ala Thr Arg Ser Lys Ser Cys
    370                 375                 380

Ser Asn Thr Ser Ala Leu Ala Ala Arg Ile Lys Tyr Leu Gln Ala Gln
385                 390                 395                 400

Leu Cys Asn Leu Pro Gln Gly Ser Leu Gln Asn Lys Thr Lys Leu Leu
                405                 410                 415

Pro Ser Ile Glu Glu Ala Trp Ser Leu Pro Ile Pro Ala Glu Leu Thr
            420                 425                 430

Ser Arg Gln Gly Ala Met Asn Thr Ala Gln Gln Asn Thr Ser Asp Asn
        435                 440                 445

Trp Ser Gly Gly His Ala Val Ser His Pro Val Gln Gln Gln Ala
    450                 455                 460

His Ser Trp Cys Leu Thr Pro Gln Lys Leu Gln His Leu Glu Gln Leu
465                 470                 475                 480

Arg Ala Asn Arg Asn Asn Leu Asn Pro Ala Lys Leu Met Leu Glu
                485                 490                 495

Gln Leu Glu Ser Gln Phe Val Leu Met Gln Gln His Gln Met Arg Pro
            500                 505                 510

Thr Gly Val Ala Gln Val Arg Ser Thr Gly Ile Pro Asn Gly Pro Thr
        515                 520                 525

Ala Asp Ser Ser Leu Pro Thr Asn Ser Val Ser Gly Gln Gln Pro Gln
    530                 535                 540

Leu Ala Leu Thr Arg Val Pro Ser Val Ser Gln Pro Gly Val Arg Pro
```

```
          545                 550                 555                 560
Ala Cys Pro Gly Gln Pro Leu Ala Asn Gly Pro Phe Ser Ala Gly His
                565                 570                 575

Val Pro Cys Ser Thr Ser Arg Thr Leu Gly Ser Thr Asp Thr Ile Leu
                580                 585                 590

Ile Gly Asn Asn His Ile Thr Gly Ser Gly Ser Asn Gly Asn Val Pro
                595                 600                 605

Tyr Leu Gln Arg Asn Ala Leu Thr Leu Pro His Asn Arg Thr Asn Leu
                610                 615                 620

Thr Ser Ser Ala Glu Glu Pro Trp Lys Asn Gln Leu Ser Asn Ser Thr
625                 630                 635                 640

Gln Gly Leu His Lys Gly Gln Ser Ser His Ser Ala Gly Pro Asn Gly
                645                 650                 655

Glu Arg Pro Leu Ser Ser Thr Gly Pro Ser Gln His Leu Gln Ala Ala
                660                 665                 670

Gly Ser Gly Ile Gln Asn Gln Asn Gly His Pro Thr Leu Pro Ser Asn
                675                 680                 685

Ser Val Thr Gln Gly Ala Ala Leu Asn His Leu Ser Ser His Thr Ala
                690                 695                 700

Thr Ser Gly Gly Gln Gln Gly Ile Thr Leu Thr Lys Glu Ser Lys Pro
705                 710                 715                 720

Ser Gly Asn Ile Leu Thr Val Pro Glu Thr Ser Arg His Thr Gly Glu
                725                 730                 735

Thr Pro Asn Ser Thr Ala Ser Val Glu Gly Leu Pro Asn His Val His
                740                 745                 750

Gln Met Thr Ala Asp Ala Val Cys Ser Pro Ser His Gly Asp Ser Lys
                755                 760                 765

Ser Pro Gly Leu Leu Ser Ser Asp Asn Pro Gln Leu Ser Ala Leu Leu
                770                 775                 780

Met Gly Lys Ala Asn Asn Asn Val Gly Thr Gly Thr Cys Asp Lys Val
785                 790                 795                 800

Asn Asn Ile His Pro Ala Val His Thr Lys Thr Asp Asn Ser Val Ala
                805                 810                 815

Ser Ser Pro Ser Ser Ala Ile Ser Thr Ala Thr Pro Ser Pro Lys Ser
                820                 825                 830

Thr Glu Gln Thr Thr Thr Asn Ser Val Thr Ser Leu Asn Ser Pro His
                835                 840                 845

Ser Gly Leu His Thr Ile Asn Gly Glu Gly Met Glu Glu Ser Gln Ser
                850                 855                 860

Pro Met Lys Thr Asp Leu Leu Leu Val Asn His Lys Pro Ser Pro Gln
865                 870                 875                 880

Ile Ile Pro Ser Met Ser Val Ser Ile Tyr Pro Ser Ser Ala Glu Val
                885                 890                 895

Leu Lys Ala Cys Arg Asn Leu Gly Lys Asn Gly Leu Ser Asn Ser Ser
                900                 905                 910

Ile Leu Leu Asp Lys Cys Pro Pro Arg Pro Pro Ser Ser Pro Tyr
                915                 920                 925

Pro Pro Leu Pro Lys Asp Lys Leu Asn Pro Thr Pro Ser Ile Tyr
                930                 935                 940

Leu Glu Asn Lys Arg Asp Ala Phe Phe Pro Pro Leu His Gln Phe Cys
945                 950                 955                 960

Thr Asn Pro Asn Asn Pro Val Thr Val Ile Arg Gly Leu Ala Gly Ala
                965                 970                 975
```

```
Leu Lys Leu Asp Leu Gly Leu Phe Ser Thr Lys Thr Leu Val Glu Ala
            980             985                 990

Asn Asn Glu His Met Val Glu Val  Arg Thr Gln Leu Leu  Gln Pro Ala
            995              1000                 1005

Asp Glu Asn Trp Asp Pro Thr  Gly Thr Lys Lys Ile  Trp His Cys
        1010             1015                1020

Glu Ser Asn Arg Ser His Thr  Thr Ile Ala Lys Tyr  Ala Gln Tyr
        1025             1030                1035

Gln Ala Ser Ser Phe Gln Glu  Ser Leu Arg Glu Glu  Asn Glu Lys
        1040             1045                1050

Arg Ser His His Lys Asp His  Ser Asp Ser Glu Ser  Thr Ser Ser
        1055             1060                1065

Asp Asn Ser Gly Arg Arg Arg  Lys Gly Pro Phe Lys  Thr Ile Lys
        1070             1075                1080

Phe Gly Thr Asn Ile Asp Leu  Ser Asp Asp Lys Lys  Trp Lys Leu
        1085             1090                1095

Gln Leu His Glu Leu Thr Lys  Leu Pro Ala Phe Val  Arg Val Val
        1100             1105                1110

Ser Ala Gly Asn Leu Leu Ser  His Val Gly His Thr  Ile Leu Gly
        1115             1120                1125

Met Asn Thr Val Gln Leu Tyr  Met Lys Val Pro Gly  Ser Arg Thr
        1130             1135                1140

Pro Gly His Gln Glu Asn Asn  Asn Phe Cys Ser Val  Asn Ile Asn
        1145             1150                1155

Ile Gly Pro Gly Asp Cys Glu  Trp Phe Val Val Pro  Glu Gly Tyr
        1160             1165                1170

Trp Gly Val Leu Asn Asp Phe  Cys Glu Lys Asn Asn  Leu Asn Phe
        1175             1180                1185

Leu Met Gly Ser Trp Trp Pro  Asn Leu Glu Asp Leu  Tyr Glu Ala
        1190             1195                1200

Asn Val Pro Val Tyr Arg Phe  Ile Gln Arg Pro Gly  Asp Leu Val
        1205             1210                1215

Trp Ile Asn Ala Gly Thr Val  His Trp Val Gln Ala  Ile Gly Trp
        1220             1225                1230

Cys Asn Asn Ile Ala Trp Asn  Val Gly Pro Leu Thr  Ala Cys Gln
        1235             1240                1245

Tyr Lys Leu Ala Val Glu Arg  Tyr Glu Trp Asn Lys  Leu Gln Ser
        1250             1255                1260

Val Lys Ser Ile Val Pro Met  Val His Leu Ser Trp  Asn Met Ala
        1265             1270                1275

Arg Asn Ile Lys Val Ser Asp  Pro Lys Leu Phe Glu  Met Ile Lys
        1280             1285                1290

Tyr Cys Leu Leu Arg Thr Leu  Lys Gln Cys Gln Thr  Leu Arg Glu
        1295             1300                1305

Ala Leu Ile Ala Ala Gly Lys  Glu Ile Ile Trp His  Gly Arg Thr
        1310             1315                1320

Lys Glu Glu Pro Ala His Tyr  Cys Ser Ile Cys Glu  Val Glu Val
        1325             1330                1335

Phe Asp Leu Leu Phe Val Thr  Asn Glu Ser Asn Ser  Arg Lys Thr
        1340             1345                1350

Tyr Ile Val His Cys Gln Asp  Cys Ala Arg Lys Thr  Ser Gly Asn
        1355             1360                1365
```

-continued

```
Leu Glu  Asn Phe Val Val Leu  Glu Gln Tyr Lys Met  Glu Asp Leu
    1370             1375              1380

Met Gln  Val Tyr Asp Gln Phe  Thr Leu Ala Pro Pro  Leu Pro Ser
    1385             1390              1395

Ala Ser  Ser
    1400

<210> SEQ ID NO 6
<211> LENGTH: 1643
<212> TYPE: PRT
<213> ORGANISM: Homo sapiens

<400> SEQUENCE: 6

Met His Arg Ala Val Asp Pro Pro Gly Ala Arg Ala Arg Glu Ala
1               5                   10                  15

Phe Ala Leu Gly Gly Leu Ser Cys Ala Gly Ala Trp Ser Ser Cys Pro
                20                  25                  30

Pro His Pro Pro Pro Arg Ser Ala Trp Leu Pro Gly Gly Arg Cys Ser
            35                  40                  45

Ala Ser Ile Gly Gln Pro Pro Leu Pro Ala Pro Leu Pro Pro Ser His
        50                  55                  60

Gly Ser Ser Ser Gly His Pro Ser Lys Pro Tyr Tyr Ala Pro Gly Ala
65                  70                  75                  80

Pro Thr Pro Arg Pro Leu His Gly Lys Leu Glu Ser Leu His Gly Cys
                85                  90                  95

Val Gln Ala Leu Leu Arg Glu Pro Ala Gln Pro Gly Leu Trp Glu Gln
                100                 105                 110

Leu Gly Gln Leu Tyr Glu Ser Glu His Asp Ser Glu Glu Ala Thr Arg
            115                 120                 125

Cys Tyr His Ser Ala Leu Arg Tyr Gly Gly Ser Phe Ala Glu Leu Gly
        130                 135                 140

Pro Arg Ile Gly Arg Leu Gln Gln Ala Gln Leu Trp Asn Phe His Thr
145                 150                 155                 160

Gly Ser Cys Gln His Arg Ala Lys Val Leu Pro Pro Leu Glu Gln Val
                165                 170                 175

Trp Asn Leu Leu His Leu Glu His Lys Arg Asn Tyr Gly Ala Lys Arg
            180                 185                 190

Gly Gly Pro Pro Val Lys Arg Ala Ala Glu Pro Pro Val Val Gln Pro
        195                 200                 205

Val Pro Pro Ala Ala Leu Ser Gly Pro Ser Gly Glu Glu Gly Leu Ser
    210                 215                 220

Pro Gly Gly Lys Arg Arg Arg Gly Cys Asn Ser Glu Gln Thr Gly Leu
225                 230                 235                 240

Pro Pro Gly Leu Pro Leu Pro Pro Pro Leu Pro Pro Pro Pro Pro Pro
                245                 250                 255

Pro Pro Pro Pro Pro Pro Pro Leu Pro Gly Leu Ala Thr Ser Pro
            260                 265                 270

Pro Phe Gln Leu Thr Lys Pro Gly Leu Trp Ser Thr Leu His Gly Asp
        275                 280                 285

Ala Trp Gly Pro Glu Arg Lys Gly Ser Ala Pro Glu Arg Gln Glu
    290                 295                 300

Gln Arg His Ser Leu Pro His Pro Tyr Pro Tyr Pro Ala Pro Ala Tyr
305                 310                 315                 320

Thr Ala His Pro Pro Gly His Arg Leu Val Pro Ala Ala Pro Pro Gly
                325                 330                 335
```

```
Pro Gly Pro Arg Pro Gly Ala Glu Ser His Gly Cys Leu Pro Ala
            340                 345                 350

Thr Arg Pro Pro Gly Ser Asp Leu Arg Glu Ser Arg Val Gln Arg Ser
            355                 360                 365

Arg Met Asp Ser Ser Val Ser Pro Ala Ala Thr Thr Ala Cys Val Pro
    370                 375                 380

Tyr Ala Pro Ser Arg Pro Pro Gly Leu Pro Gly Thr Thr Ser Ser
385                 390                 395                 400

Ser Ser Ser Ser Ser Ser Asn Thr Gly Leu Arg Gly Val Glu Pro Asn
                405                 410                 415

Pro Gly Ile Pro Gly Ala Asp His Tyr Gln Thr Pro Ala Leu Glu Val
            420                 425                 430

Ser His His Gly Arg Leu Gly Pro Ser Ala His Ser Ser Arg Lys Pro
        435                 440                 445

Phe Leu Gly Ala Pro Ala Ala Thr Pro His Leu Ser Leu Pro Pro Gly
    450                 455                 460

Pro Ser Ser Pro Pro Pro Pro Cys Pro Arg Leu Leu Arg Pro Pro
465                 470                 475                 480

Pro Pro Pro Ala Trp Leu Lys Gly Pro Ala Cys Arg Ala Ala Arg Glu
            485                 490                 495

Asp Gly Glu Ile Leu Glu Glu Leu Phe Phe Gly Thr Glu Gly Pro Pro
            500                 505                 510

Arg Pro Ala Pro Pro Leu Pro His Arg Glu Gly Phe Leu Gly Pro
    515                 520                 525

Pro Ala Ser Arg Phe Ser Val Gly Thr Gln Asp Ser His Thr Pro Pro
    530                 535                 540

Thr Pro Pro Thr Pro Thr Thr Ser Ser Asn Ser Asn Ser Gly Ser
545                 550                 555                 560

His Ser Ser Ser Pro Ala Gly Pro Val Ser Phe Pro Pro Pro Tyr
            565                 570                 575

Leu Ala Arg Ser Ile Asp Pro Leu Pro Arg Pro Pro Ser Pro Ala Gln
            580                 585                 590

Asn Pro Gln Asp Pro Pro Leu Val Pro Leu Thr Leu Ala Leu Pro Pro
        595                 600                 605

Ala Pro Pro Ser Ser Cys His Gln Asn Thr Ser Gly Ser Phe Arg Arg
    610                 615                 620

Pro Glu Ser Pro Arg Pro Arg Val Ser Phe Pro Lys Thr Pro Glu Val
625                 630                 635                 640

Gly Pro Gly Pro Pro Gly Pro Leu Ser Lys Ala Pro Gln Pro Val
            645                 650                 655

Pro Pro Gly Val Gly Glu Leu Pro Ala Arg Gly Pro Arg Leu Phe Asp
        660                 665                 670

Phe Pro Pro Thr Pro Leu Glu Asp Gln Phe Glu Glu Pro Ala Glu Phe
    675                 680                 685

Lys Ile Leu Pro Asp Gly Leu Ala Asn Ile Met Lys Met Leu Asp Glu
            690                 695                 700

Ser Ile Arg Lys Glu Glu Gln Gln Gln His Glu Ala Gly Val Ala
705                 710                 715                 720

Pro Gln Pro Pro Leu Lys Glu Pro Phe Ala Ser Leu Gln Ser Pro Phe
            725                 730                 735

Pro Thr Asp Thr Ala Pro Thr Thr Thr Ala Pro Ala Val Ala Val Thr
        740                 745                 750
```

```
Thr Thr Thr Thr Thr Thr Thr Thr Thr Ala Thr Gln Glu Glu
        755                 760             765

Lys Lys Pro Pro Pro Ala Leu Pro Pro Pro Pro Leu Ala Lys Phe
770             775             780

Pro Pro Pro Ser Gln Pro Gln Pro Pro Pro Pro Pro Ser Pro
785             790             795             800

Ala Ser Leu Leu Lys Ser Leu Ala Ser Val Leu Glu Gly Gln Lys Tyr
            805             810             815

Cys Tyr Arg Gly Thr Gly Ala Ala Val Ser Thr Arg Pro Gly Pro Leu
        820             825             830

Pro Thr Thr Gln Tyr Ser Pro Gly Pro Pro Ser Gly Ala Thr Ala Leu
        835             840             845

Pro Pro Thr Ser Ala Ala Pro Ser Ala Gln Gly Ser Pro Gln Pro Ser
850             855             860

Ala Ser Ser Ser Ser Gln Phe Ser Thr Ser Gly Gly Pro Trp Ala Arg
865             870             875             880

Glu Arg Arg Ala Gly Glu Glu Pro Val Pro Gly Pro Met Thr Pro Thr
            885             890             895

Gln Pro Pro Pro Leu Ser Leu Pro Pro Ala Arg Ser Glu Ser Glu
        900             905             910

Val Leu Glu Glu Ile Ser Arg Ala Cys Glu Thr Leu Val Glu Arg Val
        915             920             925

Gly Arg Ser Ala Thr Asp Pro Ala Asp Pro Val Asp Thr Ala Glu Pro
        930             935             940

Ala Asp Ser Gly Thr Glu Arg Leu Leu Pro Pro Ala Gln Ala Lys Glu
945             950             955             960

Glu Ala Gly Gly Val Ala Ala Val Ser Gly Ser Cys Lys Arg Arg Gln
            965             970             975

Lys Glu His Gln Lys Glu His Arg Arg His Arg Arg Ala Cys Lys Asp
            980             985             990

Ser Val Gly Arg Arg Pro Arg Glu Gly Arg Ala Lys Ala Lys Ala Lys
            995             1000            1005

Val Pro Lys Glu Lys Ser Arg Arg Val Leu Gly Asn Leu Asp Leu
    1010            1015            1020

Gln Ser Glu Glu Ile Gln Gly Arg Glu Lys Ser Arg Pro Asp Leu
    1025            1030            1035

Gly Gly Ala Ser Lys Ala Lys Pro Pro Thr Ala Pro Ala Pro Pro
    1040            1045            1050

Ser Ala Pro Ala Pro Ser Ala Gln Pro Thr Pro Ser Ala Ser
    1055            1060            1065

Val Pro Gly Lys Lys Ala Arg Glu Glu Ala Pro Gly Pro Pro Gly
    1070            1075            1080

Val Ser Arg Ala Asp Met Leu Lys Leu Arg Ser Leu Ser Glu Gly
    1085            1090            1095

Pro Pro Lys Glu Leu Lys Ile Arg Leu Ile Lys Val Glu Ser Gly
    1100            1105            1110

Asp Lys Glu Thr Phe Ile Ala Ser Glu Val Glu Glu Arg Arg Leu
    1115            1120            1125

Arg Met Ala Asp Leu Thr Ile Ser His Cys Ala Ala Asp Val Val
    1130            1135            1140

Arg Ala Ser Arg Asn Ala Lys Val Lys Gly Lys Phe Arg Glu Ser
    1145            1150            1155

Tyr Leu Ser Pro Ala Gln Ser Val Lys Pro Lys Ile Asn Thr Glu
```

```
            1160                1165                1170

Glu Lys Leu Pro Arg Glu Lys Leu Asn Pro Pro Thr Pro Ser Ile
    1175                1180                1185

Tyr Leu Glu Ser Lys Arg Asp Ala Phe Ser Pro Val Leu Leu Gln
    1190                1195                1200

Phe Cys Thr Asp Pro Arg Asn Pro Ile Thr Val Ile Arg Gly Leu
    1205                1210                1215

Ala Gly Ser Leu Arg Leu Asn Leu Gly Leu Phe Ser Thr Lys Thr
    1220                1225                1230

Leu Val Glu Ala Ser Gly Glu His Thr Val Glu Val Arg Thr Gln
    1235                1240                1245

Val Gln Gln Pro Ser Asp Glu Asn Trp Asp Leu Thr Gly Thr Arg
    1250                1255                1260

Gln Ile Trp Pro Cys Glu Ser Ser Arg Ser His Thr Thr Ile Ala
    1265                1270                1275

Lys Tyr Ala Gln Tyr Gln Ala Ser Ser Phe Gln Glu Ser Leu Gln
    1280                1285                1290

Glu Glu Lys Glu Ser Glu Asp Glu Glu Ser Glu Pro Asp Ser
    1295                1300                1305

Thr Thr Gly Thr Pro Pro Ser Ser Ala Pro Asp Pro Lys Asn His
    1310                1315                1320

His Ile Ile Lys Phe Gly Thr Asn Ile Asp Leu Ser Asp Ala Lys
    1325                1330                1335

Arg Trp Lys Pro Gln Leu Gln Glu Leu Leu Lys Leu Pro Ala Phe
    1340                1345                1350

Met Arg Val Thr Ser Thr Gly Asn Met Leu Ser His Val Gly His
    1355                1360                1365

Thr Ile Leu Gly Met Asn Thr Val Gln Leu Tyr Met Lys Val Pro
    1370                1375                1380

Gly Ser Arg Thr Pro Gly His Gln Glu Asn Asn Asn Phe Cys Ser
    1385                1390                1395

Val Asn Ile Asn Ile Gly Pro Gly Asp Cys Glu Trp Phe Ala Val
    1400                1405                1410

His Glu His Tyr Trp Glu Thr Ile Ser Ala Phe Cys Asp Arg His
    1415                1420                1425

Gly Val Asp Tyr Leu Thr Gly Ser Trp Trp Pro Ile Leu Asp Asp
    1430                1435                1440

Leu Tyr Ala Ser Asn Ile Pro Val Tyr Arg Phe Val Gln Arg Pro
    1445                1450                1455

Gly Asp Leu Val Trp Ile Asn Ala Gly Thr Val His Trp Val Gln
    1460                1465                1470

Ala Thr Gly Trp Cys Asn Asn Ile Ala Trp Asn Val Gly Pro Leu
    1475                1480                1485

Thr Ala Tyr Gln Tyr Gln Leu Ala Leu Glu Arg Tyr Glu Trp Asn
    1490                1495                1500

Glu Val Lys Asn Val Lys Ser Ile Val Pro Met Ile His Val Ser
    1505                1510                1515

Trp Asn Val Ala Arg Thr Val Lys Ile Ser Asp Pro Asp Leu Phe
    1520                1525                1530

Lys Met Ile Lys Phe Cys Leu Leu Gln Ser Met Lys His Cys Gln
    1535                1540                1545

Val Gln Arg Glu Ser Leu Val Arg Ala Gly Lys Lys Ile Ala Tyr
    1550                1555                1560
```

```
Gln Gly Arg Val Lys Asp Glu Pro Ala Tyr Tyr Cys Asn Glu Cys
    1565            1570                1575

Asp Val Glu Val Phe Asn Ile Leu Phe Val Thr Ser Glu Asn Gly
    1580            1585                1590

Ser Arg Asn Thr Tyr Leu Val His Cys Glu Gly Cys Ala Arg Arg
    1595            1600                1605

Arg Ser Ala Gly Leu Gln Gly Val Val Val Leu Gln Tyr Arg
    1610            1615                1620

Thr Glu Glu Leu Ala Gln Ala Tyr Asp Ala Phe Thr Leu Ala Pro
    1625            1630                1635

Ala Ser Thr Ser Arg
    1640

<210> SEQ ID NO 7
<211> LENGTH: 6731
<212> TYPE: DNA
<213> ORGANISM: Homo sapiens

<400> SEQUENCE: 7
```

| | | | | | |
|---|---|---|---|---|---|
| ggcaacatgc | cagccccgta | gcactgccca | ccccacccac | tgtggtctgt | tgtacccac 60 |
| tgctggggtg | gtggttccaa | tgagacaggg | cacaccaaac | tccatctggc | tgttactgag 120 |
| gcggagacac | gggtgatgat | tggctttctg | gggagagagg | aagtcctgtg | attggcaga 180 |
| tctctggagc | ttgccgacgc | ggtgtgagga | cgctcccacg | gaggccggaa | ttggctgtga 240 |
| aaggactgag | gcagccatct | gggggtagcg | ggcactctta | tcagagcggc | tggagccgga 300 |
| ccatcgtccc | agagagctgg | ggcagggggc | cgtgcccaat | ctccagggct | cctggggcca 360 |
| ctgctgacct | ggctggatgc | atcgggcagt | ggaccctcca | ggggcccgcg | ctgcacggga 420 |
| agcctttgcc | cttggggggcc | tgagctgtgc | tggggcctgg | agctcctgcc | cgcctcatcc 480 |
| ccctcctcgt | agcgcatggc | tgcctggagg | cagatgctca | gccagcattg | ggcagccccc 540 |
| gcttcctgct | ccctacccc | cttcacatgg | cagtagttct | gggcaccca | gcaaaccata 600 |
| ttatgctcca | ggggcgccca | ctccaagacc | cctccatggg | aagctggaat | ccctgcatgg 660 |
| ctgtgtgcag | gcattgctcc | gggagccagc | ccagccaggg | ctttgggaac | agcttgggca 720 |
| actgtacgag | tcagagcacg | atagtgagga | ggccacacgc | tgctaccaca | gcgcccttcg 780 |
| atacggagga | agcttcgctg | agctggggcc | ccgcattggc | cgactgcagc | aggcccagct 840 |
| ctggaacttt | catactggct | cctgccagca | ccgagccaag | gtcctgcccc | cactggagca 900 |
| agtgtggaac | ttgctacacc | ttgagcacaa | acggaactat | ggagccaagc | ggggaggtcc 960 |
| cccggtgaag | cgagctgctg | aaccccagt | ggtgcagcct | gtgcctcctg | cagcactctc 1020 |
| aggcccctca | ggggaggagg | gcctcagccc | tggaggcaag | cgaaggagag | ctgcaactc 1080 |
| tgaacagact | ggccttcccc | cagggctgcc | actgcctcca | ccaccattac | caccaccacc 1140 |
| accaccacca | ccaccaccac | caccacccct | gcctggcctg | gctaccagcc | cccatttca 1200 |
| gctaaccaag | ccagggctgt | ggagtaccct | gcatggagat | gcctggggcc | cagagcgcaa 1260 |
| gggttcagca | ccccagagc | gccaggagca | gcggcactcg | ctgcctcacc | catatccata 1320 |
| cccagctcca | gcgtacaccg | cgcacccccc | tggccaccgg | ctggtcccgg | ctgctcccc 1380 |
| aggcccaggc | cccgccccc | caggagcaga | gagccatggc | tgcctgcctg | ccacccgtcc 1440 |
| ccccggaagt | gaccttagag | agagcagagt | tcagaggtcg | cggatggact | ccagcgtttc 1500 |
| accagcagca | accaccgcct | gcgtgcctta | cgccccttcc | cggccccctg | gcctccccgg 1560 |

```
caccaccacc agcagcagca gtagcagcag cagcaacact ggtctccggg gcgtggagcc    1620
gaacccaggc attcccggcg ctgaccatta ccaaactccc gcgctggagg tctctcacca    1680
tggccgcctg gggccctcgg cacacagcag tcggaaaccg ttcttggggg ctcccgctgc    1740
cactccccac ctatccctgc cacctggacc ttcctcaccc cctccacccc cctgtccccg    1800
cctcttacgc cccccaccac cccctgcctg gttgaagggt ccggcctgcc gggcagcccg    1860
agaggatgga gagatcttag aagagctctt ctttgggact gagggacccc ccgccctgc    1920
cccaccaccc ctcccccatc gcgagggctt cttggggcct ccggcctccc gcttttctgt    1980
gggcactcag gattctcaca cccctcccac tcccccaacc ccaaccacca gcagtagcaa    2040
cagcaacagt ggcagccaca gcagcagccc tgctgggcct gtgtcctttc ccccaccacc    2100
ctatctggcc agaagtatag accccctccc ccggcctccc agcccagcac agaaccccca    2160
ggacccacct cttgtacccc tgactcttgc cctgcctcca gcccctcctt cctcctgcca    2220
ccaaaatacc tcaggaagct tcaggcgccc ggagagcccc cggcccaggg tctccttccc    2280
aaagaccccc gaggtggggc cggggccacc cccaggcccc ctgagtaaag ccccccagcc    2340
tgtgccgccc ggggttgggg agctgcctgc ccgaggccct cgactctttg attttccccc    2400
cactccgctg gaggaccagt ttgaggagcc agccgaattc aagatcctac ctgatgggct    2460
ggccaacatc atgaagatgc tggacgaatc cattcgcaag gaagaggaac agcaacaaca    2520
cgaagcaggc gtgcccccc aaccccgct gaaggagccc tttgcatctc tgcagtctcc    2580
tttccccacc gacacagccc ccaccactac tgctcctgct gtcgccgtca ccaccaccac    2640
caccaccacc accaccacca cggccaccca ggaagaggag aagaagccac caccagccct    2700
accaccacca ccgcctctag ccaagttccc tccaccctct cagccacagc caccaccacc    2760
cccaccccc agcccggcca gcctgctcaa atccttggcc tccgtgctgg agggacaaaa    2820
gtactgttat cggggggactg gagcagctgt ttccacccgg cctgggccct tgcccaccac    2880
tcagtattcc cctggccccc catcaggtgc taccgccctg ccgcccacct cagcggcccc    2940
tagcgcccag ggctccccac agccctctgc ttcctcgtca tctcagttct ctacctcagg    3000
cgggccctgg gccgggagc gcagggcggg cgaagagcca gtcccgggcc ccatgacccc    3060
cacccaaccg cccccacccc tatctctgcc ccctgctcgc tctgagtctg aggtgctaga    3120
agagatcagc cgggcttgcg agaccttgt ggagcgggtg ggccggagtg ccactgaccc    3180
agccgaccca gtggacacag cagagccagc ggacagtggg actgagcgac tgctgccccc    3240
cgcacaggcc aaggaggagg ctggcggggt ggcggcagtg tcaggcagct gtaagcggcg    3300
acagaaggag catcagaagg agcatcggcg gcacaggcgg gcctgtaagg acagtgtggg    3360
tcgtcggccc cgtgagggca gggcaaaggc caaggcaag gtccccaaag aaaagagccg    3420
ccgggtgctg gggaacctgg acctgcagag cgaggagatc cagggtcgtg agaagtcccg    3480
gcccgatctt ggcggggcct ccaaggccaa gccaccaca gctccagccc ctccatcagc    3540
tcctgcacct tctgcccagc ccacaccccc gtcagcctct gtccctggaa agaaggctcg    3600
ggaggaagcc ccagggccac cgggtgtcag ccggggccgac atgctgaagc tgcgctcact    3660
tagtgagggg ccccccaagg agctgaagat ccggctcatc aagtagaga gtggtgacaa    3720
ggagaccttt atcgcctctg aggtggaaga gcggcggctg cgcatggcag acctcaccat    3780
cagccactgt gctgctgacg tcgtgcgcgc cagcaggaat gccaaggtga aagggaagtt    3840
tcgagagtcc tacctttccc ctgcccagtc tgtgaaaccg aagatcaaca ctgaggagaa    3900
gctgccccgg gaaaaactca ccccccctac acccagcatc tatctggaga gcaaacggga    3960
```

```
tgccttctca cctgtcctgc tgcagttctg tacagaccct cgaaatccca tcacagtgat    4020
ccggggcctg gcgggctccc tgcggctcaa cttgggcctc ttctccacca agaccctggt    4080
ggaagcgagt ggcgaacaca ccgtggaagt tcgcacccag gtgcagcagc cctcagatga    4140
gaactgggat ctgacaggca ctcggcagat ctggccttgt gagagctccc gttcccacac    4200
caccattgcc aagtacgcac agtaccaggc ctcatccttc caggagtctc tgcaggagga    4260
gaaggagagt gaggatgagg agtcagagga gccagacagc accactggaa cccctcctag    4320
cagcgcacca gacccgaaga accatcacat catcaagttt ggcaccaaca tcgacttgtc    4380
tgatgctaag cggtggaagc cccagctgca ggagctgctg aagctgcccg ccttcatgcg    4440
ggtaacatcc acgggcaaca tgctgagcca cgtgggccac accatcctgg gcatgaacac    4500
ggtgcagctg tacatgaagg tgcccggcag ccgaacgcca ggccaccagg agaataacaa    4560
cttctgctcc gtcaacatca acattggccc aggcgactgc gagtggttcg cggtgcacga    4620
gcactactgg gagaccatca gcgctttctg tgatcggcac ggcgtggact acttgacggg    4680
ttcctggtgg ccaatcctgg atgatctcta tgcatccaat attcctgtgt accgcttcgt    4740
gcagcgaccc ggagacctcg tgtggattaa tgcggggact gtgcactggg tgcaggccac    4800
cggctggtgc aacaacattg cctggaacgt ggggcccctc accgcctatc agtaccagct    4860
ggccctggaa cgatacgagt ggaatgaggt gaagaacgtc aaatccatcg tgcccatgat    4920
tcacgtgtca tggaacgtgg ctcgcacggt caaaatcagc gaccccgact tgttcaagat    4980
gatcaagttc tgcctgctgc agtccatgaa gcactgccag gtgcaacgcg agagcctggt    5040
gcgggcaggg aagaaaatcg cttaccaggg ccgtgtcaag gacgagccag cctactactg    5100
caacgagtgc gatgtggagg tgtttaacat cctgttcgtg acaagtgaga atggcagccg    5160
caacacgtac ctggtacact gcgagggctg tgcccggcgc cgcagcgcag gcctgcaggg    5220
cgtggtggtg ctggagcagt accgcactga ggagctggct caggcctacg acgccttcac    5280
gctggtgagg gcccggcggg cgcgcgggca gcggaggagg gcactggggc aggctgcagg    5340
gacgggcttc gggagcccgg ccgcgccttt ccctgagccc ccgccggctt tctcccccca    5400
ggccccagcc agcacgtcgc gatgaggccg gacgccccgc ccgcctgcct gcccgcgcaa    5460
ggcgccgcgg ggccaccagc acatgcctgg gctggaccta ggtcccgcct gtggccgaga    5520
agggggtcgg gcccagccct tccacccat tggcagctcc cctcacttaa tttattaaga    5580 aaaactttt tttttttttt agcaaatatg aggaaaaaag gaaaaaaat gggagacggg    5640 ggagggggct ggcagcccct cgcccaccag cgcctcccct caccgacttt ggccttttta    5700
gcaacagaca caaggaccag gctccggcgg cggcgggggt cacatacggg ttccctcacc    5760
ctgccagccg cccgcccgcc cggcgcagat gcacgcggct cgtgtatgta catagacgtt    5820
acggcagccg aggttttaa tgagattctt tctatgggct ttaccctcc cccggaacct    5880 ccttttttac ttccaatgct agctgtgacc cctgtacatg tctctttatt cacttggtta    5940
tgatttgtat ttttgttct tttcttgttt ttttgttttt aatttataac agtcccactc    6000
acctctattt attcattttt gggaaaaccc gacctcccac accccaagc catcctgccc    6060 gccctccag ggaccgcccg tcgcggget ctccccgcgc ccagtgtgt gtccgggccc    6120 ggcccgaccg tctccacccg tccgcccgcg gctccagccg ggttctcatg gtgctcaaac    6180
ccgctcccct cccctacgtc ctgcactttc tcggaccagt ccccccactc ccgacccgac    6240
cccagcccca cctgagggtg agcaactcct gtactgtagg ggaagaagtg ggaactgaaa    6300
```

```
tggtattttg taaaaaaaat aaataaaata aaaaaattaa aggttttaaa gaaagaacta    6360
tgaggaaaag gaaccccgtc cttcccagcc ccggccaact ttaaaaaaca cagaccttca    6420
cccccacccc cttttctttt taagtgtgaa acaacccagg gccagggcct cactggggca    6480
gggacacccc ggggtgagtt tctctggggc tttattttcg ttttgttggt tgttttttct    6540
ccacgctggg gctgcggagg ggtgggtggggt ttacagtccc gcaccctcgc actgcactgt   6600
ctctctgccc caggggcaga ggggtcttcc caacccctacc cctatttttcg gtgattttttg  6660 tgtgagaata ttaatattaa aaataaacgg agaaaaaaaa aaaaaaaaaa aaaaaaaaaa    6720
aaaaaaaaaa a                                                        6731
```

<210> SEQ ID NO 8
<211> LENGTH: 1347
<212> TYPE: PRT
<213> ORGANISM: Homo sapiens

<400> SEQUENCE: 8

Met Lys Ser Cys Ala Val Ser Leu Thr Thr Ala Ala Val Ala Phe Gly
1               5                   10                  15

Asp Glu Ala Lys Lys Met Ala Glu Gly Lys Ala Ser Arg Glu Ser Glu
                20                  25                  30

Glu Glu Ser Val Ser Leu Thr Val Glu Glu Arg Glu Ala Leu Gly Gly
            35                  40                  45

Met Asp Ser Arg Leu Phe Gly Phe Val Arg Leu His Glu Asp Gly Ala
        50                  55                  60

Arg Thr Lys Thr Leu Leu Gly Lys Ala Val Arg Cys Tyr Glu Ser Leu
65                  70                  75                  80

Ile Leu Lys Ala Glu Gly Lys Val Glu Ser Asp Phe Phe Cys Gln Leu
                85                  90                  95

Gly His Phe Asn Leu Leu Leu Glu Asp Tyr Ser Lys Ala Leu Ser Ala
            100                 105                 110

Tyr Gln Arg Tyr Tyr Ser Leu Gln Ala Asp Tyr Trp Lys Asn Ala Ala
        115                 120                 125

Phe Leu Tyr Gly Leu Gly Leu Val Tyr Phe Tyr Asn Ala Phe His
    130                 135                 140

Trp Ala Ile Lys Ala Phe Gln Asp Val Leu Tyr Val Asp Pro Ser Phe
145                 150                 155                 160

Cys Arg Ala Lys Glu Ile His Leu Arg Leu Gly Leu Met Phe Lys Val
                165                 170                 175

Asn Thr Asp Tyr Lys Ser Ser Leu Lys His Phe Gln Leu Ala Leu Ile
            180                 185                 190

Asp Cys Asn Pro Cys Thr Leu Ser Asn Ala Glu Ile Gln Phe His Ile
        195                 200                 205

Ala His Leu Tyr Glu Thr Gln Arg Lys Tyr His Ser Ala Lys Glu Ala
    210                 215                 220

Tyr Glu Gln Leu Leu Gln Thr Glu Asn Leu Pro Ala Gln Val Lys Ala
225                 230                 235                 240

Thr Val Leu Gln Gln Leu Gly Trp Met His His Asn Met Asp Leu Val
                245                 250                 255

Gly Asp Lys Ala Thr Lys Glu Ser Tyr Ala Ile Gln Tyr Leu Gln Lys
            260                 265                 270

Ser Leu Glu Ala Asp Pro Asn Ser Gly Gln Ser Trp Tyr Phe Leu Gly
        275                 280                 285

Arg Cys Tyr Ser Ser Ile Gly Lys Val Gln Asp Ala Phe Ile Ser Tyr

```
                290                 295                 300
Arg Gln Ser Ile Asp Lys Ser Glu Ala Ser Ala Asp Thr Trp Cys Ser
305                 310                 315                 320

Ile Gly Val Leu Tyr Gln Gln Asn Gln Pro Met Asp Ala Leu Gln
                325                 330                 335

Ala Tyr Ile Cys Ala Val Gln Leu Asp His Gly His Ala Ala Ala Trp
                340                 345                 350

Met Asp Leu Gly Thr Leu Tyr Glu Ser Cys Asn Gln Pro Gln Asp Ala
                355                 360                 365

Ile Lys Cys Tyr Leu Asn Ala Ala Arg Ser Lys Arg Cys Ser Asn Thr
370                 375                 380

Ser Thr Leu Ala Ala Arg Ile Lys Phe Leu Gln Asn Gly Ser Asp Asn
385                 390                 395                 400

Trp Asn Gly Gly Gln Ser Leu Ser His His Pro Val Gln Gln Val Tyr
                405                 410                 415

Ser Leu Cys Leu Thr Pro Gln Lys Leu Gln His Leu Glu Gln Leu Arg
                420                 425                 430

Ala Asn Arg Asp Asn Leu Asn Pro Ala Gln Lys His Gln Leu Glu Gln
                435                 440                 445

Leu Glu Ser Gln Phe Val Leu Met Gln Gln Met Arg His Lys Glu Val
450                 455                 460

Ala Gln Val Arg Thr Thr Gly Ile His Asn Gly Ala Ile Thr Asp Ser
465                 470                 475                 480

Ser Leu Pro Thr Asn Ser Val Ser Asn Arg Gln Pro His Gly Ala Leu
                485                 490                 495

Thr Arg Val Ser Ser Val Ser Gln Pro Gly Val Arg Pro Ala Cys Val
                500                 505                 510

Glu Lys Leu Leu Ser Ser Gly Ala Phe Ser Ala Gly Cys Ile Pro Cys
                515                 520                 525

Gly Thr Ser Lys Ile Leu Gly Ser Thr Asp Thr Ile Leu Leu Gly Ser
530                 535                 540

Asn Cys Ile Ala Gly Ser Glu Ser Asn Gly Asn Val Pro Tyr Leu Gln
545                 550                 555                 560

Gln Asn Thr His Thr Leu Pro His Asn His Thr Asp Leu Asn Ser Ser
                565                 570                 575

Thr Glu Glu Pro Trp Arg Lys Gln Leu Ser Asn Ser Ala Gln Gly Leu
                580                 585                 590

His Lys Ser Gln Ser Ser Cys Leu Ser Gly Pro Asn Glu Glu Gln Pro
                595                 600                 605

Leu Phe Ser Thr Gly Ser Ala Gln Tyr His Gln Ala Thr Ser Thr Gly
610                 615                 620

Ile Lys Lys Ala Asn Glu His Leu Thr Leu Pro Ser Asn Ser Val Pro
625                 630                 635                 640

Gln Gly Asp Ala Asp Ser His Leu Ser Cys His Thr Ala Thr Ser Gly
                645                 650                 655

Gly Gln Gln Gly Ile Met Phe Thr Lys Glu Ser Lys Pro Ser Lys Asn
                660                 665                 670

Arg Ser Leu Val Pro Glu Thr Ser Arg His Thr Gly Asp Thr Ser Asn
                675                 680                 685

Gly Cys Ala Asp Val Lys Gly Leu Ser Asn His Val His Gln Leu Ile
                690                 695                 700

Ala Asp Ala Val Ser Ser Pro Asn His Gly Asp Ser Pro Asn Leu Leu
705                 710                 715                 720
```

```
Ile Ala Asp Asn Pro Gln Leu Ser Ala Leu Leu Ile Gly Lys Ala Asn
            725                 730                 735

Gly Asn Val Gly Thr Gly Thr Cys Asp Lys Val Asn Asn Ile His Pro
            740                 745                 750

Ala Val His Thr Lys Thr Asp His Ser Val Ala Ser Ser Pro Ser Ser
            755                 760                 765

Ala Ile Ser Thr Ala Thr Pro Ser Pro Lys Ser Thr Glu Gln Arg Ser
            770                 775                 780

Ile Asn Ser Val Thr Ser Leu Asn Ser Pro His Ser Gly Leu His Thr
785                 790                 795                 800

Val Asn Gly Glu Gly Leu Gly Lys Ser Gln Ser Ser Thr Lys Val Asp
            805                 810                 815

Leu Pro Leu Ala Ser His Arg Ser Thr Ser Gln Ile Leu Pro Ser Met
            820                 825                 830

Ser Val Ser Ile Cys Pro Ser Ser Thr Glu Val Leu Lys Ala Cys Arg
            835                 840                 845

Asn Pro Gly Lys Asn Gly Leu Ser Asn Ser Cys Ile Leu Leu Asp Lys
            850                 855                 860

Cys Pro Pro Pro Arg Pro Pro Thr Ser Pro Tyr Pro Pro Leu Pro Lys
865                 870                 875                 880

Asp Lys Leu Asn Pro Pro Thr Pro Ser Ile Tyr Leu Glu Asn Lys Arg
            885                 890                 895

Asp Ala Phe Phe Pro Pro Leu His Gln Phe Cys Thr Asn Pro Lys Asn
            900                 905                 910

Pro Val Thr Val Ile Arg Gly Leu Ala Gly Ala Leu Lys Leu Asp Leu
            915                 920                 925

Gly Leu Phe Ser Thr Lys Thr Leu Val Glu Ala Asn Asn Glu His Met
            930                 935                 940

Val Glu Val Arg Thr Gln Leu Leu Gln Pro Ala Asp Glu Asn Trp Asp
945                 950                 955                 960

Pro Thr Gly Thr Lys Lys Ile Trp Arg Cys Glu Ser Asn Arg Ser His
            965                 970                 975

Thr Thr Ile Ala Lys Tyr Ala Gln Tyr Gln Ala Ser Ser Phe Gln Glu
            980                 985                 990

Ser Leu Arg Glu Glu Asn Glu Lys Arg Thr Gln His Lys Asp His Ser
            995                 1000                1005

Asp Asn Glu Ser Thr Ser Ser Glu Asn Ser Gly Arg Arg Arg Lys
            1010                1015                1020

Gly Pro Phe Lys Thr Ile Lys Phe Gly Thr Asn Ile Asp Leu Ser
            1025                1030                1035

Asp Asn Lys Lys Trp Lys Leu Gln Leu His Glu Leu Thr Lys Leu
            1040                1045                1050

Pro Ala Phe Ala Arg Val Val Ser Ala Gly Asn Leu Leu Thr His
            1055                1060                1065

Val Gly His Thr Ile Leu Gly Met Asn Thr Val Gln Leu Tyr Met
            1070                1075                1080

Lys Val Pro Gly Ser Arg Thr Pro Gly His Gln Glu Asn Asn Asn
            1085                1090                1095

Phe Cys Ser Val Asn Ile Asn Ile Gly Pro Gly Asp Cys Glu Trp
            1100                1105                1110

Phe Val Val Pro Glu Asp Tyr Trp Gly Val Leu Asn Asp Phe Cys
            1115                1120                1125
```

| Glu | Lys | Asn | Asn | Leu | Asn | Phe | Leu | Met | Ser | Ser | Trp | Trp | Pro | Asn |
|---|---|---|---|---|---|---|---|---|---|---|---|---|---|---|
| | 1130 | | | | 1135 | | | | | 1140 | | | | |

| Leu | Glu | Asp | Leu | Tyr | Glu | Ala | Asn | Val | Pro | Val | Tyr | Arg | Phe | Ile |
|---|---|---|---|---|---|---|---|---|---|---|---|---|---|---|
| | 1145 | | | | 1150 | | | | | 1155 | | | | |

| Gln | Arg | Pro | Gly | Asp | Leu | Val | Trp | Ile | Asn | Ala | Gly | Thr | Val | His |
|---|---|---|---|---|---|---|---|---|---|---|---|---|---|---|
| | 1160 | | | | 1165 | | | | | 1170 | | | | |

| Trp | Val | Gln | Ala | Val | Gly | Trp | Cys | Asn | Asn | Ile | Ala | Trp | Asn | Val |
|---|---|---|---|---|---|---|---|---|---|---|---|---|---|---|
| | 1175 | | | | 1180 | | | | | 1185 | | | | |

| Gly | Pro | Leu | Thr | Ala | Cys | Gln | Tyr | Lys | Leu | Ala | Val | Glu | Arg | Tyr |
|---|---|---|---|---|---|---|---|---|---|---|---|---|---|---|
| | 1190 | | | | 1195 | | | | | 1200 | | | | |

| Glu | Trp | Asn | Lys | Leu | Lys | Ser | Val | Lys | Ser | Pro | Val | Pro | Met | Val |
|---|---|---|---|---|---|---|---|---|---|---|---|---|---|---|
| | 1205 | | | | 1210 | | | | | 1215 | | | | |

| His | Leu | Ser | Trp | Asn | Met | Ala | Arg | Asn | Ile | Lys | Val | Ser | Asp | Pro |
|---|---|---|---|---|---|---|---|---|---|---|---|---|---|---|
| | 1220 | | | | 1225 | | | | | 1230 | | | | |

| Lys | Leu | Phe | Glu | Met | Ile | Lys | Tyr | Cys | Leu | Leu | Lys | Ile | Leu | Lys |
|---|---|---|---|---|---|---|---|---|---|---|---|---|---|---|
| | 1235 | | | | 1240 | | | | | 1245 | | | | |

| Gln | Tyr | Gln | Thr | Leu | Arg | Glu | Ala | Leu | Val | Ala | Ala | Gly | Lys | Glu |
|---|---|---|---|---|---|---|---|---|---|---|---|---|---|---|
| | 1250 | | | | 1255 | | | | | 1260 | | | | |

| Val | Ile | Trp | His | Gly | Arg | Thr | Asn | Asp | Glu | Pro | Ala | His | Tyr | Cys |
|---|---|---|---|---|---|---|---|---|---|---|---|---|---|---|
| | 1265 | | | | 1270 | | | | | 1275 | | | | |

| Ser | Ile | Cys | Glu | Val | Glu | Val | Phe | Asn | Leu | Leu | Phe | Val | Thr | Asn |
|---|---|---|---|---|---|---|---|---|---|---|---|---|---|---|
| | 1280 | | | | 1285 | | | | | 1290 | | | | |

| Glu | Ser | Asn | Thr | Gln | Lys | Thr | Tyr | Ile | Val | His | Cys | His | Asp | Cys |
|---|---|---|---|---|---|---|---|---|---|---|---|---|---|---|
| | 1295 | | | | 1300 | | | | | 1305 | | | | |

| Ala | Arg | Lys | Thr | Ser | Lys | Ser | Leu | Glu | Asn | Phe | Val | Val | Leu | Glu |
|---|---|---|---|---|---|---|---|---|---|---|---|---|---|---|
| | 1310 | | | | 1315 | | | | | 1320 | | | | |

| Gln | Tyr | Lys | Met | Glu | Asp | Leu | Ile | Gln | Val | Tyr | Asp | Gln | Phe | Thr |
|---|---|---|---|---|---|---|---|---|---|---|---|---|---|---|
| | 1325 | | | | 1330 | | | | | 1335 | | | | |

| Leu | Ala | Leu | Ser | Leu | Ser | Ser | Ser |
|---|---|---|---|---|---|---|---|
| | 1340 | | | | 1345 | | |

```
<210> SEQ ID NO 9
<211> LENGTH: 6817
<212> TYPE: DNA
<213> ORGANISM: Homo sapiens

<400> SEQUENCE: 9
```

| | | | | |
|---|---|---|---|---|
| gctcatcgtt | tgttgtttag | ataatatcat | gaactgataa | atgcagttgc cacgttgatt | 60 |
| ccctagggcc | tggcttaccg | actgaggtca | taagatatta | tgccttctct ttagacttgg | 120 |
| tcagtggaga | ggaaatgggc | aaagaaccag | cctatgaggt | gacaaggcc ttagggccaa | 180 |
| aagtcttgag | ggtgaaggtt | tagggcctgc | gcagcttccc | tgccatgccc cgcaaggtct | 240 |
| cgcattcgca | aggcttgtga | cagtgggagc | ctcattacgg | actctcctaa agtccatggt | 300 |
| gtcctctttt | cgcatttgcg | ccccgtgggt | gatgcccgat | gccgcccttc ccatcgctct | 360 |
| cttcccttc | aagcgtatcg | caactgcaaa | acacccagc | acagacactc cattttctat | 420 |
| cttaatgcat | ttaactagca | caacctacag | gttgttccat | cccagagact acccttttct | 480 |
| ccatagacgt | gaccatcaac | caaccagcgg | tcagaatcag | tcagcctctg tcatgttcct | 540 |
| aggtccttgg | cgaactggct | gggcggggtc | ccagcagcct | aggagtacag tggagcaatg | 600 |
| cctgacgtaa | gtcaacaaag | atcacgtgag | acgaatcagt | cgcctagatt ggctacaact | 660 |
| aagtggttgg | gagcggggag | gtcgcggcgg | ctgcgtgggg | ttcgcccgtg acacaattac | 720 |
| aactttgtgc | tggtgctggc | aaagtttgtg | attttaagaa | attctgctgt gctctccagc | 780 |

-continued

```
actgcgagct tctgccttcc ctgtagtttc ccagatgtga tccaggtagc cgagttccgc    840
tgcccgtgct tcggtagctt aagtctttgc ctcagctttt ttccttgcag ccgctgagga    900
ggcgataaaa ttggcgtcac agtctcaagc agcgattgaa ggcgtctttt caactactcg    960
attaaggttg ggtatcgtcg tgggacttgg aaatttgttg tttccatgaa atcctgcgca   1020
gtgtcgctca ctaccgccgc tgttgccttc ggtgatgagg caaagaaaat ggcggaagga   1080
aaagcgagcc gcgagagtga agaggagtct gttagcctga cagtcgagga aagggaggcg   1140
cttggtggca tggacagccg tctcttcggg ttcgtgaggc ttcatgaaga tggcgccaga   1200
acgaagaccc tactaggcaa ggctgttcgc tgctacgaat ctttaatctt aaaagctgaa   1260
ggaaaagtgg agtctgactt cttttgccaa ttaggtcact tcaacctctt gttggaagat   1320
tattcaaaag cattatctgc atatcagaga tattacagtt tacaggctga ctactggaag   1380
aatgctgcgt ttttatatgg ccttggtttg gtctacttct actacaatgc atttcattgg   1440
gcaattaaag catttcaaga tgtcctttat gttgacccca gcttttgtcg agccaaggaa   1500
attcatttac gacttgggct catgttcaaa gtgaacacag actacaagtc tagtttaaag   1560
cattttcagt tagccttgat tgactgtaat ccatgtactt tgtccaatgc tgaaattcaa   1620
tttcatattg cccatttgta tgaaacccag aggaagtatc attctgcaaa ggaggcatat   1680
gaacaacttt tgcagacaga aaaccttcct gcacaagtaa aagcaactgt attgcaacag   1740
ttaggttgga tgcatcataa tatggatcta gtaggagaca aagccacaaa ggaaagctat   1800
gctattcagt atctccaaaa gtctttggag gcagatccta attctggcca atcgtggtat   1860
tttcttggaa ggtgttattc aagtattggg aaagttcagg atgcctttat atcttacagg   1920
caatctattg ataaatcaga agcaagtgca gatacatggt gttcaatagg tgtgttgtat   1980
cagcagcaaa atcagcctat ggatgcttta caggcatata tttgtgctgt acaattggac   2040
catgggcatg ccgcagcctg gatggaccta ggtactctct atgaatcctg caatcaacct   2100
caagatgcca ttaaatgcta cctaaatgca gctagaagca aacgttgtag taatacctct   2160
acgcttgctg caagaattaa atttctacag gctcagttgt gtaaccttcc acaaagtagt   2220
ctacagaata aaactaaatt acttcctagt attgaggagg catggagcct accaatcccc   2280
gcagagctta cctccaggca gggtgccatg aacacagcac agcaggctta tagagctcat   2340
gatccaaata ctgaacatgt attaaaccac agtcaaacac caattttaca gcaatccttg   2400
tcactacaca tgattacttc tagccaagta gaaggcctgt ccagtcctgc caagaagaaa   2460
agaacatcta gtccaacaaa gaatggttct gataactgga atggtggcca gagtcttcca   2520
catcatccag tacagcaagt ttattcgttg tgtttgacac cacagaaatt acagcacttg   2580
gaacaactgc gagcaaatag agataattta aatccagcac agaagcatca gctggaacag   2640
ttagaaagtc agtttgtctt aatgcagcaa atgagacaca aagaagttgc tcaggtacga   2700
actactggaa ttcataacgg ggccataact gattcatcac tgcctacaaa ctctgtctct   2760
aatcgacaac cacatggtgc tctgaccaga gtatctagcg tctctcagcc tggagttcgc   2820
cctgcttgtg ttgaaaaact tttgtccagt ggagcttttt ctgcaggctg tattccttgt   2880
ggcacatcaa aaattctagg aagtacagac actatcttgc taggcagtaa ttgtatagca   2940
ggaagtgaaa gtaatggaaa tgtgccttac ctgcagcaaa atacacacac tctacctcat   3000
aatcatacag acctgaacag cagcacagaa gagccatgga gaaaacagct atctaactcc   3060
gctcaggggc ttcataaaag tcagagttca tgtttgtcag gacctaatga agaacaacct   3120
ctgttttcca ctgggtcagc ccagtatcac caggcaacta gcactggtat taagaaggcg   3180
```

```
aatgaacatc tcactctgcc tagtaattca gtaccacagg gggatgctga cagtcacctc    3240
tcctgtcata ctgctacctc aggtggacaa caaggcatta tgtttaccaa agagagcaag    3300
ccttcaaaaa atagatcctt ggtgcctgaa acaagcaggc atactggaga cacatctaat    3360
ggctgtgctg atgtcaaggg actttctaat catgttcatc agttgatagc agatgctgtt    3420
tccagtccta accatggaga ttcaccaaat ttattaattg cagacaatcc tcagctctct    3480
gctttgttga ttggaaaagc caatggcaat gtgggtactg gaacctgtga caaagtgaat    3540
aatattcacc cagctgttca tacaaagact gatcattctg ttgcctcttc accctcttca    3600
gccatttcca cagcaacacc ttctcctaaa tccactgagc agagaagcat aaacagtgtt    3660
accagcctta acagtcctca cagtggatta cacacagtca atggagaggg gctggggaag    3720
tcacagagct ctacaaaagt agacctgcct ttagctagcc acagatctac ttctcagatc    3780
ttaccatcaa tgtcagtgtc tatatgcccc agttcaacag aagttctgaa agcatgcagg    3840
aatccaggta aaaatggctt gtctaatagc tgcattttgt tagataaatg tccacctcca    3900
agaccaccaa cttcaccata cccacccttg ccaaaggaca agttgaatcc acccacacct    3960
agtatttact tggaaaataa acgtgatgct ttcttttcctc cattcatca attttgtaca    4020 aatccaaaaa accctgttac agtaatacgt ggccttgctg gagctcttaa attagatctt    4080
ggacttttct ctaccaaaac tttggtagaa gctaacaatg aacatatggt agaagtgagg    4140
acacagttgc tgcaaccagc agatgaaaac tgggatccca ctggaacaaa gaaaatctgg    4200
cgttgtgaaa gcaatagatc tcatactaca attgccaaat acgcacaata ccaggcttcc    4260
tccttccagg aatcattgag agaagaaaat gagaaaagaa cacaacacaa agatcattca    4320
gataacgaat ccacatcttc agagaattct ggaaggagaa ggaaaggacc ttttaaaacc    4380
ataaaatttg ggaccaacat tgacctctct gataacaaaa agtggaagtt gcagttacat    4440
gaactgacta aacttcctgc ttttgcgcgt gtggtgtcag caggaaatct tctaacccat    4500
gttgggcata ccattctggg catgaataca gtacaactgt atatgaaagt tccagggagt    4560
cggacaccag gtcaccaaga aaataacaac ttctgctctg ttaacataaa tattggtcca    4620
ggagattgtg aatggtttgt tgtacctgaa gattattggg gtgttctgaa tgacttctgt    4680
gaaaaaaata atttgaattt tttaatgagt tcttggtggc ccaaccttga agatctttat    4740
gaagcaaatg tccctgtgta tagatttatt cagcgacctg gagatttggt ctggataaat    4800
gcaggcactg tgcattgggt tcaagctgtt ggctggtgca ataacattgc ctggaatgtt    4860
ggtccactta cagcctgcca gtataaattg gcagtggaac ggtatgaatg aacaaattg    4920 aaaagtgtga agtcaccagt acccatggtg catctttcct ggaatatggc acgaaatatc    4980
aaagtctcag atccaaagct ttttgaaatg attaagtatt gtcttttgaa aattctgaag    5040
caatatcaga cattgagaga agctcttgtt gcagcaggaa aagaggttat atggcatggg    5100
cggacaaatg atgaaccagc tcattactgt agcatttgtg aggtggaggt ttttaatctg    5160 cttttttgtca ctaatgaaag caatactcaa aaaacctaca tagtacattg ccatgattgt    5220
gcacgaaaaa caagcaaaag tttggaaaat tttgtggtgc tcgaacagta caaaatggag    5280
gacctaatcc aagtttatga tcaatttaca ctagctcttt cattatcatc ctcatcttga    5340
tatagttcca tgaatattaa atgagattat ttctgctctt caggaaattt ctgcaccact    5400
ggttttgtag ctgtttcata aaactgttga ctaaaagcta tgtctatgca accttccaag    5460
aatagtatgt caagcaactg gacacagtgc tgcctctgct tcaggactta acatgctgat    5520
```

-continued

```
ccagctgtac ttcagaaaaa taatattaat catatgtttt gtgtacgtat gacaaactgt    5580
caaagtgaca cagaatactg atttgaagat agcctttttt atgtttctct atttctgggc    5640
tgatgaatta atattcattt gtattttaac cctgcagaat tttccttagt taaaaacact    5700
ttcctagctg gtcatttctt cataagatag caaatttaaa tctctcctcg atcagctttt    5760
aaaaaatgtg tactattatc tgaggaagtt ttttactgct ttatgttttt gtgtgttttg    5820
aggccatgat gattacattt gtggttccaa ataattttt ttaaatatta atagcccata    5880
tacaaagata atggattgca catagacaaa gaaataaact tcagatttgt gatttttgtt    5940
tctaaacttg atacagattt acactattta taaatacgta tttattgcct gaaaatattt    6000
gtgaatggaa tgttgttttt ttccagacgt aactgccatt aaatactaag gagttctgta    6060
gttttaaaca ctactcctat tacattttat atgtgtagat aaaactgctt agtattatac    6120
agaaattttt attaaaattg ttaaatgttt aaagggtttc ccaatgtttg agtttaaaaa    6180
agacttctg aaaaaatcca cttttgttc attttcaaac ctaatgatta tatgtatttt    6240
atatgtgtgt gtatgtgtac acacatgtat aatatataca gaaacctcga tatataattg    6300
tatagatttt aaaagtttta ttttttacat ctatggtagt ttttgaggtg cctattataa    6360
agtattacgg aagtttgctg ttttttaaagt aaatgtctttt tagtgtgatt tattaagttg    6420
tagtcaccat agtgatagcc cataaataat tgctggaaaa ttgtatttta aacagtaga    6480
aaacatatag tcagtgaagt aaatattta aaggaaacat tatatagatt tgataaatgt    6540
tgtttataat taagagtttc ttatggaaaa gagattcaga atgataacct cttttagaga    6600
acaaataagt gacttatttt tttaaagcta gatgactttg aaatgctata ctgtcctgct    6660
tgtacaacat ggtttggggt gaaggggagg aaagtattaa aaaatctata tcgctagtaa    6720
attgtaataa gttctattaa aacttgtatt tcatatgaaa aatttgctaa tttaatatta    6780
actcatttga taataatact tgtctttttct acctctc                            6817
```

<210> SEQ ID NO 10
<211> LENGTH: 724
<212> TYPE: PRT
<213> ORGANISM: Homo sapiens

<400> SEQUENCE: 10

```
Met Ser Gly Gly Glu Val Val Cys Ser Gly Trp Leu Arg Lys Ser Pro
1               5                   10                  15

Pro Glu Lys Lys Leu Lys Arg Tyr Ala Trp Lys Arg Arg Trp Phe Val
            20                  25                  30

Leu Arg Ser Gly Arg Leu Thr Gly Asp Pro Asp Val Leu Glu Tyr Tyr
        35                  40                  45

Lys Asn Asp His Ala Lys Lys Pro Ile Arg Ile Ile Asp Leu Asn Leu
    50                  55                  60

Cys Gln Gln Val Asp Ala Gly Leu Thr Phe Asn Lys Lys Glu Phe Glu
65                  70                  75                  80

Asn Ser Tyr Ile Phe Asp Ile Asn Thr Ile Asp Arg Ile Phe Tyr Leu
                85                  90                  95

Val Ala Asp Ser Glu Glu Glu Met Asn Lys Trp Val Arg Cys Ile Cys
            100                 105                 110

Asp Ile Cys Gly Phe Asn Pro Thr Glu Glu Asp Pro Val Lys Pro Pro
        115                 120                 125

Gly Ser Ser Leu Gln Ala Pro Ala Asp Leu Pro Leu Ala Ile Asn Thr
    130                 135                 140
```

```
Ala Pro Pro Ser Thr Gln Ala Asp Ser Ser Ala Thr Leu Pro Pro
145                 150                 155                 160

Pro Tyr Gln Leu Ile Asn Val Pro Pro His Leu Glu Thr Leu Gly Ile
                165                 170                 175

Gln Glu Asp Pro Gln Asp Tyr Leu Leu Leu Ile Asn Cys Gln Ser Lys
            180                 185                 190

Lys Pro Glu Pro Thr Arg Thr His Ala Asp Ser Ala Lys Ser Thr Ser
        195                 200                 205

Ser Glu Thr Asp Cys Asn Asp Asn Val Pro Ser His Lys Asn Pro Ala
    210                 215                 220

Ser Ser Gln Ser Lys His Gly Met Asn Gly Phe Phe Gln Gln Gln Met
225                 230                 235                 240

Ile Tyr Asp Ser Pro Pro Ser Arg Ala Pro Ser Ala Ser Val Asp Ser
                245                 250                 255

Ser Leu Tyr Asn Leu Pro Arg Ser Tyr Ser His Asp Val Leu Pro Lys
            260                 265                 270

Val Ser Pro Ser Ser Thr Glu Ala Asp Gly Glu Leu Tyr Val Phe Asn
        275                 280                 285

Thr Pro Ser Gly Thr Ser Ser Val Glu Thr Gln Met Arg His Val Ser
    290                 295                 300

Ile Ser Tyr Asp Ile Pro Pro Thr Pro Gly Asn Thr Tyr Gln Ile Pro
305                 310                 315                 320

Arg Thr Phe Pro Glu Gly Thr Leu Gly Gln Thr Ser Lys Leu Asp Thr
                325                 330                 335

Ile Pro Asp Ile Pro Pro Arg Pro Pro Lys Pro His Pro Ala His
            340                 345                 350

Asp Arg Ser Pro Val Glu Thr Cys Ser Ile Pro Arg Thr Ala Ser Asp
        355                 360                 365

Thr Asp Ser Ser Tyr Cys Ile Pro Thr Ala Gly Met Ser Pro Ser Arg
    370                 375                 380

Ser Asn Thr Ile Ser Thr Val Asp Leu Asn Lys Leu Arg Lys Asp Ala
385                 390                 395                 400

Ser Ser Gln Asp Cys Tyr Asp Ile Pro Arg Ala Phe Pro Ser Asp Arg
                405                 410                 415

Ser Ser Ser Leu Glu Gly Phe His Asn His Phe Lys Val Lys Asn Val
            420                 425                 430

Leu Thr Val Gly Ser Val Ser Ser Glu Glu Leu Asp Glu Asn Tyr Val
        435                 440                 445

Pro Met Asn Pro Asn Ser Pro Pro Arg Gln His Ser Ser Ser Phe Thr
    450                 455                 460

Glu Pro Ile Gln Glu Ala Asn Tyr Val Pro Met Thr Pro Gly Thr Phe
465                 470                 475                 480

Asp Phe Ser Ser Phe Gly Met Gln Val Pro Pro Ala His Met Gly
                485                 490                 495

Phe Arg Ser Ser Pro Lys Thr Pro Arg Arg Pro Val Pro Val Ala
            500                 505                 510

Asp Cys Glu Pro Pro Val Asp Arg Asn Leu Lys Pro Asp Arg Lys
        515                 520                 525

Gly Gln Ser Pro Lys Ile Leu Arg Leu Lys Pro His Gly Leu Glu Arg
    530                 535                 540

Thr Asp Ser Gln Thr Ile Gly Asp Phe Ala Thr Arg Arg Lys Val Lys
545                 550                 555                 560

Pro Ala Pro Leu Glu Ile Lys Pro Leu Pro Glu Trp Glu Glu Leu Gln
```

```
                565                 570                 575
Ala Pro Val Arg Ser Pro Ile Thr Arg Ser Phe Ala Arg Asp Ser Ser
            580                 585                 590

Arg Phe Pro Met Ser Pro Arg Pro Asp Ser Val His Ser Thr Thr Ser
        595                 600                 605

Ser Ser Asp Ser His Asp Ser Glu Glu Asn Tyr Val Pro Met Asn Pro
    610                 615                 620

Asn Leu Ser Ser Glu Asp Pro Asn Leu Phe Gly Ser Asn Ser Leu Asp
625                 630                 635                 640

Gly Gly Ser Ser Pro Met Ile Lys Pro Lys Gly Asp Lys Gln Val Glu
            645                 650                 655

Tyr Leu Asp Leu Asp Leu Asp Ser Gly Lys Ser Thr Pro Pro Arg Lys
        660                 665                 670

Gln Lys Ser Ser Gly Ser Gly Ser Ser Val Ala Asp Glu Arg Val Asp
    675                 680                 685

Tyr Val Val Asp Gln Gln Lys Thr Leu Ala Leu Lys Ser Thr Arg
    690                 695                 700

Glu Ala Trp Thr Asp Gly Arg Gln Ser Thr Glu Ser Glu Thr Pro Ala
705                 710                 715                 720

Lys Ser Val Lys

<210> SEQ ID NO 11
<211> LENGTH: 7836
<212> TYPE: DNA
<213> ORGANISM: Homo sapiens

<400> SEQUENCE: 11
agggggcgga gcgcaaagga cagaagctcc ggcaccgagt cggggcagag tcccgctgag      60
tccgagcgct gctgaggcag ctggcgagac ggcacgtctg gaggcgaggc gggcgcactg     120
aaaggaggcc ggcgcgcccg cggcccggc tcgcgttctg ttcaggttcg tgggcctgca     180
gaggagagac tcgaactcgt ggaacccgcg caccgtggag tctgtccgcc cagtccgtcc     240
ggggtgcgcg accaggagag ctaggttctc gccactgcgc gctcggcagg cgtcggctgt     300
gtcgggagcg cgcccgccgc ccctcagctg cccggcccgg agcccgagac gcgcgcacca     360
tgagcggtgg tgaagtggtc tgctccggat ggctccgcaa gtccccccg gagaaaaagt      420 tgaagcgtta tgcatggaag aggagatggt tcgtgttacg cagtggccgt ttaactggag     480
atccagatgt tttggaatat tacaaaaatg atcatgccaa gaagcctatt cgtattattg     540
atttaaattt atgtcaacaa gtagatgctg gattgacatt taacaaaaaa gagttttgaaa    600 acagctacat ttttgatatc aacactattg accggatttt ctacttggta gcagacagcg     660
aggaggagat gaataagtgg gttcgttgta tttgtgacat ctgtgggttt aatccaacag     720
aagaagatcc tgtgaagcca cctggcagct ctttacaagc accagctgat ttacctttag     780 ctataaaatac agcaccacca tccacccagg cagattcatc ctctgctact ctacctcctc    840
catatcagct aatcaatgtt ccaccacacc tggaaactct tggcattcag gaggatcctc    900
aagactacct gttgctcatc aactgtcaaa gcaagaagcc cgaacccacc agaacgcatg    960
ctgattctgc aaaatccacc tcttctgaaa cagactgcaa tgataacgtc ccttctcata    1020
aaaatcctgc ttcctcccag agcaaacatg gaatgaatgg ctttttttcag cagcaaatga    1080 tatacgactc tccaccttca cgtgcccat ctgcttcagt tgactccagc ctttataacc     1140
tgcccaggag ttattcccat gatgttttac caaaggtgtc tccatcaagt actgaagcag   1200
```

-continued

```
atggagaact ctatgttttt aatacccat ctgggacatc gagtgtagag actcaaatga   1260
ggcatgtatc tattagttat gacattcctc caacacctgg taatacttat cagattccac   1320
gaacatttcc agaaggaacc ttgggacaga catcaaagct agacactatt ccagatattc   1380
ctccacctcg gccaccgaaa ccacatccag ctcatgaccg atctcctgtg aaacgtgta   1440 gtatcccacg caccgcctca gacactgaca gtagttactg tatccctaca gcagggatgt   1500
cgccttcacg tagtaatacc atttccactg tggatttaaa caattgcga aaagatgcta   1560 gttctcaaga ctgctatgat attccacgag catttccaag tgatagatct agttcacttg   1620
aaggcttcca taaccacttt aaagtcaaaa atgtgttgac agtgggaagt gtttcaagtg   1680
aagaactgga tgaaaattac gtcccaatga atcccaattc accaccacga caacattcca   1740
gcagttttac agaaccaatt caggaagcaa attatgtgcc aatgactcca ggaacatttg   1800
atttttcctc atttggaatg caagttcctc ctcctgctca tatgggcttc aggtccagcc   1860
caaaaacccc tcccagaagg ccagttcctg ttgcagactg tgaaccaccc ccgtggata   1920 ggaacctcaa gccagacaga aaagtcaagc cagcgccttt agaaataaaa cctttgccag   1980
aatgggaaga attacaagcc ccagttagat ctcccatcac taggagtttt gctcgagact   2040
cttccaggtt tccatgtcc ccccgaccag attcagtgca tagcacaact tcaagcagtg   2100
actcacacga cagtgaagag aattatgttc ccatgaaccc aaacctgtcc agtgaagacc   2160
caaatctctt tggcagtaac agtcttgatg gaggaagcag ccctatgatc aagcccaaag   2220
gagacaaaca ggtggaatac ttagatctcg acttagattc tgggaaatcc acaccaccac   2280
gtaagcaaaa gagcagtggc tcaggcagca gtgtagcaga tgagagagtg gattatgttg   2340
ttgttgacca acagaagacc ttggctctaa agagtacccg ggaagcctgg acagatggga   2400
gacagtccac agaatcagaa acgccagcga agagtgtgaa atgaaaatat tgccttgcca   2460
tttctgaaca aaagaaaact gaattgtaaa gataaatccc ttttgaagaa tgacttgaca   2520
cttccactct aggtagatcc tcaaatgagt agagttgaag tcaaaggacc tttctgacat   2580
aatcaagcaa tttagactta agtggtgctt tgtggtatct gaacaattca taacatgtaa   2640
ataatgtggg aaaatagtat tgtttagctc ccagagaaac atttgttcca cagttaacac   2700
actcgtagta ttactgtatt tatgcacttt ttcatctaaa acattgttct gggttttccc   2760
aatgtacctt accataattc ctttgggagt tcttgttttt tgtcacacta ctttatataa   2820
caatactaag tcaactaagc tacttttaga tttggaaatt gctgtttaca gtctaacaac   2880
attaaaatga gaggtagatt cacaagttag cttttctacct gaagcttcag gtgataacca   2940
ttagcttata cttggactca tcatttgttg ccttccaaaa tgctgaggat aatgtatgta   3000
ctggtgtcag gacctagttc tctggttaat gtacatttag ttttaatgg tggaactttg   3060 ttatattttg ttaattacag tgttttggt tcattgagtg aagattctgc cgggtgggat   3120
cttgcacctt tgaaagactg aataattaca ctaccaagta agcctgcaaa tcattgatgg   3180
catgcagtga tgatgtgctc ttacacttgt taacatgtat taagtgttat ttgcaaaagg   3240
tagattatgt aaccaatcag gtacgtacca ggcagtgatg tgctaataca ctgatcaggt   3300
ttagacaatg agcttggtt gtgttcttgt tagtcctaat attggttttc agtttggaat   3360
taataaagca gttgacattc actgttagtt acagcaacat actgtgattt ttaattagat   3420
agtaattcag atttattact ctatgaaatt ctgtcttttg acaccatagt gcccttcta   3480 tgatttttt tacttaatat tcttcttggc cttatattta attccctatg caattaatat   3540
tttatatctg cattttttta aaaaaaatag atgttatata agtgattctc gtatgtagca   3600
```

```
cctgttgctt ttccactgaa agaattacgg attttgtact gtgatttata ttcactgccc    3660
caattcaaga aatattggag ccttgctaca atgtgaaatg ttatagtcat ggactccttc    3720
caaccagatt tctgaaaaca ccagagggat ggtataattc tgtctcacct ataacatggt    3780
cctgtgacat agatattaag accacaagtt gtagtgaggc tacaattata ttcgtctgtc    3840
ttggctttgc aacataattt agaaagcacg tatagttgtt ttttaaccaa gttacataca    3900
atctcatgta ctgatttgag acttataaca atttttggag ggggcataga gaaggagtg    3960 cccacagttg aggcatgacc ccctccattc agacctctaa ctgttgcctg agtacacaga    4020
tgtgccctga tttctggccc attggccata gtactgtgcc taatcaatgt aataggttta    4080
ttttcccaat cctcaaacta aaatgttcca taacaagatg aattgtagac tagtaacatt    4140
tgatgctttt aaatatttgc ttcttttta acaaaaacta aacccagaa gtgaatttt    4200 aggtggattt ttaaataaaa aagattgatt gagtttggtg tgcaagctgt tttataatga    4260
aacaacaaaa tgaaatctaa aatcctgaaa tgtgcctaaa ctatcaaaac acacgataca    4320
gctaatgtgt aaagatgcta aattctgtta cttggaggat gaatatattt aagatttaaa    4380
acacaataat aaatacatga ttaattcaaa aataaaaatc tttacagctg cctatcaagg    4440
gtctaaagca cttaatgaat gttttagtc taacttatca ttaactttt acaagtcacc    4500 atatttgaag atctgtagca ctctgatttt cagaaaattt ttcattctga ataatttaaa    4560
aatggtgatg tattagaaag gcagtttgct ttagaaaact aaatcacatt gaacattgta    4620
ttagagaatt aaattaaaag tttcttacag agcagtattt tccaaacatt tttagcacta    4680
gaatcttttt agatgaaatt ttatgtataa ccccaataca taaagcctga aaactcaatt    4740
ttatcaatat aaatgtattt tgggttcaca tttatgctta ttcattttgg ctcattacta    4800
agcataataa gattctgagt tatttctgaa taacacaaat gtggagttat acatagttga    4860
tgaaaccagc agccaattta tagctatgcc ctgttttatt tgtatactat caagaaaatt    4920
ttgattcaca caaatgtaag caaaaataat aggttttaaa catacatctc aggaaattct    4980
ttaattagag atagctaaag ttattcaagg tctatacaaa aataagttat cctggtagtg    5040
gaagttaata cataagcagt ctccagtgtg gtaaagtagg gtatgtaaca catcagaatg    5100
tgcgttttta ttaggtttta aaatatgcac gtataaaaac taaatttgaa tcaaaccctt    5160
ttaactcacc tccaagaagc tagactttgg ccaggaatgg gctaaaaacc actggttaac    5220
gatgtgacag ttatgatctt ggagattgga aatctttctt ccacattaga gttctttacc    5280
ttaattcctt attctgaaaa attgtaagat tttatgaagg tttgaatact gaagcacagt    5340
tctgctttca aaaattaaaa ttcaaacttg aaaaagctgt ttaacccatg gaagatatca    5400
tttagtaaga tgtaaaagat tttttaaatc tacacttcag tttatacatc tttatcatta    5460
tcaatactat ataagttact gtgagcattt tagagaattc cataaaggta ctatgagtgt    5520
gtctgtatgt gtgtgtatat atagcattgt atttaatcat agactaaatt taatttgata    5580
tagaaatact actttacttg tacattaagg tcataatttc tgctggactc ttttatattt    5640
aattaatggg gattatagtc ttccttcata aatgcattta aacctgaaat tgaacaccag    5700
tgtttttctt tttctactta tgggaagttg tctgcttccc cctttagaga aaacagtatt    5760
tttatatttt gttaaaatat taactacttt atgcctacac actatgctgt agatactgat    5820
cataattctt gggtgttcac aaacactcct agtgcctctt ttttggcccg ttgaaagtgt    5880
tggtattact actttcacta cagagccttt ggccctctaa taatgctgag gtgggctgat    5940
```

```
ccttcccatt tctgtcttcg ggtcattctg gtaggtcttc tcctccactg tcaagtaagc    6000
aatcaggtcc gtgacaggga ttggacatat gaacaaatta agtggataca cacagtgaga    6060
aagatacatg cattctatgg taacaactac tgtcaataac atctgatgtt acatgcacat    6120
ttatatatat ataattttaa aaactgaact atgagaagcc atggtataaa tgaatattgt    6180
ggacatcatg gacttgatat gatagaaatc aattgtcagc ttgagaaagt tgttttttaat   6240 ctgtctaaat agttcatgca ttactacagt taaaaatagt ttcatttgtc ttctatagac    6300
ttaattttat tccggttcag tataatctct gttaacagag tttcagcaaa ctgattggtc    6360
aaggtattaa catagcttct acttccttta cttaaaaaga gtggttttta tgtaagttct    6420
tgattactga tgatcatccc aaattttgac aacaaaatca tatgtataaa tttatttctc    6480
ccctcttgtt catcatcttt tgtaaaggtc ccattgtaga tctttttctgc taccaaataa    6540 aacttttcaa acaatttggt ttcaagacct taaaatagaca agttggatac taagattgtg   6600
aactgataag gacatataaa tttatatttc cagcccttcc ttagagtctt tatctgcatc    6660
aaaaacccaa ttctgccatt aactgtgctt cccagtccca cctctatatg tcactcattt    6720
tctgcaacaa agatctcact aaatcatgtt gaaacacaag tcatgatcct ctctaagtaa    6780
atagaaaaag ctccctggaa aaactctgtt gccacatgca cgtgccctgt tactcctcca    6840
gccagccagt gctgccagca ttttattgtg taaaagtcca aataaataag ggcctgcatg    6900
caacctttat cttcagaaac taggttttat atgtaaaatg tgacttggga aatgattctg    6960
tttattaact ggctgggatt tttcatttct atgaaagttt caaacatctc cagtacttta    7020
taaaatccca acaattgctg taagtcagca ctttggtcca ctcagcccac ccagcccact    7080
tgcaactctg actcttcact gaatcatatt tgggaagttt gggtagggtg aggctatctt    7140
cttcaagatt attttctcat atgtctgtct gtcaccttgt aaaccatgag actcctgggt    7200
atttgcatgt aacttctttg aggaagttac caccatctct gatatagaca cacttttga    7260 gttgcagttt ctgttagaat ttttttggaga ctaacttgcc aattctgtga atgttattga    7320
atatttaaaa agctgggtct gtaatgggag gcattttatt agctgttgtg attgggtaac    7380 atgtccccctt agatttcctg atttaaaatt atacaaaatt actattttg ataaaataaa    7440 ggaacaccta cagaaaatta agtttctaag atgtttctat acttcattag aaaagatttt    7500
attactatta cttatggtta ttggtgatta acacttaatg cgtctcctct gattttgtgt    7560
tccatgaggt gcttggaaca tttggagtgc tctgtgcgag ggacatacag tgatataggaa    7620 aatttaaaaa ttaaataat acccaaaacc cactttatca gatatggtat tgtgatggtt    7680
aatattatgt gtcaacttgg tgaggctatg gcgcccatgt gtttggtcaa acactagcct    7740
agatgttgct gtgaatatat tttgtagatg tgattaacat ttacaatcag ttgattttaa    7800
gtaaagcaga ttctcatcca aaaaaaaaaa aaaaaa                              7836

<210> SEQ ID NO 12
<211> LENGTH: 894
<212> TYPE: PRT
<213> ORGANISM: Homo sapiens

<400> SEQUENCE: 12

Met Glu Ser Thr Leu Ser Ala Ser Asn Met Gln Asp Pro Ser Ser
1               5                   10                  15

Pro Leu Glu Lys Cys Leu Gly Ser Ala Asn Gly Asn Gly Asp Leu Asp
                20                  25                  30

Ser Glu Glu Gly Ser Ser Leu Glu Glu Thr Gly Phe Asn Trp Gly Glu
```

```
                35                  40                  45
Tyr Leu Glu Glu Thr Gly Ala Ser Ala Ala Pro His Thr Ser Phe Lys
 50                  55                  60

His Val Glu Ile Ser Ile Gln Ser Asn Phe Gln Pro Gly Met Lys Leu
 65                  70                  75                  80

Glu Val Ala Asn Lys Asn Asn Pro Asp Thr Tyr Trp Val Ala Thr Ile
                 85                  90                  95

Ile Thr Thr Cys Gly Gln Leu Leu Leu Arg Tyr Cys Gly Tyr Gly
                100                 105                 110

Glu Asp Arg Arg Ala Asp Phe Trp Cys Asp Val Ile Ala Asp Leu
                115                 120                 125

His Pro Val Gly Trp Cys Thr Gln Asn Asn Lys Val Leu Met Pro Pro
130                 135                 140

Asp Ala Ile Lys Glu Lys Tyr Thr Asp Trp Thr Glu Phe Leu Ile Arg
145                 150                 155                 160

Asp Leu Thr Gly Ser Arg Thr Ala Pro Ala Asn Leu Leu Glu Gly Pro
                165                 170                 175

Leu Arg Gly Lys Gly Pro Ile Asp Leu Ile Thr Val Gly Ser Leu Ile
                180                 185                 190

Glu Leu Gln Asp Ser Gln Asn Pro Phe Gln Tyr Trp Ile Val Ser Val
                195                 200                 205

Ile Glu Asn Val Gly Gly Arg Leu Arg Leu Arg Tyr Val Gly Leu Glu
210                 215                 220

Asp Thr Glu Ser Tyr Asp Gln Trp Leu Phe Tyr Leu Asp Tyr Arg Leu
225                 230                 235                 240

Arg Pro Val Gly Trp Cys Gln Glu Asn Lys Tyr Arg Met Asp Pro Pro
                245                 250                 255

Ser Glu Ile Tyr Pro Leu Lys Met Ala Ser Glu Trp Lys Cys Thr Leu
                260                 265                 270

Glu Lys Ser Leu Ile Asp Ala Ala Lys Phe Pro Leu Pro Met Glu Val
                275                 280                 285

Phe Lys Asp His Ala Asp Leu Arg Ser His Phe Phe Thr Val Gly Met
                290                 295                 300

Lys Leu Glu Thr Val Asn Met Cys Glu Pro Phe Tyr Ile Ser Pro Ala
305                 310                 315                 320

Ser Val Thr Lys Val Phe Asn Asn His Phe Gln Val Thr Ile Asp
                325                 330                 335

Asp Leu Arg Pro Glu Pro Ser Lys Leu Ser Met Leu Cys His Ala Asp
                340                 345                 350

Ser Leu Gly Ile Leu Pro Val Gln Trp Cys Leu Lys Asn Gly Val Ser
                355                 360                 365

Leu Thr Pro Pro Lys Gly Tyr Ser Gly Gln Asp Phe Asp Trp Ala Asp
                370                 375                 380

Tyr His Lys Gln His Gly Ala Gln Glu Ala Pro Pro Phe Cys Phe Arg
385                 390                 395                 400

Asn Thr Ser Phe Ser Arg Gly Phe Thr Lys Asn Met Lys Leu Glu Ala
                405                 410                 415

Val Asn Pro Arg Asn Pro Gly Glu Leu Cys Val Ala Ser Val Val Ser
                420                 425                 430

Val Lys Gly Arg Leu Met Trp Leu His Leu Glu Gly Leu Gln Thr Pro
                435                 440                 445

Val Pro Glu Val Ile Val Asp Val Glu Ser Met Asp Ile Phe Pro Val
                450                 455                 460
```

```
Gly Trp Cys Glu Ala Asn Ser Tyr Pro Leu Thr Ala Pro His Lys Thr
465                 470                 475                 480

Val Ser Gln Lys Lys Arg Lys Ile Ala Val Gln Pro Glu Lys Gln
            485                 490                 495

Leu Pro Pro Thr Val Pro Val Lys Lys Ile Pro His Asp Leu Cys Leu
                500                 505                 510

Phe Pro His Leu Asp Thr Thr Gly Thr Val Asn Gly Lys Tyr Cys Cys
            515                 520                 525

Pro Gln Leu Phe Ile Asn His Arg Cys Phe Ser Gly Pro Tyr Leu Asn
530                 535                 540

Lys Gly Arg Ile Ala Glu Leu Pro Gln Ser Val Gly Pro Gly Lys Cys
545                 550                 555                 560

Val Leu Val Leu Lys Glu Val Leu Ser Met Ile Ile Asn Ala Ala Tyr
                565                 570                 575

Lys Pro Gly Arg Val Leu Arg Glu Leu Gln Leu Val Glu Asp Pro His
                580                 585                 590

Trp Asn Phe Gln Glu Glu Thr Leu Lys Ala Lys Tyr Arg Gly Lys Thr
            595                 600                 605

Tyr Arg Ala Val Val Lys Ile Val Arg Thr Ser Asp Gln Val Ala Asn
610                 615                 620

Phe Cys Arg Arg Val Cys Ala Lys Leu Glu Cys Cys Pro Asn Leu Phe
625                 630                 635                 640

Ser Pro Val Leu Ile Ser Glu Asn Cys Pro Glu Asn Cys Ser Ile His
                645                 650                 655

Thr Lys Thr Lys Tyr Thr Tyr Tyr Gly Lys Arg Lys Lys Ile Ser
            660                 665                 670

Lys Pro Pro Ile Gly Glu Ser Asn Pro Asp Ser Gly His Pro Lys Pro
                675                 680                 685

Ala Arg Arg Arg Lys Arg Arg Lys Ser Ile Phe Val Gln Lys Lys Arg
    690                 695                 700

Arg Ser Ser Ala Val Asp Phe Thr Ala Gly Ser Gly Glu Glu Ser Glu
705                 710                 715                 720

Glu Glu Asp Ala Asp Ala Met Asp Asp Thr Ala Ser Glu Glu Thr
                725                 730                 735

Gly Ser Glu Leu Arg Asp Asp Gln Thr Asp Thr Ser Ser Ala Glu Val
            740                 745                 750

Pro Ser Ala Arg Pro Arg Arg Ala Val Thr Leu Arg Ser Gly Ser Glu
        755                 760                 765

Pro Val Arg Arg Pro Pro Glu Arg Thr Arg Arg Gly Arg Gly Ala
        770                 775                 780

Pro Ala Ala Ser Ser Ala Glu Glu Gly Glu Lys Cys Pro Pro Thr Lys
785                 790                 795                 800

Pro Glu Gly Thr Glu Asp Thr Lys Gln Glu Glu Glu Arg Leu Val
                805                 810                 815

Leu Glu Ser Asn Pro Leu Glu Trp Thr Val Thr Asp Val Val Arg Phe
            820                 825                 830

Ile Lys Leu Thr Asp Cys Ala Pro Leu Ala Lys Ile Phe Gln Glu Gln
    835                 840                 845

Asp Ile Asp Gly Gln Ala Leu Leu Leu Leu Thr Leu Pro Thr Val Gln
    850                 855                 860

Glu Cys Met Glu Leu Lys Leu Gly Pro Ala Ile Lys Leu Cys His Gln
865                 870                 875                 880
```

Ile Glu Arg Val Lys Val Ala Phe Tyr Ala Gln Tyr Ala Asn
              885                  890

<210> SEQ ID NO 13
<211> LENGTH: 7922
<212> TYPE: DNA
<213> ORGANISM: Homo sapiens

<400> SEQUENCE: 13

| | | | | |
|---|---|---|---|---|
| cgccttgtgt | gtgctggatc | ctgcgcgggt | agatccccga | gtaattttt ctgcaggatg | 60 |
| aattaagaga | agagacactt | gctcatcagg | catggagagc | actttgtcag cttccaatat | 120 |
| gcaagaccct | tcatcttcac | ccttggaaaa | gtgtctcggc | tcagctaatg gaaatggaga | 180 |
| ccttgattct | gaagaaggct | caagcttgga | ggaaactggc | tttaactggg gagaatattt | 240 |
| ggaagagaca | ggagcaagtg | ctgctcccca | cacatcattc | aaacacgttg aaatcagcat | 300 |
| tcagagcaac | ttccagccag | gaatgaaatt | ggaagtggct | aataagaaca cccggacac | 360 |
| gtactgggtg | ccacgatca | ttaccacgtg | cgggcagctg | ctgcttctgc gctactgcgg | 420 |
| ttacggggag | gaccgcaggg | ccgacttctg | gtgtgacgta | gtcatcgcgg atttgcaccc | 480 |
| cgtggggtgg | tgcacacaga | acaacaaggt | gttgatgccg | ccggacgcaa tcaaagagaa | 540 |
| gtacacagac | tggacagaat | tctcatacg | tgacttgact | ggttcgagga cagcacccgc | 600 |
| caacctcctg | gaaggtcctc | tgcgagggaa | aggccctata | gacctcatta cagttggttc | 660 |
| cttaatagaa | cttcaggatt | cccagaaccc | ttttcagtac | tggatagtta gtgtgattga | 720 |
| aaatgttgga | ggaagattac | gccttcgcta | tgtgggattg | gaggacactg aatcctatga | 780 |
| ccagtggttg | ttttacttgg | attacagact | tcgaccagtt | ggttggtgtc aagagaataa | 840 |
| atacagaatg | gacccacctt | cagaaatcta | tcctttgaag | atggcctctg aatgaaatg | 900 |
| tactctggaa | aaatccctta | ttgatgctgc | caaatttcct | cttccaatgg aagtgtttaa | 960 |
| ggatcacgca | gatttgcgaa | gccatttctt | cacagttggg | atgaagcttg agacagtgaa | 1020 |
| tatgtgcgag | cccttttaca | tctctcctgc | gtcggtgact | aaggttttta caatcactt | 1080 |
| ttttcaagtg | actattgatg | acctaagacc | tgaaccaagt | aaactgtcaa tgctgtgcca | 1140 |
| tgcagattct | ttggggattt | tgccagtaca | gtggtgcctt | aaaaatggag tcagcctcac | 1200 |
| tcctcccaaa | ggttactctg | gccaggactt | cgactgggca | gattatcaca agcagcatgg | 1260 |
| ggcgcaggaa | gcccctccct | tctgcttccg | aaatacatca | ttcagtcgag gtttcacaaa | 1320 |
| gaacatgaaa | cttgaagctg | tgaaccccag | gaatccagga | gaactgtgtg tggcctccgt | 1380 |
| tgtgagtgtg | aagggggcggc | taatgtggct | tcacctggaa | gggctgcaga ctcctgttcc | 1440 |
| agaggtcatt | gttgatgtgg | aatccatgga | catcttccca | gtgggctggt gtgaagccaa | 1500 |
| ttcttatcct | ttgactgcac | cacacaaaac | agtctcacaa | agaagagaa agattgcagt | 1560 |
| cgtgcaacca | gagaaacaat | gccgcccac | agtgcctgtt | aagaaaatac ctcatgacct | 1620 |
| ttgtttattc | cctcacctgg | acaccacagg | aaccgtcaac | gggaaatact gctgtcctca | 1680 |
| gctcttcatc | aaccacaggt | gtttctcagg | cccttacctg | aacaaaggaa ggattgcaga | 1740 |
| gctacctcag | tcggtgggac | cgggcaaatg | cgtgctggtt | cttaaagagg ttcttagcat | 1800 |
| gataatcaac | gcagcctaca | agcctggaag | ggtattaaga | gaattacagc tggtagaaga | 1860 |
| tccccactgg | aatttccagg | aagagacgct | gaaggccaaa | tacagaggca aacatacag | 1920 |
| ggctgtggtc | aaaatcgtac | ggacatctga | ccaagtcgca | aatttctgcc gccgagtctg | 1980 |
| tgccaagcta | gagtgctgtc | caatttgtt | tagtcctgtg | ctgatatctg aaaactgccc | 2040 |

```
agagaactgc tccattcata ccaaaaccaa atacacctat tactatggaa agagaaagaa   2100
gatctccaag cccccatcg gggaaagcaa cccgacagc ggacacccca aacccgccag    2160
gcggaggaag cgacggaaat ccattttcgt gcagaagaaa cggaggtctt ctgccgtgga   2220
cttcaccgcg ggctcggggg aggaaagtga agaggaggac gctgacgcca tggacgatga   2280
caccgccagt gaggagaccg gctccgagct ccgggatgac cagacggaca cctcgtcggc   2340
ggaggtgccc tcggcccggc ccggagggc cgtcaccctg cggagcggct cagagcccgt    2400
gcgccggcca cccccagaga ggacacgaag gggccgcggg gcgccggctg cctcctcagc   2460
agaggaaggg gagaagtgcc cgccgaccaa gcccgagggg acagaggaca cgaaacagga   2520
ggaggaggag agactggttc tggagagcaa cccgttggag tggacggtca ccgacgtggt   2580
gaggttcatt aagctgacag actgtgcccc cttggccaag atatttcagg agcaggatat   2640
tgacggccaa gcactcctgc ttctgacccT tccgacggtg caggagtgca tggagctgaa   2700
gctggggcct gccatcaagt tatgccacca gatcgagaga gtcaaagtgg ctttctacgc   2760
ccagtacgcc aactgagtct gccctcggga ggtggcccat tattgctggg atgcggtgtt   2820
ggtaaaggtt tccaggactg aaactttgat tttccgggat atgttaaatg gtacagccac   2880
taagtatcac cagaaaacca gaagcccagg atcttctgcc tccgccagcc tgtgagctgt   2940
ttccatgttt tcaaagcaca gcagcagtcg cttctgggga gtgccagtta aagtcatgca   3000
tcagaccctg ccagacgtgg gcctgcttct ggctcaccc acgttttgcc tttctcctgc    3060
cccaaatcag gcagctccct tggagcaggg tttcctcaga tgaggactgc attctttgaa   3120
aacaaagaat gtcgccaagg aagaaacctc acgccatgct gtagtgtttc ctgtaatcac   3180
acgagcacat ttatatatgc agtttcccat ggataggcgt gtgaccctgg ttgagtggca   3240
cttgcggttt catcttggtg gcaactcctt tgcaatgcag ctggcagcga catccttata   3300
aaaacatgtg ctaaagctct gtcctctgtt agaggtgcct tttaggaata cggggagtga   3360
aggaaggccg gcaggcatct ccatgcaact agatggtttg tttgtttgtt tgtttgtttg   3420
ttgttcattt tgttgtgttt tttgagacag ggtcttgctc tgtcgcccag gttgtaatgc   3480
agtggcgcaa tctcagctca ctgcaacctc tctctcccgg gttcaagtga ttctcctgcc   3540
tcagcctccc aagtagctgg gattacaggc acccaccacc atgcctggct aattttgta    3600 ttttggtag agacagggtt tcaccatgtt ggtcaggcta gtcttgaact cccaacctca    3660
agtgatctgc ccgcctcggc ctcccaacgt gctgggatta caggtgtgag ccactacgcc   3720
ccggcccaac tggatggttt ttgattgaag cctagaacat ctgtagagac aaactctacc   3780
cagtcttttc tagaccctca actatctcca gtgttgttgt ttaatcgtag ccggatcagg   3840
gagtgagtct tttaggcaaa tgttggatta tatatcaaag gaaaagctta gtttcagaga   3900
ggaggaaggg aaagagatgt gagggaagca tttcatcaac cagctacgtc cccttagaa    3960 ggatcactgc gcaggtcac cgagcaggag tccctctgag cgtcccttct gtctcgttct   4020
gccctagctg gcagcatatg aaccaggcat gatgcagcag gagcagtgaa tctggagtca   4080
gccacttggc accctggttt cgctgagaac aaactctgag atcttgggtg acttctcatc   4140
actctggacc tccattcctg tgaagtgaca ggtgtggacc ctgagggtgc ggtggtgagc   4200
acactgtctc ctgctggcat tcaccccact catgctggaa aggaagatcc agatcgtaca   4260
aaaattagaa aaagaaagaa taagaagggt ctggtcccag ttctgactcg gccattctta   4320
cagctctttc tggctttgag tttgcttgtg gaatttcctg ggcagttgtg ttaaatccgc   4380
caggtcacgt gcagacaaag ctgtggctgc gagagttggc tggcctcttg gaccagaagc   4440
```

```
catctccata tcctcatgag cgattccata tctccactca gaccctgtgg actacagtgt   4500
tccgctgtgg tggctgccaa gatgccttct taaacttatg caaggaaacc aaaccctccc   4560
acagttccca agcagacact ggaagcagag gcttctcacc cttcctgctt tttcaccaca   4620
atcaccttga gctcgtccct tggactagag tctccacagt tccagtaaaa ttctgcggtg   4680
ggctgatgag ctgcttgcat ttctgtgaca tttccagata tgattctcag tgggattttg   4740
gaaactttga ttgctcaagc tcaccccttct taacattctg taatggttac agatgagaat   4800
ggaaaacaca tattttatgg atgaggcgtt ttggtctccc ctgcagtcga tttctagaat   4860
caagttttag agttcggctg atgcatctgc ctggggacct cagatgggag gagtgtgtca   4920
gttgtacccc gacagaaatg tctctgggat ctgtggctgg cttgccccgg gcatctctcc   4980
tttaagctca agttttgaac tctctgcggt tttccacccc tgccttctca gccacatgct   5040
tttggcctta aacgctcagt cttgtggagt tcaactctgt caaacgattg gaaagggcat   5100
ccatttccag atctttggca ttttccccgc gctgactctt tgatgatcct tcactgtggc   5160
cttttcaagc tcagctgttc ctgttgtatt tgagacgagg gtgagggaat gtggtggcca   5220
caaaagaaca gggacttgca gcacaaatgt cacttctgtc tccttttca gtggtagcac   5280 ggaggaggag gtgctgcgtt ggagggaggg gatcctccag gagctctctg gagcccatct   5340
aggaagctag agtgtgtggc ccgccaggag ctcaggaagg atacagccac tgtcgcaggg   5400
gaaagtgttt gcttcccgtg gagccaagcg cccaagactc tccgtatcct tcaccctgac   5460
agtttaactt cagcgtttct ctgtgcagtt gcggtcacca tgggtgagca ctgtctgtgc   5520
acgtgccagg gaggagatgg ctgggaccac tgcacaggag ggcgcagcct ggcgtcgcca   5580
tgaaagttgt ctctgtgcca tctctccggt ccttgaggag agcccagaaa gattttagga   5640
cccaggaggt gcttttcctc cagctgttgc cagtgtcctt ctgagcctgg attctccggg   5700
gatttccgtc gtggtggatg gacttcacat cagcagcagt tctggtacag aattgtaatg   5760
tgttttcatt tctctgtagg attcacctct caccagcgtc tgtcttaaag gtagggccaa   5820
tttcatggag cattttcctg tgtgtgtcct tgttgctttt gccagaaaaa gtggatttga   5880
catgcgtgcc ccgatgccac catagcccct aggccaacaa tgtcatggtc taaacaccaa   5940
aaagtgatgc cccgcattcc ttccctggat ggtaccgttt cttctccgtc tctctttgat   6000 gattcttttgg gaccaaagtc ctctccttag tgcgcctact tcctgtgggc atcatgccac   6060
ttggaactta ttggaactgg cccgggagac tctgcagtct gcgccgtttg aaaaccctga   6120
gaaagagatg ccacctcaac ttgaatcatg acagcccatc gctcagtctc accctaaact   6180
catggagctt gtttcagctc ctcacttctt gactgtattt gtactatgtt gaaaaaatat   6240
cctgtccaca aagacataag cctaacaacc tagaaaaaca acagggtact actggcatta   6300
cagaacttct ttgccttttca aaacaaaagc aaaacacagt gaacttcacc acggagctgc   6360
acagcgtggg gaactcatcc atcactttca aaattagagt catttgatcc aagttggagt   6420
cagacacagt atttgagctg cacggcttct gggttctccc accttatttg atcatattcg   6480
aaagattatt tcctgtgttt gctttgattt gttcctcagt acattaaaat gatccacacc   6540
ttgaacactg ccctctctag aaggttgatt ttgatcagcc ttttgaagat gggtgtcgtt   6600
tccctaactt atctcacaga attttgagtg ttgtatttgg caagttctga gatttgcctt   6660
ctgtcttatg ccaaacaccc cttttctaaga gctgtccccg cttagtttta gaagtactag   6720
gggttttcat acttattttta tagaacaccc atttatattt atttctgtat atagaactaa   6780
```

```
aaaaaacagt agtgttaaaa atctttgttg tggtttgagc atctttgctg cttttggatt    6840
gagatggcga atcaaggctt cacttcctct ctcttctgtc tttagaaagc tgtgatcgtg    6900
cgtgcaatta tttgaaaggc aacatagtca attaagaaac ctgtagttgt taaggaagaa    6960
attgttggca agatatccat actgcccata tctcgttggt gcaataatta aatagcaaag    7020
gaaatctgta ttggcaacta ttataattca ataattcttt tgtttactgc ccttttctgt    7080
tcaagaattt tctggaaatt actcccttc acatggttga actcttaagt tgaccagttc     7140
tcatagctct atcactagaa tggtttgcag ataccccaaa catactatga taaaatcaaa    7200
ttgtgctact tttgacccat gtaatttacc taaaagttgt aattgctgac agagtactgc    7260
cttgaatttt ggtttaaaac ctctctagtt tcaatgacaa gtaacaactc aaataattcc    7320
atattgtttg aggaagaggc cataatcctt ctgaattgtt ggcactaagt aatgggattt    7380
ggcccagtaa gtatgacggt cgtgtcgcct aaccaacgca gagcagtgct ttttgtgtgg    7440
ctgaagcgat gtgctgacga aaaaggaaa attctaggac aatcgttggc taaaaatcac     7500
cttaggatga aaaatttgag gcaaattttt ttaaatgaca gaaaaagata atcatctcac    7560
ttgcttgaaa caggagccag catgatctct ggaagcatca actatccctc gtcgtgattg    7620
ttgaaagctc tttcactgtt ttgcattcta gtttgaatag tttgtattga aattggattc    7680
ctatcttgtg tatgttttg gtgcgtaaaa gggaaaaatt ggtgtcatta cttttgaaat      7740
ttgcaggacg aagggcatgc ttttggtttg ctgtaagatt gtattctgta tatatgtttt    7800
catgtaaata aatgaaaatc tatatcagag ttatatttta attttattc taaatgaaaa     7860 aaaccctttt tacttcaaaa aaattgtaag ccacattgtt aataaagtaa aaataaattc    7920
ta                                                                   7922
```

<210> SEQ ID NO 14
<211> LENGTH: 435
<212> TYPE: PRT
<213> ORGANISM: Homo sapiens

<400> SEQUENCE: 14

```
Met Leu Pro Ala Arg Cys Ala Arg Leu Leu Thr Pro His Leu Leu
1               5                   10                  15

Val Leu Val Gln Leu Ser Pro Ala Arg Gly His Arg Thr Thr Gly Pro
                20                  25                  30

Arg Phe Leu Ile Ser Asp Arg Asp Pro Gln Cys Asn Leu His Cys Ser
            35                  40                  45

Arg Thr Gln Pro Lys Pro Ile Cys Ala Ser Asp Gly Arg Ser Tyr Glu
        50                  55                  60

Ser Met Cys Glu Tyr Gln Arg Ala Lys Cys Arg Asp Pro Thr Leu Gly
65              70                  75                  80

Val Val His Arg Gly Arg Cys Lys Asp Ala Gly Gln Ser Lys Cys Arg
                85                  90                  95

Leu Glu Arg Ala Gln Ala Leu Glu Gln Ala Lys Lys Pro Gln Glu Ala
            100                 105                 110

Val Phe Val Pro Glu Cys Gly Glu Asp Gly Ser Phe Thr Gln Val Gln
        115                 120                 125

Cys His Thr Tyr Thr Gly Tyr Cys Trp Cys Val Thr Pro Asp Gly Lys
    130                 135                 140

Pro Ile Ser Gly Ser Ser Val Gln Asn Lys Thr Pro Val Cys Ser Gly
145                 150                 155                 160

Ser Val Thr Asp Lys Pro Leu Ser Gln Gly Asn Ser Gly Arg Lys Asp
```

-continued

```
                165                 170                 175
Asp Gly Ser Lys Pro Thr Pro Thr Met Glu Thr Gln Pro Val Phe Asp
            180                 185                 190
Gly Asp Glu Ile Thr Ala Pro Thr Leu Trp Ile Lys His Leu Val Ile
        195                 200                 205
Lys Asp Ser Lys Leu Asn Asn Thr Asn Ile Arg Asn Ser Glu Lys Val
    210                 215                 220
Tyr Ser Cys Asp Gln Glu Arg Gln Ser Ala Leu Glu Glu Ala Gln Gln
225                 230                 235                 240
Asn Pro Arg Glu Gly Ile Val Ile Pro Glu Cys Ala Pro Gly Gly Leu
                245                 250                 255
Tyr Lys Pro Val Gln Cys His Gln Ser Thr Gly Tyr Cys Trp Cys Val
            260                 265                 270
Leu Val Asp Thr Gly Arg Pro Leu Pro Gly Thr Ser Thr Arg Tyr Val
        275                 280                 285
Met Pro Ser Cys Glu Ser Asp Ala Arg Ala Lys Thr Thr Glu Ala Asp
    290                 295                 300
Asp Pro Phe Lys Asp Arg Glu Leu Pro Gly Cys Pro Glu Gly Lys Lys
305                 310                 315                 320
Met Glu Phe Ile Thr Ser Leu Leu Asp Ala Leu Thr Thr Asp Met Val
                325                 330                 335
Gln Ala Ile Asn Ser Ala Ala Pro Thr Gly Gly Gly Arg Phe Ser Glu
            340                 345                 350
Pro Asp Pro Ser His Thr Leu Glu Glu Arg Val Val His Trp Tyr Phe
        355                 360                 365
Ser Gln Leu Asp Ser Asn Ser Ser Asn Asp Ile Asn Lys Arg Glu Met
    370                 375                 380
Lys Pro Phe Lys Arg Tyr Val Lys Lys Ala Lys Pro Lys Lys Cys
385                 390                 395                 400
Ala Arg Arg Phe Thr Asp Tyr Cys Asp Leu Asn Lys Asp Lys Val Ile
                405                 410                 415
Ser Leu Pro Glu Leu Lys Gly Cys Leu Gly Val Ser Lys Glu Val Gly
            420                 425                 430
Arg Leu Val
        435
```

<210> SEQ ID NO 15
<211> LENGTH: 3740
<212> TYPE: DNA
<213> ORGANISM: Homo sapiens

<400> SEQUENCE: 15

| | |
|---|---|
| ataacgggaa ttcccatggc ccgggctcag gcgtccaacc tgctgccgcc tgggccccgc | 60 |
| cgagcggagc tagcgccgcg cgcagagcac acgctcgcgc tccagctccc ctcctgcgcg | 120 |
| gttcatgact tgtcccctg accgcagcct ctgcgagccc cgccgcagg accacgccc | 180 |
| gctccccgcc gccgcgaggg ccccgagcga aggaaggaag ggaggcgcgc tgtgcgcccc | 240 |
| gcggagcccg cgaaccccgc tcgctgccgg ctgcccagcc tggctggcac catgctgccc | 300 |
| gcgcgctgcg cccgcctgct cacgccccac ttgctgctgg tgttggtgca gctgtccct | 360 |
| gctcgcggcc accgcaccac aggccccagg tttctaataa gtgaccgtga cccacagtgc | 420 |
| aacctccact gctccaggac tcaacccaaa cccatctgtg cctctgatgg caggtcctac | 480 |
| gagtccatgt gtgagtacca gcgagccaag tgccgagacc cgaccctggg cgtggtgcat | 540 |

```
cgaggtagat gcaaagatgc tggccagagc aagtgtcgcc tggagcgggc tcaagccctg    600
gagcaagcca agaagcctca ggaagctgtg tttgtcccag agtgtggcga ggatggctcc    660
tttacccagg tgcagtgcca tacttacact gggtactgct ggtgtgtcac cccggatggg    720
aagcccatca gtggctcttc tgtgcagaat aaaactcctg tatgttcagg ttcagtcacc    780
gacaagccct tgagccaggg taactcagga aggaaagtct cctttcgatt cttttttaacc   840 ctcaattcag atgacgggtc taagccgaca cccacgatgg agaccccagcc ggtgttcgat    900 ggagatgaaa tcacagcccc aactctatgg attaaacact tggtgatcaa ggactccaaa    960
ctgaacaaca ccaacataag aaattcagag aaagtctatt cgtgtgacca ggagaggcag   1020
agtgccctgg aagaggccca gcagaatccc cgtgagggta ttgtcatccc tgaatgtgcc   1080
cctgggggac tctataagcc agtgcaatgc caccagtcca ctggctactg ctggtgtgtg   1140
ctggtggaca cagggcgccc gctgcctggg acctccacac gctacgtgat gcccagttgt   1200
gagagcgacg ccagggccaa gactacagag gcggatgacc ccttcaagga cagggagcta   1260
ccaggctgtc cagaagggaa gaaaatgagg tttatcacca gcctactgga tgctctcacc   1320
actgacatgg ttcaggccat taactcagca gcgcccactg gaggtgggag gttctcagag   1380
ccagacccca gccacaccct ggaggagcgg gtagtgcact ggtatttcag ccagctggac   1440
agcaatagca gcaacgacat taacaagcgg gagatgaagc ccttcaagcg ctacgtgaag   1500
aagaaagcca agcccaagaa atgtgcccgg cgtttcaccg actactgtga cctgaacaaa   1560
gacaaggtca tttcactgcc tgagctgaag ggctgcctgg gtgttagcaa agaagtagga   1620
cgcctcgtct aaggagcaga aaacccaagg gcaggtggag agtccaggga ggcaggatgg   1680
atcaccagac acctaacctt cagcgttgcc catggccctg ccacatcccg tgtaacataa   1740
gtggtgccca ccatgtttgc acttttaata actcttactt gcgtgttttg ttttttggttt   1800 cattttaaaa caccaatatc taataccaca gtgggaaaag gaaagggaag aaagacttta   1860
ttctctctct tattgtaagt ttttggatct gctactgaca acttttagag ggttttgggg   1920 gggtgggga gggtgttgtt ggggctgaga agaaagagat ttatatgctg tatataaata   1980
tatatgtaaa ttgtatagtt cttttgtaca ggcattggca ttgctgtttg tttatttctc   2040
tccctctgcc tgctgtgggt ggtgggcact ctggacacat agtccagctt tctaaaatcc   2100
aggactctat cctgggccta ctaaacttct gtttggagac tgacccttgt gtataaagac   2160
gggagtcctg caattgtact gcggactcca cgagttcttt tctggtggga ggactatatt   2220
gccccatgcc attagttgtc aaaattgata agtcacttgg ctctcggcct tgtccaggga   2280
ggttgggcta aggagagatg gaaactgccc tgggagagga agggagtcca gatcccatga   2340
atagcccaca caggtaccgg ctctcagagg gtccgtgcat tcctgctctc cggacccca    2400 aagggcccag cattggtggg tgcaccagta tcttagtgac cctcggagca aattatccac   2460
aaaggatttg cattacgtca ctcgaaacgt tttcatccat gcttagcatc tactctgtat   2520
aacgcatgag aggggaggca aagaagaaaa agacacacag aagggccttt aaaaaagtag   2580
atatttaata tctaagcagg ggaggggaca ggacagaaag cctgcactga ggggtgcggt   2640
gccaacaggg aaactcttca cctccctgca aacctaccag tgaggctccc agagacgcag   2700
ctgtctcagt gccaggggca gattgggtgt gacctctcca ctcctccatc tcctgctgtt   2760
gtcctagtgg ctatcacagg cctgggtggg tgggttgggg gaggtgtcag tcaccttgtt   2820
ggtaacacta agttgttttt gttggttttt taaaaaccca atactgaggt tcttcctgtt   2880
ccctcaagtt ttcttatggg cttccaggct ttaagctaat tccagaagta aaactgatct   2940
```

```
tgggtttcct attctgcctc ccctagaagg gcagggtga taacccagct acagggaaat    3000
cccggcccag ctttccacag gcatcacagg catcttccgc ggattctagg gtgggctgcc    3060
cagccttctg gtctgaggcg cagctccctc tgcccaggtg ctgtgcctat tcaagtggcc    3120
ttcaggcaga gcagcaagtg gcccttagcg ccccttccca taagcagctg tggtggcagt    3180
gagggaggtt gggtagccct ggactggtcc cctcctcaga tcacccttgc aaatctggcc    3240
tcatcttgta ttccaaccccg acatccctaa aagtacctcc acccgttccg ggtctggaag    3300
gcgttggcac cacaagcact gtccctgtgg gaggagcaca accttctcgg gacaggatct    3360
gatggggtct tgggctaaag gaggtccctg ctgtcctgga gaaagtccta gaggttatct    3420
caggaatgac tggtggccct gccccaacgt ggaaaggtgg gaaggaagcc ttctcccatt    3480
agccccaatg agagaactca acgtgccgga gctgagtggg ccttgcacga gacactggcc    3540
ccactttcag gcctggagga agcatgcaca catggagacg gcgcctgcct gtagatgttt    3600
ggatcttcga gatctcccca ggcatcttgt ctcccacagg atcgtgtgtg taggtggtgt    3660
tgtgtggttt tcctttgtga aggagagagg gaaactattt gtagcttgtt ttataaaaaa    3720
taaaaaatgg gtaaatcttg                                                3740

<210> SEQ ID NO 16
<211> LENGTH: 45
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 16
ccaggcgctc aagagaataa caatttctgc tcagtcaaca tcaac                    45

<210> SEQ ID NO 17
<211> LENGTH: 40
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 17
ctcttgagcg cctggcgttc ggctgccagg gaccttcatg                          40
```

COMPOSITIONS AND METHODS FOR TREATING DISEASES ASSOCIATED WITH AN IMPRINTING DEFECT

CROSS-REFERENCE TO RELATED APPLICATION

This application is the U.S. national phase application, pursuant to 35 U.S.C. § 371, of PCT International Application Ser. No.: PCT/US2018/042876, filed Jul. 19, 2018, designating the United States and published in English, which claims the benefit of the following U.S. Provisional Application No. 62/534,532, filed Jul. 19, 2017, the entire contents of which are incorporated herein by reference.

GOVERNMENT LICENSE RIGHTS STATEMENT

This invention was made with government support under Grant Number HD092465 awarded by the National Institutes of Health. The Government has certain rights in the invention.

BACKGROUND

Sperm and oocytes are generated from primordial germ cells through distinct processes. Consequently, their genomes are packaged differently with distinct epigenetic landscapes. Following fertilization, paternal chromatin releases protamines and is repackaged with maternally-stored histones that are devoid of most histone modifications, while maternal chromatin harbors various histone modifications inherited from oocytes. The different processes of parental chromatin formation result in parental epigenetic asymmetry in zygotes, which becomes largely equalized during subsequent development with the exception of certain genomic loci, including imprinting control regions (ICRs). Errors in genomic imprinting can cause severe disorders and profound developmental defects, including, for example, Beckwith-Wiedemann, Angleman, and Prader-Willi syndromes, that lead to lifelong health problems. There is a significant need for improved therapies for the treatment of imprinting associated disorders.

SUMMARY

The invention provides methods for activating a repressed allele within an imprinting control region, thereby treating an imprinting associated disorder.

In one aspect, the invention provides a method of activating a histone H3 lysine 27 trimethylation (H3K27me3) repressed allele within an imprinting control region of a cell, the method comprising contacting the cell with an agent that inhibits histone H3 lysine 27 trimethylation, thereby activating the H3K27me3-repressed allele. In one embodiment, the agent is an inhibitor of the H3K27 methyltransferase. In another embodiment, the H3K27 methyltransferase is selected from the group consisting of EZH1, EZH2, PRC2, PRC2-Ezh1, or PRC2-Ezh2. In another embodiment, the agent is a small compound, polypeptide, or polynucleotide. In another embodiment, the agent is selected from the group consisting of tazemetostat, DZNep, GSK373, GSK126, Ell, Epz005687, CPI-169.

In another aspect, the invention provides a method of activating a H3K27me3 repressed allele within an imprinting control region of a cell, the method comprising contacting the cell with an agent that selectively removes trimethylation at lysine 27 of histone 3, thereby activating the H3K27me3 repressed allele. In one embodiment, the agent is an H3K27me3-specific demethylase. In another embodiment, the agent is lysine-specific demethylase 6A (KDM6A), KDM6B, or KDM6C. In yet another embodiment, the cell is a mammalian cell in vitro or in vivo. In yet another embodiment, the cell is present in a mammal undergoing pre- or post-natal development.

In another aspect, the invention provides a method of treating a subject having a disorder associated with H3K27me3-dependent imprinting, the method comprising administering to the subject an agent that inhibits histone H3 lysine 27 trimethylation, thereby treating the disorder.

In another aspect, the invention provides a method of treating a subject having a disorder associated with H3K27me3-dependent imprinting, the method comprising administering to the subject an agent that selectively removes trimethylation at lysine 27, thereby treating the disorder.

In various embodiments, the disorder is associated with a mutation in a gene of Table 1 or selected from the group consisting of Adamts2, Bbx, BCO49762, Bmp7, C430002E04Rik, E2f3, Enc1, Epas1, Etv6, Fam198b, G730013B05Rik, Gab1, Gramd1b, Mbnl2, Otx2, Otx2os1, Phf17, Rbms1, Rbp2, Runx1, Sfinbt2, Sh3gl3, Slc38a1, Slc38a2, Slc38a4, Smoc1, Sox21, and Tle3.

In various embodiments, the disorder is associated with a mutation in a gene selected from the group consisting of Sfinbt2, Bbx, C430002E04Rik, Phf17, Slc38a4, Gramd1b, Tle3, E2f3, Smoc1, Sox21, Slc38a1, Runx1, Bmp7, Rnc1, Fam198b, Rbms1, Zrsr1, Impact, and Fkbp6. In still other embodiments, the disorder is associated with a mutation in a gene selected from the group consisting of Sfinbt2, Gab1, Slc38a4, and Phf17. In still other embodiments, the disorder is associated with a mutation in a gene selected from the group consisting of Etv6, 17001125H03Rik, Smoc1, and Bmp7. In still other embodiments, the disorder is associated with a mutation in a gene selected from the group consisting of Gab1, Phf17, Sfinbt2, Slc38a4, or Smoc1. In still other embodiments, the disorder is microphthalmia with limb anomalies (MLA) associated with a mutation in Smoc1. In still other embodiments, the disorder is associated with limb development associated with a mutation in Smoc1. In still other embodiments, the disorder is associated with a placental defect associated with a mutation in Gab1 or Sfinbt2. In still other embodiments, one parental allele comprises a mutation and the other parental allele is a wild-type allele.

In another aspect, the invention provides a method of identifying a gene comprising H3K27me3-dependent imprinting, the method comprising analyzing chromatin derived from a biological sample for the presence of an H3K27me3 modification and identifying a gene having said modification.

In another aspect, the invention provides a method for characterizing H3K27me3-dependent imprinting in a sample, the method comprising analyzing chromatin derived from the sample for the presence of an H3K27me3 modification relative to a reference sample, thereby characterizing H3K27me3-dependent imprinting in the sample. In one embodiment, the sample is obtained from an embryo. In another embodiment, an increase or decrease in imprinting relative to the reference is associated with a developmental disorder. In particular embodiments,
the imprinting is in a gene selected from the group consisting of Adamts2, Bbx, BC049762, Bmp7, C430002E04Rik, E2f3, Enc1, Epas1, Etv6, Fam198b, G730013B05Rik, Gab1, Gramd1b, Mbnl2, Otx2, Otx2os1, Phf17, Rbms1, Rbp2, Runx1, Sfinbt2, Sh3gl3, Slc38a1, Slc38a2, Slc38a4, Smoc1, Sox21, and Tle3. In still other embodiments, the imprinting is in a gene selected from the group consisting of Sfinbt2, Bbx, C430002E04Rik, Phf17, Slc38a4, Gramd1b, Tle3, E2f3, Smoc1, Sox21, Slc38a1, Runx1, Bmp7, Rnc1, Fam198b, Rbms1, Zrsr1, Impact, and Fkbp6. In still other embodiments, the imprinting is in a gene selected from the group Sfinbt2, Gab1, Slc38a4, and Phf17. In other embodiments, the imprinting is in a gene selected from the group Etv6, 17001125H03Rik, Smoc1, and Bmp7.

In another aspect, the invention provides a method for increasing histone H3 lysine 27 trimethylation (H3K27me3) within an imprinting control region of a hybrid cell, the method comprising contacting a donor mammalian cell, donor nucleus, recipient mammalian oocyte, hybrid cell, with an agent that increases histone H3 lysine 27 trimethylation (H3K27me3), thereby increasing histone H3 lysine 27 trimethylation (H3K27me3) within an imprinting control region of a hybrid cell. In one embodiment, the agent is an mRNA encoding an H3K27 methyltransferase.

Definitions

Unless defined otherwise, all technical and scientific terms used herein have the meaning commonly understood by a person skilled in the art to which this invention belongs. The following references provide one of skill with a general definition of many of the terms used in this invention: Singleton et al., Dictionary of Microbiology and Molecular Biology (2nd ed. 1994); The Cambridge Dictionary of Science and Technology (Walker ed., 1988); The Glossary of Genetics, 5th Ed., R. Rieger et al. (eds.), Springer Verlag (1991); and Hale & Marham, The Harper Collins Dictionary of Biology (1991). As used herein, the following terms have the meanings ascribed to them below, unless specified otherwise.

By "EZH1 polypeptide" (histone-lysine N-methyltransferase EZH1) is meant a protein having at least about 85% amino acid identity to the sequence provided at NCBI Reference Sequence: NP_001982, or a fragment thereof, and having methyltransferase activity. An exemplary H3K27 methyltransferase amino acid sequence is provided below:

```
  1 meipnpptsk citywkrkvk seymrlrqlk rlqanmgaka lyvanfakvq ektqilneew
 61 kklrvqpvqs mkpvsghpfl kkctiesifp gfasqhmlmr slntvalvpi myswsplqqn
121 fmvedetvlc nipymgdevk eedetfieel innydgkvhg eeemipgsvl isdavflelv
181 dalnqysdee eeghndtsdg kqddskedlp vtrkrkrhai egnkksskkq fpndmifsai
241 asmfpengvp ddmkeryrel temsdpnalp pqctpnidgp naksvqreqs lhsfhtlfcr
301 rcfkydcflh pfhatpnvyk rknkeikiep epcgtdcfll legakeyaml hnprskcsgr
361 rrrrhhivsa scsnasasav aetkegdsdr dtgndwasss seansrcqtp tkqkaspapp
421 qlcvveapse pvewtgaees lfrvfhgtyf nnfcsiarll gtktckqvfq favkeslilk
481 lptdelmnps qkkkrkhrlw aahcrkiqlk kdnsstqvyn yqpcdhpdrp cdstcpcimt
541 qnfcekfcqc npdcqnrfpg crcktqcntk qcpcylavre cdpdlcltcg asehwdckvv
601 sckncsiqrg lkkhlllaps dvagwgtfik esvqknefis eycgelisqd eadrrgkvyd
661 kymssflfnl nndfvvdatr kgnkirfanh svnpncyakv vmvngdhrig ifakraiqag
721 eelffdyrys qadalkyvgi eretdvl
```

By "EZH1 polynucleotide" is meant a nucleic acid molecule encoding the EZH1 polypeptide. An exemplary EZH1 polynucleotide sequence is provided at NM_001991.4 and reproduced below:

```
  1 aggaggcgcg gggcggggca cggcgcaggg gtggggccgc ggcgcgcatg cgtcctagca
 61 gcgggacccg cggctcggga tggaggctgg acacctgttc tgctgttgtg tcctgccatt
121 ctcctgaaga acagaggcac actgtaaaac ccaacacttc cccttgcatt ctataagatt
181 acagcaagat ggaaatacca aatccccta cctccaaatg tatcacttac tggaaaagaa
241 aagtgaaatc tgaatacatg cgacttcgac aacttaaacg gcttcaggca aatatgggtg
301 caaaggcttt gtatgtggca aattttgcaa aggttcaaga aaaacccag atcctcaatg
361 aagaatggaa gaagcttcgt gtccaacctg ttcagtcaat gaagcctgtg agtggacacc
421 cttttctcaa aaagtgtacc atagagagca ttttcccggg atttgcaagc caacatatgt
481 taatgaggtc actgaacaca gttgcattgg ttccatcat gtattcctgg tcccctctcc
541 aacagaactt tatggtagaa gatgagacgg ttttgtgcaa tattccctac atgggagatg
601 aagtgaaaga agaagatgag actttattg aggagctgat caataactat gatgggaaag
```

-continued

```
 661 tccatggtga agaagagatg atccctggat ccgttctgat tagtgatgct gtttttctgg
 721 agttggtcga tgccctgaat cagtactcag atgaggagga ggaagggcac aatgacacct
 781 cagatggaaa gcaggatgac agcaagaag atctgccagt aacaagaaag agaaagcgac
 841 atgctattga aggcaacaaa aagagttcca agaaacagtt cccaaatgac atgatcttca
 901 gtgcaattgc ctcaatgttc cctgagaatg tgtcccaga tgacatgaag gagaggtatc
 961 gagaactaac agagatgtca gaccccaatg cacttccccc tcagtgcaca cccaacatcg
1021 atggccccaa tgccaagtct gtgcagcggg agcaatctct gcactccttc cacacacttt
1081 tttgccggcg ctgctttaaa tacgactgct tccttcaccc ttttcatgcc accctaatg
1141 tatataaacg caagaataaa gaaatcaaga ttgaaccaga accatgtggc acagactgct
1201 tccttttgct ggaaggagca aaggagtatg ccatgctcca aaccccgc tccaagtgct
1261 ctggtcgtcg ccggagaagg caccacatag tcagtgcttc ctgctccaat gcctcagcct
1321 ctgctgtggc tgagactaaa gaaggagaca gtgacaggga cacaggcaat gactgggcct
1381 ccagttcttc agaggctaac tctcgctgtc agactccac aaaacagaag gctagtccag
1441 ccccacctca actctgcgta gtggaagcac cctcggagcc tgtggaatgg actggggctg
1501 aagaatctct ttttcgagtc ttccatggca cctacttcaa caacttctgt tcaatagcca
1561 ggcttctggg gaccaagacg tgcaagcagg tctttcagtt tgcagtcaaa gaatcactta
1621 tcctgaagct gccaacagat gagctcatga accccctcaca gaagaagaaa agaaagcaca
1681 gattgtgggc tgcacactgc aggaagattc agctgaagaa agataactct tccacacaag
1741 tgtacaacta ccaaccctgc gaccacccag accgcccctg tgacagcacc tgccctgca
1801 tcatgactca gaatttctgt gagaagttct gccagtgcaa cccagactgt cagaatcgtt
1861 tccctggctg tcgctgtaag acccagtgca ataccaagca atgtccttgc tatctggcag
1921 tgcgagaatg tgaccctgac ctgtgtctca cctgtgggc ctcagagcac tgggactgca
1981 aggtggtttc ctgtaaaaac tgcagcatcc agcgtggact aagaagcac ctgctgctgg
2041 cccctctga tgtggccgga tggggcacct tcataagga gtctgtgcag aagaacgaat
2101 tcatttctga atactgtggt gagctcatct tcaggatga ggctgatcga cgcggaaagg
2161 tctatgacaa atacatgtcc agcttcctct tcaacctcaa taatgatttt gtagtggatg
2221 ctactcggaa aggaaacaaa attcgatttg caaatcattc agtgaatccc aactgttatg
2281 ccaaagtggt catggtgaat ggagaccatc ggattgggat ctttgccaag agggcaattc
2341 aagctggcga agagctcttc tttgattaca ggtacagcca agctgatgct ctcaagtacg
2401 tgggatcga gaggagacc gacgtccttt agccctccca ggccccacgg cagcacttat
2461 ggtagcggca ctgtcttggc tttcgtgctc acaccactgc tgctcgagtc tcctgcactg
2521 tgtctcccac actgagaaac ccccaaccc actccctctg tagtgaggcc tctgccatgt
2581 ccagagggca caaactgtc tcaatgagag gggagacaga ggcagctagg gcttggtctc
2641 ccaggacaga gagttacaga atgggagac tgtttctctg gcctcagaag aagcgagcac
2701 aggctggggt ggatgactta tgcgtgattt cgtgtcggct ccccaggctg tggcctcagg
2761 aatcaactta ggcagttccc aacaagcgct agcctgtaat tgtagctttc cacatcaaga
2821 gtccttatgt tattgggatg caggcaaacc tctgtggtcc taagacctgg agaggacagg
2881 ctaagtgaag tgtggtccct ggagcctaca agtggtctgg gttagaggcg agcctggcag
2941 gcagcacaga ctgaactcag aggtagacag gtcaccttac tacctcctcc ctcgtggcag
3001 ggctcaaact gaaagagtgt gggttctaag tacaggcatt caaggctggg ggaaggaaag
```

```
-continued
3061 ctacgccatc cttccttagc cagagaggga gaaccagcca gatgatagta gttaaactgc 3121 taagcttggg cccaggaggc tttgagaaag ccttctctgt gtactctgga gatagatgga 3181 gaagtgtttt cagattcctg ggaacagaca ccagtgctcc agctcctcca aagttctggc 3241 ttagcagctg caggcaagca ttatgctgct attgaagaag cattaggggt atgcctggca 3301 ggtgtgagca tcctggctcg ctggatttgt gggtgttttc aggccttcca ttccccatag 3361 aggcaaggcc caatgccag tgttgcttat cgcttcaggg taggtgggca caggcttgga 3421 ctagagagga gaaagattgg tgtaatctgc tttcctgtct gtagtgcctg ctgtttggaa 3481 agggtgagtt agaatatgtt ccaaggttgg tgagggcta aattgcacgc gtttaggctg 3541 gcaccccgtg tgcagggcac actggcagag ggtatctgaa gtgggagaag aagcaggtag 3601 accacctgtc ccaggctgtg gtgccaccct ctctggcatt catgcagagc aaagcacttt 3661 aaccatttct tttaaaaggt ctatagattg gggtagagtt tggcctaagg tctctagggt 3721 ccctgcctaa atcccactcc tgagggaggg ggaagaagag agggtgggag attctcctcc 3781 agtcctgtct catctcctgg gagaggcaga cgagtgagtt tcacacagaa gaatttcatg 3841 tgaatggggc cagcaagagc tgccctgtgt ccatggtggg tgtgccgggc tggctgggaa 3901 caaggagcag tatgttgagt agaaagggtg tgggcgggta tagattggcc tgggagtgtt 3961 acagtaggga gcaggcttct cccttctttc tgggactcag agcccgctt cttcccactc 4021 cacttgttgt cccatgaagg aagaagtggg gttcctcctg acccagctgc ctcttacggt 4081 ttggtatggg acatgcacac acactcacat gctctcactc accacactgg agggcacaca 4141 cgtaccccgc acccagcaac tcctgacaga aagctcctcc cacccaaatg gccaggccc 4201 cagcatgatc ctgaaatctg catccgccgt ggtttgtatt cattgtgcat atcagggata 4261 ccctcaagct ggactgtggg ttccaaatta ctcatagagg agaaaaccag agaaagatga 4321 agaggaggag ttaggtctat ttgaaatgcc aggggctcgc tgtgaggaat aggtgaaaaa 4381 aaacttttca ccagcctttg agagactaga ctgaccccac ccttccttca gtgagcagaa 4441 tcactgtggt cagtctcctg tcccagcttc agttcatgaa tactcctgtt cctccagttt 4501 cccatccttt gtccctgctg tcccccactt taaagatgg gtctcaaccc ctccccacca 4561 cgtcatgatg gatgggggcaa ggtggtgggg actagggag cctggtatac atgcggcttc 4621 attgccaata aatttcatgc actttaaagt cctgtggctt gtgacctctt aataaagtgt 4681 tagaatccaa aaaaaaa
```

By "EZH2 polypeptide" (histone-lysine N-methyltransferase EZH2) is meant a protein having at least about 85% amino acid identity to the sequence provided at UniProtKB/Swiss-Prot: Q15910.2, or a fragment thereof, and having methyltransferase activity. An exemplary H3K27 methyltransferase amino acid sequence is provided below:

```
  1 mgqtgkksek gpvcwrkrvk seymrlrqlk rfrradevks mfssnrqkil erteilnqew 61 kqrriqpvhi ltsvsslrgt recsvtsdld fptqviplkt lnavasvpim yswsplqqnf 121 mvedetvlhn ipymgdevld qdgtfieeli knydgkvhgd recgfindei fvelvnalgq 181 yndddddddg ddpeereekq kdledhrddk esrpprkfps dkifeaissm fpdkgtaeel 241 kekykelteq qlpgalppec tpnidgpnak svgreqslhs fhtlfcrrcf kydcflhpfh 301 atpntykrkn tetaldnkpc gpqcyqhleg akefaaalta eriktppkrp ggrrrgrlpn 361 nssrpstpti nvleskdtds dreagtetgg enndkeeeek kdetssssea nsrcqtpikm 421 kpnieppenv ewsgaeasmf rvligtyydn fcaiarligt ktcrqvyefr vkessiiapa 481 paedvdtppr kkkrkhrlwa ahcrkiqlkk dgssnhvyny qpcdhprqpc dsscpcviaq
```

```
541 nfcekfcqcs secqnrfpgc rckaqcntkq cpcylavrec dpdlcltcga adhwdsknvs 601 ckncsiqrgs kkhlllapsd vagwgifikd pvqknefise ycgeiisqde adrrgkvydk 661 ymcsflfnln ndfvvdatrk gnkirfanhs vnpncyakvm mvngdhrigi fakraiqtge 721 elffdyrysq adalkyvgie remeip
```

By "EZH2 polynucleotide" is meant a nucleic acid molecule encoding an EZH2 polypeptide. An exemplary EZH2 polynucleotide sequence is provided at NM_001203248.1 and is provided below:

```
   1 ggcggcgctt gattgggctg gggggggccaa ataaaagcga tggcgattgg gctgccgcgt
  61 ttggcgctcg gtccggtcgc gtccgacacc cggtgggact cagaaggcag tggagccccg
 121 gcggcggcgg cggcggcgcg cggggcgac gcgcgggaac aacgcgagtc ggcgcgcggg
 181 acgaagaata atcatgggcc agactgggaa gaaatctgag aagggaccag tttgttggcg
 241 gaagcgtgta aaatcagagt acatgcgact gagacagctc aagaggttca gacgagctga
 301 tgaagtaaag agtatgttta gttccaatcg tcagaaaatt ttggaaagaa cggaaatctt
 361 aaaccaagaa tggaaacagc gaaggataca gcctgtgcac atcctgactt cttgttcggt
 421 gaccagtgac ttggattttc aacacaagt catcccatta aagactctga atgcagttgc
 481 ttcagtaccc ataatgtatt cttggtctcc cctacagcag aattttatgg tggaagatga
 541 aactgtttta cataacattc cttatatggg agatgaagtt ttagatcagg atggtacttt
 601 cattgaagaa ctaataaaaa attatgatgg gaaagtacac ggggatagag aatgtgggtt
 661 tataaatgat gaaattttg tggagttggt gaatgccctt ggtcaatata atgatgatga
 721 cgatgatgat gatggagacg atcctgaaga aagagaagaa aagcagaaag atctggagga
 781 tcaccgagat gataaagaaa gccgcccacc tcggaaattt ccttctgata aaattttga
 841 agccatttcc tcaatgtttc agataaggg cacagcagaa gaactaaagg aaaaatataa
 901 agaactcacc gaacagcagc tcccaggcgc acttcctcct gaatgtaccc ccaacataga
 961 tggaccaaat gctaaatctg ttcagagaga gcaaagctta cactcctttc atacgctttt
1021 ctgtaggcga tgttttaaat atgactgctt cctacatcct tttcatgcaa cacccaacac
1081 ttataagcgg aagaacacag aaacagctct agacaacaaa ccttgtggac cacagtgtta
1141 ccagcatttg gagggagcaa aggagtttgc tgctgctctc accgctgagc ggataaagac
1201 cccaccaaaa cgtccaggag gccgcagaag aggacggctt cccaataaca gtagcaggcc
1261 cagcaccccc accattaatg tgctggaatc aaaggataca gacagtgata gggaagcagg
1321 gactgaaacg gggggagaga acaatgataa agaagaagaa gagaagaaag atgaaacttc
1381 gagctcctct gaagcaaatt ctcggtgtca acaccaata aagatgaagc caaatattga
1441 acctcctgag aatgtggagt ggagtggtgc tgaagcctca atgtttagag tcctcattgg
1501 cacttactat gacaatttct gtgccattgc taggttaatt gggaccaaaa catgtagaca
1561 ggtgtatgag tttagagtca aagaatctag catcatagct ccagctcccg ctgaggatgt
1621 ggatactcct ccaaggaaaa agaagaggaa acaccggttg tgggctgcac actgcagaaa
1681 gatacagctg aaaaaggacg gctcctctaa ccatgtttac aactatcaac cctgtgatca
1741 tccacggcag ccttgtgaca gttcgtgccc ttgtgtgata gcacaaaatt tttgtgaaaa
1801 gttttgtcaa tgtagttcag agtgtcaaaa ccgctttccg ggatgccgct gcaaagcaca
1861 gtgcaacacc aagcagtgcc cgtgctacct ggctgtccga gagtgtgacc ctgacctctg
1921 tcttacttgt ggagccgctg accattggga cagtaaaaat gtgtcctgca agaactgcag
```

-continued

```
1981 tattcagcgg ggctccaaaa agcatctatt gctggcacca tctgacgtgg caggctgggg 2041 gatttttatc aaagatcctg tgcagaaaaa tgaattcatc tcagaatact gtggagagat 2101 tatttctcaa gatgaagctg acagaagagg gaaagtgtat gataaataca tgtgcagctt 2161 tctgttcaac ttgaacaatg attttgtggt ggatgcaacc cgcaagggta acaaaattcg 2221 ttttgcaaat cattcggtaa atccaaactg ctatgcaaaa gttatgatgg ttaacggtga 2281 tcacaggata ggtattttg ccaagagagc catccagact ggcgaagagc tgttttttga 2341 ttacagatac agccaggctg atgccctgaa gtatgtcggc atcgaaagag aaatggaaat 2401 cccttgacat ctgctacctc ctccccctc tctgaaaca gctgccttag cttcaggaac 2461 ctcgagtact gtgggcaatt tagaaaaaga acatgcagtt tgaaattctg aatttgcaaa 2521 gtactgtaag aataatttat agtaatgagt ttaaaaatca acttttattt gccttctcac 2581 cagctgcaaa gtgttttgta ccagtgaatt tttgcaataa tgcagtatgg tacatttttc 2641 aactttgaat aaagaatact tgaacttgtc cttgttgaat c
```

By "KDM6A polypeptide" (lysine-specific demethylase 6A, also referred to as histone demethylase UTX) is meant a protein having at least about 85% amino acid identity to the sequence provided at NCBI Reference Sequence: 015550.2, or a fragment thereof, and having demethylase activity. An exemplary KDM6A amino acid sequence is provided below:

```
   1 mkscgvslat aaaaaaafgd eekkmaagka sgeseeasps ltaeerealg gldsrlfgfv 61 rfhedgartk allgkavrcy eslilkaegk vesdffcqlg hfnllledyp kalsayqryy 121 slqsdywkna aflyglglvy fhynafqwai kafqevlyvd psfcrakeih lrlglmfkvn 181 tdyesslkhf qlalvdcnpc tlsnaeiqfh iahlyetqrk yhsakeayeq llqtenlsaq 241 vkatvlqqlg wmhhtvdllg dkatkesyai qylqkslead pnsgqswyfl grcyssigkv 301 qdafisyrqs idkseasadt wcsigvlyqq qnqpmdalqa yicavqldhg haaawmdlgt 361 lyescnqpqd aikcylnatr skscsntsal aarikylqaq lcnlpqgslq nktkllpsie 421 eawslpipae ltsrqgamnt aqqntsdnws gghavshppv qqqahswclt pqklqhleql 481 ranrnnlnpa qklmleqles qfvlmqqhqm rptgvaqvrs tgipngptad sslptnsvsg 541 qqpqlaltrv psvsqpgvrp acpgqplang pfsaghvpcs tsrtlgstdt ilignnhitg 601 sgsngnvpyl qrnaltlphn rtnitssaee pwknqlsnst gglhkgqssh sagpngerpl 661 sstgpsqhlq aagsgiqnqn ghptlpsnsv tqgaalnhls shtatsggqq gitltkeskp 721 sgniltvpet srhtgetpns tasveglpnh vhqmtadavc spshgdsksp gllssdnpql 781 sallmgkann nvgtgtcdkv nnihpavhtk tdnsvassps saistatpsp ksteqtttns 841 vtslnsphsg lhtingegme esqspmktdl llvnhkpspq iipsmsvsiy pssaevlkac 901 rnlgknglsn ssilldkcpp prppsspypp lpkdklnppt psiylenkrd affpplhqfc 961 tnpnnpvtvi rglagalkld lglfstktlv eannehmvev rtqllqpade nwdptgtkki 1021 whcesnrsht tiakyaqyqa ssfqeslree nekrshhkdh sdsestssdn sgrrrkgpfk 1081 tikfgtnidl sddkkwklql heltklpafv rvvsagnlls hvghtilgmn tvqlymkvpg 1141 srtpghqenn nfcsvninig pgdcewfvvp egywgvlndf ceknnlnflm gswwpnledl 1201 yeanvpvyrf iqrpgdlvwi nagtvhwvqa igwcnniawn vgpltacqyk laveryewnk
```

-continued

```
1261 lqsvksivpm vhlswnmarn ikvsdpklfe mikycllrtl kqcqtlreal iaagkeiiwh 1321 grtkeepahy csicevevfd llfvtnesns rktyivhcqd carktsgnle nfvvleqykm 1381 edlmqvydqf tlapplpsas s
```

By "KDM6A polynucleotide" is meant a nucleic acid molecule encoding a KDM6A polypeptide. An exemplary KDM6A polynucleotide sequence is provided at NM_001291415.1.

By "KDM6B polypeptide" (lysine-specific demethylase 6, also referred to as JmjC domain-containing protein 3) is meant a protein having at least about 85% amino acid identity to the sequence provided at NCBI Reference Sequence: 015054.4, or a fragment thereof, and having demethylase activity. An exemplary KDM6B amino acid sequence is provided below:

```
   1 mhravdppga raareafalg glscagawss cpphppprsa wlpggrcsas igqpplpapl 61 ppshgsssgh pskpyyapga ptprplhgkl eslhgcvqal lrepaqpglw eqlgqlyese 121 hdseeatrcy hsalryggsf aelgprigrl qqaqlwnfht gscqhrakvl ppleqvwnll 181 hlehkrnyga krggppvkra aeppvvqpvp paalsgpsge eglspggkrr rgcnseqtgl 241 ppglplpppp lppppppppp pppplpglat sppfqltkpg lwstlhgdaw gperkgsapp 301 erqeqrhslp hpypypapay tahppghrlv paappgpgpr ppgaeshgcl patrppgsdl 361 resrvqrsrm dssyspaatt acvpyapsrp pglpgtttss sssssssntgl rgvepnpgip 421 gadhyqtpal evshhgrlgp sahssrkpfl gapaatphls lppgpssppp ppcprllrpp 481 pppawlkgpa craaredgei leelffgteg pprpappplp hregflgppa srfsvgtqds 541 htpptpptpt tsssnsnsgs hssspagpvs fppppylars idplprppsp aqnpqdpplv 601 pltlalppap psschqntsg sfrrpesprp rvsfpktpev gpgpppgpls kapqpvppgv 661 gelpargprl fdfpptpled qfeepaefki lpdglanimk mldesirkee eqqqheagva 721 pqpplkepfa slqspfptdt apttapava vtttttttt ttatqeeekk pppalppppp 781 lakfpppsqp qpppppppsp asllkslasv legqkycyrg tgaaystrpg plpttqyspg 841 ppsgatalpp tsaapsaqgs pqpsassssq fstsggpwar errageepvp gpmtptqppp 901 plslpparse sevleeisra cetlvervgr satdpadpvd taepadsgte rllppaqake 961 eaggvaaysg sckrrqkehq kehrrhrrac kdsvgrrpre grakakakvp keksrrvlgn 1021 ldlqseeiqg reksrpdlgg askakpptap appsapapsa qptppsasvp gkkareeapg 1081 ppgvsradml klrslsegpp kelkirlikv esgdketfia seveerrlrm adltishcaa 1141 dvvrasrnak vkgkfresyl spaqsvkpki nteeklprek lnpptpsiyl eskrdafspv 1201 llqfctdprn pitvirglag slrlnlglfs tktiveasge htvevrtqvq qpsdenwdlt 1261 gtrqiwpces srshttiaky aqyqassfqe slqeekesed eeseepdstt gtppssapdp 1321 knhhiikfgt nidlsdakrw kpqlqellkl pafmrvtstg nmlshvghti lgmntvqlym 1381 kvpgsrtpgh qennnfcsvn inigpgdcew favhehywet isafcdrhgv dyltgswwpi 1441 lddlyasnip vyrfvqrpgd lvwinagtvh wvqatgwcnn iawnvgplta yqyqlalery 1501 ewnevknvks ivpmihvswn vartvkisdp dlfkmikfcl lqsmkhcqvq reslvragkk 1561 iayqgrvkde payycnecdv evfnilfvts engsrntylv hcegcarrrs aglqgvvvle 1621 qyrteelaqa ydaftlapas tsr
```

By "KDM6B polynucleotide" is meant a nucleic acid molecule encoding a KDM6B polypeptide. An exemplary KDM6B polynucleotide sequence is provided at NM_001080424.2 and reproduced below:

```
   1  ggcaacatgc cagccccgta gcactgccca ccccacccac tgtggtctgt tgtacccac
  61  tgctggggtg gtggttccaa tgagacaggg cacaccaaac tccatctggc tgttactgag
 121  gcggagacac gggtgatgat tggctttctg gggagagagg aagtcctgtg attggccaga
 181  tctctggagc ttgccgacgc ggtgtgagga cgctcccacg gaggccggaa ttggctgtga
 241  aaggactgag gcagccatct gggggtagcg ggcactctta tcagagcggc tggagccgga
 301  ccatcgtccc agagagctgg ggcaggggggc cgtgcccaat ctccagggct cctggggcca
 361  ctgctgacct ggctggatgc atcgggcagt ggaccctcca ggggcccgcg ctgcacggga
 421  agcctttgcc cttggggggcc tgagctgtgc tggggcctgg agctcctgcc cgcctcatcc
 481  ccctcctcgt agcgcatggc tgcctggagg cagatgctca gccagcattg ggcagccccc
 541  gcttcctgct cccctacccc cttcacatgg cagtagttct gggcaccccca gcaaaccata
 601  ttatgctcca ggggcgccca ctccaagacc cctccatggg aagctggaat ccctgcatgg
 661  ctgtgtgcag gcattgctcc gggagccagc ccagccaggg cttgggaac agcttgggca
 721  actgtacgag tcagagcacg atagtgagga ggccacacgc tgctaccaca cgcccttcg
 781  atacggagga agcttcgctg agctggggcc ccgcattggc cgactgcagc aggcccagct
 841  ctggaacttt catactggct cctgccagca ccgagccaag gtcctgcccc cactggagca
 901  agtgtggaac ttgctacacc ttgagcacaa acggaactat ggagccaagc ggggaggtcc
 961  cccggtgaag cgagctgctg aacccccagt ggtgcagcct gtgcctcctg cagcactctc
1021  aggccccttca ggggaggagg gcctcagccc tggaggcaag cgaaggagag gctgcaactc
1081  tgaacagact ggccttcccc cagggctgcc actgcctcca ccaccattac caccaccacc
1141  accaccacca ccaccaccac caccaccct gcctggcctg gctaccagcc cccatttca
1201  gctaaccaag ccagggctgt ggagtaccct gcatggagat gcctggggcc cagagcgcaa
1261  gggttcagca ccccagagc gccaggagca gcggcactcg ctgcctcacc catatccata
1321  cccagctcca gcgtacaccg cgcaccccc tggccaccgg ctggtcccgg ctgctccccc
1381  aggcccaggc ccccgccccc caggagcaga gagccatggc tgcctgcctg ccaccgtcc
1441  ccccggaagt gaccttagag agagcagagt tcagaggtcg cggatggact ccagcgtttc
1501  accagcagca accaccgcct gcgtgcctta cgcccttcc cggcccctg gcctccccgg
1561  caccaccacc agcagcagca gtagcagcag cagcaacact ggtctccggg gcgtggagcc
1621  gaacccaggc attcccggcg ctgaccatta ccaaactccc gcgctggagg tctctcacca
1681  tggccgcctg gggccctcgg cacacagcag tcggaaaccg ttcttggggg ctcccgctgc
1741  cactccccac ctatccctgc cacctggacc ttcctcaccc cctccacccc cctgtccccg
1801  cctcttacgc ccccccaccac ccctgcctg gttgaagggt ccggcctgcc gggcagcccg
1861  agaggatgga gagatcttag aagagctctt ctttgggact gagggacccc ccgccctgc
1921  cccaccaccc ctccccatc gcgaggggctt cttggggcct ccggcctccc gcttttctgt
1981  gggcactcag gattctcaca cccctcccac tccccaacc caaccacca gcagtagcaa
2041  cagcaacagt ggcagccaca gcagcagccc tgctgggcct gtgtcctttc ccccaccacc
2101  ctatctggcc agaagtatag acccccttcc ccggcctccc agcccagcac agaaccccca
2161  ggacccacct cttgtacccc tgactcttgc cctgcctcca gccctccttt cctcctgcca
2221  ccaaaatacc tcaggaagct tcaggcgccc ggagagcccc cggccaggg tctccttccc
2281  aaagaccccc gaggtgggggc cggggccacc cccaggcccc ctgagtaaag cccccccagcc
```

-continued

```
2341 tgtgccgccc ggggttgggg agctgcctgc ccgaggccct cgactctttg attttccccc
2401 cactccgctg gaggaccagt ttgaggagcc agccgaattc aagatcctac ctgatgggct
2461 ggccaacatc atgaagatgc tggacgaatc cattcgcaag gaagaggaac agcaacaaca
2521 cgaagcaggc gtggccaccc aaccccgct gaaggagccc tttgcatctc tgcagtctcc
2581 tttccccacc gacacagccc ccaccactac tgctcctgct gtcgccgtca ccaccaccac
2641 caccaccacc accaccacca cggccaccca ggaagaggag aagaagccac caccagccct
2701 accaccacca ccgcctctag ccaagttccc tccaccctct cagccacagc caccaccacc
2761 cccaccccc agcccggcca gcctgctcaa atccttggcc tccgtgctgg agggacaaaa
2821 gtactgttat cgggggactg gagcagctgt ttccacccgg cctgggccct tgcccaccac
2881 tcagtattcc cctggccccc catcaggtgc taccgccctg ccgccacct cagcggcccc
2941 tagcgcccag ggctccccac agccctctgc ttcctcgtca tctcagttct ctacctcagg
3001 cgggccctgg gcccgggagc gcagggcggg cgaagagcca gtcccgggcc ccatgacccc
3061 cacccaaccg cccccacccc tatctctgcc ccctgctcgc tctgagtctg aggtgctaga
3121 agagatcagc cgggcttgcg agaccccttgt ggagcgggtg ggccggagtg ccactgaccc
3181 agccgaccca gtggacacag cagagccagc ggacagtggg actgagcgac tgctgccccc
3241 cgcacaggcc aaggaggagg ctggcggggt ggcggcagtg tcaggcagct gtaagcggcg
3301 acagaaggag catcagaagg agcatcggcg gcacaggcgg gcctgtaagg acagtgtggg
3361 tcgtcggccc cgtgagggca gggcaaaggc caaggccaag gtccccaaag aaaagagccg
3421 ccgggtgctg gggaacctgg acctgcagag cgaggagatc cagggtcgtg agaagtcccg
3481 gcccgatctt ggcggggcct ccaaggccaa gccacccaca gctccagccc ctccatcagc
3541 tcctgcacct tctgcccagc ccacaccccc gtcagcctct gtccctggaa agaaggctcg
3601 ggaggaagcc cagggccac cgggtgtcag ccgggccgac atgctgaagc tgcgctcact
3661 tagtgagggg ccccccaagg agctgaagat ccggctcatc aaggtagaga gtggtgacaa
3721 ggagaccttt atcgcctctg aggtggaaga gcggcggctg cgcatggcag acctcaccat
3781 cagccactgt gctgctgacg tcgtgcgcgc cagcaggaat gccaaggtga agggaagtt
3841 tcgagagtcc taccttttccc ctgcccagtc tgtgaaaccg aagatcaaca ctgaggagaa
3901 gctgccccgg gaaaaactca accccctac acccagcatc tatctggaga gcaaacggga
3961 tgccttctca cctgtcctgc tgcagttctg tacagaccct cgaaatccca tcacagtgat
4021 ccggggcctg gcgggctccc tgcggctcaa cttgggcctc ttctccacca agaccctggt
4081 ggaagcgagt ggcgaacaca ccgtggaagt tcgcacccag gtgcagcagc cctcagatga
4141 gaactgggat ctgacaggca ctcggcagat ctggccttgt gagagctccc gttcccacac
4201 caccattgcc aagtacgcac agtaccaggc ctcatccttc caggagtctc tgcaggagga
4261 gaaggagagt gaggatgagg agtcagagga gccagacagc accactggaa ccccctcctag
4321 cagcgcacca gacccgaaga accatcacat catcaagttt ggcaccaaca tcgacttgtc
4381 tgatgctaag cggtggaagc cccagctgca ggagctgctg aagctgcccg ccttcatgcg
4441 ggtaacatcc acgggcaaca tgctgagcca cgtgggccac accatcctgg gcatgaacac
4501 ggtgcagctg tacatgaagg tgcccggcag ccgaacgcca ggccaccagg agaataacaa
4561 cttctgctcc gtcaacatca acattggccc aggcgactgc gagtggttcg cggtgcacga
4621 gcactactgg gagaccatca gcgctttctg tgatcggcac ggcgtggact acttgacggg
4681 ttcctggtgg ccaatcctgg atgatctcta tgcatccaat attcctgtgt accgcttcgt
4741 gcagcgaccc ggagaccctcg tgtggattaa tgcggggact gtgcactggg tgcaggccac
```

```
4801 cggctggtgc aacaacattg cctggaacgt ggggcccctc accgcctatc agtaccagct 4861 ggccctggaa cgatacgagt ggaatgaggt gaagaacgtc aaatccatcg tgcccatgat 4921 tcacgtgtca tggaacgtgg ctcgcacggt caaaatcagc gaccccgact tgttcaagat 4981 gatcaagttc tgcctgctgc agtccatgaa gcactgccag gtgcaacgcg agagcctggt 5041 gcgggcaggg aagaaaatcg cttaccaggg ccgtgtcaag gacgagccag cctactactg 5101 caacgagtgc gatgtggagg tgtttaacat cctgttcgtg acaagtgaga atggcagccg 5161 caacacgtac ctggtacact gcgagggctg tgcccggcgc cgcagcgcag gcctgcaggg 5221 cgtggtggtg ctggagcagt accgcactga ggagctggct caggcctacg acgccttcac 5281 gctggtgagg gcccggcggg cgcgcgggca gcggaggagg gcactggggc aggctgcagg 5341 gacgggcttc gggagcccgg ccgcgccttt ccctgagccc ccgccggctt tctcccccca 5401 ggccccagcc agcacgtcgc gatgaggccg gacgccccgc ccgcctgcct gcccgcgcaa 5461 ggcgccgcgg ggccaccagc acatgcctgg gctggaccta ggtcccgcct gtggccgaga 5521 aggggtcgg gcccagccct tccacccat tggcagctcc cctcacttaa tttattaaga 5581 aaacttttt tttttttttt agcaaatatg aggaaaaaag gaaaaaaat gggagacggg 5641 ggaggggct ggcagcccct cgcccaccag cgcctcccct caccgacttt ggccttttta 5701 gcaacagaca caaggaccag gctccggcgg cggcgggggt cacatacggg ttccctcacc 5761 ctgccagccg cccgcccgcc cggcgcagat gcacgcggct cgtgtatgta catagacgtt 5821 acggcagccg aggtttttaa tgagattctt tctatgggct ttaccctcc cccggaacct 5881 ccttttttac ttccaatgct agctgtgacc cctgtacatg tctctttatt cacttggtta 5941 tgatttgtat tttttgttct tttcttgttt tttgttttt aatttataac agtcccactc 6001 acctctattt attcattttt gggaaaaccc gacctcccac acccccaagc catcctgccc 6061 gcccctccag ggaccgcccg tcgccgggct ctccccgcgc cccagtgtgt gtccgggccc 6121 ggcccgaccg tctccacccg tccgcccgcg gctccagccg ggttctcatg gtgctcaaac 6181 ccgctcccct ccctacgtc ctgcactttc tcggaccagt cccccactc ccgacccgac 6241 cccagcccca cctgagggtg agcaactcct gtactgtagg ggaagaagtg ggaactgaaa 6301 tggtattttg taaaaaaaat aaataaaata aaaaattaa aggttttaaa gaaagaacta 6361 tgaggaaaag gaaccccgtc cttcccagcc ccggccaact ttaaaaaaca cagaccttca 6421 cccccacccc cttttctttt taagtgtgaa acaacccagg gccagggcct cactggggca 6481 gggacacccc ggggtgagtt tctctggggc tttattttcg ttttgttggt tgttttttct 6541 ccacgctggg gctgcggagg ggtgggggt ttacagtccc gcaccctcgc actgcactgt
```

```
6601 ctctctgccc caggggcaga ggggtcttcc caaccctacc cctattttcg gtgattttg 6661 tgtgagaata ttaatattaa aaataaacgg agaaaaaaaa aaaaaaaaaa aaaaaaaaa 6721 aaaaaaaaaa a
```

By "KDM6C polypeptide" (histone demethylase UTY, also referred to as ubiquitously-transcribed TPR protein on the Y chromosome) is meant a protein having at least about 85% amino acid identity to the sequence provided at NCBI Reference Sequence: O14607.2, or a fragment thereof, and having demethylase activity. An exemplary KDM6C amino acid sequence is provided below:

```
   1 mkscavsltt aavafgdeak kmaegkasre seeesysltv eerealggmd srlfgfvrlh
  61 edgartktll gkavroyesl ilkaegkves dffcqlghfn llledyskal sayqryyslq
 121 adywknaafl yglglvyfyy nafhwaikaf qdvlyvdpsf crakeihlrl glmfkvntdy
 181 ksslkhfqla lidcnpctls naeiqfhiah lyetqrkyhs akeayeqllq tenlpaqvka
 241 tvlqqlgwmh hnmdlvgdka tkesyaiqyl qksleadpns gqswyflgrc yssigkvqda
 301 fisyrqsidk seasadtwcs igvlyqqqnq pmdalqayic avqldhghaa awmdlgtlye
 361 scnqpqdaik cylnaarskr csntstlaar ikflqngsdn wnggqslshh pvqqvyslcl
 421 tpqklqhleq lranrdnlnp aqkhqleqle sqfvlmggmr hkevaqyrtt gihngaitds
 481 slptnsysnr qphgaltrvs sysqpgvrpa cvekllssga fsagcipcgt skilgstdti
 541 llgsnciags esngnvpylq qnthtlphnh tdlnssteep wrkqlsnsaq glhksqsscl
 601 sgpneeqplf stgsaqyhqa tstgikkane hltlpsnsvp qgdadshlsc htatsggqqg
 661 imftkeskps knrslvpets rhtgdtsngc advkglsnhv hqliadavss pnhgdspnll
 721 iadnpqlsal ligkangnvg tgtcdkvnni hpavhtktdh svasspssai statpspkst
 781 eqrsinsvts lnsphsglht vngeglgksq sstkvdlpla shrstsqilp smsvsicpss
 841 tevlkacrnp gknglsnsci lldkcppprp ptspypplpk dklnpptpsi ylenkrdaff
 901 pplhqfctnp knpvtvirgl agalkldlgl fstktivean nehmvevrtq llqpadenwd
 961 ptgtkkiwrc esnrshttia kyaqyqassf qeslreenek rtqhkdhsdn estssensgr
1021 rrkgpfktik fgtnidlsdn kkwklqlhel tklpafarvv sagnllthvg htilgmntvq
1081 lymkvpgsrt pghqennnfc svninigpgd cewfvvpedy wgvindfcek nnlnflmssw
1141 wpnledlyea nvpvyrfiqr pgdlvwinag tvhwvqavgw cnniawnvgp ltacqyklav
1201 eryewnklks vkspvpmvhl swnmarnikv sdpklfemik ycllkilkqy qtlrealvaa
1261 gkeviwhgrt ndepahycsi cevevfnllf vtnesntqkt yivhchdcar ktskslenfv
1321 vleqykmedl iqvydqftla lslssss
```

By "KDM6C polynucleotide is meant a nucleic acid molecule encoding a KDM6C polypeptide. An exemplary KDM6A polynucleotide sequence is provided at NM_001258249.1, which sequence is reproduced below:

```
   1 gctcatcgtt tgttgtttag ataatatcat gaactgataa atgcagttgc cacgttgatt
  61 ccctagggcc tggcttaccg actgaggtca taagatatta tgccttctct ttagacttgg
 121 tcagtggaga ggaaatgggc aaagaaccag cctatggagg tgacaaggcc ttagggccaa
 181 aagtcttgag ggtgaaggtt tagggcctgc gcagcttccc tgccatgccc cgcaaggtct
 241 cgcattcgca aggcttgtga cagtgggagc ctcattacgg actctcctaa agtccatggt
 301 gtcctcttttt cgcatttgcg cccgtgggt gatgcccgat gccgcccttc ccatcgctct
```

-continued

```
 361 cttccccttc aagcgtatcg caactgcaaa acacccagc acagacactc cattttctat
 421 cttaatgcat ttaactagca caacctacag gttgttccat cccagagact acccttttct
 481 ccatagacgt gaccatcaac caaccagcgg tcagaatcag tcagcctctg tcatgttcct
 541 aggtccttgg cgaactggct gggcggggtc ccagcagcct aggagtacag tggagcaatg
 601 cctgacgtaa gtcaacaaag atcacgtgag acgaatcagt cgcctagatt ggctacaact
 661 aagtggttgg gagcggggag gtcgcggcgg ctgcgtgggg ttcgcccgtg acacaattac
 721 aactttgtgc tggtgctggc aaagtttgtg attttaagaa attctgctgt gctctccagc
 781 actgcgagct tctgccttcc ctgtagtttc ccagatgtga tccaggtagc cgagttccgc
 841 tgcccgtgct tcggtagctt aagtctttgc ctcagctttt ttccttgcag ccgctgagga
 901 ggcgataaaa ttggcgtcac agtctcaagc agcgattgaa ggcgtctttt caactactcg
 961 attaaggttg ggtatcgtcg tgggacttgg aaatttgttg tttccatgaa atcctgcgca
1021 gtgtcgctca ctaccgccgc tgttgccttc ggtgatgagg caaagaaaat ggcggaagga
1081 aaagcgagcc gcgagagtga agaggagtct gttagcctga cagtcgagga aagggaggcg
1141 cttggtggca tggacagccg tctcttcggg ttcgtgaggc ttcatgaaga tggcgccaga
1201 acgaagaccc tactaggcaa ggctgttcgc tgctacgaat ctttaatctt aaaagctgaa
1261 ggaaaagtgg agtctgactt cttttgccaa ttaggtcact tcaacctctt gttggaagat
1321 tattcaaaag cattatctgc atatcagaga tattacagtt tacaggctga ctactggaag
1381 aatgctgcgt ttttatatgg ccttggtttg gtctacttct actacaatgc atttcattgg
1441 gcaattaaag catttcaaga tgtcctttat gttgaccca gcttttgtcg agccaaggaa
1501 attcatttac gacttgggct catgttcaaa gtgaacacag actacaagtc tagtttaaag
1561 cattttcagt tagccttgat tgactgtaat ccatgtactt tgtccaatgc tgaaattcaa
1621 tttcatattg cccatttgta tgaaacccag aggaagtatc attctgcaaa ggaggcatat
1681 gaacaacttt tgcagacaga aaaccttcct gcacaagtaa aagcaactgt attgcaacag
1741 ttaggttgga tgcatcataa tatggatcta gtaggagaca aagccacaaa ggaaagctat
1801 gctattcagt atctccaaaa gtctttggag gcagatccta attctggcca atcgtggtat
1861 tttcttggaa ggtgttattc aagtattggg aaagttcagg atgcctttat atcttacagg
1921 caatctattg ataaatcaga agcaagtgca gatacatggt gttcaatagg tgtgttgtat
1981 cagcagcaaa atcagcctat ggatgcttta caggcatata tttgtgctgt acaattggac
2041 catgggcatg ccgcagcctg gatggaccta ggtactctct atgaatcctg caatcaacct
2101 caagatgcca ttaaatgcta cctaaatgca gctagaagca aacgttgtag taatacctct
2161 acgcttgctg caagaattaa atttctacag gctcagttgt gtaaccttcc acaaagtagt
2221 ctacagaata aaactaaatt acttcctagt attgaggagg catggagcct accaatcccc
2281 gcagagctta cctccaggca gggtgccatg aacacagcac agcaggctta tagagctcat
2341 gatccaaata ctgaacatgt attaaaccac agtcaaacac caattttaca gcaatccttg
2401 tcactacaca tgattacttc tagccaagta gaaggcctgt ccagtcctgc caagaagaaa
2461 agaacatcta gtccaacaaa gaatggttct gataactgga atggtggcca gagtctttca
2521 catcatccag tacagcaagt ttattcgttg tgtttgacac cacagaaatt acagcacttg
2581 gaacaactgc gagcaaatag agataattta aatccagcac agaagcatca gctggaacag
2641 ttagaaagtc agtttgtctt aatgcagcaa atgagacaca agaagttgc tcaggtacga
2701 actactggaa ttcataacgg ggccataact gattcatcac tgcctacaaa ctctgtctct
2761 aatcgacaac cacatggtgc tctgaccaga gtatctagcg tctctcagcc tggagttcgc
```

-continued

```
2821  cctgcttgtg ttgaaaaact tttgtccagt ggagctttt  ctgcaggctg tattccttgt 2881  ggcacatcaa aaattctagg aagtacagac actatcttgc taggcagtaa ttgtatagca 2941  ggaagtgaaa gtaatggaaa tgtgccttac ctgcagcaaa atacacacac tctacctcat 3001  aatcatacag acctgaacag cagcacagaa gagccatgga gaaaacagct atctaactcc 3061  gctcaggggc ttcataaaag tcagagttca tgtttgtcag gacctaatga agaacaacct 3121  ctgttttcca ctgggtcagc ccagtatcac caggcaacta gcactggtat taagaaggcg 3181  aatgaacatc tcactctgcc tagtaattca gtaccacagg gggatgctga cagtcacctc 3241  tcctgtcata ctgctacctc aggtggacaa caaggcatta tgtttaccaa agagagcaag 3301  ccttcaaaaa atagatcctt ggtgcctgaa acaagcaggc atactggaga cacatctaat 3361  ggctgtgctg atgtcaaggg actttctaat catgttcatc agttgatagc agatgctgtt 3421  tccagtccta accatggaga ttcaccaaat ttattaattg cagacaatcc tcagctctct 3481  gctttgttga ttgaaaagc  caatggcaat gtgggtactg gaacctgtga caaagtgaat 3541  aatattcacc cagctgttca tacaaagact gatcattctg ttgcctcttc accctcttca 3601  gccatttcca cagcaacacc ttctcctaaa tccactgagc agagaagcat aaacagtgtt 3661  accagcctta acagtcctca cagtggatta cacacagtca atggagaggg gctggggaag 3721  tcacagagct ctacaaaagt agacctgcct ttagctagcc acagatctac ttctcagatc 3781  ttaccatcaa tgtcagtgtc tatatgcccc agttcaacag aagttctgaa agcatgcagg 3841  aatccaggta aaaatggctt gtctaatagc tgcattttgt tagataaatg tccacctcca 3901  agaccaccaa cttcaccata cccacccttg ccaaaggaca agttgaatcc acccacacct 3961  agtatttact tggaaaataa acgtgatgct ttctttcctc cattacatca attttgtaca 4021  aatccaaaaa accctgttac agtaatacgt ggccttgctg gagctcttaa attagatctt 4081  ggacttttct ctaccaaaac tttggtagaa gctaacaatg aacatatggt agaagtgagg 4141  acacagttgc tgcaaccagc agatgaaaac tgggatccca ctggaacaaa gaaaatctgg 4201  cgttgtgaaa gcaatagatc tcatactaca attgccaaat acgcacaata ccaggcttcc 4261  tccttccagg aatcattgag agaagaaaat gagaaaagaa cacaacacaa agatcattca 4321  gataacgaat ccacatcttc agagaattct ggaaggagaa ggaaaggacc ttttaaaacc 4381  ataaaatttg ggaccaacat tgacctctct gataacaaaa agtggaagtt gcagttacat 4441  gaactgacta aacttcctgc ttttgcgcgt gtggtgtcag caggaaatct tctaacccat 4501  gttgggcata ccattctggg catgaataca gtacaactgt atatgaaagt tccagggagt 4561  cggacaccag gtcaccaaga aaataacaac ttctgctctg ttaacataaa tattggtcca 4621  ggagattgtg aatggtttgt tgtacctgaa gattattggg gtgttctgaa tgacttctgt 4681  gaaaaaaata atttgaattt tttaatgagt tcttggtggc ccaaccttga agatctttat 4741  gaagcaaatg tccctgtgta tagatttatt cagcgacctg gagatttggt ctggataaat 4801  gcaggcactg tgcattgggt tcaagctgtt ggctggtgca ataacattgc ctggaatgtt 4861  ggtccactta cagcctgcca gtataaattg gcagtggaac ggtatgaatg gaacaaattg 4921  aaaagtgtga agtcaccagt acccatggtg catctttcct ggaatatggc acgaaatatc 4981  aaagtctcag atccaaagct ttttgaaatg attaagtatt gtcttttgaa aattctgaag 5041  caatatcaga cattgagaga agctcttgtt gcagcaggaa aagaggttat atggcatggg 5101  cggacaaatg atgaaccagc tcattactgt agcatttgtg aggtggaggt ttttaatctg 5161  cttttttgtca ctaatgaaag caatactcaa aaaacctaca tagtacattg ccatgattgt
```

-continued

```
5221 gcacgaaaaa caagcaaaag tttggaaaat tttgtggtgc tcgaacagta caaaatggag 5281 gacctaatcc aagtttatga tcaatttaca ctagctcttt cattatcatc ctcatcttga 5341 tatagttcca tgaatattaa atgagattat ttctgctctt caggaaattt ctgcaccact 5401 ggttttgtag ctgtttcata aaactgttga ctaaaagcta tgtctatgca accttccaag 5461 aatagtatgt caagcaactg gacacagtgc tgcctctgct tcaggactta acatgctgat 5521 ccagctgtac ttcagaaaaa taatattaat catatgtttt gtgtacgtat gacaaactgt 5581 caaagtgaca cagaatactg atttgaagat agccttttt atgtttctct atttctgggc 5641 tgatgaatta atattcattt gtattttaac cctgcagaat tttccttagt taaaaacact 5701 ttcctagctg gtcatttctt cataagatag caaatttaaa tctctcctcg atcagctttt 5761 aaaaaatgtg tactattatc tgaggaagtt ttttactgct ttatgttttt gtgtgttttg 5821 aggccatgat gattacattt gtggttccaa ataatttttt ttaaatatta atagcccata 5881 tacaaagata atggattgca catagacaaa gaaataaact tcagatttgt gattttgtt 5941 tctaaacttg atacagattt acactattta taaatacgta tttattgcct gaaaatattt 6001 gtgaatggaa tgttgttttt ttccagacgt aactgccatt aaatactaag gagttctgta 6061 gttttaaaca ctactcctat tacattttat atgtgtagat aaaactgctt agtattatac 6121 agaaattttt attaaaattg ttaaatgttt aaagggtttc ccaatgtttg agtttaaaaa 6181 agactttctg aaaaaatcca cttttgttc attttcaaac ctaatgatta tatgtatttt 6241 atatgtgtgt gtatgtgtac acacatgtat aatatataca gaaacctcga tatataattg 6301 tatagatttt aaaagtttta tttttttacat ctatggtagt ttttgaggtg cctattataa 6361 agtattacgg aagtttgctg tttttaaagt aaatgtcttt tagtgtgatt tattaagttg 6421 tagtcaccat agtgatagcc cataaataat tgctggaaaa ttgtatttta aacagtaga 6481 aaacatatag tcagtgaagt aaatatttta aaggaaacat tatatagatt tgataaatgt 6541 tgtttataat taagagtttc ttatggaaaa gagattcaga atgataacct cttttagaga 6601 acaaataagt gacttatttt tttaaagcta gatgactttg aaatgctata ctgtcctgct 6661 tgtacaacat ggtttggggt gaaggggagg aaagtattaa aaaatctata tcgctagtaa 6721 attgtaataa gttctattaa aacttgtatt tcatatgaaa aatttgctaa tttaatatta 6781 actcatttga taataatact tgtcttttct acctctc
```

45

By "Gab1 polypeptide" (GRB2-associated-binding protein 1) is meant a protein having at least about 85% amino acid identity to the sequence provided at NCBI Reference Sequence: NP_997006.1, or a fragment thereof. An exemplary Gab1 amino acid sequence is provided below:

```
  1 msggevvcsg wlrksppekk lkryawkrrw fvlrsgrltg dpdvleyykn dhakkpirii 61 dlnlcqqvda gltfnkkefe nsyifdinti drifylvads eeemnkwvrc icdicgfnpt 121 eedpvkppgs slqapadlpl aintappstq adsssatlpp pyqlinvpph letlgiqedp 181 qdylllincq skkpeptrth adsakstsse tdcndnvpsh knpassqskh gmngffqqqm 241 iydsppsrap sasvdsslyn lprsyshdvl pkvspsstea dgelyvfntp sgtssvetqm 301 rhvsisydip ptpgntyqip rtfpegtlgq tskldtipdi ppprppkphp andrspvetc 361 siprtasdtd ssyciptagm spsrsntist vdlnklrkda ssqdcydipr afpsdrsssl 421 egfhnhfkvk nvltvgsyss eeldenyvpm npnspprqhs ssftepiqea nyvpmtpgtf 481 dfssfgmqvp ppahmgfrss pktpprrpvp vadcepppvd rnlkpdrkgq spkilrlkph
```

```
541 glertdsqti gdfatrrkvk papleikplp eweelqapvr spitrsfard ssrfpmsprp 601 dsvhsttsss dshdseenyv pmnpnlssed pnlfgsnsld ggsspmikpk gdkqveyldl 661 dldsgkstpp rkqkssgsgs svadervdyv vvdqqktlal kstreawtdg rqstesetpa 721 ksvk
```

By "Gab1 polynucleotide" is meant a nucleic acid molecule encoding a Gab1 polypeptide. An exemplary Gab1 polynucleotide sequence is provided at NM_002039.3, which is reproduced below:

```
   1 aggggggcgga gcgcaaagga cagaagctcc ggcaccgagt cggggcagag tcccgctgag
  61 tccgagcgct gctgaggcag ctggcgagac ggcacgtctg gaggcgaggc gggcgcactg
 121 aaaggaggcc ggcgcgcccg cggccccggc tcgcgttctg ttcaggttcg tgggcctgca
 181 gaggagagac tcgaactcgt ggaacccgcg caccgtggag tctgtccgcc cagtccgtcc
 241 ggggtgcgcg accaggagag ctaggttctc gccactgcgc gctcggcagg cgtcggctgt
 301 gtcgggagcg cgcccgccgc ccctcagctg cccggcccgg agcccgagac gcgcgcacca
 361 tgagcggtgg tgaagtggtc tgctccggat ggctccgcaa gtccccccg gagaaaaagt
 421 tgaagcgtta tgcatggaag aggagatggt tcgtgttacg cagtggccgt ttaactggag
 481 atccagatgt tttggaatat tacaaaaatg atcatgccaa gaagcctatt cgtattattg
 541 atttaaattt atgtcaacaa gtagatgctg gattgacatt taacaaaaaa gagtttgaaa
 601 acagctacat ttttgatatc aacactattg accggatttt ctacttggta gcagacagcg
 661 aggaggagat gaataagtgg gttcgttgta tttgtgacat ctgtgggttt aatccaacag
 721 aagaagatcc tgtgaagcca cctggcagct ctttacaagc accagctgat ttacctttag
 781 ctataaatac agcaccacca tccacccagg cagattcatc ctctgctact ctacctcctc
 841 catatcagct aatcaatgtt ccaccacacc tggaaactct tggcattcag gaggatcctc
 901 aagactacct gttgctcatc aactgtcaaa gcaagaagcc cgaacccacc agaacgcatg
 961 ctgattctgc aaaatccacc tcttctgaaa cagactgcaa tgataacgtc ccttctcata
1021 aaaatcctgc ttcctcccag agcaaacatg gaatgaatgg cttttttcag cagcaaatga
1081 tatacgactc tccaccttca cgtgccccat ctgcttcagt tgactccagc ctttataacc
1141 tgcccaggag ttattcccat gatgttttac caaaggtgtc tccatcaagt actgaagcag
1201 atggagaact ctatgttttt aatacccccat ctgggacatc gagtgtagag actcaaatga
1261 ggcatgtatc tattagttat gacattcctc caacacctgg taatacttat cagattccac
1321 gaacatttcc agaaggaacc ttgggacaga catcaaagct agacactatt ccagatattc
1381 ctccacctcg gccaccgaaa ccacatccag ctcatgaccg atctcctgtg gaaacgtgta
1441 gtatcccacg caccgcctca gacactgaca gtagttactg tatccctaca gcagggatgt
1501 cgccttcacg tagtaatacc atttccactg tggatttaaa caattgcgca aaagatgcta
1561 gttctcaaga ctgctatgat attccacgag catttccaag tgatagatct agttcacttg
1621 aaggcttcca taaccacttt aaagtcaaaa atgtgttgac agtgggaagt gtttcaagtg
1681 aagaactgga tgaaaattac gtcccaatga atcccaattc accaccacga caacattcca
1741 gcagttttac agaaccaatt caggaagcaa attatgtgcc aatgactcca ggaacatttg
1801 attttttcctc atttggaatg caagttcctc ctcctgctca tatgggcttc aggtccagcc
1861 caaaaacccc tcccagaagg ccagttcctg ttgcagactg tgaaccaccc cccgtggata
1921 ggaacctcaa gccagacaga aaagtcaagc cagcgccttt agaaataaaa cctttgccag
```

-continued

```
1981 aatgggaaga attacaagcc ccagttagat ctcccatcac taggagtttt gctcgagact
2041 cttccaggtt tcccatgtcc ccccgaccag attcagtgca tagcacaact tcaagcagtg
2101 actcacacga cagtgaagag aattatgttc ccatgaaccc aaacctgtcc agtgaagacc
2161 caaatctctt tggcagtaac agtcttgatg gaggaagcag ccctatgatc aagcccaaag
2221 gagacaaaca ggtggaatac ttagatctcg acttagattc tgggaaatcc acaccaccac
2281 gtaagcaaaa gagcagtggc tcaggcagca gtgtagcaga tgagagagtg gattatgttg
2341 ttgttgacca acagaagacc ttggctctaa agagtacccg ggaagcctgg acagatggga
2401 gacagtccac agaatcagaa acgccagcga agagtgtgaa atgaaaatat tgccttgcca
2461 tttctgaaca aagaaaaact gaattgtaaa gataaatccc ttttgaagaa tgacttgaca
2521 cttccactct aggtagatcc tcaaatgagt agagttgaag tcaaaggacc tttctgacat
2581 aatcaagcaa tttagactta agtggtgctt tgtggtatct gaacaattca taacatgtaa
2641 ataatgtggg aaaatagtat tgtttagctc ccagagaaac atttgttcca cagttaacac
2701 actcgtagta ttactgtatt tatgcacttt ttcatctaaa acattgttct gggttttccc
2761 aatgtacctt accataattc ctttgggagt tcttgttttt tgtcacacta ctttatataa
2821 caatactaag tcaactaagc tacttttaga tttggaaatt gctgtttaca gtctaacaac
2881 attaaaatga gaggtagatt cacaagttag ctttctacct gaagcttcag gtgataacca
2941 ttagcttata cttggactca tcatttgttg ccttccaaaa tgctgaggat aatgtatgta
3001 ctggtgtcag gacctagttc tctggttaat gtacatttag ttttaatgg tggaactttg
3061 ttatattttg ttaattacag tgttttggt tcattgagtg aagattctgc cgggtgggat
3121 cttgcacctt tgaaagactg aataattaca ctaccaagta agcctgcaaa tcattgatgg
3181 catgcagtga tgatgtgctc ttacacttgt taacatgtat aagtgttat ttgcaaaagg
3241 tagattatgt aaccaatcag gtacgtacca ggcagtgatg tgctaataca ctgatcaggt
3301 ttagacaatg agctttggtt gtgttcttgt tagtcctaat attggttttc agtttggaat
3361 taataaagca gttgacattc actgttagtt acagcaacat actgtgattt ttaattagat
3421 agtaattcag atttattact ctatgaaatt ctgtcttttg acaccatagt gcccttteta
3481 tgattttttt tacttaatat tcttcttggc cttatattta attccctatg caattaatat
3541 tttatatctg catttttta aaaaaaatag atgttatata agtgattctc gtatgtagca
3601 cctgttgctt ttccactgaa agaattacgg atttttgtact gtgatttata ttcactgccc
3661 caattcaaga aatattggag ccttgctaca atgtgaaatg ttatagtcat ggactccttc
3721 caaccagatt tctgaaaaca ccagagggat ggtataattc tgtctcacct ataacatggt
3781 cctgtgacat agatattaag accacaagtt gtagtgaggc tacaattata ttcgtctgtc
3841 ttggctttgc aacataattt agaaagcacg tatagttgtt ttttaaccaa gttacataca
3901 atctcatgta ctgatttgag acttataaca atttttggag ggggcataga gaaggagtg
3961 cccacagttg aggcatgacc ccctccattc agacctctaa ctgttgcctg agtacacaga
4021 tgtgccctga tttctggccc attggccata gtactgtgcc taatcaatgt aataggttta
4081 ttttcccaat cctcaaacta aaaatgttca taacaagatg aattgtagac tagtaacatt
4141 tgatgctttt aaatatttgc ttcttttaa acaaaaacta aacccagaa gtgaattttt
4201 aggtggattt ttaaataaaa aagattgatt gagtttggtg tgcaagctgt tttataatga
4261 aacaacaaaa tgaaatctaa aatcctgaaa tgtgcctaaa ctatcaaaac acacgataca
4321 gctaatgtgt aaagatgcta aattctgtta cttggaggat gaatatattt aagatttaaa
```

-continued

```
4381 acacaataat aaatacatga ttaattcaaa aataaaaatc tttacagctg cctatcaagg 4441 gtctaaagca cttaatgaat gttttttagtc taacttatca ttaactttt acaagtcacc 4501 atatttgaag atctgtagca ctctgatttt cagaaaattt ttcattctga ataatttaaa 4561 aatggtgatg tattagaaag gcagtttgct ttagaaaact aaatcacatt gaacattgta 4621 ttagagaatt aaattaaaag tttcttacag agcagtattt tccaaacatt tttagcacta 4681 gaatctttt agatgaaatt ttatgtataa ccccaataca taaagcctga aaactcaatt 4741 ttatcaatat aaatgtattt tgggttcaca tttatgctta ttcattttgg ctcattacta 4801 agcataataa gattctgagt tatttctgaa taacacaaat gtggagttat acatagttga 4861 tgaaaccagc agccaattta tagctatgcc ctgttttatt tgtatactat caagaaaatt 4921 ttgattcaca caaatgtaag caaaaataat aggttttaaa catacatctc aggaaattct 4981 ttaattagag atagctaaag ttattcaagg tctatacaaa aataagttat cctggtagtg 5041 gaagttaata cataagcagt ctccagtgtg gtaaagtagg gtatgtaaca catcagaatg 5101 tgcgttttta ttaggtttta aaatatgcac gtataaaaac taaatttgaa tcaaacccctt 5161 ttaactcacc tccaagaagc tagactttgg ccaggaatgg gctaaaaacc actggttaac 5221 gatgtgacag ttatgatctt ggagattgga aatctttctt ccacattaga gttctttacc 5281 ttaattcctt attctgaaaa attgtaagat tttatgaagg tttgaatact gaagcacagt 5341 tctgctttca aaaattaaaa ttcaaacttg aaaaagctgt ttaacccatg gaagatatca 5401 tttagtaaga tgtaaaagat tttttaaatc tacacttcag tttatacatc tttatcatta 5461 tcaatactat ataagttact gtgagcattt tagagaattc cataaaggta ctatgagtgt 5521 gtctgtatgt gtgtgtatat atagcattgt atttaatcat agactaaatt taatttgata 5581 tagaaatact actttacttg tacattaagg tcataatttc tgctggactc ttttatattt 5641 aattaatggg gattatagtc ttccttcata aatgcattta aacctgaaat tgaacaccag 5701 tgttttctt tttctactta tgggaagttg tctgcttccc cctttagaga aaacagtatt 5761 tttatatttt gttaaaatat taactacttt atgcctacac actatgctgt agatactgat 5821 cataattctt gggtgttcac aaacactcct agtgcctctt ttttggcccg ttgaaagtgt 5881 tggtattact actttcacta cagagccttt ggccctctaa taatgctgag gtgggctgat 5941 ccttcccatt tctgtcttcg ggtcattctg gtaggtcttc tcctccactg tcaagtaagc 6001 aatcaggtcc gtgacaggga ttggacatat gaacaaatta agtggataca cacagtgaga 6061 aagatacatg cattctatgg taacaactac tgtcaataac atctgatgtt acatgcacat 6121 ttatatatat ataattttaa aaactgaact atgagaagcc atggtataaa tgaatattgt 6181 ggacatcatg gacttgatat gatagaaatc aattgtcagc ttgagaaagt tgtttttaat 6241 ctgtctaaat agttcatgca ttactacagt taaaaatagt ttcatttgtc ttctatagac 6301 ttaattttat tccggttcag tataatctct gttaacagag tttcagcaaa ctgattggtc 6361 aaggtattaa catagcttct acttcctta cttaaaaaga tgtggtttta tgtaagttct 6421 tgattactga tgatcatccc aaattttgac aacaaaatca tatgtataaa tttatttctc 6481 ccctcttgtt catcatcttt tgtaaaggtc ccattgtaga tcttttctgc taccaaataa 6541 aacttttcaa acaatttggt ttcaagacct taaatagaca agttggatac taagattgtg 6601 aactgataag gacatataaa tttatatttc cagcccttcc ttagagtctt tatctgcatc 6661 aaaaacccaa ttctgccatt aactgtgctt cccagtccca cctctatatg tcactcattt 6721 tctgcaacaa agatctcact aaatcatgtt gaaacacaag tcatgatcct ctctaagtaa 6781 atagaaaaag ctccctggaa aaactctgtt gccacatgca cgtgccctgt tactcctcca
```

-continued

```
6841 gccagccagt gctgccagca ttttattgtg taaaagtcca aataaataag ggcctgcatg
6901 caacctttat cttcagaaac taggttttat atgtaaaatg tgacttggga aatgattctg
6961 tttattaact ggctgggatt tttcatttct atgaaagttt caaacatctc cagtactttca
7021 taaaatccca acaattgctg taagtcagca ctttggtcca ctcagcccac ccagcccact
7081 tgcaactctg actcttcact gaatcatatt tgggaagttt gggtagggtg aggctatctt
7141 cttcaagatt attttctcat atgtctgtct gtcaccttgt aaaccatgag actcctgggt
7201 atttgcatgt aacttctttg aggaagttac caccatctct gatatagaca cactttttga
7261 gttgcagttt ctgttagaat ttttttggaga ctaacttgcc aattctgtga atgttattga
7321 atatttaaaa agctgggtct gtaatgggag gcattttatt agctgttgtg attgggtaac
7381 atgtcccctt agatttcctg atttaaaatt atacaaaatt actattttg ataaaataaa
7441 ggaacaccta cagaaaatta agtttctaag atgtttctat acttcattag aaaagattt
7501 attactatta cttatggtta ttggtgatta acacttaatg cgtctcctct gattttgtgt
7561 tccatgaggt gcttggaaca tttggagtgc tctgtgcgag ggacatacag tgatatagga
7621 aatttaaaaa ttaaaataat acccaaaacc cactttatca gatatggtat tgtgatggtt
7681 aatattatgt gtcaacttgg tgaggctatg gcgcccatgt gtttggtcaa acactagcct
7741 agatgttgct gtgaatatat tttgtagatg tgattaacat ttacaatcag ttgattttaa
7801 gtaaagcaga ttctcatcca aaaaaaaaaa aaaaaa
```

By "Sfmbt2 polypeptide" (scm-like with four MBT domains protein 2) is meant a protein having at least about 85% amino acid identity to the sequence provided at NCBI Reference Sequence: NP_001018049.1, or a fragment thereof. An exemplary Sfmbt2 amino acid sequence is provided below:

```
  1 mestlsasnm qdpsssplek clgsangngd ldseegssle etgfnwgeyl eetgasaaph
 61 tsfkhveisi qsnfqpgmkl evanknnpdt ywvatiittc gqllllrycg ygedrradfw
121 cdvviadlhp vgwctqnnkv lmppdaikek ytdwteflir dltgsrtapa nllegplrgk
181 gpidlitvgs lielqdsqnp fqywivsvie nvggrlrlry vgledtesyd qwlfyldyrl
241 rpvgwcgenk yrmdppseiy plkmasewkc tlekslidaa kfplpmevfk dhadlrshff
301 tvgmkletvn mcepfyispa svtkvfnnhf fqvtiddlrp epsklsmlch adslgilpvq
361 wclkngvslt ppkgysgqdf dwadyhkqhg aqeappfcfr ntsfsrgftk nmkleavnpr
421 npgelcvasv vsvkgrlmwl hleglqtpvp evivdvesmd ifpvgwcean sypltaphkt
481 vsqkkrkiav vqpekqlppt vpvkkiphdl clfphldttg tvngkyccpq lfinhrcfsg
541 pylnkgriae lpqsvgpgkc vlvlkevlsm iinaaykpgr vlrelqlved phwnfqeetl
601 kakyrgktyr avvkivrtsd qvanfcrrvc akleccpnlf spvlisencp encsihtktk
661 ytyyygkrkk iskppigesn pdsghpkpar rrkrrksifv qkkrrssavd ftagsgeese
721 eedadamddd taseetgsel rddqtdtssa evpsarprra vtlrsgsepv rrppppertrr
781 grgapaassa eegekcpptk pegtedtkqe eeerlvlesn plewtvtdvv rfikltdcap
841 lakifqeqdi dgqallltl ptvqecmelk lgpaiklchq iervkvafya qyan
```

By "Sfmbt2 polynucleotide" is meant a polypeptide encoding an Sfmbt2 polypeptide. An exemplary Sfmbt2 polynucleotide sequence is provided at NM_001018039.1, which is reproduced below:

```
   1 cgccttgtgt gtgctggatc ctgcgcgggt agatccccga gtaattttttt ctgcaggatg
  61 aattaagaga agagacactt gctcatcagg catggagagc actttgtcag cttccaatat
 121 gcaagaccct tcatcttcac ccttggaaaa gtgtctcggc tcagctaatg gaaatggaga
 181 ccttgattct gaagaaggct caagcttgga ggaaactggc tttaactggg gagaatattt
 241 ggaagaqaca ggagcaagtg ctgctcccca cacatcattc aaacacgttg aaatcagcat
 301 tcagagcaac ttccagccag gaatgaaatt ggaagtggct aataagaaca acccggacac
 361 gtactgggtg gccacgatca ttaccacgtg cgggcagctg ctgcttctgc gctactgcgg
 421 ttacggggag gaccgcaggg ccgacttctg gtgtgacgta gtcatcgcgg atttgcaccc
 481 cgtggggtgg tgcacacaga acaacaaggt gttgatgccg ccggacgcaa tcaaagagaa
 541 gtacacagac tggacagaat ttctcatacg tgacttgact ggttcgagga cagcacccgc
 601 caacctcctg gaaggtcctc tgcgagggaa aggccctata gacctcatta cagttggttc
 661 cttaatagaa cttcaggatt cccagaaccc ttttcagtac tggatagtta gtgtgattga
 721 aaatgttgga ggaagattac gccttcgcta tgtgggattg gaggacactg aatcctatga
 781 ccagtggttg ttttacttgg attacagact tcgaccagtt ggttggtgtc aagagaataa
 841 atacagaatg gacccacctt cagaaatcta tcctttgaag atggcctctg aatggaaatg
 901 tactctggaa aaatccctta ttgatgctgc caaatttcct cttccaatgg aagtgtttaa
 961 ggatcacgca gatttgcgaa gccatttctt cacagttggg atgaagcttg agacagtgaa
1021 tatgtgcgag ccctttttaca tctctcctgc gtcggtgact aaggttttta caatcactt
1081 ttttcaagtg actattgatg acctaagacc tgaaccaagt aaactgtcaa tgctgtgcca
1141 tgcagattct ttggggattt tgccagtaca gtggtgcctt aaaaatggag tcagcctcac
1201 tcctcccaaa ggttactctg ccaggactt cgactgggca gattatcaca agcagcatgg
1261 ggcgcaggaa gcccctccct tctgcttccg aaatacatca ttcagtcgag gtttcacaaa
1321 gaacatgaaa cttgaagctg tgaaccccag gaatccagga gaactgtgtg tggcctccgt
1381 tgtgagtgtg aaggggcggc taatgtggct tcacctggaa gggctgcaga ctcctgttcc
1441 agaggtcatt gttgatgtgg aatccatgga catcttccca gtgggctggt gtgaagccaa
1501 ttcttatcct ttgactgcac cacacaaaac agtctcacaa aagaagagaa agattgcagt
1561 cgtgcaacca gagaaacaat gccgcccac agtgcctgtt aagaaaatac ctcatgacct
1621 ttgtttattc cctcacctgg acaccacagg aaccgtcaac gggaaatact gctgtcctca
1681 gctcttcatc aaccacaggt gtttctcagg cccttacctg aacaaaggaa ggattgcaga
1741 gctacctcag tcggtgggac cgggcaaatg cgtgctggtt cttaaagagg ttcttagcat
1801 gataatcaac gcagcctaca gcctggaag ggtattaaga gaattacagc tggtagaaga
1861 tccccactgg aatttccagg aagagacgct gaaggccaaa tacagaggca aaacatacag
1921 ggctgtggtc aaaatcgtac ggacatctga ccaagtcgca aatttctgcc gccgagtctg
1981 tgccaagcta gagtgctgtc caaatttgtt tagtcctgtg ctgatatctg aaaactgccc
2041 agagaactgc tccattcata ccaaaaccaa atacacctat tactatggaa agagaaagaa
2101 gatctccaag ccccccatcg gggaaagcaa ccccgacagc ggacaccca aacccgccag
2161 gcggaggaag cgacggaaat ccatttttcgt gcagaagaaa cggaggtctt ctgccgtgga
2221 cttcaccgcg ggctcggggg aggaaagtga agaggaggac gctgacgcca tggacgatga
2281 caccgccagt gaggagaccg gctccgagct ccgggatgac cagacggaca cctcgtcggc
2341 ggaggtgccc tcgccccggc ccggagggc cgtcaccctg cggagcggct cagagcccgt
2401 gcgccggcca ccccagaga ggacacgaag gggccgcggg gcgccggctg cctcctcagc
```

-continued

```
2461 agaggaaggg gagaagtgcc cgccgaccaa gcccgagggg acagaggaca cgaaacagga 2521 ggaggaggag agactggttc tggagagcaa cccgttggag tggacggtca ccgacgtggt 2581 gaggttcatt aagctgacag actgtgcccc cttggccaag atatttcagg agcaggatat 2641 tgacggccaa gcactcctgc ttctgaccct tccgacggtg caggagtgca tggagctgaa 2701 gctggggcct gccatcaagt tatgccacca gatcgagaga gtcaaagtgg ctttctacgc 2761 ccagtacgcc aactgagtct gccctcggga ggtggcccat tattgctggg atgcggtgtt 2821 ggtaaaggtt tccaggactg aaactttgat tttccgggat atgttaaatg gtacagccac 2881 taagtatcac cagaaaacca gaagcccagg atcttctgcc tccgccagcc tgtgagctgt 2941 ttccatgttt tcaaagcaca gcagcagtcg cttctgggga gtgccagtta aagtcatgca 3001 tcagaccctg ccagacgtgg gcctgcttct tggctcaccc acgttttgcc tttctcctgc 3061 cccaaatcag gcagctccct tggagcaggg tttcctcaga tgaggactgc attctttgaa 3121 aacaaagaat gtcgccaagg aagaaacctc acgccatgct gtagtgtttc ctgtaatcac 3181 acgagcacat ttatatatgc agtttcccat ggataggcgt gtgaccctgg ttgagtggca 3241 cttgcggttt catcttggtg gcaactcctt tgcaatgcag ctggcagcga catccttata 3301 aaaacatgtg ctaaagctct gtcctctgtt agaggtgcct tttaggaata cggggagtga 3361 aggaaggccg gcaggcatct ccatgcaact agatggtttg tttgtttgtt tgtttgtttg 3421 ttgttcattt tgttgtgttt tttgagacag ggtcttgctc tgtcgcccag gttgtaatgc 3481 agtggcgcaa tctcagctca ctgcaacctc tctctcccgg gttcaagtga ttctcctgcc 3541 tcagcctccc aagtagctgg gattacaggc acccaccacc atgcctggct aatttttgta 3601 tttttggtag agacagggtt tcaccatgtt ggtcaggcta gtcttgaact cccaacctca 3661 agtgatctgc ccgcctcggc ctcccaacgt gctgggatta caggtgtgag ccactacgcc 3721 ccggcccaac tggatggttt tgattgaag cctagaacat ctgtagagac aaactctacc 3781 cagtcttttc tagaccctca actatctcca gtgttgttgt ttaatcgtag ccggatcagg 3841 gagtgagtct tttaggcaaa tgttggatta tatcaaag gaaaagctta gtttcagaga 3901 ggaggaaggg aaagagatgt gagggaagca tttcatcaac cagctacgtc cccctttagaa 3961 ggatcactgc agcaggtcac cgagcaggag tccctctgag cgtcccttct gtctcgttct 4021 gccctagctg gcagcatatg aaccaggcat gatgcagcag gagcagtgaa tctggagtca 4081 gccacttggc accctggttt cgctgagaac aaactctgag atcttgggtg acttctcatc 4141 actctggacc tccattcctg tgaagtgaca ggtgtggacc ctgagggtgc ggtggtgagc 4201 acactgtctc ctgctggcat tcaccccact catgctggaa aggaagatcc agatcgtaca 4261 aaaattagaa aaagaaagaa taagaagggt ctggtcccag ttctgactcg gccattctta 4321 cagctctttc tggctttgag tttgcttgtg aatttcctg ggcagttgtg ttaaatccgc 4381 caggtcacgt gcagacaaag ctgtggctgc gagagttggc tggcctcttg gaccagaagc 4441 catctccata tcctcatgag cgattccata tctccactca gaccctgtgg actacagtgt 4501 tccgctgtgg tggctgccaa gatgccttct taaacttatg caaggaaacc aaaccctccc 4561 acagttccca agcagacact ggaagcagag gcttctcacc cttcctgctt tttcaccaca 4621 atcaccttga gctcgtccct tggactagag tctccacagt tccagtaaaa ttctgcggtg 4681 ggctgatgag ctgcttgcat ttctgtgaca tttccagata tgattctcag tgggattttg 4741 gaaactttga ttgctcaagc tcaccttct taacattctg taatggttac agatgagaat 4801 ggaaaacaca tatttatgg atgaggcgtt ttggtctccc ctgcagtcga tttctagaat
```

-continued

```
4861 caagttttag agttcggctg atgcatctgc ctggggacct cagatgggag gagtgtgtca
4921 gttgtacccc gacagaaatg tctctgggat ctgtggctgg cttgcccgg gcatctctcc
4981 tttaagctca agttttgaac tctctgcggt tttccacccc tgccttctca gccacatgct
5041 tttggcctta aacgctcagt cttgtggagt tcaactctgt caaacgattg aaagggcat
5101 ccatttccag atctttggca ttttccccgc gctgactctt tgatgatcct tcactgtggc
5161 cttttcaagc tcagctgttc ctgttgtatt tgagacgagg gtgagggaat gtggtggcca
5221 caaagaaca gggacttgca gcacaaatgt cacttctgtc tcccttttca gtggtagcac
5281 ggaggaggag gtgctgcgtt ggagggaggg gatcctccag gagctctctg gagcccatct
5341 aggaagctag agtgtgtggc ccgccaggag ctcaggaagg atacagccac tgtcgcaggg
5401 gaaagtgttt gcttcccgtg gagccaagcg cccaagactc tccgtatcct tcaccctgac
5461 agtttaactt cagcgtttct ctgtgcagtt gcggtcacca tgggtgagca ctgtctgtgc
5521 acgtgccagg gaggagatgg ctgggaccac tgcacaggag ggcgcagcct ggcgtcgcca
5581 tgaaagttgt ctctgtgcca tctctccggt ccttgaggag agcccagaaa gattttagga
5641 cccaggaggt gcttttcctc cagctgttgc cagtgtcctt ctgagcctgg attctccggg
5701 gatttccgtc gtggtggatg gacttcacat cagcagcagt tctggtacag aattgtaatg
5761 tgttttcatt tctctgtagg attcacctct caccagcgtc tgtcttaaag gtagggccaa
5821 tttcatggag cattttcctg tgtgtgtcct tgttgctttt gccagaaaaa gtggatttga
5881 catgcgtgcc ccgatgccac catagcccct aggccaacaa tgtcatggtc taaacaccaa
5941 aaagtgatgc cccgcattcc ttccctggat ggtaccgttt cttctccgtc tctctttgat
6001 gattctttgg gaccaaagtc ctctccttag tgcgcctact tcctgtgggc atcatgccac
6061 ttggaactta ttggaactgg cccggggagac tctgcagtct gcgccgtttg aaaaccctga
6121 gaaagagatg ccacctcaac ttgaatcatg acagcccatc gctcagtctc accctaaact
6181 catggagctt gtttcagctc ctcacttctt gactgtattt gtactatgtt gaaaaaatat
6241 cctgtccaca aagacataag cctaacaacc tagaaaaaca acagggtact actggcatta
6301 cagaacttct ttgcctttca aaacaaaagc aaaacacagt gaacttcacc acggagctgc
6361 acagcgtggg gaactcatcc atcactttca aaattagagt catttgatcc aagttggagt
6421 cagacacagt atttgagctg cacggcttct gggttctccc accttatttg atcatattcg
6481 aaagattatt tcctgtgttt gctttgattt gttcctcagt acattaaaat gatccacacc
6541 ttgaacactg ccctctctag aaggttgatt ttgatcagcc ttttgaagat gggtgtcgtt
6601 tccctaactt atctcacaga attttgagtg ttgtatttgg caagttctga gatttgcctt
6661 ctgtcttatg ccaaacaccc ctttctaaga gctgtccccg cttagtttta gaagtactag
6721 gggttttcat acttatttta tagaacaccc atttatattt atttctgtat atagaactaa
6781 aaaaaacagt agtgttaaaa atcttttgttg tggtttgagc atctttgctg cttttggatt
6841 gagatggcga atcaaggctt cacttcctct ctcttctgtc tttagaaagc tgtgatcgtg
6901 cgtgcaatta tttgaaaggc aacatagtca attaagaaac ctgtagttgt taaggaagaa
6961 attgttggca agatatccat actgcccata tctcgttggg gcaataatta aatagcaaag
7021 gaaatctgta ttggcaacta ttataattca ataattcttt tgtttactgc ccttttctgt
7081 tcaagaattt tctggaaatt actcccttc acatggttga actcttaagt tgaccagttc
7141 tcatagctct atcactagaa tggttttgcag ataccccaaa catactatga taaaatcaaa
7201 ttgtgctact tttgacccat gtaatttacc taaaagttgt aattgctgac agagtactgc
7261 cttgaatttt ggtttaaaac ctctctagtt tcaatgacaa gtaacaactc aaataattcc
```

```
-continued
7321 atattgtttg aggaagaggc cataatcctt ctgaattgtt ggcactaagt aatgggattt 7381 ggcccagtaa gtatgacggt cgtgtcgcct aaccaacgca gagcagtgct ttttgtgtgg 7441 ctgaagcgat gtgctgacga aaaaaggaaa attctaggac aatcgttggc taaaaatcac 7501 cttaggatga aaaatttgag gcaaattttt ttaaatgaca gaaaaagata atcatctcac 7561 ttgcttgaaa caggagccag catgatctct ggaagcatca actatccctc gtcgtgattg 7621 ttgaaagctc tttcactgtt ttgcattcta gtttgaatag tttgtattga aattggattc 7681 ctatcttgtg tatgttttg gtgcgtaaaa gggaaaaatt ggtgtcatta cttttgaaat 7741 ttgcaggacg aagggcatgc ttttggtttg ctgtaagatt gtattctgta tatatgtttt 7801 catgtaaata aatgaaaatc tatatcagag ttatatttta attttattc taaatgaaaa 7861 aaacccttt tacttcaaaa aaattgtaag ccacattgtt aataaagtaa aaataaattc 7921 ta
```

By "Smoc1 polypeptide" (SPARC related modular calcium binding 1) is meant a protein having at least about 85% amino acid identity to the sequence provided at NCBI Reference Sequence: NP_001030024, or a fragment thereof. An exemplary Smoc1 amino acid sequence is provided below:

```
  1  mlparcarll tphlllvlvq lsparghrtt gprflisdrd pqcnlhcsrt qpkpicasdg 61  rsyesmceyq rakcrdptlg vvhrgrckda gqskcrlera qaleqakkpq eavfvpecge 121  dgsftqvqch tytgycwcvt pdgkpisgss vqnktpvcsg svtdkplsqg nsgrkddgsk 181  ptptmetqpv fdgdeitapt lwikhlvikd sklnntnirn sekvyscdqe rqsaleeaqq 241  npregivipe capgglykpv qchqstgycw cvlvdtgrpl pgtstryvmp scesdarakt 301  teaddpfkdr elpgcpegkk mefitsllda lttdmvqain saaptgggrf sepdpshtle 361  ervvhwyfsq ldsnssndin kremkpfkry vkkkakpkkc arrftdycdl nkdkvislpe 421  lkgclgvske vgrlv
```

By "Smoc1 polynucleotide" is meant a nucleic acid molecule encoding a Smoc1 polypeptide. An exemplary Smoc1 polynucleotide sequence is provided at XM_005267995.1, which is reproduced below:

```
  1  ataacgggaa ttcccatggc ccgggctcag gcgtccaacc tgctgccgcc tgggcccgc 61  cgagcggagc tagcgccgcg cgcagagcac acgctcgcgc tccagctccc ctcctgcgcg 121  gttcatgact gtgtccctg accgcagcct ctgcgagccc ccgccgcagg accacggccc 181  gctccccgcc gccgcgaggg ccccgagcga aggaaggaag ggaggcgcgc tgtgcgcccc 241  gcggagcccg cgaaccccgc tcgctgccgg ctgcccagcc tggctggcac catgctgccc 301  gcgcgctgcg cccgcctgct cacgccccac ttgctgctgg tgttggtgca gctgtccct 361  gctcgcggcc accgcaccac aggccccagg tttctaataa gtgaccgtga cccacagtgc 421  aacctccact gctccaggac tcaacccaaa cccatctgtg cctctgatgg caggtcctac 481  gagtccatgt gtgagtacca gcgagccaag tgccgagacc cgaccctggg cgtggtgcat 541  cgaggtagat gcaaagatgc tggccagagc aagtgtcgc tggagcgggc tcaagccctg 601  gagcaagcca agaagcctca ggaagctgtg tttgtcccag agtgtggcga ggatggctcc 661  tttacccagg tgcagtgcca tacttacact gggtactgct ggtgtgtcac cccggatggg 721  aagcccatca gtggctcttc tgtgcagaat aaaactcctg tatgttcagg ttcagtcacc
```

-continued

```
 781 gacaagccct tgagccaggg taactcagga aggaaagtct cctttcgatt cttttttaacc 841 ctcaattcag atgacgggtc taagccgaca cccacgatgg agacccagcc ggtgttcgat 901 ggagatgaaa tcacagcccc aactctatgg attaaacact tggtgatcaa ggactccaaa 961 ctgaacaaca ccaacataag aaattcagag aaagtctatt cgtgtgacca ggagaggcag 1021 agtgccctgg aagaggccca gcagaatccc cgtgagggta ttgtcatccc tgaatgtgcc 1081 cctgggggac tctataagcc agtgcaatgc caccagtcca ctggctactg ctggtgtgtg 1141 ctggtggaca cagggcgccc gctgcctggg acctccacac gctacgtgat gcccagttgt 1201 gagagcgacg ccagggccaa gactacagag gcggatgacc ccttcaagga cagggagcta 1261 ccaggctgtc cagaagggaa gaaaatggag tttatcacca gcctactgga tgctctcacc 1321 actgacatgg ttcaggccat taactcagca gcgcccactg gaggtgggag gttctcagag 1381 ccagacccca gccacaccct ggaggagcgg gtagtgcact ggtatttcag ccagctggac 1441 agcaatagca gcaacgacat taacaagcgg gagatgaagc ccttcaagcg ctacgtgaag 1501 aagaaagcca agcccaagaa atgtgcccgg cgtttcaccg actactgtga cctgaacaaa 1561 gacaaggtca tttcactgcc tgagctgaag ggctgcctgg gtgttagcaa agaagtagga 1621 cgcctcgtct aaggagcaga aaacccaagg gcaggtggag agtccaggga ggcaggatgg 1681 atcaccagac acctaacctt cagcgttgcc catggccctg ccacatcccg tgtaacataa 1741 gtggtgccca ccatgtttgc acttttaata actcttactt gcgtgttttg ttttggttt 1801 cattttaaaa caccaatatc taataccaca gtgggaaaag gaaagggaag aaagacttta 1861 ttctctctct tattgtaagt ttttggatct gctactgaca acttttagag ggttttgggg 1921 gggtggggga gggtgttgtt ggggctgaga agaaagagat ttatatgctg tatataaata 1981 tatatgtaaa ttgtatagtt cttttgtaca ggcattggca ttgctgtttg tttatttctc 2041 tccctctgcc tgctgtgggt ggtgggcact ctggacacat agtccagctt tctaaaatcc 2101 aggactctat cctgggccta ctaaacttct gtttggagac tgacccttgt gtataaagac 2161 gggagtcctg caattgtact gcggactcca cgagttcttt tctggtggga ggactatatt 2221 gccccatgcc attagttgtc aaaattgata agtcacttgg ctctcggcct tgtccaggga 2281 ggttgggcta aggagagatg gaaactgccc tgggagagga agggagtcca gatcccatga 2341 atagcccaca caggtaccgg ctctcagagg gtccgtgcat tcctgctctc cggaccccca 2401 aagggcccag cattggtggg tgcaccagta tcttagtgac cctcggagca aattatccac 2461 aaaggatttg cattacgtca ctcgaaacgt tttcatccat gcttagcatc tactctgtat 2521 aacgcatgag aggggaggca aagaagaaaa agacacacag aagggccttt aaaaaagtag 2581 atatttaata tctaagcagg ggaggggaca ggacagaaag cctgcactga ggggtgcggt 2641 gccaacaggg aaactcttca cctccctgca aacctaccag tgaggctccc agagacgcag 2701 ctgtctcagt gccaggggca gattgggtgt gacctctcca ctcctccatc tcctgctgtt 2761 gtcctagtgg ctatcacagg cctgggtggg tgggttgggg gaggtgtcag tcaccttgtt 2821 ggtaacacta agttgtttt gttggttttt taaaaaccca atactgaggt tcttcctgtt 2881 ccctcaagtt ttcttatggg cttccaggct ttaagctaat tccagaagta aaactgatct 2941 tgggtttcct attctgcctc ccctagaagg gcaggggtga taacccagct acagggaaat 3001 cccggcccag ctttccacag gcatcacagg catcttccgc ggattctagg gtgggctgcc 3061 cagccttctg gtctgaggcg cagctccctc tgcccaggtg ctgtgcctat tcaagtggcc 3121 ttcaggcaga gcagcaagtg gcccttagcg cccttccca taagcagctg tggtggcagt 3181 gagggaggtt gggtagccct ggactggtcc cctcctcaga tcacccttgc aaatctggcc
```

-continued

```
3241 tcatcttgta ttccaacccg acatccctaa aagtacctcc acccgttccg ggtctggaag 3301 gcgttggcac cacaagcact gtccctgtgg gaggagcaca accttctcgg gacaggatct 3361 gatggggtct tgggctaaag gaggtccctg ctgtcctgga gaaagtccta gaggttatct 3421 caggaatgac tggtggccct gccccaacgt ggaaaggtgg gaaggaagcc ttctcccatt 3481 agccccaatg agagaactca acgtgccgga gctgagtggg ccttgcacga gacactggcc 3541 ccactttcag gcctggagga agcatgcaca catggagacg gcgcctgcct gtagatgttt 3601 ggatcttcga gatctcccca ggcatcttgt ctcccacagg atcgtgtgtg taggtggtgt 3661 tgtgtggttt tcctttgtga aggagagagg gaaactattt gtagcttgtt ttataaaaaa 3721 taaaaaatgg gtaaatcttg
```

By "tri-methylated histone H3 at lysine 27 (H3K27me3)" is meant the trimethylation of lysine 27 on histone H3 protein subunit. The H3K27me3 modification is generally associated with gene repression.

By "agent" is meant a peptide, nucleic acid molecule, or small compound.

By "allele" is meant one of two or more alternative forms of a gene that are found at the same place on a chromosome.

By "alteration" is meant a change (increase or decrease) in the expression levels or activity of a gene or polypeptide as detected by standard art known methods such as those described herein. As used herein, an alteration includes a 10% change in expression levels, preferably a 25% change, more preferably a 40% change, and most preferably a 50% or greater change in expression levels."

By "ameliorate" is meant decrease, suppress, attenuate, diminish, arrest, or stabilize the development or progression of a disease.

In this disclosure, "comprises," "comprising," "containing" and "having" and the like can have the meaning ascribed to them in U.S. patent law and can mean "includes," "including," and the like; "consisting essentially of" or "consists essentially" likewise has the meaning ascribed in U.S. patent law and the term is open-ended, allowing for the presence of more than that which is recited so long as basic or novel characteristics of that which is recited is not changed by the presence of more than that which is recited, but excludes prior art embodiments.

"Detect" refers to identifying the presence, absence or amount of the analyte to be detected.

By "disease" is meant any condition or disorder that damages, or interferes with the normal function of a cell, tissue, or organ. Examples of disorders include those associated with undesirable repression of an allele by H3K27me3-dependent imprinting. Microphthalmia exemplary disorder associated with H3K27me3-dependent imprinting relating to imprinting disorders.

By "DNA" is meant deoxyribonucleic acid. In various embodiments, the term DNA refers to genomic DNA, recombinant DNA, or cDNA. In particular embodiments, the DNA comprises a "target region." DNA libraries contemplated herein include genomic DNA libraries, and cDNA libraries constructed from RNA, e.g., an RNA expression library. In various embodiments, the DNA libraries comprise one or more additional DNA sequences and/or tags.

By "effective amount" is meant the amount of a required to ameliorate the symptoms of a disease relative to an untreated patient. The effective amount of active compound(s) used to practice the present invention for therapeutic treatment of a disease varies depending upon the manner of administration, the age, body weight, and general health of the subject. Ultimately, the attending physician or veterinarian will decide the appropriate amount and dosage regimen. Such amount is referred to as an "effective" amount.

By "fragment" is meant a portion of a polypeptide or nucleic acid molecule. This portion contains, preferably, at least 10%, 20%, 30%, 40%, 50%, 60%, 70%, 80%, or 90% of the entire length of the reference nucleic acid molecule or polypeptide. A fragment may contain 10, 20, 30, 40, 50, 60, 70, 80, 90, or 100, 200, 300, 400, 500, 600, 700, 800, 900, or 1000 nucleotides or amino acids.

The terms "isolated," "purified," or "biologically pure" refer to material that is free to varying degrees from components which normally accompany it as found in its native state. "Isolate" denotes a degree of separation from original source or surroundings. "Purify" denotes a degree of separation that is higher than isolation. A "purified" or "biologically pure" protein is sufficiently free of other materials such that any impurities do not materially affect the biological properties of the protein or cause other adverse consequences. That is, a nucleic acid or peptide of this invention is purified if it is substantially free of cellular material, viral material, or culture medium when produced by recombinant DNA techniques, or chemical precursors or other chemicals when chemically synthesized. Purity and homogeneity are typically determined using analytical chemistry techniques, for example, polyacrylamide gel electrophoresis or high performance liquid chromatography. The term "purified" can denote that a nucleic acid or protein gives rise to essentially one band in an electrophoretic gel. For a protein that can be subjected to modifications, for example, phosphorylation or glycosylation, different modifications may give rise to different isolated proteins, which can be separately purified.

By "isolated polynucleotide" is meant a nucleic acid (e.g., a DNA) that is free of the genes which, in the naturally-occurring genome of the organism from which the nucleic acid molecule of the invention is derived, flank the gene. The term therefore includes, for example, a recombinant DNA that is incorporated into a vector; into an autonomously replicating plasmid or virus; or into the genomic DNA of a prokaryote or eukaryote; or that exists as a separate molecule (for example, a cDNA or a genomic or cDNA fragment produced by PCR or restriction endonuclease digestion) independent of other sequences. In addition, the term includes an RNA molecule that is transcribed from a DNA molecule, as well as a recombinant DNA that is part of a hybrid gene encoding additional polypeptide sequence.

By an "isolated polypeptide" is meant a polypeptide of the invention that has been separated from components that naturally accompany it. Typically, the polypeptide is isolated when it is at least 60%, by weight, free from the proteins and naturally-occurring organic molecules with which it is naturally associated. Preferably, the preparation is at least 75%, more preferably at least 90%, and most preferably at least 99%, by weight, a polypeptide of the invention. An isolated polypeptide of the invention may be obtained, for example, by extraction from a natural source, by expression of a recombinant nucleic acid encoding such a polypeptide; or by chemically synthesizing the protein. Purity can be measured by any appropriate method, for example, column chromatography, polyacrylamide gel electrophoresis, or by HPLC analysis.

Ranges provided herein are understood to be shorthand for all of the values within the range. For example, a range of 1 to 50 is understood to include any number, combination of numbers, or sub-range from the group consisting 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50.

By "reduces" is meant a negative alteration of at least 10%, 25%, 50%, 75%, or 100%.

By "reference" is meant a standard or control condition.

A "reference sequence" is a defined sequence used as a basis for sequence comparison. A reference sequence may be a subset of or the entirety of a specified sequence; for example, a segment of a full-length cDNA or gene sequence, or the complete cDNA or gene sequence. For polypeptides, the length of the reference polypeptide sequence will generally be at least about 16 amino acids, preferably at least about 20 amino acids, more preferably at least about 25 amino acids, and even more preferably about 35 amino acids, about 50 amino acids, or about 100 amino acids. For nucleic acids, the length of the reference nucleic acid sequence will generally be at least about 50 nucleotides, preferably at least about 60 nucleotides, more preferably at least about 75 nucleotides, and even more preferably about 100 nucleotides or about 300 nucleotides or any integer thereabout or therebetween.

Nucleic acid molecules useful in the methods of the invention include any nucleic acid molecule that encodes a polypeptide of the invention or a fragment thereof. Such nucleic acid molecules need not be 100% identical with an endogenous nucleic acid sequence, but will typically exhibit substantial identity. Polynucleotides having "substantial identity" to an endogenous sequence are typically capable of hybridizing with at least one strand of a double-stranded nucleic acid molecule. Nucleic acid molecules useful in the methods of the invention include any nucleic acid molecule that encodes a polypeptide of the invention or a fragment thereof. Such nucleic acid molecules need not be 100% identical with an endogenous nucleic acid sequence, but will typically exhibit substantial identity. Polynucleotides having "substantial identity" to an endogenous sequence are typically capable of hybridizing with at least one strand of a double-stranded nucleic acid molecule. By "hybridize" is meant pair to form a double-stranded molecule between complementary polynucleotide sequences (e.g., a gene described herein), or portions thereof, under various conditions of stringency. (See, e.g., Wahl, G. M. and S. L. Berger (1987) Methods Enzymol. 152:399; Kimmel, A. R. (1987) Methods Enzymol. 152:507).

For example, stringent salt concentration will ordinarily be less than about 750 mM NaCl and 75 mM trisodium citrate, preferably less than about 500 mM NaCl and 50 mM trisodium citrate, and more preferably less than about 250 mM NaCl and 25 mM trisodium citrate. Low stringency hybridization can be obtained in the absence of organic solvent, e.g., formamide, while high stringency hybridization can be obtained in the presence of at least about 35% formamide, and more preferably at least about 50% formamide. Stringent temperature conditions will ordinarily include temperatures of at least about 30° C., more preferably of at least about 37° C., and most preferably of at least about 42° C. Varying additional parameters, such as hybridization time, the concentration of detergent, e.g., sodium dodecyl sulfate (SDS), and the inclusion or exclusion of carrier DNA, are well known to those skilled in the art. Various levels of stringency are accomplished by combining these various conditions as needed. In a preferred: embodiment, hybridization will occur at 30° C. in 750 mM NaCl, 75 mM trisodium citrate, and 1% SDS. In a more preferred embodiment, hybridization will occur at 37° C. in 500 mM NaCl, 50 mM trisodium citrate, 1% SDS, 35% formamide, and 100.mu.g/ml denatured salmon sperm DNA (ssDNA). In a most preferred embodiment, hybridization will occur at 42° C. in 250 mM NaCl, 25 mM trisodium citrate, 1% SDS, 50% formamide, and 200 µg/ml ssDNA. Useful variations on these conditions will be readily apparent to those skilled in the art.

For most applications, washing steps that follow hybridization will also vary in stringency. Wash stringency conditions can be defined by salt concentration and by temperature. As above, wash stringency can be increased by decreasing salt concentration or by increasing temperature. For example, stringent salt concentration for the wash steps will preferably be less than about 30 mM NaCl and 3 mM trisodium citrate, and most preferably less than about 15 mM NaCl and 1.5 mM trisodium citrate. Stringent temperature conditions for the wash steps will ordinarily include a temperature of at least about 25° C., more preferably of at least about 42° C., and even more preferably of at least about 68° C. In a preferred embodiment, wash steps will occur at 25° C. in 30 mM NaCl, 3 mM trisodium citrate, and 0.1% SDS. In a more preferred embodiment, wash steps will occur at 42 C in 15 mM NaCl, 1.5 mM trisodium citrate, and 0.1% SDS. In a more preferred embodiment, wash steps will occur at 68° C. in 15 mM NaCl, 1.5 mM trisodium citrate, and 0.1% SDS. Additional variations on these conditions will be readily apparent to those skilled in the art. Hybridization techniques are well known to those skilled in the art and are described, for example, in Benton and Davis (Science 196: 180, 1977); Grunstein and Hogness (Proc. Natl. Acad. Sci., USA 72:3961, 1975); Ausubel et al. (Current Protocols in Molecular Biology, Wiley Interscience, New York, 2001); Berger and Kimmel (Guide to Molecular Cloning Techniques, 1987, Academic Press, New York); and Sambrook et al., Molecular Cloning: A Laboratory Manual, Cold Spring Harbor Laboratory Press, New York.

By "substantially identical" is meant a polypeptide or nucleic acid molecule exhibiting at least 50% identity to a reference amino acid sequence (for example, any one of the amino acid sequences described herein) or nucleic acid sequence (for example, any one of the nucleic acid sequences described herein). Preferably, such a sequence is at least 60%, more preferably 80% or 85%, and more preferably 90%, 95% or even 99% identical at the amino acid level or nucleic acid to the sequence used for comparison.

Sequence identity is typically measured using sequence analysis software (for example, Sequence Analysis Software Package of the Genetics Computer Group, University of Wisconsin Biotechnology Center, 1710 University Avenue, Madison, Wis. 53705, BLAST, BESTFIT, GAP, or PILEUP/PRETTYBOX programs). Such software matches identical or similar sequences by assigning degrees of homology to various substitutions, deletions, and/or other modifications. Conservative substitutions typically include substitutions within the following groups: glycine, alanine; valine, isoleucine, leucine; aspartic acid, glutamic acid, asparagine, glutamine; serine, threonine; lysine, arginine; and phenylalanine, tyrosine. In an exemplary approach to determining the degree of identity, a BLAST program may be used, with a probability score between $e^{-3}$ and $e^{-100}$ indicating a closely related sequence.

By "Somatic Cell Nuclear Transfer" or "SCNT" is meant the transfer of a donor nucleus from a somatic cell into an enucleated oocyte. The process can be used in either reproductive or therapeutic cloning. By "subject" is meant a mammal, including, but not limited to, a human or non-human mammal, such as an agriculturally significant mammal (e.g., bovine, equine, ovine), a pet (e.g., canine, feline), or a rare or endangered mammal (e.g., panda).

As used herein, the terms "treat," "treating," "treatment," and the like refer to reducing or ameliorating a disorder and/or symptoms associated therewith. It will be appreciated that, although not precluded, treating a disorder or condition does not require that the disorder, condition or symptoms associated therewith be completely eliminated.

Unless specifically stated or obvious from context, as used herein, the term "or" is understood to be inclusive. Unless specifically stated or obvious from context, as used herein, the terms "a", "an", and "the" are understood to be singular or plural.

Unless specifically stated or obvious from context, as used herein, the term "or" is understood to be inclusive. Unless specifically stated or obvious from context, as used herein, the terms "a", "an", and "the" are understood to be singular or plural (i.e., at least one). By way of example, "an element" means one element or more than one element.

Unless specifically stated or obvious from context, as used herein, the term "about" is understood as within a range of normal tolerance in the art, for example within 2 standard deviations of the mean. About can be understood as within 10%, 9%, 8%, 7%, 6%, 5%, 4%, 3%, 2%, 1%, 0.5%, 0.1%, 0.05%, or 0.01% of the stated value. Unless otherwise clear from context, all numerical values provided herein are modified by the term about.

The recitation of a listing of chemical groups in any definition of a variable herein includes definitions of that variable as any single group or combination of listed groups. The recitation of an embodiment for a variable or aspect herein includes that embodiment as any single embodiment or in combination with any other embodiments or portions thereof.

Any compositions or methods provided herein can be combined with one or more of any of the other compositions and methods provided herein.

BRIEF DESCRIPTION OF THE DRAWINGS

FIG. 1A provides a schematic for identifying parental allele-specific DHSs in zygotes. IVF, in vitro fertilization. PN, pronucleus. FIG. 1B depicts a heat map showing bi-allelic, paternal allele-specific (Ps-DHSs), and maternal allele-specific DHSs (Ms-DHSs) in zygotes. Each row represents liDNase-seq (low-input DNase-seq) signal intensity at a DHS±5 kb.

FIG. 1C provides representative androgenesis (AG)- and gynogenesis (GG)-specific differentially expressed genes (DEGs) harboring allelic promoter DHSs in zygotes. Upper panels are genome browser views of DHSs in paternal and maternal pronuclei with biological duplicates. The DHS signal intensity and the genomic length of each view (kb) are indicated at the upper left and the bottom of each panel, respectively. Lower graphs are gene expression levels in AG, GG and α-amanitin-treated (Ama) 2-cell embryos. Error bar, standard deviation of biological duplicates. Note that GG-specific expression of Akap1 and Isl2 is evident after subtraction of maternal pool transcripts.

FIG. 2A-FIG. 2H shows identification of parental allelic DHSs, related to FIG. 1. FIG. 2A provides scatter plots showing the correlation of DHSs between three biological replicates in paternal and maternal pronuclei (PN).

FIG. 2B provides a scatter plot showing bi-allelic DHSs (upper-right), Ps-DHSs (upper-middle left), and Ms-DHSs (left). The cutoffs used to define these DHS groups are indicated.

FIG. 2C provides averaged DHS signals of Ps-DHSs and Ms-DHSs within ±5 kb around DHSs.

FIG. 2D provides genomic distribution of DHSs. Promoters represent ±1 kb around transcriptional start sites (TSSs). 'Random' indicates the percentages of each genomic element of the mouse genome. FIG. 2E. provides percentages of DHSs located at CpG islands (CGIs). Promoters represent ±1 kb around TSSs. The genomic locations of CGIs were described in Kobayashi et al., 2012.

FIG. 2F provides a genome browser view of Ps-DHSs at imprinting control regions (ICRs) of representative imprinted genes. The genomic locations of ICRs were referred in Kobayashi et al., 2012.

FIG. 2G provides a list of genes harboring promoter Ps-DHSs or Ms-DHSs in zygotes.

FIG. 2H provides a genome browser view of representative allelic DHSs at gene promoters not previously known to be imprinted.

FIG. 3A-FIG. 3F shows correlation between allelic ZGA in two-cell embryos and allelic DHSs in zygotes. The experimental scheme, RNA-seq reproducibility and analysis scheme are related to FIG. 1

FIG. 3A provides a schematic for identifying parental allele-specific gene expression at ZGA. Androgenetic (AG) embryos and gynogenetic (GG) embryos were produced by pronuclear transfer. AG 2-cell embryos contain paternally-expressed nascent transcripts and maternally-stored transcripts. GG 2-cell embryos contain maternally-expressed nascent transcripts and maternally-stored transcripts. α-amanitin-treated (Ama) 2-cell embryos contain maternally-stored transcripts only.

FIG. 3B provides a scatter plot showing the correlation between biological duplicate of 2-cell RNA-seq samples.

FIG. 3C provides a flowchart for avoiding maternally-stored transcripts and identifying nascent allelic transcripts at ZGA.

FIG. 3D provides a scatterplot of nascent transcripts in AG and GG 2-cell embryos. For each gene, the FPKM value in Ama embryos was subtracted from that in AG and GG embryos, respectively. AG- and GG-specific differentially expressed genes (DEGs) (FC>10) are indicated either below the dashed-line or above the dashed-line, respectively. Known imprinted genes are indicated with their associated name below the dashed-line.

FIG. 3E and FIG. 3F provide a scatterplot showing DHS allelic bias at promoters (±0.5 kb at TSS) of androgenesis-(FIG. 3E) and gynogenesis-(FIG. 3F) specific differentially expressed genes (DEGs). FC>2 was considered as 'bias' dark gray in FIGS. 3E and 3F.

FIG. 4A provides a scatter plot showing the correlation between three biological replicates of liDNase-seq for germinal vesicle (GV) nuclei isolated from fully-grown oocytes.

FIG. 4B provides a genome browser view of sperm DHSs that are passed on to paternal PNs of zygotes. The nearest gene names are indicated at the top of each panel.

FIG. 4C provides a heat map showing Ps-DHSs. Each row represents liDNase-seq signal intensity at a DHS±5 kb. Note that Ps-DHSs are largely absent in both sperm or oocytes.

FIG. 4D provides a genome browser view of representative Ps-DHSs.

FIG. 4E provides a heat map showing Ms-DHSs. Note that Ms-DHSs are mostly already present in oocytes.

FIG. 4F provides a genome browser view of representative Ms-DHSs.

FIG. 4G provides a heat map showing biallelic DHSs.

FIG. 4H provides a genome browser view of representative biallelic DHSs.

FIG. 5A-FIG. 5J shows distinct epigenetic features of Kdm6b- and Kdm4d-affected Ps-DHSs, related to FIG. 6.

FIG. 5A provides a pie chart showing percentages of Ps-DHSs that overlap (black) or associated (gray) with oocyte-gametic differentially methylated regions (gDMRs) within ±100 kb. Oocyte gDMR was defined by >80% methylation in oocytes and <20% methylation in sperm.

FIG. 5B provides a pie chart showing the percentages of Ps-DHSs organized based on their oocyte DNA methylation levels.

FIG. 5C provides boxplots showing the H3K27me3 signal levels at Ps-DHSs±1 kb in gametes (left panel) and zygotes (right panel). Ps-DHSs were divided into oocyte DNA hypomethylated (0-20%, n=296) and hypermethylated groups (80-100%, n=305). Middle lines in the boxes represent the medians. Box edges and whiskers indicate the 25th/75th and 2.5th/97.5th percentiles, respectively.

FIG. 5D provides representative images of Kdm6b- or Kdm4d-injected zygotes stained with anti-Flag antibody, using non-injected zygotes as negative controls.

FIG. 5E provides representative images of zygotes stained with anti-H3K27me3 antibody. M, maternal pronucleus. P, paternal pronucleus. The bar graph on the right represents relative immunostaining signal intensity of maternal pronuclei. The averaged signal of non-injected zygotes was set as 1.0. The total numbers of embryos examined were 8 (No injection), 13 (Kdm6b$^{WT}$), and 10 (Kdm6b$^{MUT}$). Error bars indicate SD. ***, p<0.001 (two-tailed Student t-test). N. S, statistically not significant.

FIG. 5F provides representative images of zygotes stained with anti-H3K9me3 antibody. The bar graph on right represents relative immunostaining signal intensity in the maternal pronuclei. The averaged signal of non-injected zygotes was set as 1.0. The total numbers of embryos examined were 5 (no-inject), 5 (Kdm4d$^{WT}$), and 7 (Kdm4d$^{MUT}$). Error bars indicate SD. ***, p<0.001 (two-tailed Student t-test). N.S, statistically not significant.

FIG. 5G provides a scatter plot showing the correlation between biological duplicates of liDNase-seq for maternal (Mat) and paternal pronuclei (Pat) of Kdm6b$^{WT}$- and Kdm6b$^{MUT}$-injected zygotes.

FIG. 5H provides a scatter plot showing the correlation between biological duplicates of liDNase-seq for maternal (Mat) and paternal pronuclei (Pat) of Kdm4d$^{WT}$- and Kdm4d$^{MUT}$-injected zygotes.

FIG. 5I provides a genome browser view of representative Ps-DHSs affected by Kdm4d$^{WT}$.

FIG. 5J provides a boxplot showing H3K27me3 signals at Kdm6b- or Kdm4d-affected Ps-DHSs±1 kb in gametes (left panel) and zygotes (right panel). Middle lines in the boxes indicate the medians. Box edges and whiskers indicate the 25th/75th and 2.5th/97.5th percentiles, respectively.

FIG. 6A provides a schematic for studying the role of histone methylations in maternal chromatin inaccessibility.

FIG. 6B provides a heat map showing the allelic bias at Ps-DHSs in Kdm6b- or Kdm4d-injected zygotes.

FIG. 6C provides a genome browser view of representative Ps-DHSs affected by Kdm6b$^{WT}$.

FIG. 6D provides pie charts showing Kdm6b- or Kdm4d-affected Ps-DHSs organized based on their oocyte DNA methylation levels.

FIG. 7A provides a schematic for identifying parental allele-specific DHSs in morula embryos.

FIG. 7B provides a heat map showing AG-specific (AG-DHSs) and GG-specific DHSs (GG-DHSs) in morula embryos. Each row represents liDNase-seq signal intensity at a DHS±5 kb.

FIG. 7C provides a scatterplot showing allelic enrichment of H3K27me3 ChIP-seq signal at AG-DHSs±1 kb in inner cell mass (ICM) of blastocyst embryos. AG-DHSs with [RPM>0.5, FC(Mat/Pat)>2] were considered to harbor maternal allele-biased H3K27me3 (dark gray dots).

FIG. 7D provides a heat map showing parental allele-specific gene expression of putative H3K27me3-dependent imprinted genes. Genes expressed in AG morula embryos (RPKM>0.5) are shown. The left column represents the ratio of AG/GG gene expression. The two right columns represent relative gene expression in hybrid morula embryos. BxC; B6/CAST. CxB; CAST/B6. The 4 known non-canonical imprinted genes are indicated in bold. White boxes indicate 'not determined (N.D.)' due to lack of SNP reads (<20 reads).

FIG. 8A provides a scatter plot showing the correlation between biological duplicates of liDNase-seq for AG and GG morula embryos.

FIG. 8B provides averaged SNP-tracked liDNase-seq signal intensity of paternal and maternal alleles in hybrid morula embryos. The data were obtained from morula embryos of a BDF1 and JF1 cross. Plots from the biological duplicates (e.g. BDF1_1 and BDF1_2) are shown. Note that paternal (JF1), but not maternal (BDF1), SNP reads are enriched in AG-DHSs (left panel), while neither SNP reads are enriched in GG-DHSs (right panel).

FIG. 8C provides a genome browser view of DHSs at known imprinting control regions (ICRs).

FIG. 8D provides a pie chart showing AG-DHSs grouped based on their oocyte DNA methylation levels.

FIG. 9A provides a scatter plot showing the correlation between biological duplicates of RNA-seq samples.

FIG. 9B provides a scatterplot of gene expression levels in AG- and GG morula embryos. AG- and GG-specific differentially expressed genes (DEGs) (FC>10) are indicated either below the dashed-line or above the dashed-line, respectively. Paternally-expressed known imprinted genes are below the dashed-line and include their associated gene names. A maternally-expressed known gene, Meg3, is indicated above the dashed-line.

FIG. 9C provides genome browser views of allelic H3K27me3 levels in non-canonical imprinted genes. Sp; sperm. Oo; MII-stage oocyte. ICM; inner cell mass of blastocysts. Paternal (Pat) and maternal (Mat) allele signals in 1-cell and ICM were based on SNP analyses.

FIG. 9D provides genome browser views of allelic H3K27me3 levels in representative canonical imprinted genes. Known ICRs are indicated at the bottom of each canonical imprinted gene.

FIG. 10A provides a schematic for studying the role of H3K27me3 in maternal allele repression. $Kdm6b^{MUT}$-injected parthenogenetic (PG) embryos were used as a negative control.

FIG. 10B provides relative gene expression levels (log scale) of putative H3K27me3-dependent imprinted genes. Shown are genes expressed in AG morula embryos (RPKM>0.5) and significantly derepressed by $Kdm6b^{WT}$. The expression level of gynogenetic (GG) morula embryos was set as 1. The genes are ordered by statistical significance (p-values by DEseq) between $Kdm6b^{WT}$ and $Kdm6b^{MUT}$ samples. Arrows indicate known non-canonical imprinted genes.

FIG. 10C provides a heat map showing parental allele-specific gene expression of putative H3K27me3-dependent imprinted genes in $Kdm6b^{WT}$- and $Kdm6b^{MUT}$-injected hybrid morula embryos. Among the 28 genes listed in FIG. 3d, those with >10 SNP reads in both samples are shown. Known non-canonical imprinted genes are indicated in bold. Allelic expression levels of representative canonical imprinted genes are shown at the bottom.

FIG. 10D provides a heat map showing the levels of chromatin accessibility at AG-DHSs in $Kdm6b^{WT}$- and $Kdm6b^{MUT}$-injected morula PG embryos. The DHS signal intensity in AG embryos was set as 100%. AG-DHSs are ordered by $\Delta(Kdm6b^{WT}-Kdm6b^{MUT})$. Known imprinted genes are indicated at right, with non-canonical imprinted genes shown in at the upper right side of the panel in light gray font.

FIG. 10E provides a genome browser view of gain-of-accessibility at AG-DHSs of putative H3K27me3-dependent imprinted genes.

FIG. 11A provides a developmental ratio of $Kdm6b^{WT}$- and $Kdm6b^{MUT}$-injected parthenogenetic (PG) embryos. The total embryo numbers examined were 60 (WT) and 58 (MUT).

FIG. 11B provides a scatter plot showing the correlation between biological duplicates of RNA-seq for $Kdm6b^{WT}$- and $Kdm6b^{MUT}$-injected PG embryos.

FIG. 11C provides relative gene expression levels of canonical imprinted genes that are expressed in AG morula embryos (RPKM>0.5). Note that none are derepressed by $Kdm6b^{WT}$ injection.

FIG. 11D provides a scatter plot showing the correlation between biological duplicates of liDNase-seq for $Kdm6b^{WT}$- and $Kdm6b^{MUT}$-injected PG embryos.

FIG. 11E and FIG. 11F provide wide genome browser views of non-canonical (e) and canonical imprinted genes (f). The arrowheads indicate AG-DHSs at which chromatin accessibility is gained in $Kdm6b^{WT}$-injected PG embryos (shown in FIG. 4e). Known imprinting control regions (ICRs) are indicated above each panel of canonical imprinted genes (f).

FIG. 11G provides a genome browser view of AG-DHSs of representative canonical imprinted genes.

FIG. 12A provides a heat map showing parental allele-specific gene expression of putative H3K27me3-dependent imprinted genes in hybrid blastocyst embryos. BxC; B6/CAST. CxB; CAST/B6. Known non-canonical imprinted genes are indicated in bold in panels a-d. The grayscale scheme in panels a-d follows FIG. 7d.

FIG. 12B provides a heat map showing androgenesis/gynogenesis (AG/GG) relative expression of putative H3K27me3-dependent imprinted genes in ICM and TE of blastocyst embryos. Arrows indicate genes showing a milder level of AG-bias in ICM when compared to TE. White boxes indicate 'not determined' due to low gene expression levels (RPKM<0.5).

FIG. 12C provides a heat map showing parental allele-specific gene expression of putative H3K27me3-dependent imprinted genes in epiblast (EPI), visceral endoderm (VE), and extra-embryonic ectoderm (EXE) of E6.5 embryos. Genes with >20 SNP reads in both reciprocal crosses are shown. BxP; B6/PWK. PxB; PWK/B6. Arrowheads indicate genes showing imprinted expression.

FIG. 12D provides a heat map showing parental allele-specific gene expression of putative H3K27me3-dependent imprinted genes in pure fetus-derived E9.5 placenta cells. Genes with >20 SNP reads in both reciprocal crosses are shown. Arrowheads genes showing imprinted expression.

FIG. 12E provides a model illustrating the fate of H3K27me3-dependent genomic imprinting during development.

FIG. 13A provides expression levels of marker genes for TE (Cdx2) and ICM (Sox2) in the samples.

FIG. 13B provides scatter plot showing the correlation between biological duplicates of the E6.5 epiblast (EPI), visceral endoderm (VE), and extra-embryonic ectoderm (EXE) RNA-seq samples from both B6xPWK and PWKxB6 crosses.

FIG. 13C provides bar graphs showing the expression levels of marker genes for epiblast (Pou5f1 and Nanog), extra-embryonic ectoderm (Elf5 and Gata3), and visceral endoderm genes (Gata6 and Gata4) in the samples.

FIG. 13D provides a heat map showing paternally-expressed genes (PEGs) and maternally-expressed genes (MEGs) in epiblast, visceral endoderm, and extra-embryonic ectoderm of E6.5 embryos. BxP; B6/PWK. PxB; PWK/B6. All genes showing parental allele-specific expression (FC>2 in both BxP and PxB) in each sample are shown. Genes not previously known to be imprinted are indicated in bold.

FIG. 13E provides a genome browser view of RNA-seq data of newly identified imprinted genes. D7Ertd715e and Smoc1 are paternally expressed, and Mas1 is maternally expressed. EXE, extra-embryonic ectoderm. VE, visceral endoderm.

FIG. 14A provides an experimental scheme of placenta cell purification. Sperm or oocytes were collected from B6$^{GFP}$ mice, and in vitro fertilized with the counterparts collected from the PWK strain. Embryos were transplanted into surrogate mothers. The placentae were harvested at E9.5, and dissociated into single cells by trypsin treatment before FACS sorting of GFP-positive cells.

FIG. 14B provides a scatter plot showing the correlation between biological duplicates of RNA-seq samples.

FIG. 14C provides total numbers of the paternal and maternal SNP reads in the purified placental cells.

FIG. 15A provides a heat map showing paternally-expressed genes (PEGs) and maternally-expressed genes (MEGs) in E9.5 placentae. BxP; B6/PWK. PxB; PWK/B6. All genes exhibiting parental allele-specific expression (FC>2 in both BxP and PxB) are shown. Genes not previously known to be imprinted are indicated in bold.

FIG. 15B provides a genome browser view of RNA-seq data of newly identified imprinted genes. D7Ertd715e and Smoc1 are paternally expressed, and Cbx7 and Thbs2 are maternally expressed.

FIG. 16A provides a genome browser view of the H3K27me3 enrichment in gametes and growing oocytes, as well as DNaseI-seq signals and DNA methylation levels in GV oocytes at the Xist locus. The top center bar indicates the maternal H3K27me3 domain coating Xist. The H3K27me3 ChIP-seq, DNaseI-seq, and DNA methylome datasets were from (Zheng et al., 2016), (Inoue et al., 2017), and (Kobayashi et al., 2012), respectively. Oo, MII oocyte. Sp, sperm. 7d and 14d indicate growing oocytes collected from 7- and 14-day old females, respectively. GV, fully-grown GV-stage oocytes collected from 8-week old females.

FIG. 16B provides a genome browser view of the allelic H3K27me3 in 1-cell, 2-cell, and blastocyst embryos at the Xist locus. The highlighted square indicates a computationally determined region where the maternal allele-biased enrichment of H3K27me3 is retained in blastocyst embryos. Mat, maternal chromatin. Pat, paternal chromatin. The H3K27me3 ChIP-seq datasets were from (Zheng et al., 2016).

FIG. 17A provides an experimental scheme for addressing the role of H3K27me3 in maternal Xist repression during preimplantation development.

FIG. 17B provides representative images of Xist RNA FISH (top row, light grey) in Kdm6b-injected morula embryos. The gender of each embryo was assessed by simultaneous DNA FISH using a green fluorescent BAC probe containing the Rnf12 locus on the X chromosome (middle row, arrow).

FIG. 17C and FIG. 17D provide the ratio of blastomeres showing the indicated number of Xist RNA clouds in male (FIG. 17C) and female (FIG. 17D) morula embryos. Each bar represents an individual embryo. The numbers of embryos examined were 19 (Kdm6b$^{WT}$) and 35 (Kdm6b$^{MUT}$) males and 34 (Kdm6b$^{WT}$) and 35 (Kdm6b$^{MUT}$) females.

FIG. 18A provides a box plot showing the relative expression of genes on individual maternal chromosomes between Kdm6b$^{MUT}$- and Kdm6b$^{WT}$-injected blastocysts. Genes with enough SNP reads (RPM>0.5) were analyzed. Middle lines in the boxes represent the medians. Box edges and whiskers indicate the 25th/75th and 2.5th/97.5th percentiles, respectively. ***, p<0.001 (Mann-Whitney-Wilcoxon Test).

FIG. 18B and FIG. 18C provide the relative expression levels of Xm-linked genes between Kdm6b$^{WT}$ and Kdm6b$^{MUT}$ injected blastocyst embryos. Each dot represents an individual gene showing enough SNP reads (RPM>0.5). Panel c shows known escapees, and panel b shows the rest of genes.

FIG. 19A provides representative images of zygotes stained with anti-H3K27me3 antibody. M, maternal pronucleus. P, paternal pronucleus.

FIG. 19B provides relative immunostaining signal intensity of maternal pronuclei. The averaged signal of non-injected zygotes was set as 1.0. The total numbers of embryos examined were 8 (No injection), 13 (Kdm6b$^{WT}$), and 10 (Kdm6b$^{MUT}$). Error bars indicate SD. ***, p<0.001 (two-tailed Student t-test). N.S, statistically not significant.

FIG. 20A provides representative images of zygotes stained with anti-H3K9me3 antibody. M, maternal pronucleus. P, paternal pronucleus.

FIG. 20B provides relative immunostaining signal intensity in the maternal pronuclei. The averaged signal intensity of non-injected zygotes was set as 1.0. The total numbers of embryos examined were 5 (no injection), 5 (Kdm4d$^{WT}$), and 7 (Kdm4d$^{MUT}$). Error bars indicate SD. ***, p<0.001 (two-tailed Student t-test). N.S, statistically not significant.

FIG. 20C provides representative images of Xist RNA FISH (magenta) in Kdm4b-injected morula embryos. The gender of each embryo was assessed by simultaneous DNA FISH using a green fluorescent BAC probe containing the Rnf12 locus on the X chromosome (arrow).

FIG. 20D and FIG. 20E provide the ratio of blastomeres that show the indicated number of Xist RNA clouds in male (FIG. 20D) and female (FIG. 20E) morula embryos. Each bar represents an individual embryo. The numbers of embryos examined were 9 (Kdm4d$^{WT}$) and 12 (Kdm4d$^{MUT}$) males and 9 (Kdm4d$^{WT}$) and 15 (Kdm4d$^{MUT}$) females.

DETAILED DESCRIPTION

Figure 1A:
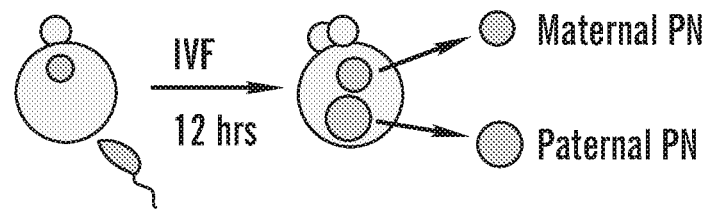
FIG. 1A-FIG. 1C shows allelic DNase I hypersensitive sites (DHSs) in zygotes mark allelic gene expression at ZGA.

The invention provides methods for activating a H3K27me3 silenced allele within an imprinting control region by contacting the silenced allele with an agent that removes H3K27me3 or with an agent that inhibits H3K27 trimethylation, thereby treating a H3K27me3-dependent imprinting associated disorder.

The invention is based, at least in part, on the discovery that maternal H3K27me3 acts as a DNA methylation-independent imprinting mechanism, and that H3K27me3 is the imprinting mark of Xist an X-linked long non-coding RNA, which functions in X-chromosome inactivation.

H3K27Me3 is a DNA Methylation-Independent Imprinting Mechanism

Mammalian sperm and oocytes have different epigenetic landscapes and are organized in different fashion. Following fertilization, the initially distinct parental epigenomes become largely equalized with the exception of certain loci including imprinting control regions (ICRs). How parental chromatin becomes equalized and how ICRs escape from this reprogramming is largely unknown. Here parental allele-specific DNase I hypersensitive sites (DHSs) was characterized in mouse zygotes and morula embryos, and the epigenetic mechanisms underlying allelic DHSs was investigated. Integrated analyses of DNA methylome and H3K27me3 ChIP-seq data sets revealed 76 genes with paternal allele-specific DHSs that were devoid of DNA methylation, but harbored maternal allele-specific H3K27me3. Interestingly, these genes are paternally expressed in preimplantation embryos, and ectopic removal of H3K27me3 induced maternal allele expression. H3K27me3-dependent imprinting was largely lost in the embryonic cell lineage, but at least 5 genes maintained their imprinting in the extra-embryonic cell lineage. The 5 genes include all previously identified DNA methylation-independent imprinted autosomal genes. Thus, the results reported herein identified maternal H3K27me3 as a DNA methylation-independent imprinting mechanism.

Accordingly, the invention provides methods for relieving undesirable H3K27me3-dependent imprinting in a cell, including in the cell of a subject having an H3K27me3-dependent imprinting associated disorder. In one embodiment, such methods involve the use of an H3K27me3 selective methylase.

H3K27Me3 is Important for X Chromosome Inactivation

In females of certain therian mammals including rodents, one of the two X chromosomes is inactivated to achieve gene dosage compensation. This phenomenon, called X chromosome inactivation (XCI), provides an excellent model for understanding mechanisms of epigenetic silencing. During development, XCI can take place in either imprinted or random manners. For imprinted XCI, the paternal X chromosome (Xp) is selectively inactivated during preimplantation development. Although imprinted XCI is maintained in the extra-embryonic cell lineage, it is lost in the inner cell mass (ICM) of late blastocysts. At peri-implantation stage, epiblast cells undergo random XCI resulting in the silencing of either Xp or maternal X chromosome (Xm). Previous studies have demonstrated a critical role of Xist, an X-linked long non-coding RNA, in both imprinted and random XCI. The Xist RNA participates in XCI by coating and inactivating X chromosome in cis.

Genomic imprinting allows parent-of-origin specific gene regulation. To selectively silence the Xp during imprinted XCI, the Xist gene is imprinted for silencing in the Xm with a long sought-after, but yet-to-be-identified, mechanism. Previous studies using nuclear transfer approaches have suggested that genomic imprinting of Xist is established during oogenesis, like that of autosomal imprinted genes. In mouse preimplantation embryos and extra-embryonic cells, only the paternal X chromosome (Xp) is inactivated. Central to the imprinted paternal X chromosome inactivation (XCI) is a long non-coding RNA, Xist, which is expressed from Xp and acts in cis to coat and silence the entire Xp. To achieve Xp-specific inactivation, the maternal Xist gene must be silenced, yet the silencing mechanism is not yet clear. As reported herein, the Xist locus is coated with a broad H3K27me3 domain in mouse oocytes, which persists through preimplantation development. Ectopic removal of H3K27me3 induces maternal Xist expression and maternal XCI. Thus, maternal H3K27me3 serves as the imprinting mark of Xist.

In some embodiments, disclosed herein methods related to treating a disorder associated with a H3K27me3-dependent imprinting defect in a subject, comprising administering a pharmaceutical composition comprising a selective H3K27me3 demethylase inhibitor, thereby treating the H3K27me3-dependent imprinting defect.

Therapeutic Methods

Agents that remove H3K27me3 imprinting present in an imprinting control region are useful for preventing or ameliorating a developmental disorder associated with an imprinting control region. Developmental disorders associated with an imprinting control region include, for example, a disorder where one mutant allele (e.g., a paternal allele) is active while a wild-type allele (e.g., a maternal allele) is undesirably silent. Disorders associated with an imprinting control region may be treated by removing H3K27me3 from the undesirably silenced allele, thereby allowing that allele to be expressed.

In one therapeutic approach, an agent that inhibits H3K27me3 demethylase is administered systemically, thereby alleviating the symptoms of the disorder in a subject. The dosage of the administered agent depends on a number of factors, including the size and health of the individual patient. For any particular subject, the specific dosage regimes should be adjusted over time according to the individual need and the professional judgement of the person administering or supervising the administration of the compositions.

The following examples are put forth so as to provide those of ordinary skill in the art with a complete disclosure and description of how to make and use the assay, screening, and therapeutic methods of the invention, and are not intended to limit the scope of what the inventors regard as their invention.

Agents that Modify H3K27Me3

Disclosed herein are agents that inhibit histone H3 lysine 27 trimethylation (H3K27me3) thereby activating an H3K27me3 repressed allele. Also disclosed herein are agents (e.g., demethylases, such as KDM6A, KDM6B, and KDM6C) that selectively remove trimethylation at lysine 27 of histone H3 and activate an H3K27me3 repressed allele. Agents that inhibit H3K27me3 are known in the art, and described, for example, in the following patents and patent publications: U.S. Pat. No. 8,895,245 (e.g., Compound, 75, 37, 65, etc.), U.S. Pat. No. 9,688,665, U.S. application Ser. No. 15/101,577, U.S. application Ser. No. 15/211,792, PCT/US2016/065447, PCT/US2016/055554, PCT/US2016/060814; which are incorporated by reference herein. In particular embodiments, the agent is tazemetostat, DZNep, GSK373, GSK126, El1, Epz005687, CPI-169 (See, Morera et al., Clinical Epigenetics 2016 8:57)

In other embodiments, the agents disclosed herein selectively remove trimethylation at lysine 27 of histone H3 and activate an H3K27me3 repressed allele (e.g., KDM6A, KDM6B, or KDM6C). Such demethylases may be expressed as a polynucleotide (e.g., mRNA) in a cell or injected into a cell as a protein.

In accordance with the methods disclosed herein, in therapeutic applications, the dosages of the agents used in accordance with the invention vary depending on the agent, the age, weight, and clinical condition of the of recipient patient, and the experience and judgment of the clinician or practitioner administering the therapy, among other factors affecting the selected dosage. Generally, the dose should be sufficient to result in slowing, and preferably regressing, the disorder and most preferably causing complete regression of the disorder.

Nuclear Transfer

Somatic cell nuclear transfer (SCNT) is a technique that may be used, for example, for the reproductive cloning of livestock (e.g., cows, horses, sheep, goats) or for therapeutic cloning, in which desired tissues are produced for cell replacement therapy. Unfortunately cloned animals suffer from certain defects arising from improper imprinting, such as a deficiency in trimethylation of lysine 27 on histone H3 protein subunit. This deficiency can be remedied by providing an mRNA encoding an enzyme that carries out the trimethylation event during the SCNT procedure. In one embodiment, an mRNA encoding an enzyme capable of carrying out the trimethylation event (e.g., EZH1, EZH2, PRC2) is injected into the recipient cell or the nuclear donor cell prior to or during the SCNT procedure.

Somatic cell nuclear transfer involves obtaining a nuclear donor cell, then fusing this nuclear donor cell into an enucleated recipient cell, most preferably an enucleated oocyte, to form a nuclear transfer embryo, activating this embryo, and finally culturing the embryo or transferring this embryo into a maternal host. During nuclear transfer a full complement of nuclear DNA from one cell is introduced to an enucleated cell. Nuclear transfer methods are well known to a person of ordinary skill in the art. See, U.S. Pat. No. 4,994,384 to Prather et al., entitled "Multiplying Bovine Embryos," issued on Feb. 19, 1991; U.S. Pat. No. 5,057,420 to Massey, entitled "Bovine Nuclear Transplantation," issued on Oct. 15, 1991; U.S. Pat. No. 5,994,619, issued on Nov. 30, 1999 to Stice et al., entitled "Production of Chimeric Bovine or Porcine Animals Using Cultured Inner Cell Mass Cells; U.K. Patents Nos. GB 2,318,578 GB 2,331,751, issued on Jan. 19, 2000 to Campbell et al. and Wilmut et al., respectively, entitled "Quiescent Cell Populations For Nuclear Transfer"; U.S. Pat. No. 6,011,197 to Strelchenko et al., entitled "Method of Cloning Bovines Using Reprogrammed Non-Embryonic Bovine Cells," issued on Jan. 4, 2000; and in U.S. patent application Ser. No. 09/753,323 entitled "Method of Cloning Porcine Animals, filed Dec. 28, 2000), each of which are hereby incorporated by reference in its entirety including all figures, tables and drawings. Nuclear transfer may be accomplished by using oocytes that are not surrounded by a zona pellucida.

In a nuclear transfer procedure, a nuclear donor cell, or the nucleus thereof, is introduced into a recipient cell. A recipient cell is preferably an oocyte and is preferably enucleated. However, the invention relates in part to nuclear transfer, where a nucleus of an oocyte is not physically extracted from the oocyte. It is possible to establish a nuclear transfer embryo where nuclear DNA from the donor cell is replicated during cellular divisions. See, e.g., Wagoner et al., 1996, "Functional enucleation of bovine oocytes: effects of centrifugation and ultraviolet light," Theriogenology 46: 279-284. In addition, nuclear transfer may be accomplished by combining one nuclear donor and more than one enucleated oocyte. Also, nuclear transfer may be accomplished by combining one nuclear donor, one or more enucleated oocytes, and the cytoplasm of one or more enucleated oocytes. The resulting combination of a nuclear donor cell and a recipient cell can be referred to as a "hybrid cell."

The term "nuclear donor" as used herein refers to any cell, or nucleus thereof, having nuclear DNA that can be translocated into an oocyte. A nuclear donor may be a nucleus that has been isolated from a cell. Multiple techniques are available to a person of ordinary skill in the art for isolating a nucleus from a cell and then utilizing the nucleus as a nuclear donor. See, e.g., U.S. Pat. Nos. 4,664,097, 6,011,197, and 6,107,543, each of which is hereby incorporated by reference in its entirety including all figures, tables and drawings. Any type of cell can serve as a nuclear donor. Examples of nuclear donor cells include, but are not limited to, cultured and non-cultured cells isolated from an embryo arising from the union of two gametes in vitro or in vivo; embryonic stem cells (ES cells) arising from cultured embryonic cells (e.g., pre-blastocyst cells and inner cell mass cells); cultured and non-cultured cells arising from inner cell mass cells isolated from embryos; cultured and non-cultured pre-blastocyst cells; cultured and non-cultured fetal cells; cultured and non-cultured adult cells; cultured and non-cultured primordial germ cells; cultured and non-cultured germ cells (e.g., embryonic germ cells); cultured and non-cultured somatic cells isolated from an animal; cultured and non-cultured cumulus cells; cultured and non-cultured amniotic cells; cultured and non-cultured fetal fibroblast cells; cultured and non-cultured genital ridge cells; cultured and non-cultured differentiated cells; cultured and non-cultured cells in a synchronous population; cultured and non-cultured cells in an asynchronous population; cultured and non-cultured serum-starved cells; cultured and non-cultured permanent cells; and cultured and non-cultured totipotent cells. See, e.g., Piedrahita et al., 1998, Biol. Reprod. 58: 1321-1329; Shim et al., 1997, Biol. Reprod. 57: 1089-1095; Tsung et al., 1995, Shih Yen Sheng Wu Hsueh Pao 28: 173-189; and Wheeler, 1994, Reprod. Fertil. Dev. 6: 563-568, each of which is incorporated herein by reference in its entirety including all figures, drawings, and tables. In addition, a nuclear donor may be a cell that was previously frozen or cryopreserved.

Hybrid cells made by the process of nuclear transfer may be used, for example, in reproductive cloning or in regenerative cloning.

The practice of the present invention employs, unless otherwise indicated, conventional techniques of molecular biology (including recombinant techniques), microbiology, cell biology, biochemistry and immunology, which are well within the purview of the skilled artisan. Such techniques are explained fully in the literature, such as, "Molecular Cloning: A Laboratory Manual", second edition (Sambrook, 1989); "Oligonucleotide Synthesis" (Gait, 1984); "Animal Cell Culture" (Freshney, 1987); "Methods in Enzymology" "Handbook of Experimental Immunology" (Weir, 1996); "Gene Transfer Vectors for Mammalian Cells" (Miller and Calos, 1987); "Current Protocols in Molecular Biology" (Ausubel, 1987); "PCR: The Polymerase Chain Reaction", (Mullis, 1994); "Current Protocols in Immunology" (Coligan, 1991). These techniques are applicable to the production of the polynucleotides and polypeptides of the invention, and, as such, may be considered in making and practicing the invention. Particularly useful techniques for particular embodiments will be discussed in the sections that follow.

The following examples are put forth so as to provide those of ordinary skill in the art with a complete disclosure and description of how to make and use the assay, screening, and therapeutic methods of the invention, and are not intended to limit the scope of what the inventors regard as their invention.

EXAMPLES

Example 1: Allelic DHSs in Zygotes Mark Promoters that are Primed for Allelic Zygotic Genome Activation Transcriptional regulatory elements, such as promoters and enhancers, can be mapped by DNase I hyper-sensitivity assay. By using a low-input DNase I-sequencing (liDNase-seq) technique, the transcriptional regulatory landscape of preimplantation embryos were mapped and SNP-based analysis revealed that chromatin accessibility of the two parental alleles is overall comparable except imprinted gene promoters. A similar conclusion was also reached using an assay for transposase-accessible chromatin with high throughput sequencing (ATAC-seq). However, the mechanisms underlying parent-of-origin specific chromatin accessibility are unknown.

Figure 1B:
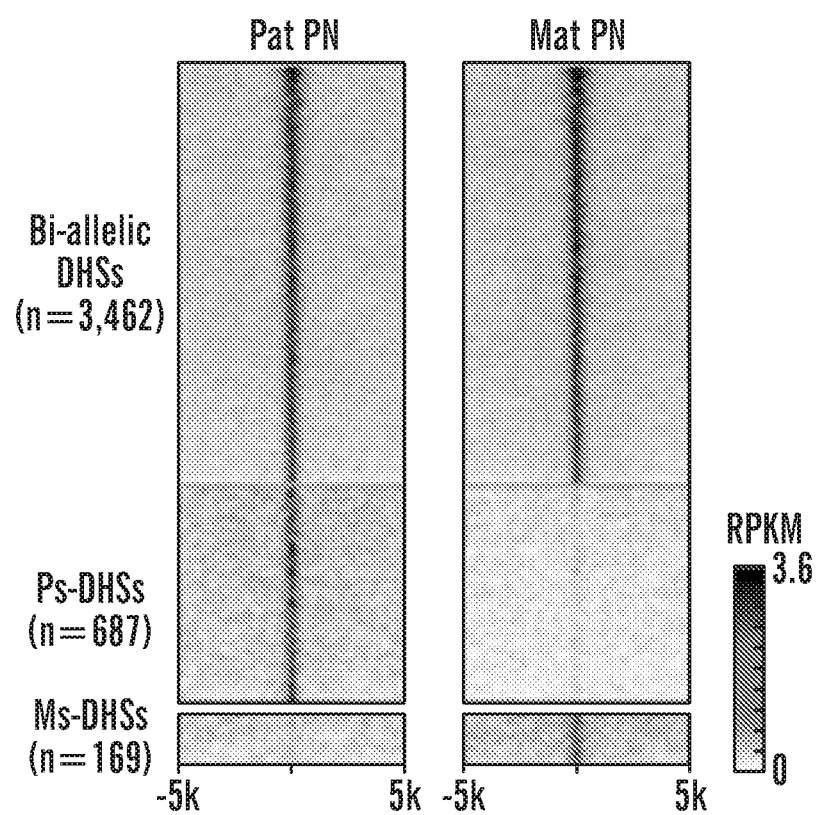
Figure 2A:
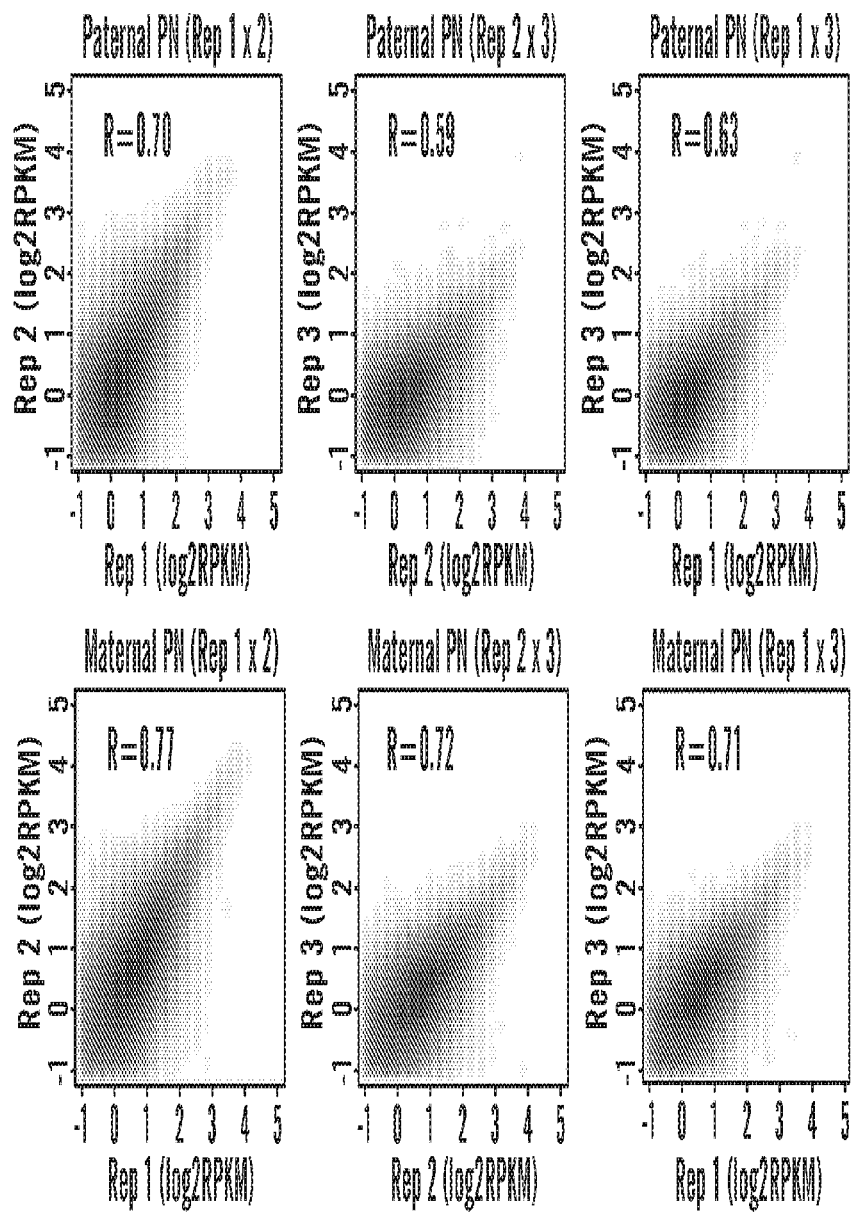
Figure 2B:
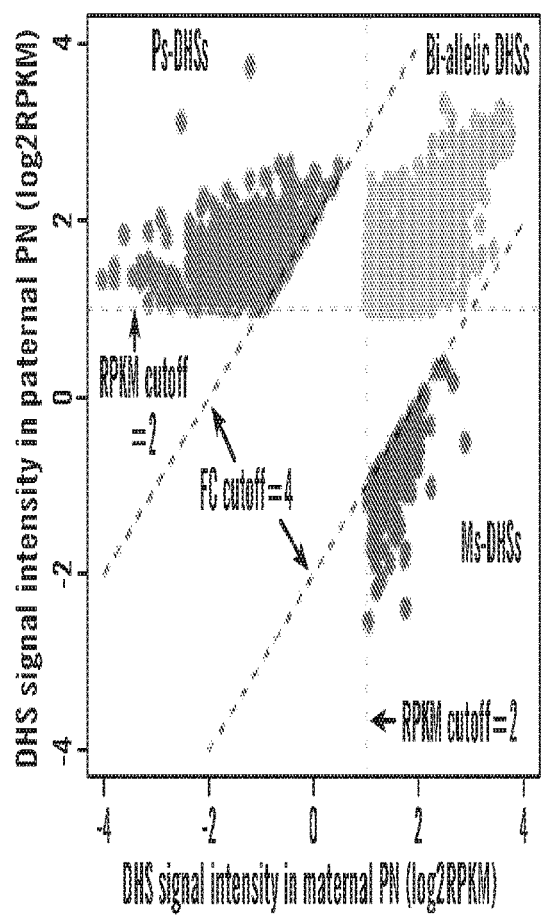
Figure 2C:
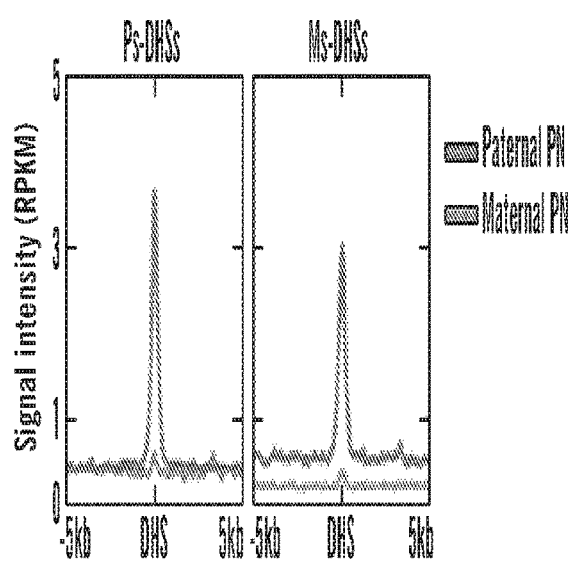
Figure 2F:
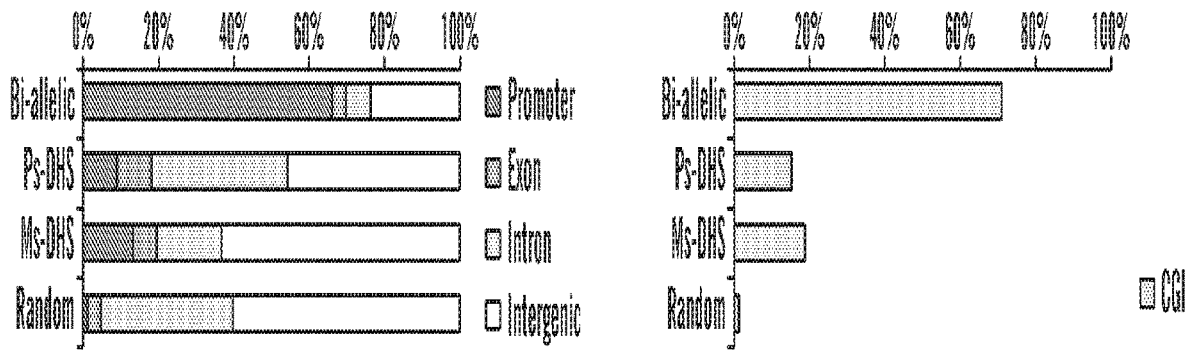
Figure 2F:
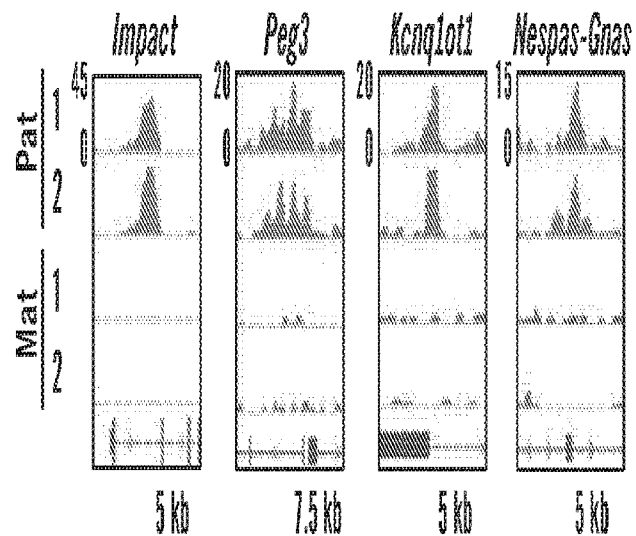
Figure 2H:
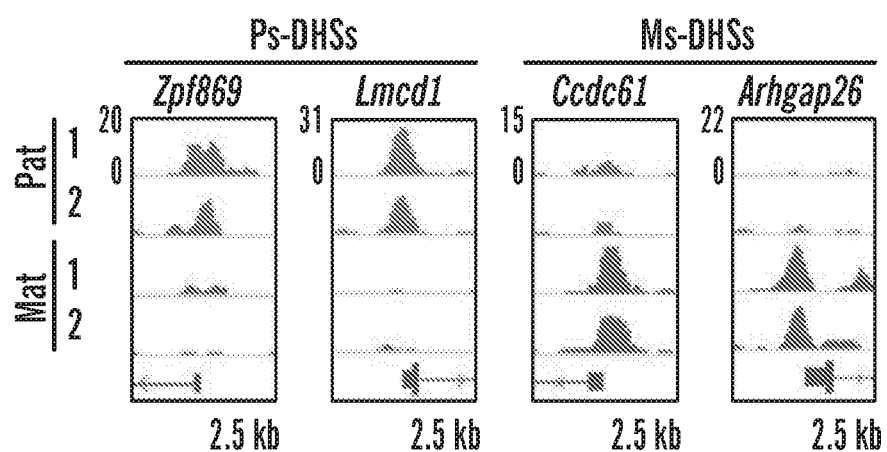

To comprehensively profile parental allele-specific DHSs in zygotes, paternal and maternal pronuclei from PN5-stage zygotes were isolated and performed liDNase-seq (FIG. 1A, FIG. 2A). Using stringent criteria (FIG. 2B) and excluding data of sex chromosomes, 3,462, 687, and 169 of bi-allelic DHSs were identified, paternal allele-specific DHSs (Ps-DHSs), and maternal allele-specific DHSs (Ms-DHSs), respectively (FIG. 1B, FIG. 2C). The genomic location of allelic DHSs was heavily biased to non-promoter elements when compared to bi-allelic DHSs that were enriched in promoters and CpG islands (FIG. 2D, FIG. 2E). Ps-DHSs include ICRs of known imprinted genes (FIG. 2F). Interestingly, both Ps- and Ms-DHSs also included promoters of genes previously not known to be imprinted (FIG. 2G, FIG. 2H).

Since promoter DHSs can prime gene expression at the next developmental stage, it was explored whether allelic DHSs in zygotes can prime allelic gene expression at zygotic genome activation (ZGA). RNA-seq analysis of 2-cell stage androgenetic (AG) and gynogenetic (GG) embryos, using α-amanitin treatment as a negative control, identified 107 AG- and 14 GG-specific differentially expressed genes (DEGs), including 8 known imprinted genes (FIG. 3A, FIG. 3B, FIG. 3C, and FIG. 3D).

Figure 1C:
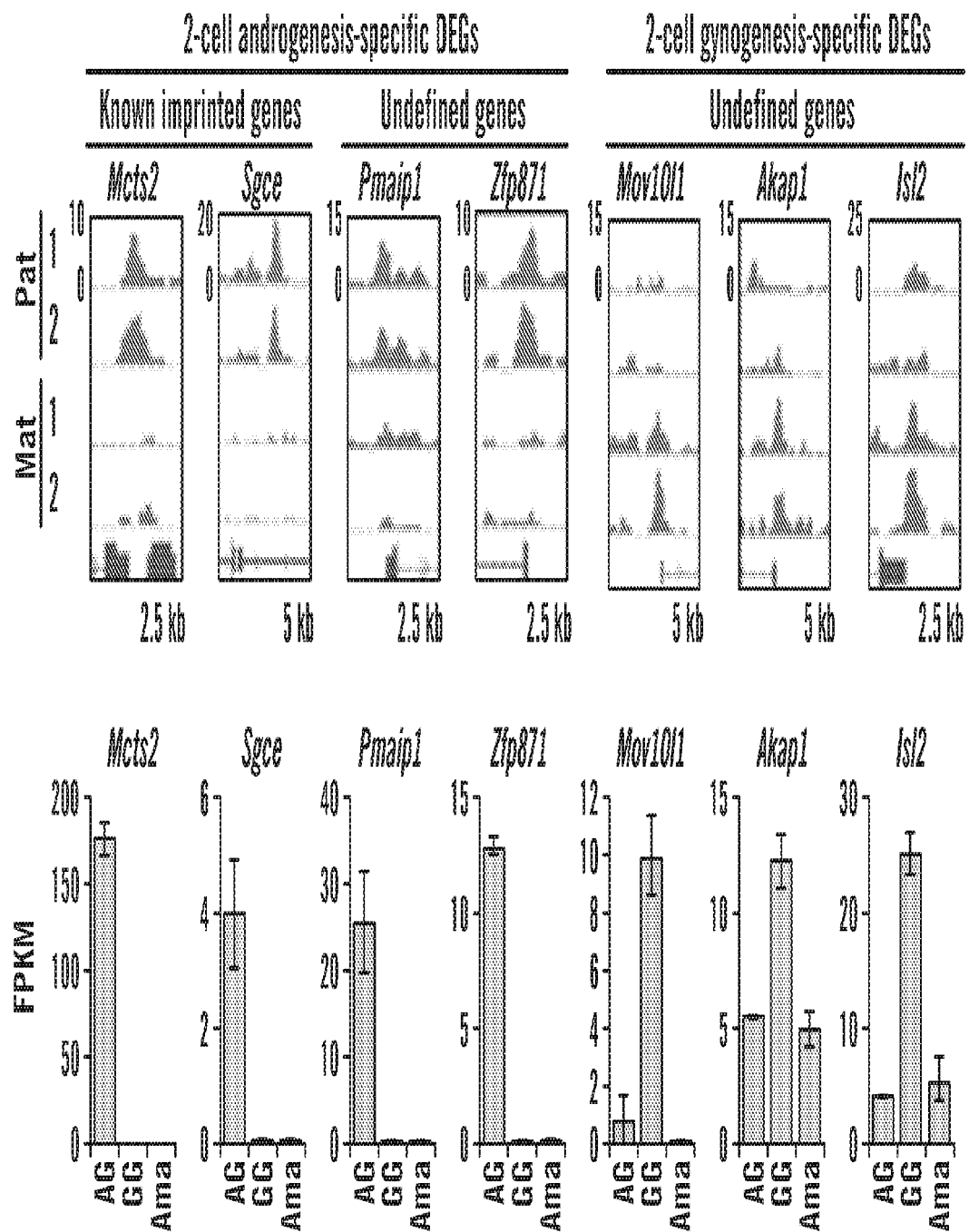
Figure 3A:
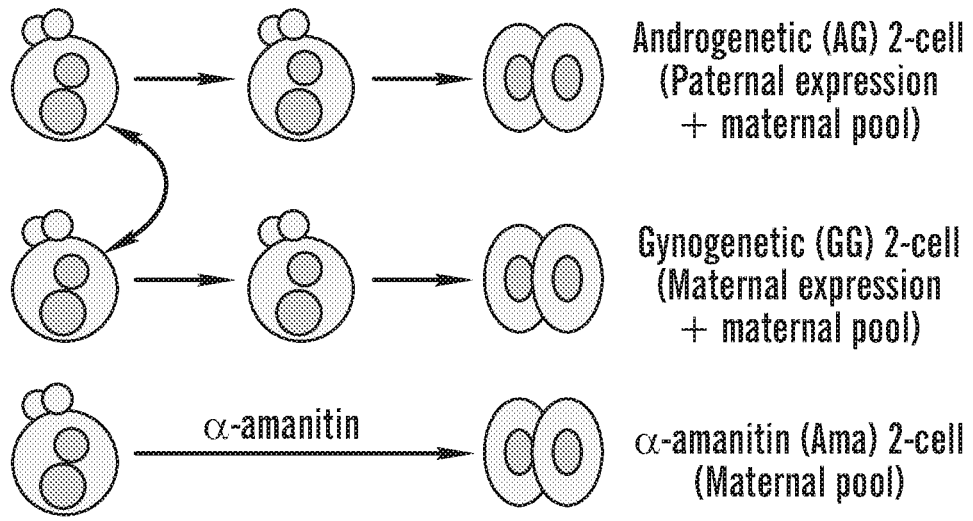
Figure 3B:
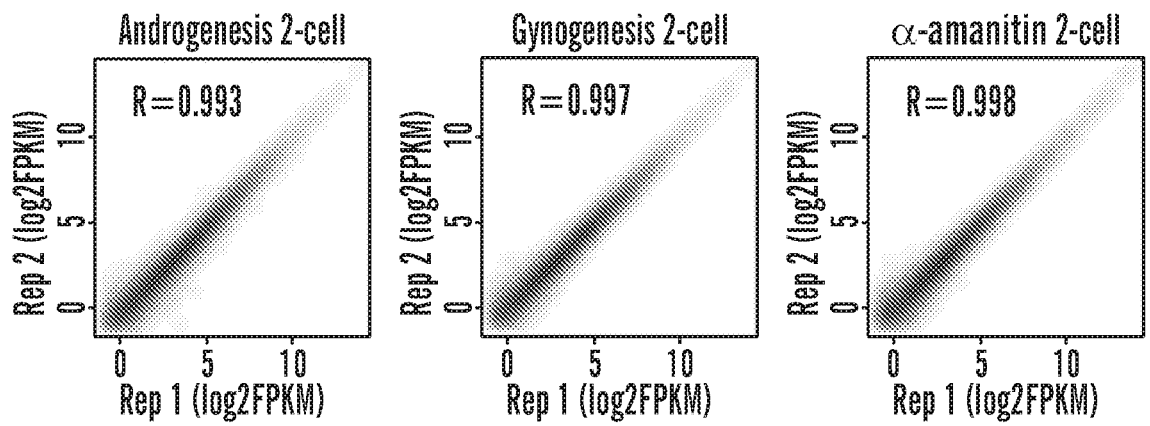
Figure 3E:
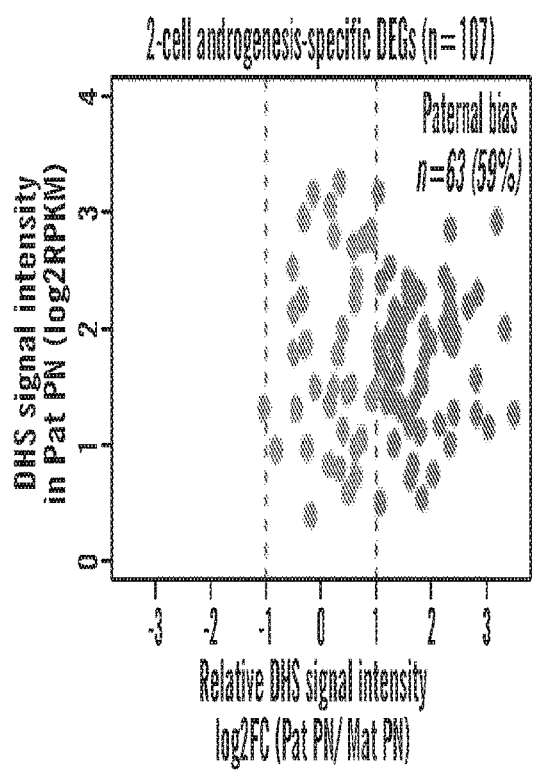
Figure 3F:
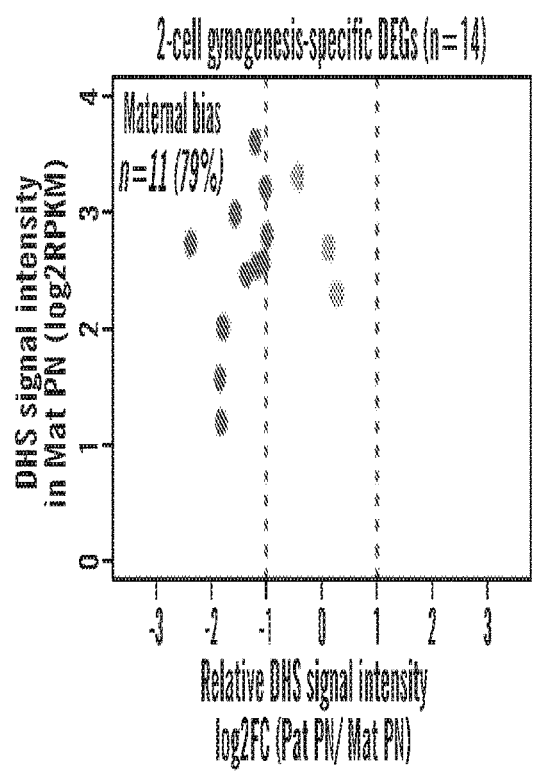

Integrated analysis of allelic ZGA and allelic promoter DHSs in zygotes revealed that the majority (59% and 79%) of the AG- and GG-specific DEGs were associated with paternal and maternal allele-biased chromatin accessibility, respectively (FIG. 3E, FIG. 3F). Genes showing such a correlation include not only known imprinted genes but also genes not known to be imprinted (FIG. 1C). These results indicated that allelic DHSs in zygotes can mark promoters that are primed for allelic ZGA.

Example 2: DNA Methylation and Allelic DHSs

Figure 4A:
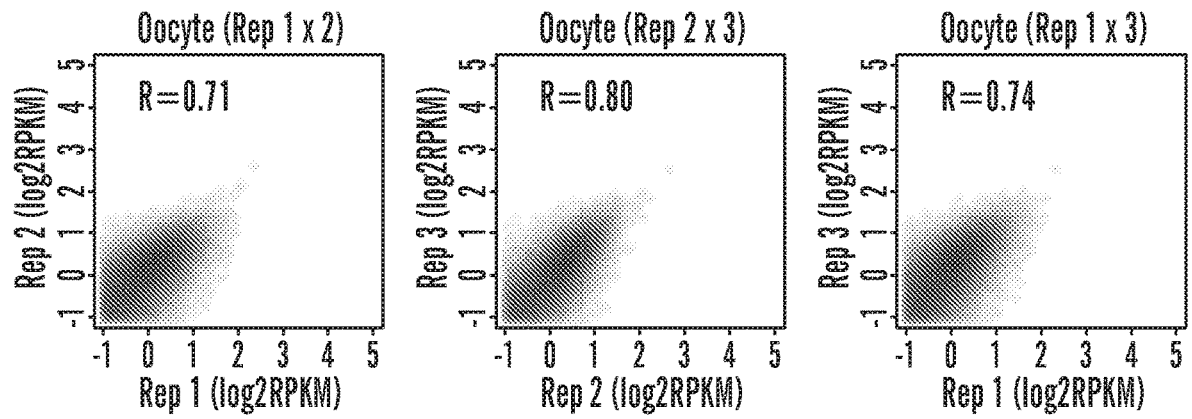
FIG. 4A-FIG. 4H shows zygotic Ms-DHSs are inherited from oocyte DHSs, related to FIG. 6.
Figure 4B:
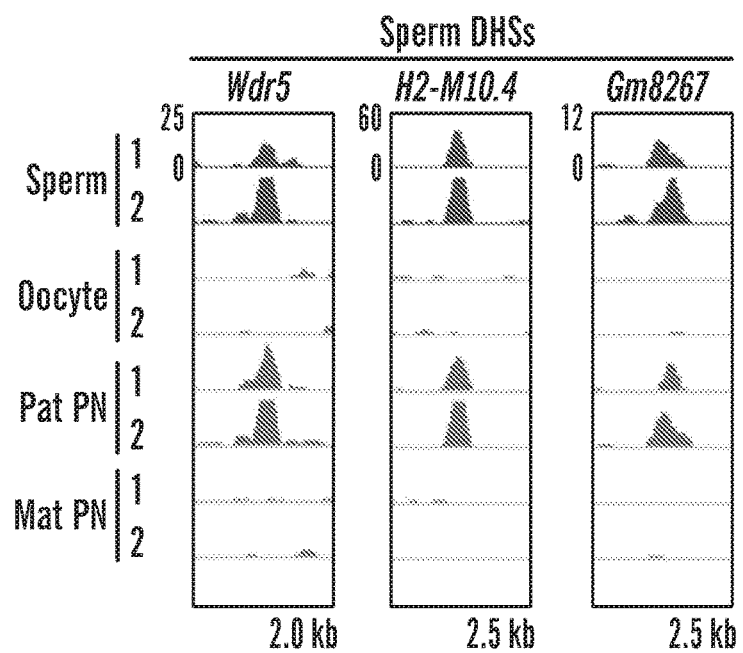
Figure 4C:
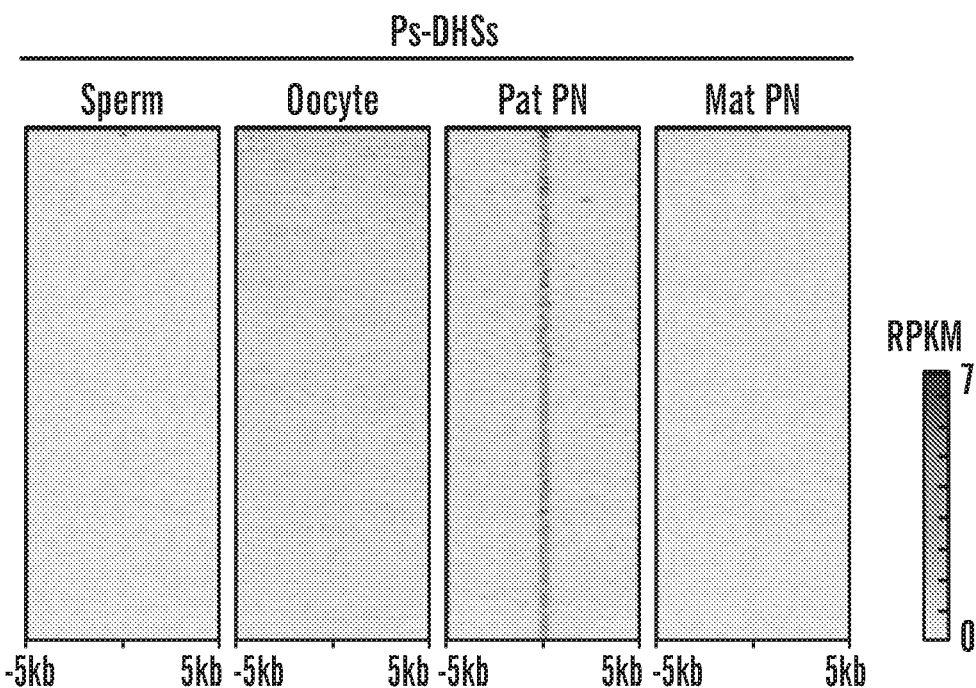
Figure 4D:
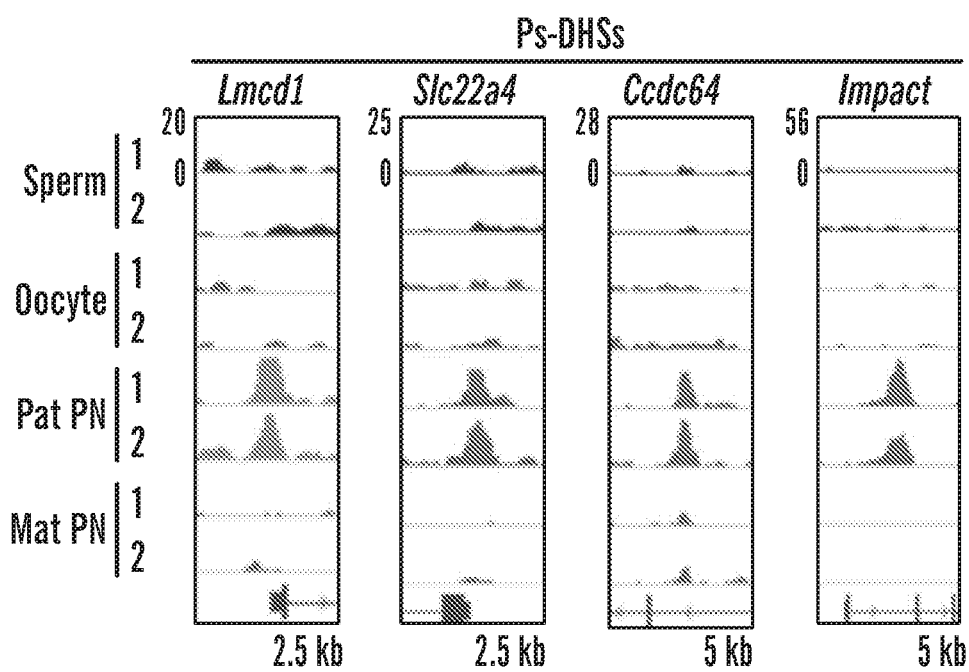
Figure 4E:
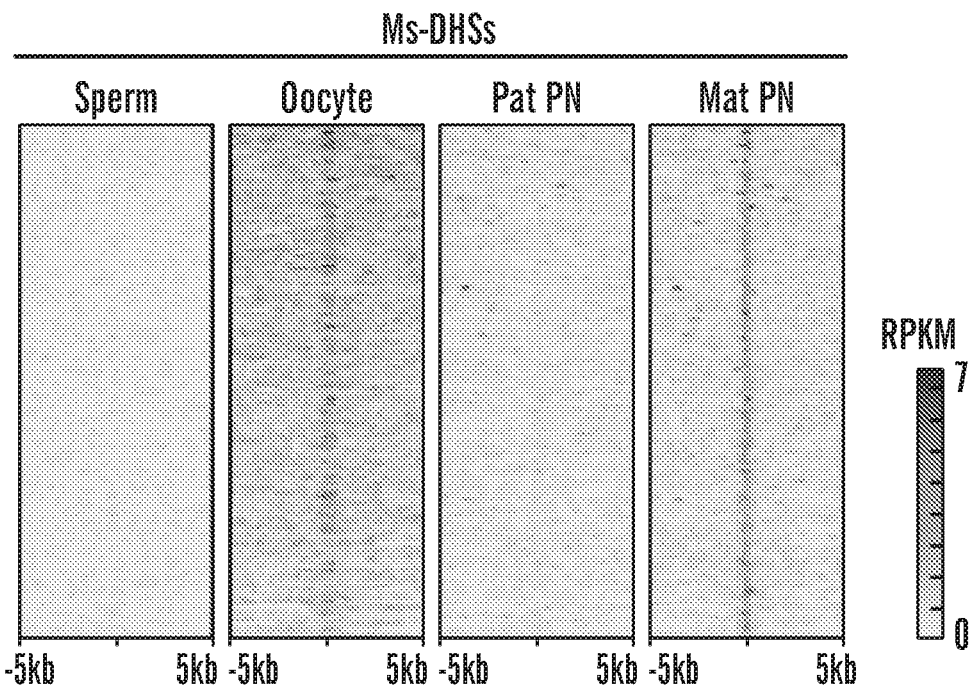
Figure 4F:
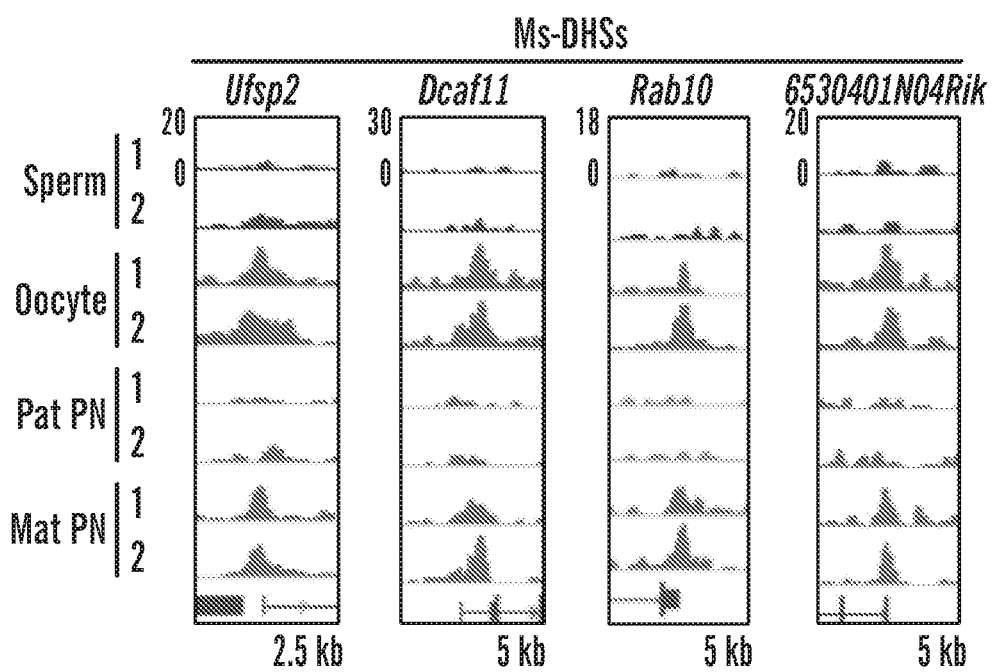
Figure 4G:
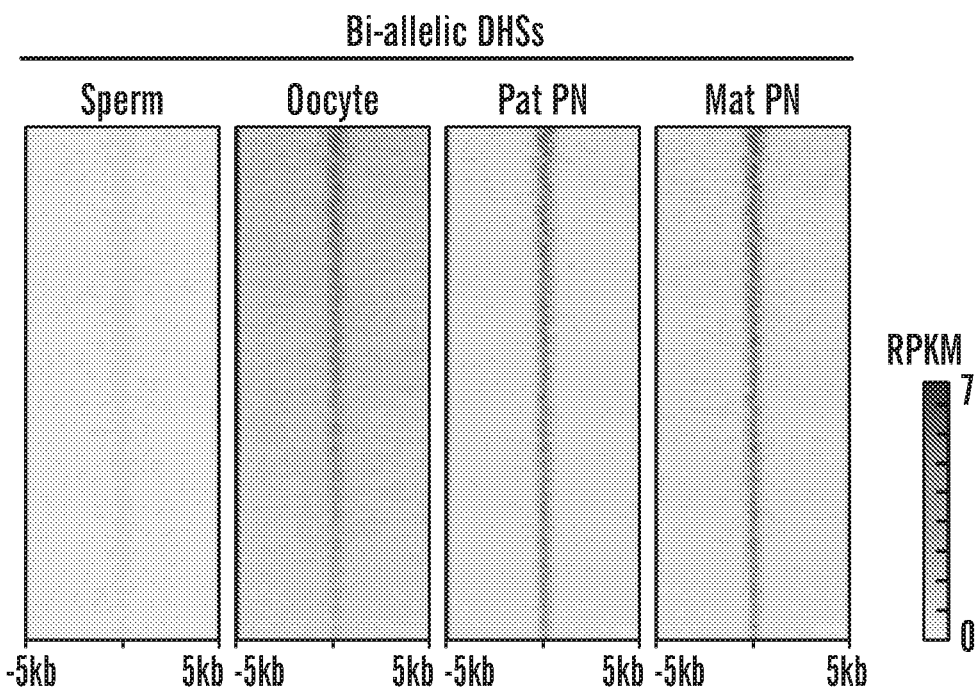
Figure 4H:
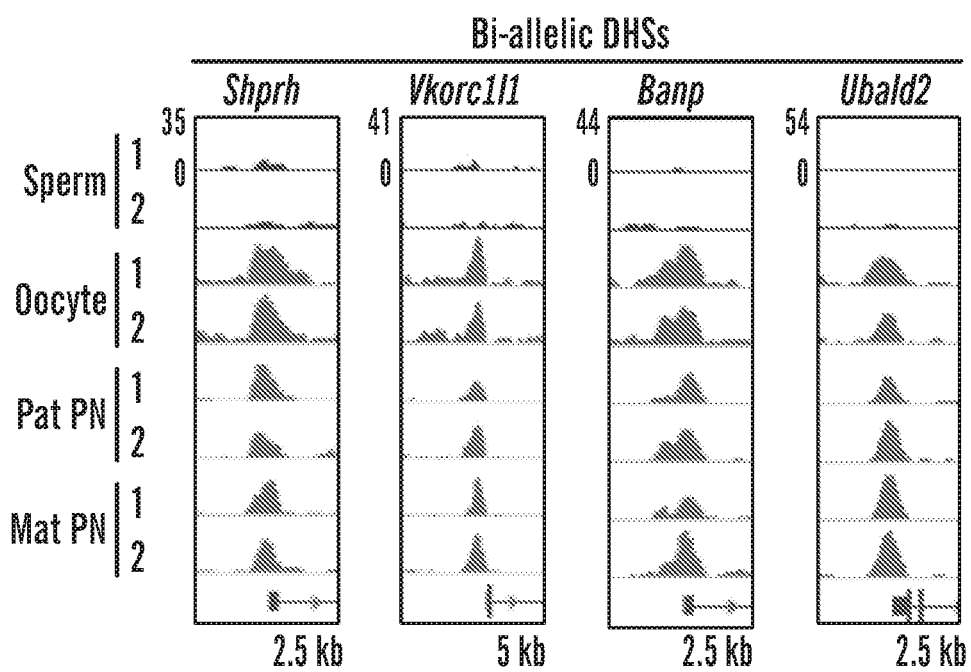

To understand how allelic DHSs in zygotes were specified, it was examined whether they are inherited from gametes. DHSs of fully-grown oocytes were profiled (FIG. 4A) and analyzed sperm DHSs. Although sperms only have 34 reproducible DHSs, some of them contribute to Ps-DHSs (FIG. 4B). However, most of Ps-DHSs are absent in sperm and oocytes, indicating that they are generated after fertilization (FIG. 4C, FIG. 4D). In contrast, most of Ms-DHSs and bi-allelic DHSs are already present in oocytes (FIG. 4E, FIG. 4F, FIG. 4G, FIG. 4H), indicating that most maternal DHSs are inherited from oocytes.

Figure 5D:
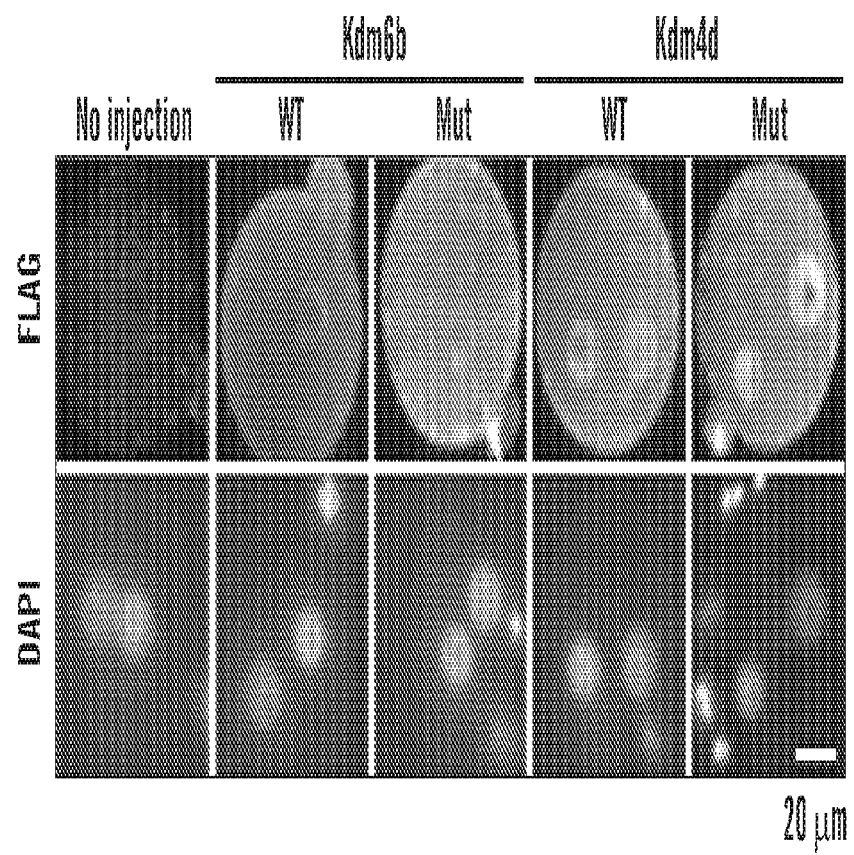

To determine how the maternal allele at Ps-DHSs remains inaccessible, it was hypothesized that maternal DNA methylation prevents DHS formation. Analysis of a public whole genome bisulfite sequencing (WGBS) dataset of oocytes and sperm revealed that only 17% of Ps-DHSs overlap with oocyte germline differentially methylated regions (gDMRs) (FIG. 5A). Despite extending to a ±100 kb region flanking Ps-DHSs, only additional 21% are found to be associated with oocyte gDMRs (FIG. 5A). Even when the oocyte DNA methylation level alone is considered, 48% of Ps-DHSs are devoid of oocyte DNA methylation (FIG. 5B), indicating the existence of a DNA methylation-independent mechanism that prevents maternal allelic accessibility.

Example 3: Maternal Allelic Protection by H3K27me3

The fact that Polycomb-mediated H3K27me3 can mediate silencing of DNA hypomethylated promoters led to the postulation that H3K27me3 might be responsible for maternal allele inaccessibility. Analyses of public ChIP-seq datasets revealed that the H3K27me3 level in oocytes was much higher than that of sperm at DNA hypomethylated Ps-DHSs, while it was reversed at DNA hypermethylated Ps-DHSs (FIG. 5C, left panel). SNP-tracking analysis revealed that the hypomethylated Ps-DHSs maintain maternal allele-specific H3K27me3 in zygotes (FIG. 5C, right panel), indicating that H3K27me3 may be responsible for maternal allele inaccessibility at DNA hypomethylated regions.

Figure 5E:
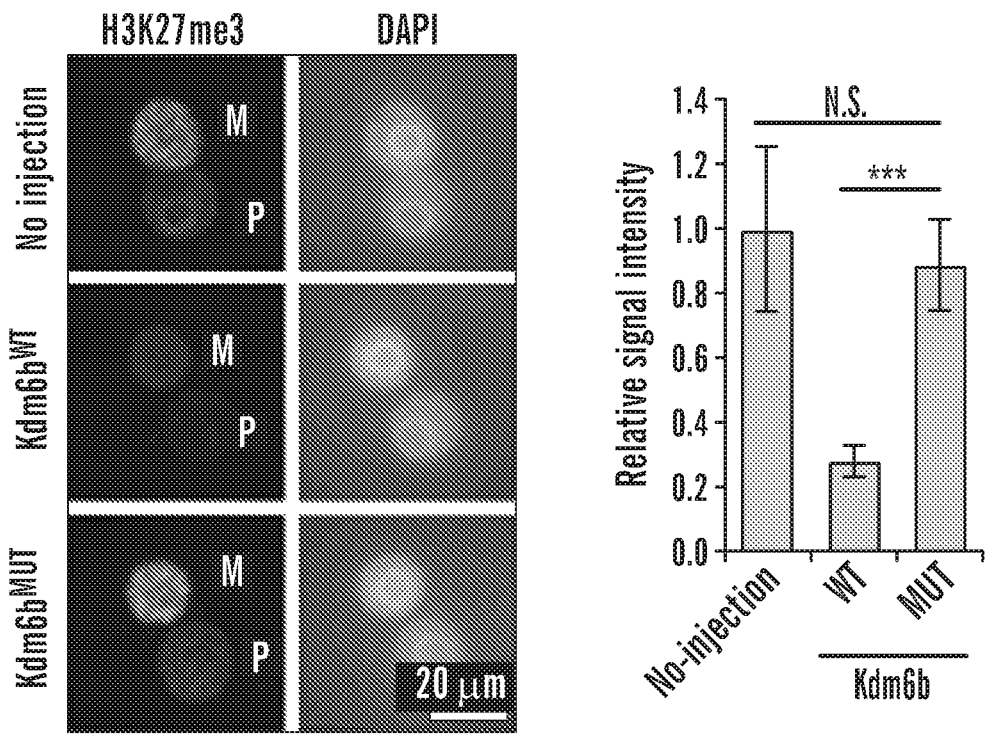
Figure 5F:
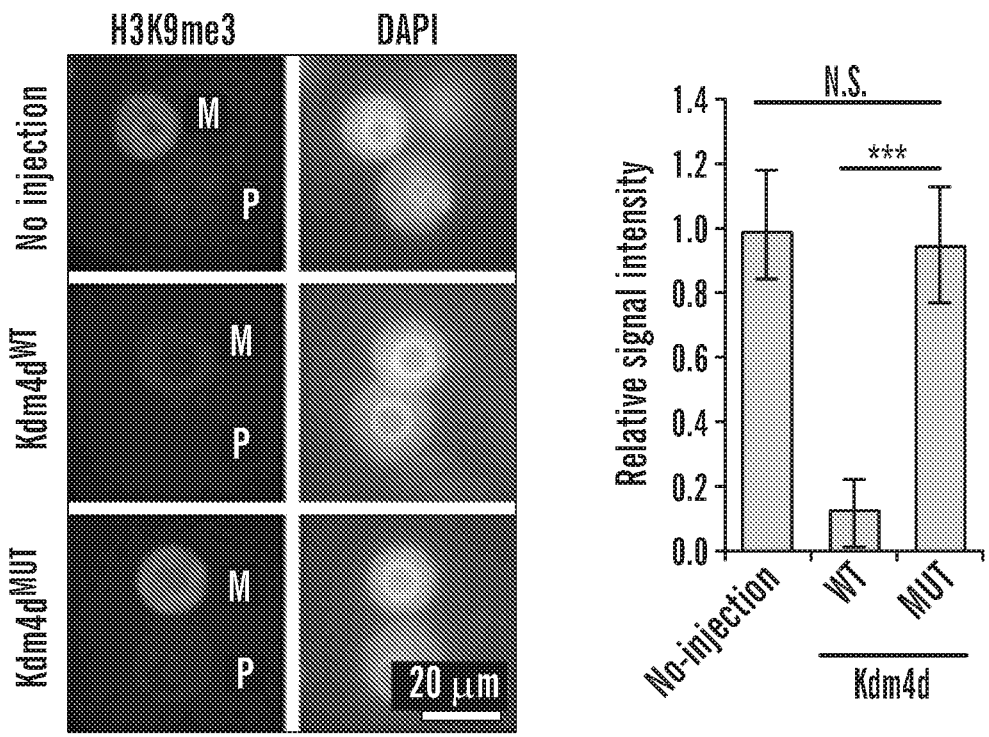
Figure 5G:
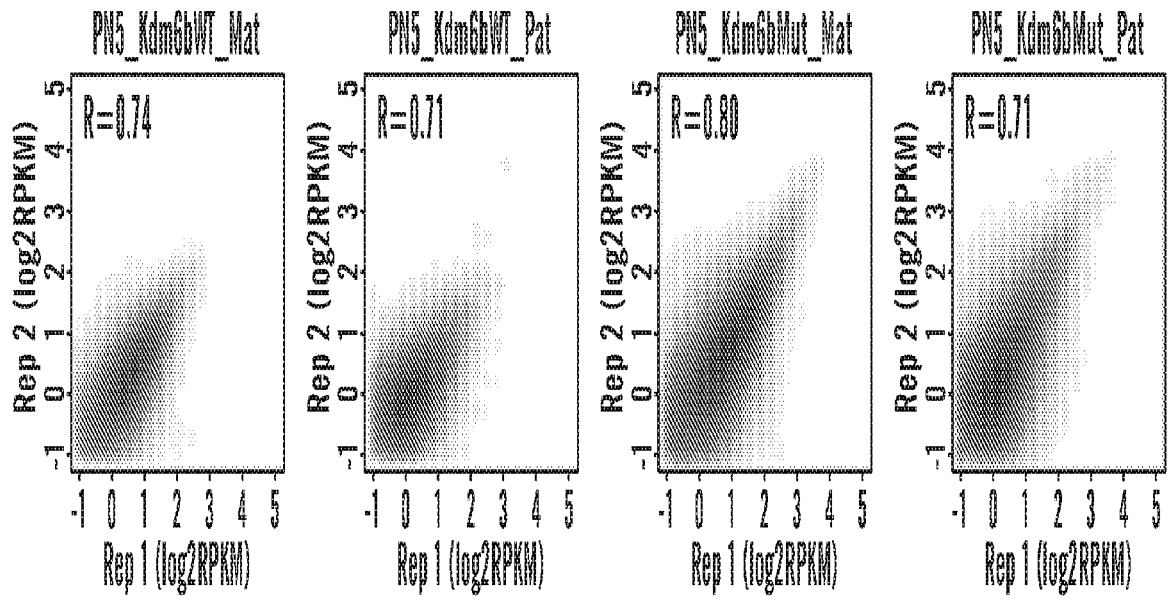
Figure 5H:
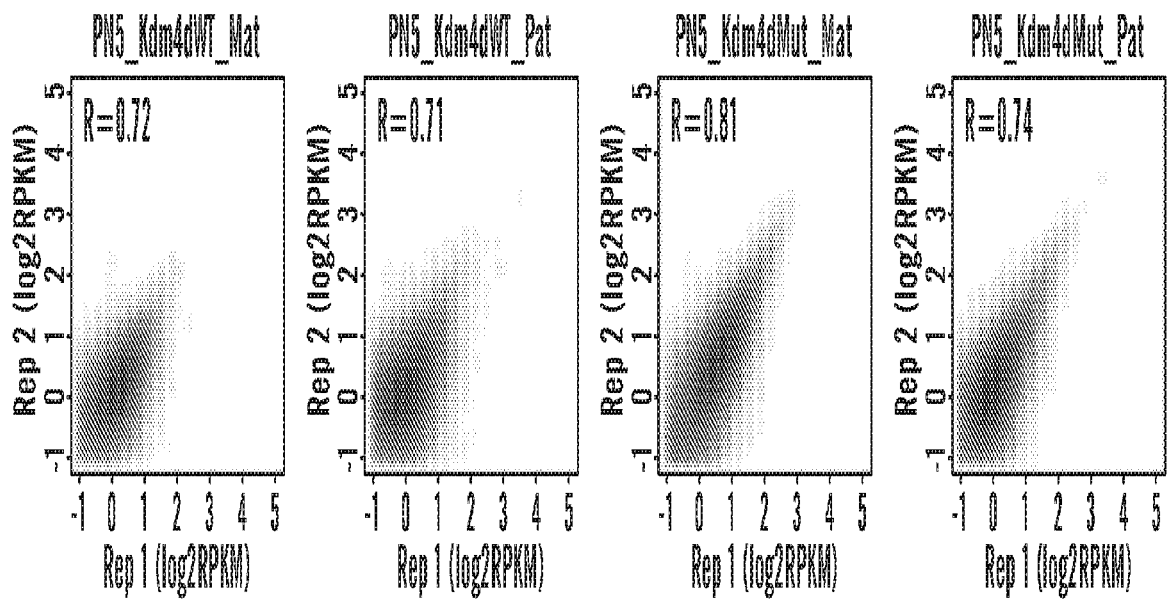
Figure 5I:
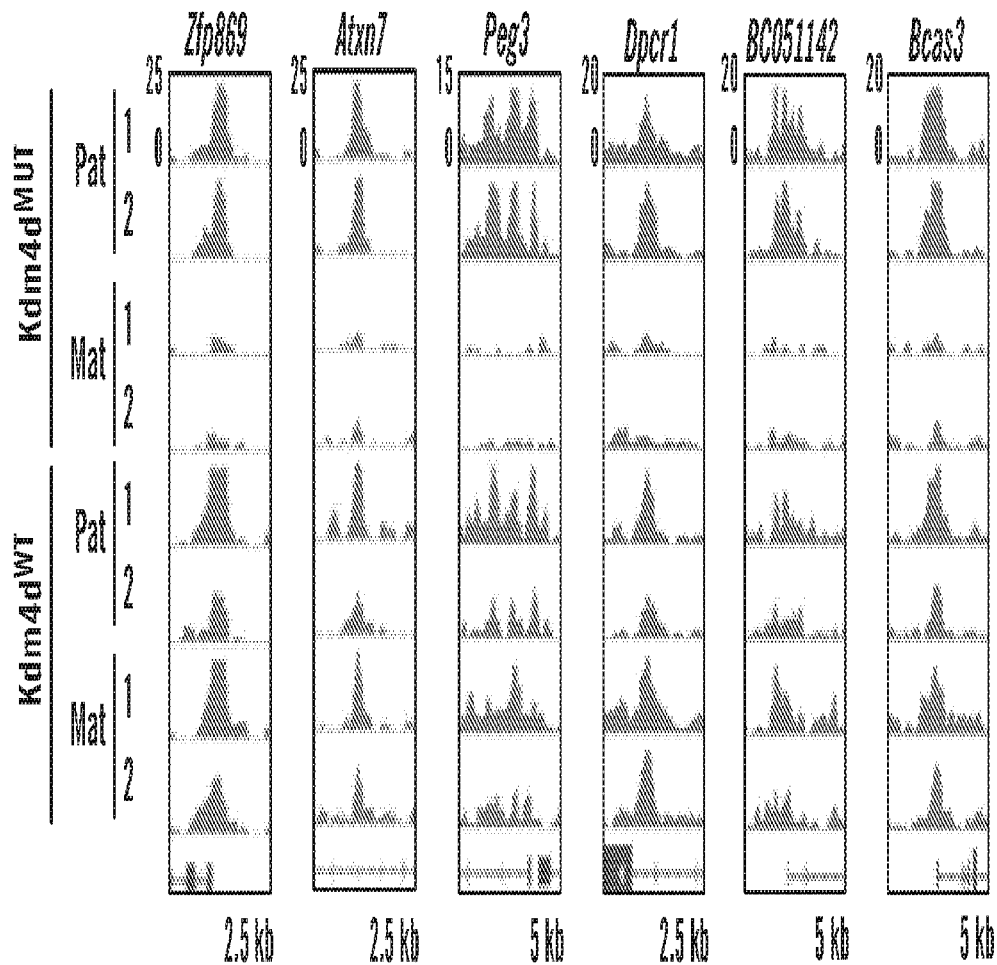
Figure 5J:
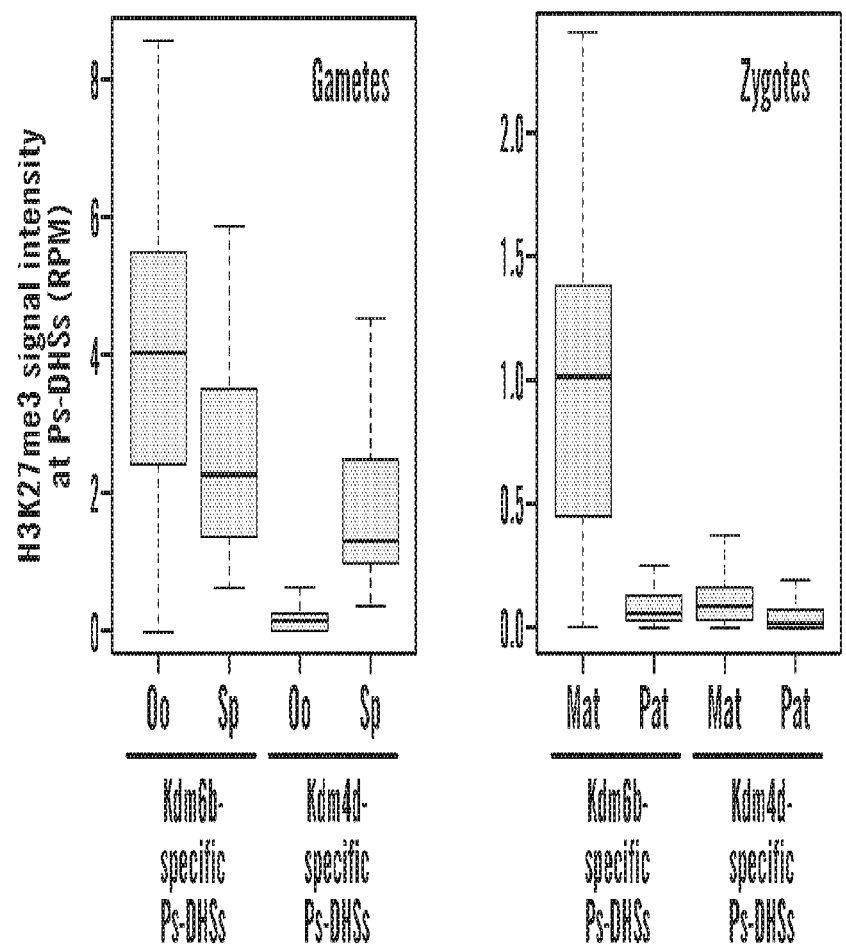
Figure 6A:
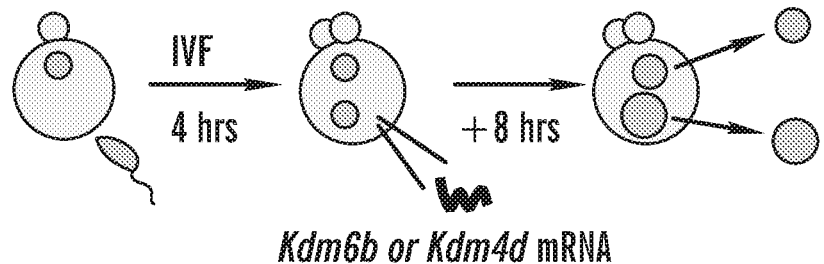
FIG. 6A-FIG. 6D shows oocyte-specific H3K27me3 prevents maternal chromatin accessibility at DNA hypomethylated regions.
Figure 6B:
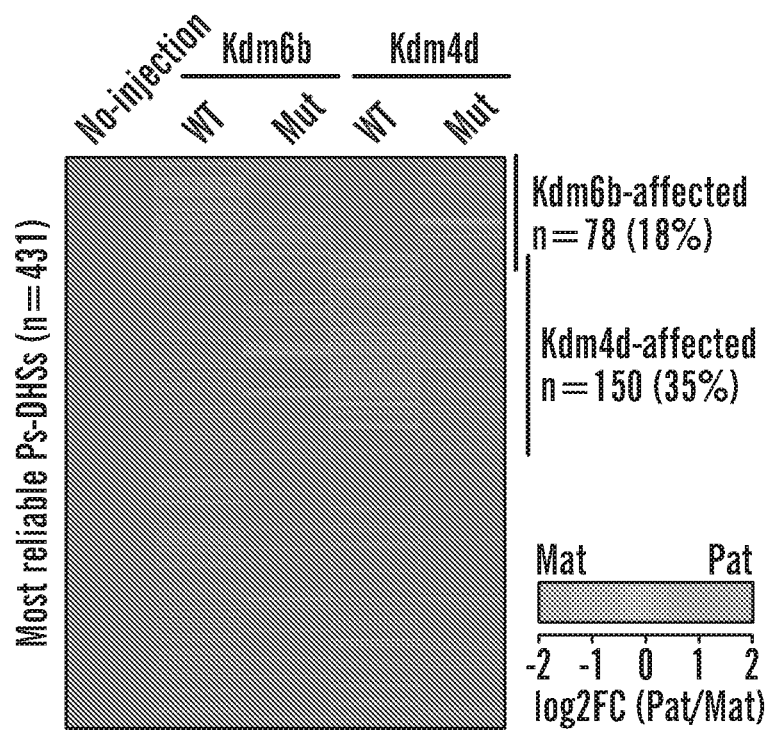
Figure 6C:
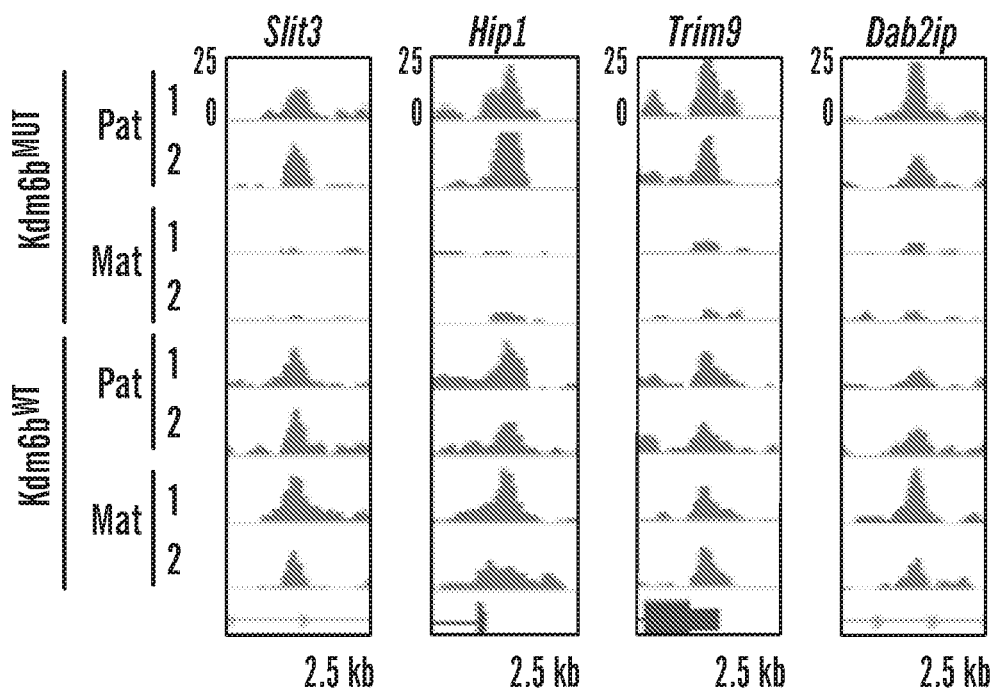
Figure 6D:
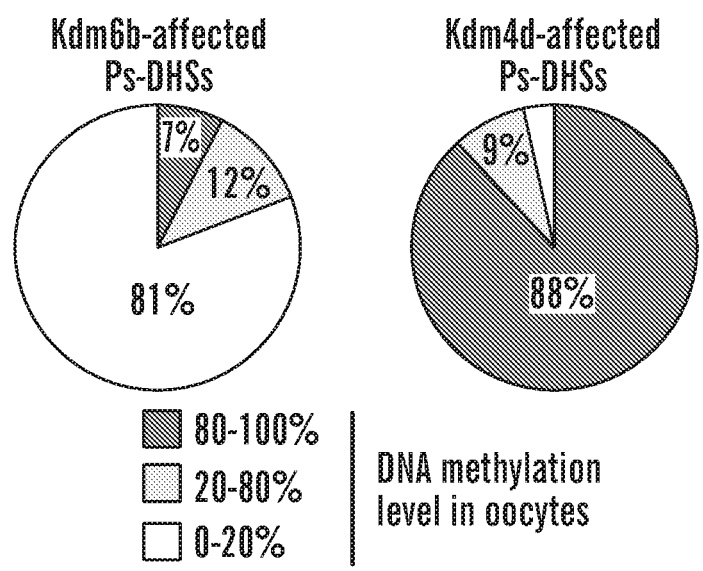

To test this possibility, mRNA encoding an H3K27me3-specific demethylase Kdm6b ($Kdm6b^{WT}$) with its catalytic mutant (H1390A) ($Kdm6b^{MUT}$) was injected as a control (FIG. 6A). Similarly, zygotes injected with an H3K9me3-specific demethylase Kdm4d or its catalytic mutant (H189A) were prepared. Both WT and mutant Kdm6b and Kdm4d were expressed at a similar level (FIG. 5D), and $Kdm6b^{WT}$ and $Kdm4d^{WT}$, but not their mutants, significantly reduced H3K27me3 and H3K9me3 levels, respectively (FIG. 5E, FIG. 5F). LiDNase-seq of isolated pronuclei (FIG. 5G, FIG. 5H) revealed that 78 and 150 of the 431 most reliable Ps-DHSs became bi-allelic in $Kdm6b^{WT}$- and $Kdm4d^{WT}$-injected zygotes, respectively, while their catalytic mutants had little effect (FIG. 6B, FIG. 6C, FIG. 5I). This result indicated that both maternal H3K27me3 and H3K9me3 were involved in maternal allele inaccessibility. Importantly, Kdm6b-affected Ps-DHSs were largely devoid of oocyte DNA methylation, which was markedly different from Kdm4d-affected Ps-DHSs that locate at DNA hypermethylated regions (FIG. 6D). Consistently, Ps-DHSs specifically affected by Kdm6b, but not Kdm4d, overlap maternal allele-specific H3K27me3 (FIG. 5J). These results indicated that maternal H3K27me3 and H3K9me3 restrict maternal allele accessibility at regions with hypomethylated and hypermethylated DNA, respectively.

Example 4: H3K27Me3-Dependent Imprinting

Figure 7A:
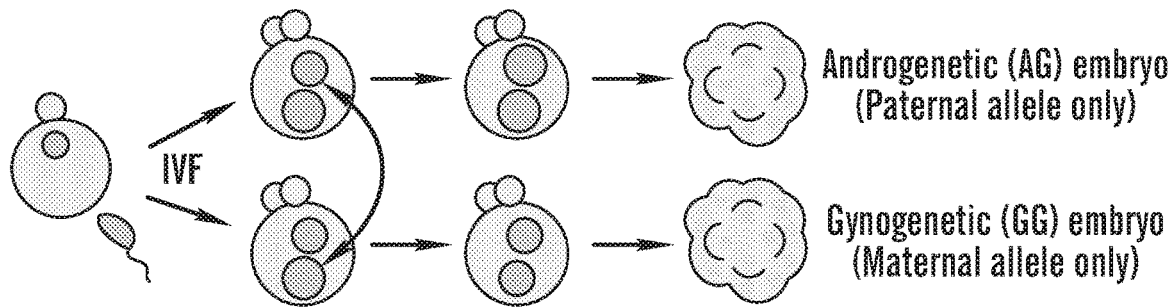
FIG. 7A-FIG. 7D shows genes with H3K27me3-marked AG-DHSs are paternally expressed in morula embryos.
Figure 7B:
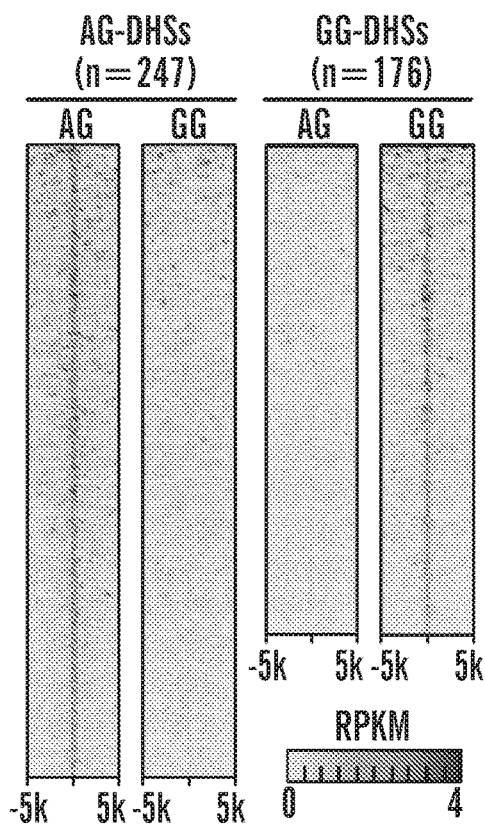
Figure 8A:
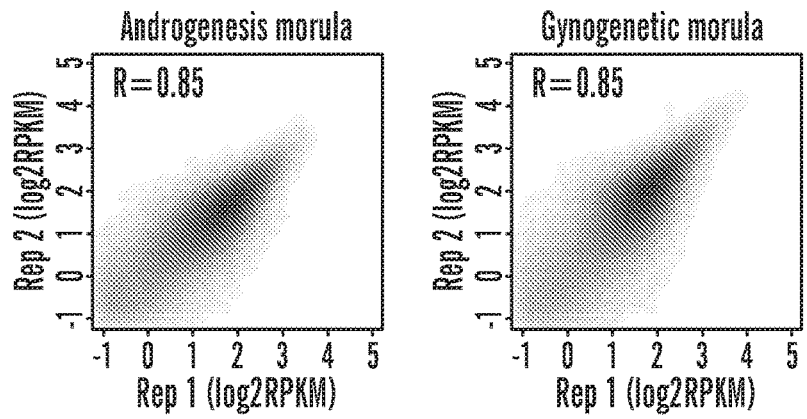
FIG. 8A-FIG. 8D shows androgenetic (AG)- and gynogenetic (GG)-specific DHSs in morula embryos, related to FIG. 7.
Figure 8B:
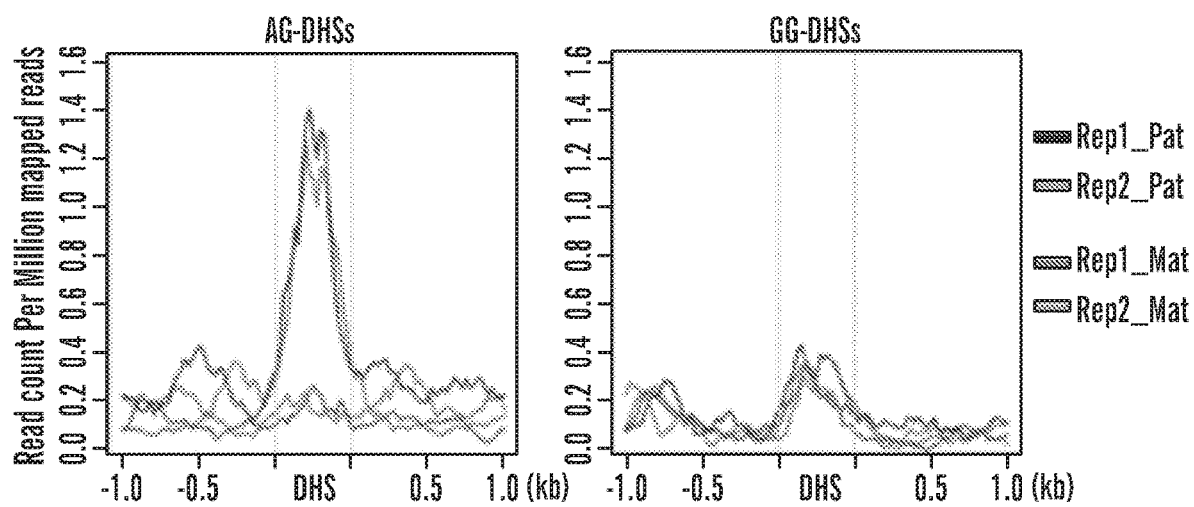
Figure 8C:
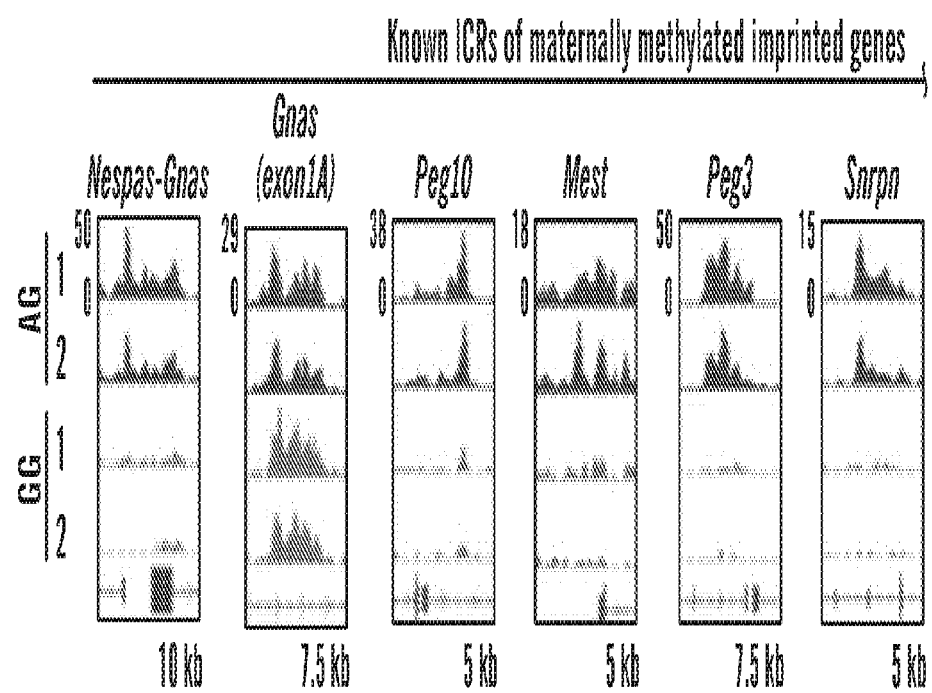
Figure 8C:
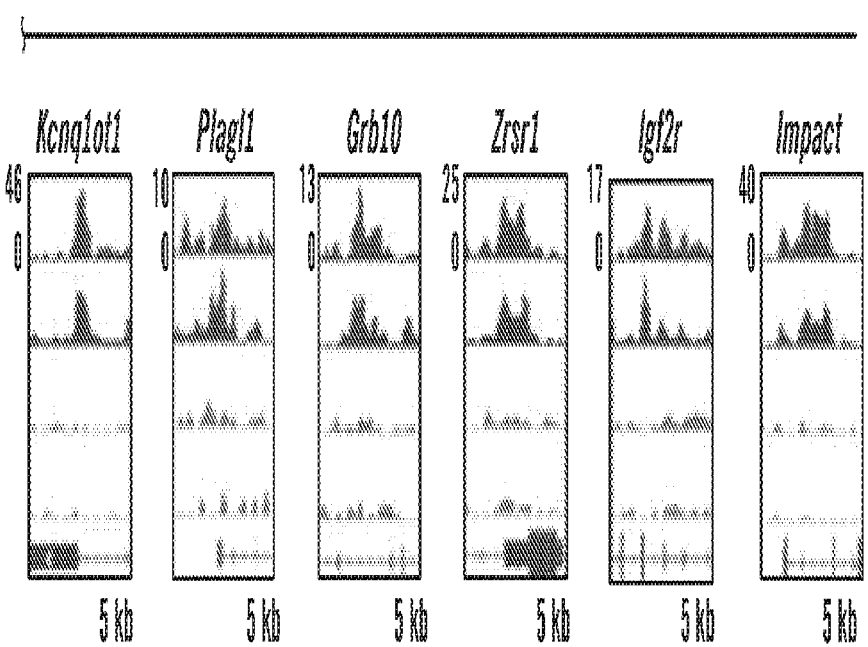

Maternal H3K27me3 serves as a DNA methylation-independent imprinting mark and restricts maternal allele accessibility to mediate H3K27me3-dependent genomic imprinting. To understand to what extent allelic DHSs exist at a later embryonic stage, AG and GG morula embryos were generated (FIG. 7A) and performed liDNase-seq (FIG. 8A). Using the same criteria for allelic DHSs as in zygotes and excluding data of sex chromosomes, 36,569, 247, and 176 of common DHSs were identified, AG-specific DHSs (AG-DHSs), and GG-specific DHSs (GG-DHSs), respectively (FIG. 7B). By SNP-tracking analyses of a public DHS profile of hybrid morula embryos, it was confirmed that AG-DHSs, but not GG-DHSs, recapitulate the corresponding parental allele-specific DHSs (FIG. 8B), indicating that AG-DHSs were physiological. Interestingly, AG-DHSs included almost all known maternally-methylated ICRs (FIG. 8C). This finding raised the possibility that AG-DHSs could serve as indicators of genomic imprinting.

Figure 7C:
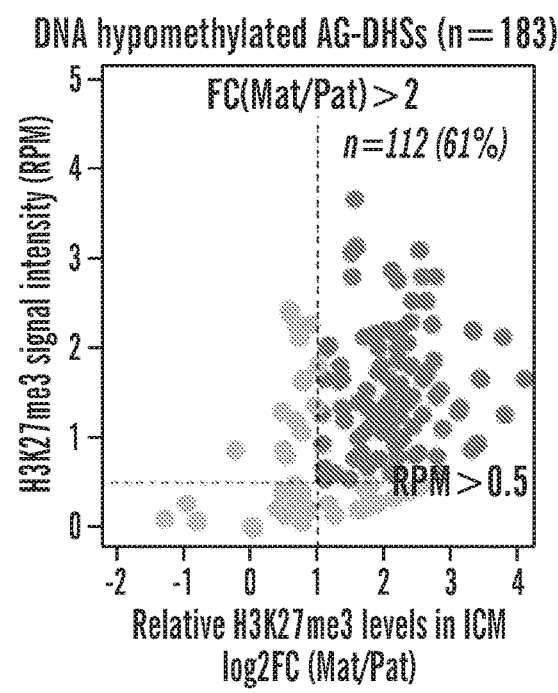
Figure 8D:
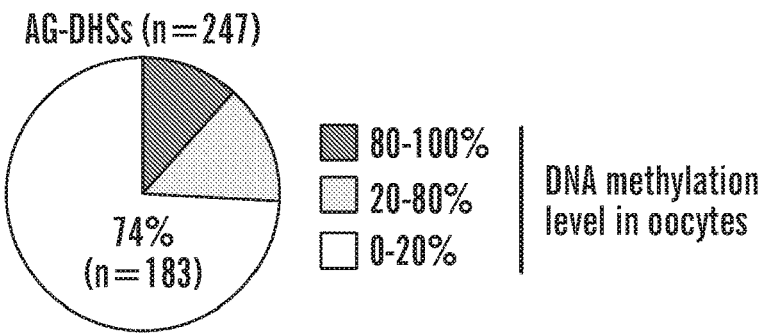

Because both gDMR and maternal H3K27me3 can contribute to maternal allele inaccessibility (FIG. 6), their respective contribution to the generation of the 247 AG-DHSs was determined. Analyses of the oocyte DNA methylome identified 183 (74%) AG-DHSs in DNA hypomethylated regions (FIG. 8D). Allelic H3K27me3 enrichment analysis revealed that 112 of the 183 were marked with maternal allele-biased H3K27me3 in inner cell mass (ICM) of blastocysts (FIG. 7C). Of the 112 AG-DHSs, 105 showed maternal allele-specific H3K27me3 enrichment in zygotes [RPM>0.5, FC(Mat/Pat)>4], which suggested that the maternal allele-biased H3K27me3 is inherited from zygotic maternal chromatin. By associating the 105 H3K27me3-marked AG-DHSs with their nearest genes, 76 genes (Table 1, below) were obtained as putative H3K27me3-dependent imprinted genes.

TABLE 1

| gene_name | gene_chr | gene_start | gene_end |
|---|---|---|---|
| Rbp2 | chr9 | 98390956 | 98410190 |
| Runx1 | chr16 | 92601711 | 92826311 |
| Sfmbt2 | chr2 | 10292078 | 10516880 |
| Slc38a2 | chr15 | 96517823 | 96530129 |
| Slc38a4 | chr15 | 96825254 | 96886387 |
| Gramd1b | chr9 | 40105492 | 40263349 |
| Bbx | chr16 | 50191957 | 50432502 |
| Sox21 | chr14 | 118632456 | 118636252 |
| Mbnl2 | chr14 | 120674891 | 120830920 |
| Prdm11 | chr2 | 92815063 | 92886301 |
| 1700067G17Rik | chr1 | 90912688 | 90918785 |
| 1700095B10Rik | chr5 | 113222312 | 113230721 |
| Mir692-2b | chr4 | 125181992 | 125182101 |
| Sh3gl3 | chr7 | 89319728 | 89455927 |
| Etv6 | chr6 | 133985725 | 134220165 |
| Tle3 | chr9 | 61220173 | 61266304 |
| Hunk | chr16 | 90386642 | 90499798 |
| Gab1 | chr8 | 83288333 | 83404378 |
| Matn1 | chr4 | 130500300 | 130511391 |
| Chst1 | chr2 | 92439864 | 92455409 |
| Clic6 | chr16 | 92498392 | 92541486 |
| 1700110K17Rik | chr9 | 40141057 | 40150922 |
| Foxl1 | chr8 | 123651585 | 123654544 |
| Mir6241 | chr14 | 118657855 | 118657958 |
| Otog | chr7 | 53496357 | 53566804 |
| 1700017J07Rik | chr2 | 168803769 | 168804406 |
| 4930404H11Rik | chr12 | 72641594 | 72657120 |
| Gm5086 | chr13 | 98329955 | 98353949 |
| Tshz2 | chr2 | 169459146 | 169714004 |
| Bmp7 | chr2 | 172695189 | 172765794 |
| G730013B05Rik | chr16 | 50526358 | 50559572 |
| Rftn1 | chr17 | 50132632 | 50329822 |
| C430002E04Rik | chr3 | 41291603 | 41297121 |
| Myoz2 | chr3 | 122709124 | 122737905 |
| Six3os1 | chr17 | 86001272 | 86017736 |
| Slc38a1 | chr15 | 96401849 | 96473344 |
| Rbms1 | chr2 | 60590010 | 60801261 |
| Flt1 | chr5 | 148373772 | 148537564 |
| Sall3 | chr18 | 81163113 | 81183317 |
| Otx2os1 | chr14 | 49288963 | 49413023 |
| 1700006F04Rik | chr14 | 120148449 | 120150786 |
| 2300005B03Rik | chr15 | 74573269 | 74577117 |
| 4931430N09Rik | chr6 | 118830176 | 118835561 |
| Gas7 | chr11 | 67346500 | 67502494 |
| Phf17 | chr3 | 41359656 | 41420786 |
| Igsf21 | chr4 | 139582767 | 139802726 |
| Otx2 | chr14 | 49277859 | 49282547 |
| Klhdc7a | chr4 | 139518088 | 139523941 |
| 1700125H03Rik | chr8 | 70892358 | 70899609 |
| Lpar3 | chr3 | 145883925 | 145949178 |
| Mir6239 | chr14 | 118352964 | 118353069 |
| Epas1 | chr17 | 87153204 | 87232750 |
| Slc6a1 | chr6 | 114232629 | 114267519 |
| Cdh26 | chr2 | 178165312 | 178222071 |
| 1700025C18Rik | chr2 | 164904193 | 164916250 |
| Prox1 | chr1 | 191945658 | 191994559 |
| 1700121N20Rik | chr12 | 107680862 | 107685876 |
| Adamts2 | chr11 | 50415587 | 50617551 |
| Gadl1 | chr9 | 115818573 | 115985294 |

TABLE 1-continued

| gene_name | gene_chr | gene_start | gene_end |
|---|---|---|---|
| Dnase2b | chr3 | 146244337 | 146278562 |
| Inhbb | chr1 | 121312042 | 121318825 |
| E2f3 | chr13 | 29998444 | 30077932 |
| Ajap1 | chr4 | 152747330 | 152856939 |
| BC049762 | chr11 | 51067153 | 51076453 |
| Edn3 | chr2 | 174586274 | 174609543 |
| Enc1 | chr13 | 98011060 | 98022995 |
| 4930465M20Rik | chr12 | 108961953 | 108973698 |
| 9630028H03Rik | chr2 | 135406266 | 135408956 |
| Cd44 | chr2 | 102651300 | 102741822 |
| Epgn | chr5 | 91456543 | 91464238 |
| Syt13 | chr2 | 92755258 | 92796208 |
| Myb | chr10 | 20844736 | 20880790 |
| Lrig3 | chr10 | 125403275 | 125452415 |
| Fam198b | chr3 | 79689852 | 79750200 |
| Smoc1 | chr12 | 82127795 | 82287401 |
| 1700084F23Rik | chr13 | 70142928 | 70167226 |

Figure 7D:
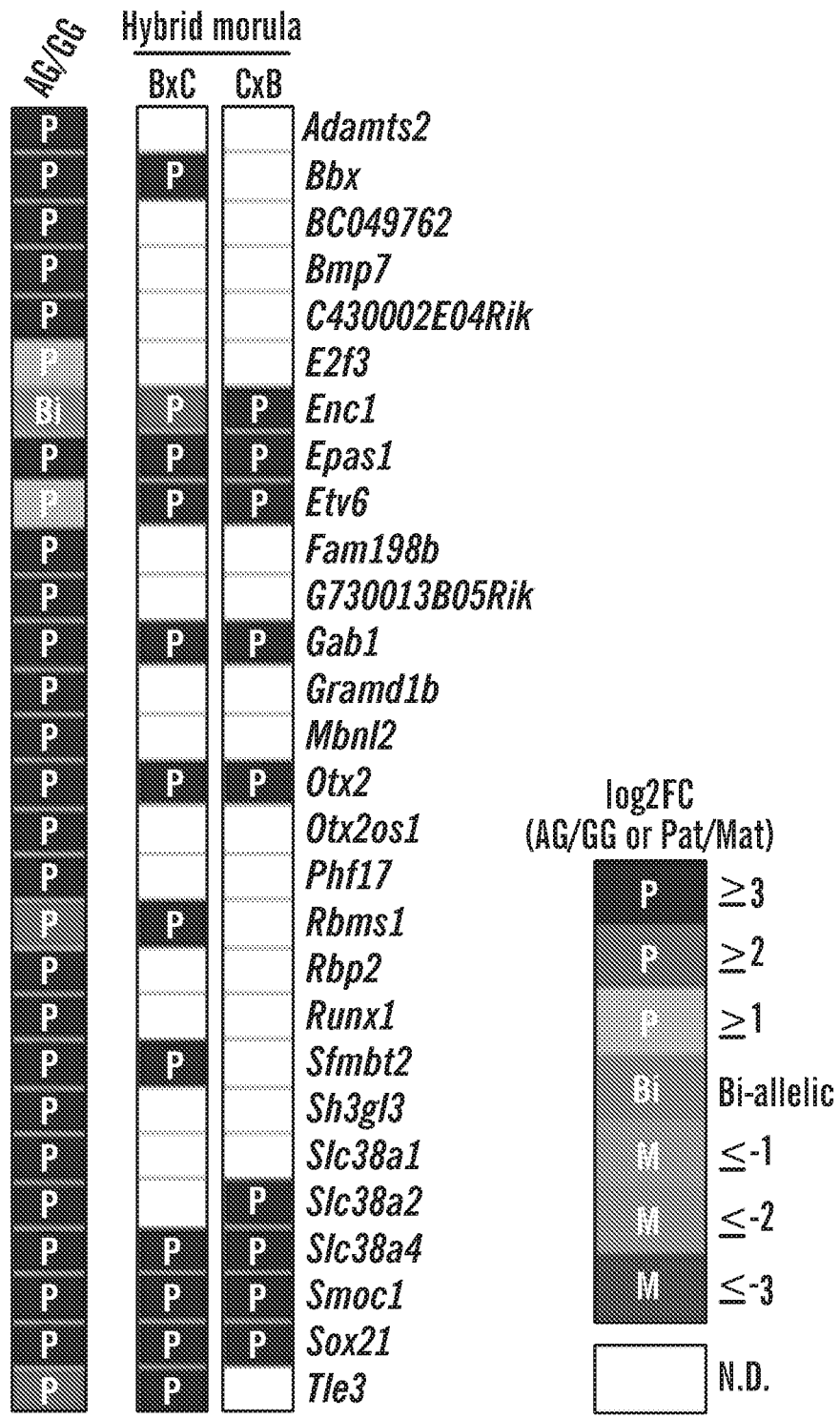
Figure 9A:
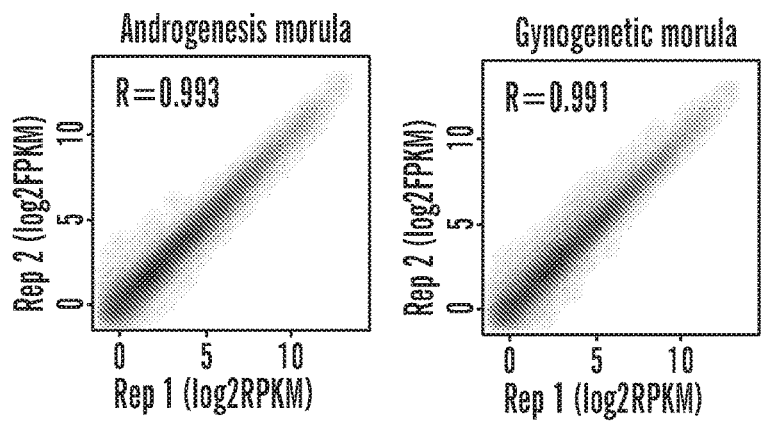
FIG. 9A-FIG. 9D shows allelic gene expression in morula embryos, related to FIG. 7.
Figure 9B:
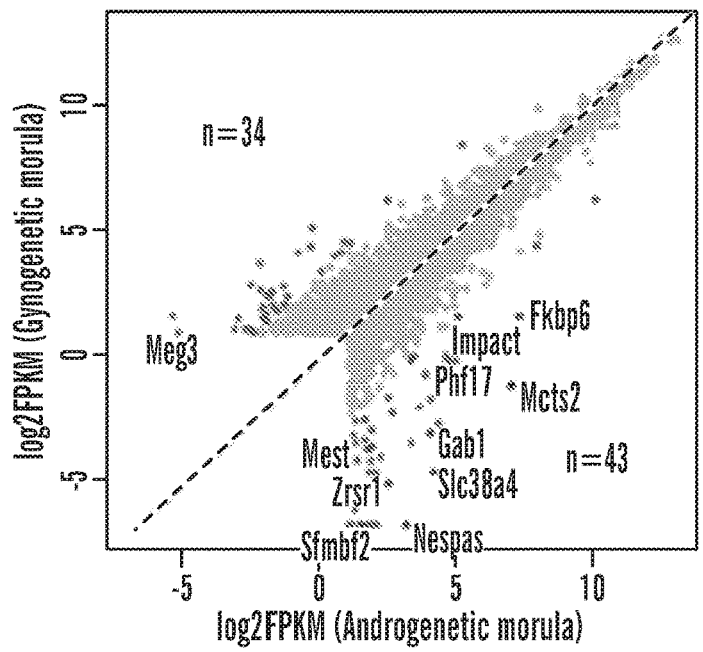
Figure 9C:
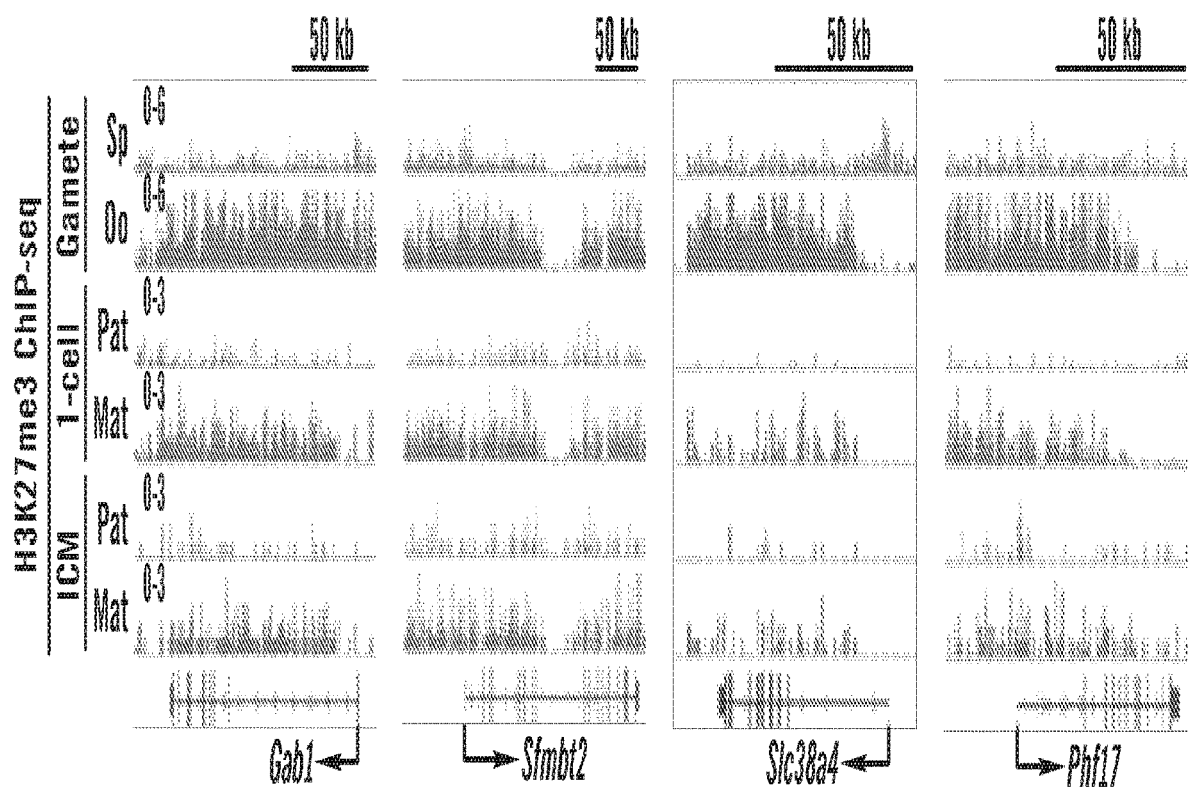
Figure 9D:
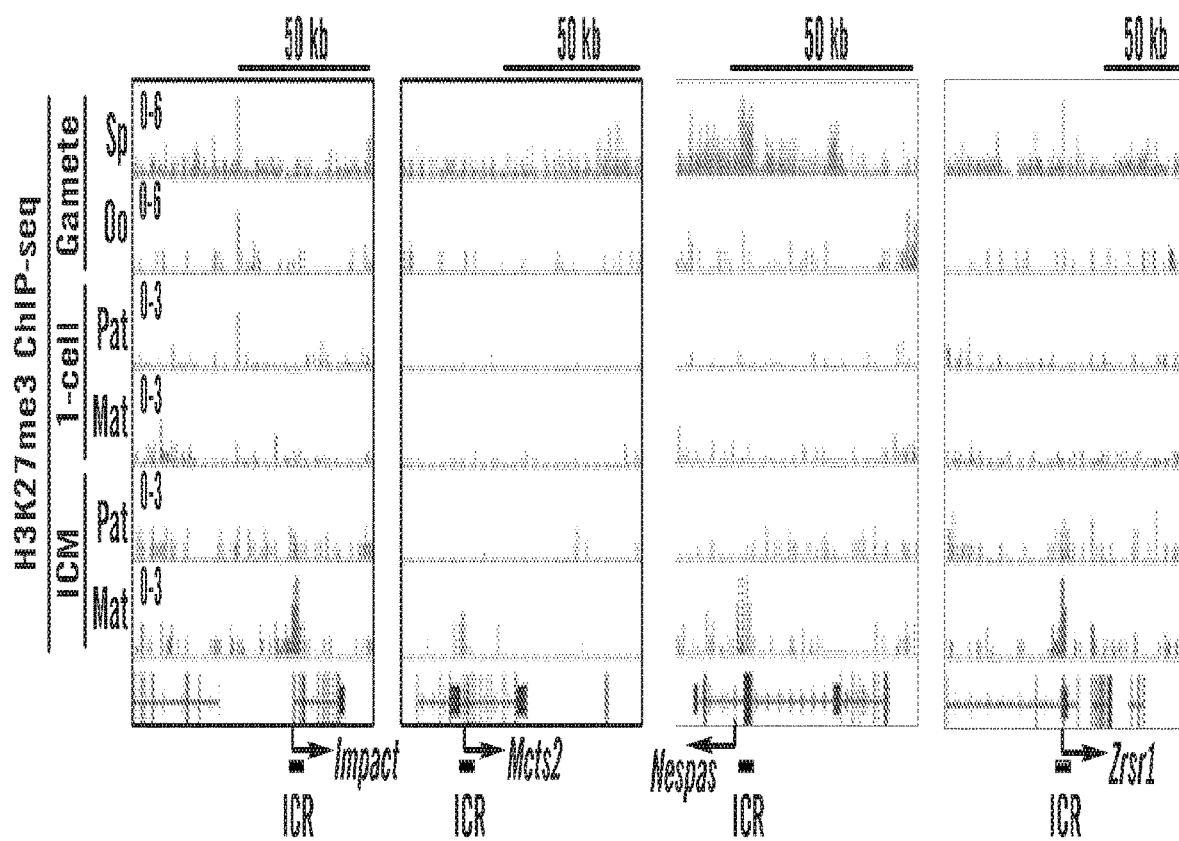

To determine if any of the 76 genes are indeed imprinted in preimplantation embryos, RNA-seq analysis was performed for AG and GG morula embryos (FIG. 9A). After confirming AG- or GG-specific expression of known imprinted genes (FIG. 9B), the relative AG/GG expression levels for each candidate was calculated. Among the 76 genes, 28 were expressed in either AG or GG embryos (FPKM>0.5). Interestingly, 27 of the 28 genes exhibited biased (FC>2), and 23 genes exhibited highly biased (FC>8) expression in AG embryos (FIG. 7D, left column). Using a RNA-seq dataset of hybrid IVF morula embryos, it was further confirmed that all 13 SNP-trackable genes exhibit paternal allele-specific expression (FIG. 7D, right columns). Importantly, these genes included Sfmbt2, Gab1, Slc38a4, and Phf17 whose imprinted expression was suggested to be independent of oocyte DNA methylation. These 'non-canonical' imprinted genes were coated with oocyte-specific H3K27me3 domains that are retained even in blastocysts (FIG. 9C), which is in contrast to DNA methylation-dependent 'canonical' imprinted genes that are devoid of oocyte H3K27me3 (FIG. 9D). Collectively, these results demonstrated that maternal H3K27me3 may serve as a DNA methylation-independent imprinting mark.

Figure 10A:
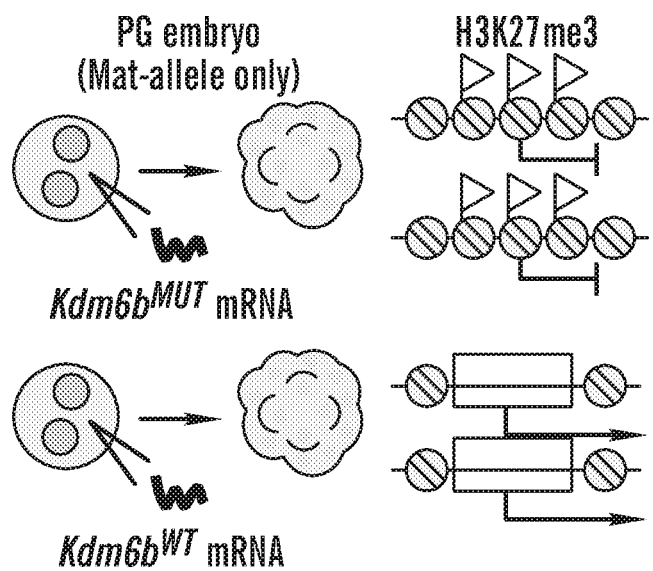
FIG. 10A-FIG. 10E shows maternal H3K27me3 serves as an imprinting mark.
Figure 10B:
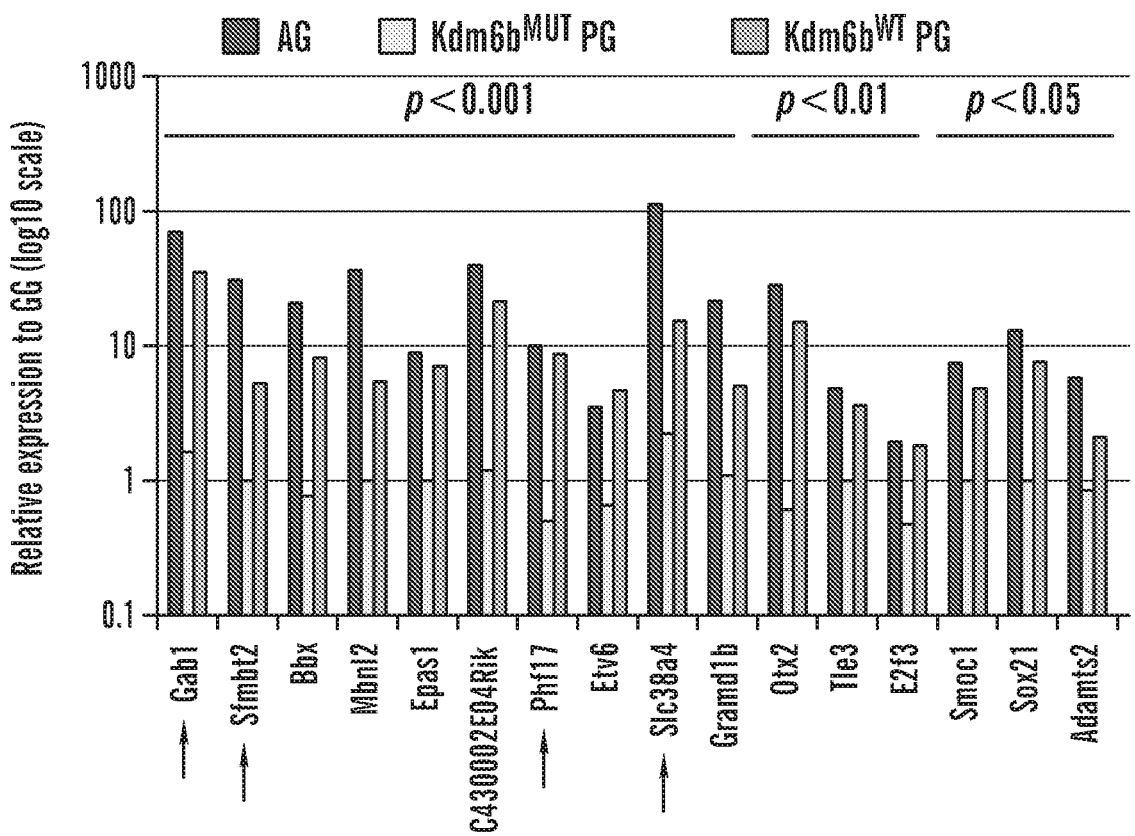
Figure 11A:
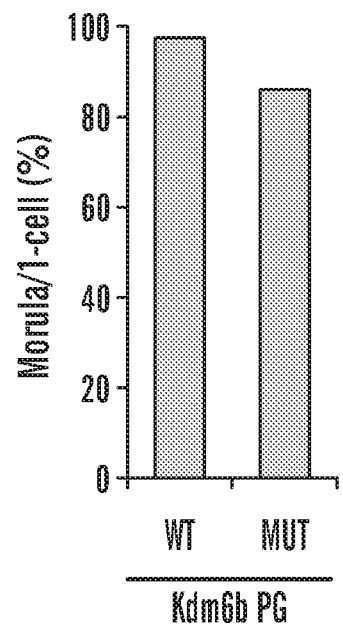
FIG. 11A-FIG. 11G shows the effect of Kdm6b mRNA injection on maternal allele expression and accessibility, related to FIG. 10.
Figure 11B:
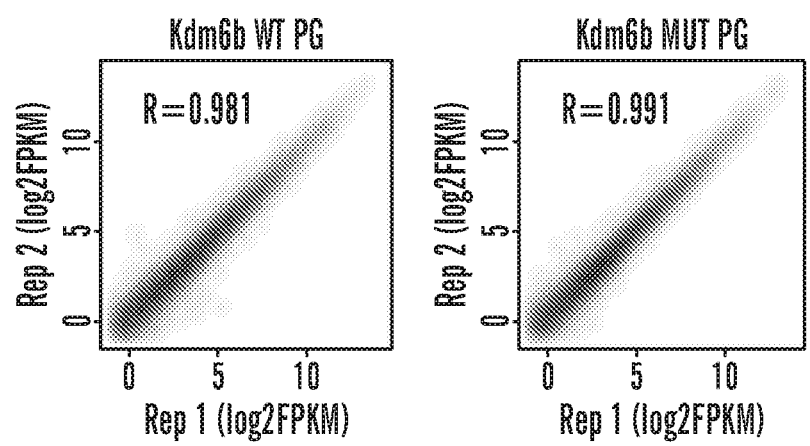
Figure 11C:
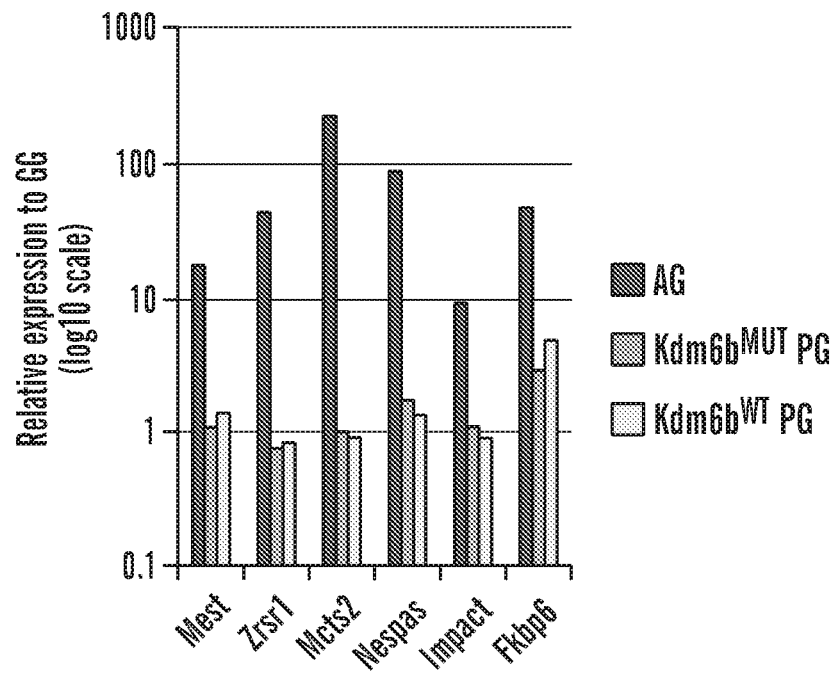
Figure 11D:
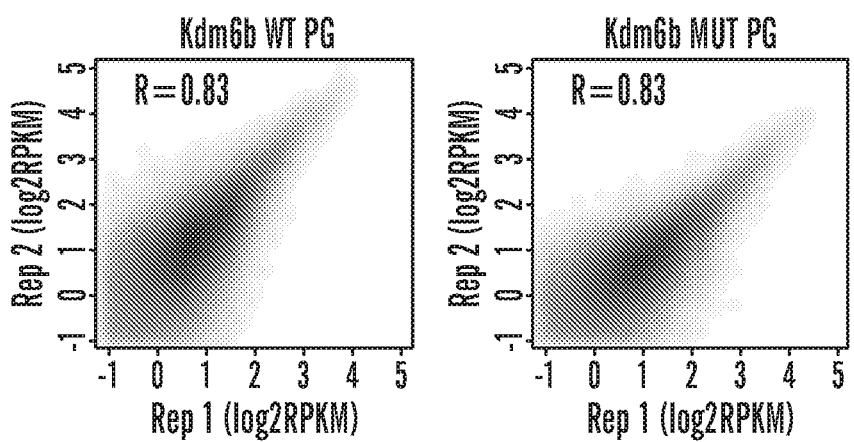

To determine whether maternal H3K27me3 was responsible for maternal allele repression of the putative H3K27me3-dependent imprinted genes, $Kdm6b^{WT}$ or $Kdm6b^{MUT}$ mRNAs was injected into 1-cell stage parthenogenetic (PG) embryos (FIG. 10A). After verifying that the injection did not affect embryo development to the morula stage (FIG. 11A), RNA-seq analysis was performed (FIG. 11B). Of the 28 putative imprinted genes expressed in AG morula embryos (FIG. 7D), 16 were significantly depressed in a catalytic activity-dependent manner, which include all 4 known non-canonical imprinted genes (FIG. 10B). In contrast, canonical imprinted genes were not affected by $Kdm6b^{WT}$ injection (FIG. 11C), demonstrating that H3K27me3 was specifically required for maternal allele repression of the putative H3K27me3-dependent imprinted genes.

Figure 10C:
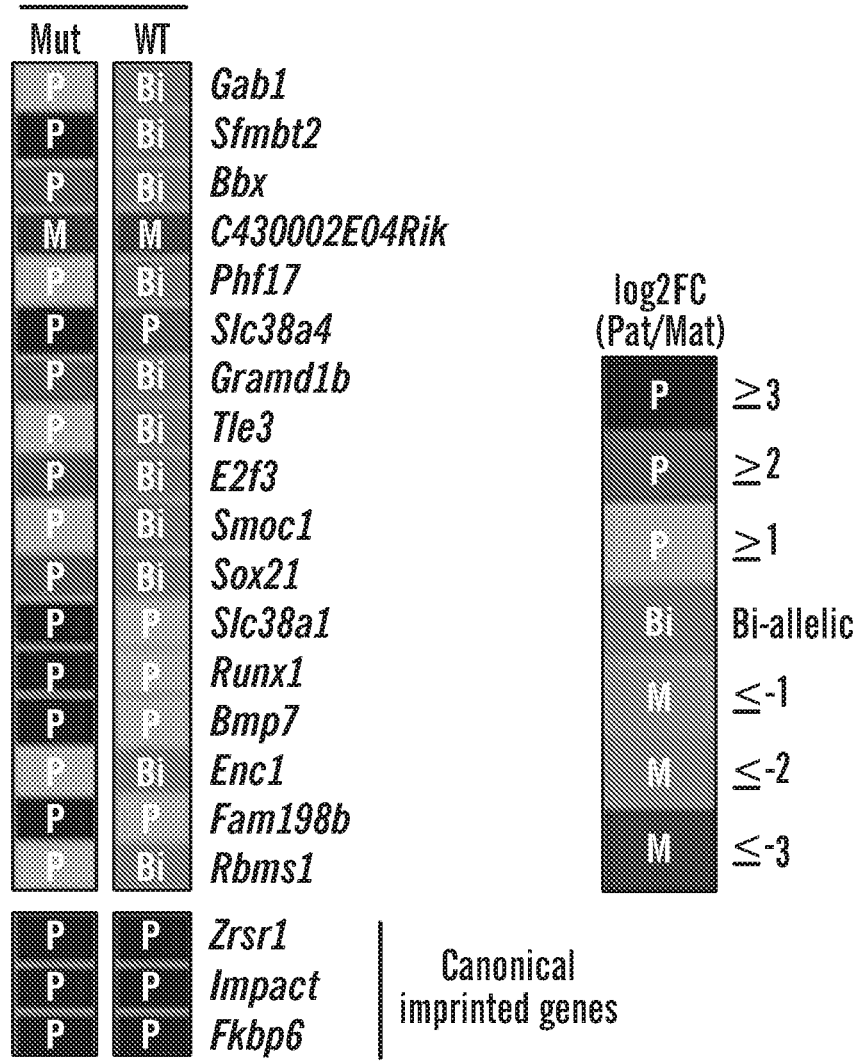

To demonstrate that Kdm6b-mediated maternal allele derepression occurs in a physiological context, RNA-seq analysis was performed in IVF-derived hybrid morula embryos that had been injected with $Kdm6b^{WT}$ or $Kdm6b^{MUT}$ mRNA at the 1-cell stage. Of the 28 putative imprinted genes, 17 had sufficient SNP reads, and 16 of them showed paternal allele-biased expression in $Kdm6b^{MUT}$-injected embryos (FIG. 10C). Notably, the extent of the paternal allelic bias of all these genes became milder in Kdm6b$^{WT}$-injected embryos, while that of canonical imprinted genes was not affected (FIG. 10C). These data indicated that imprinted expression of these genes depends on maternal H3K27me3.

Figure 10D:
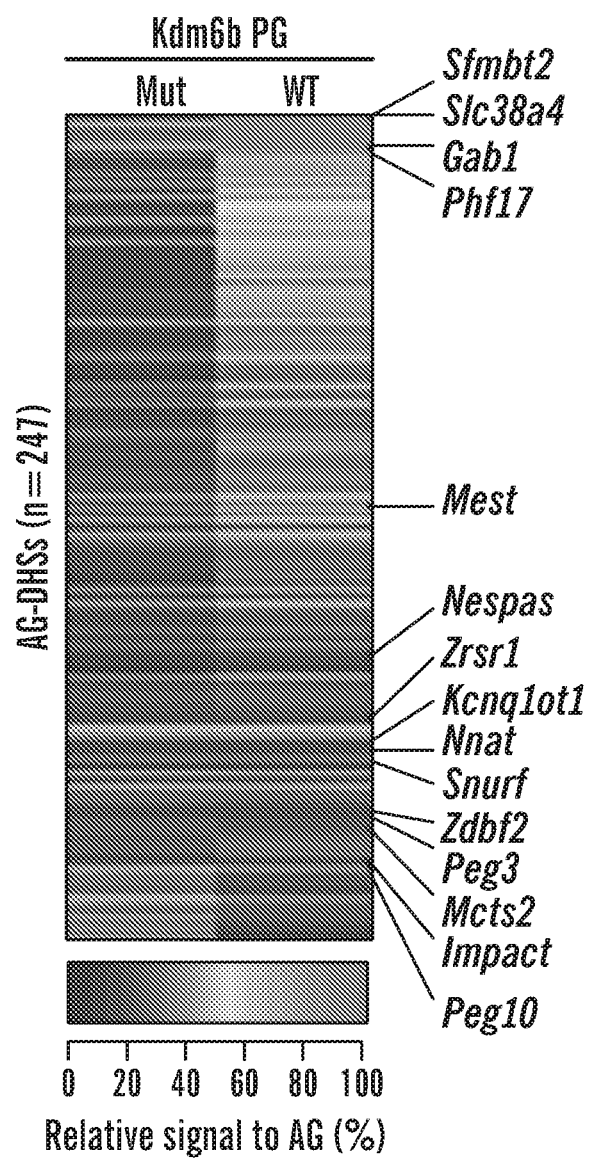
Figure 10E:
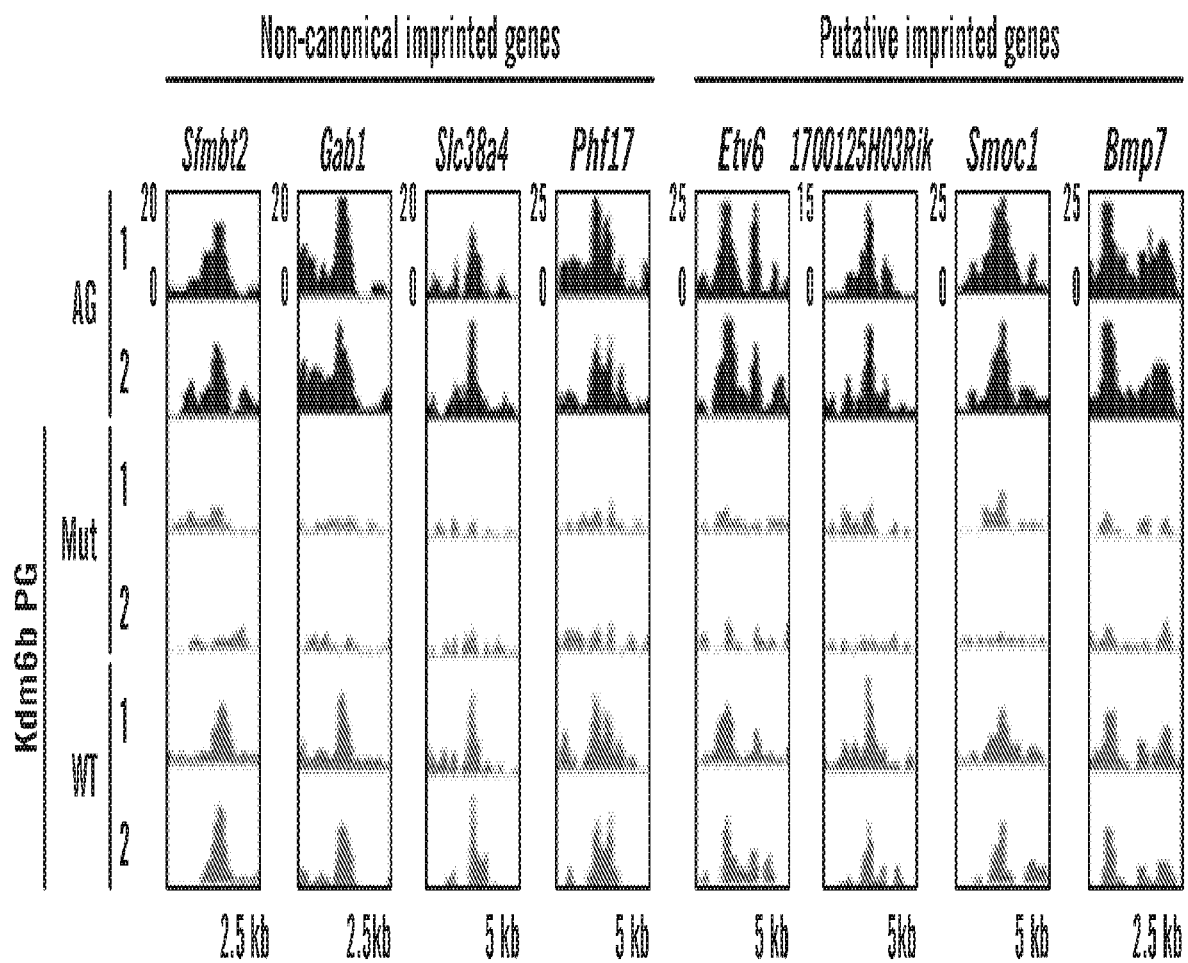
Figure 11E:
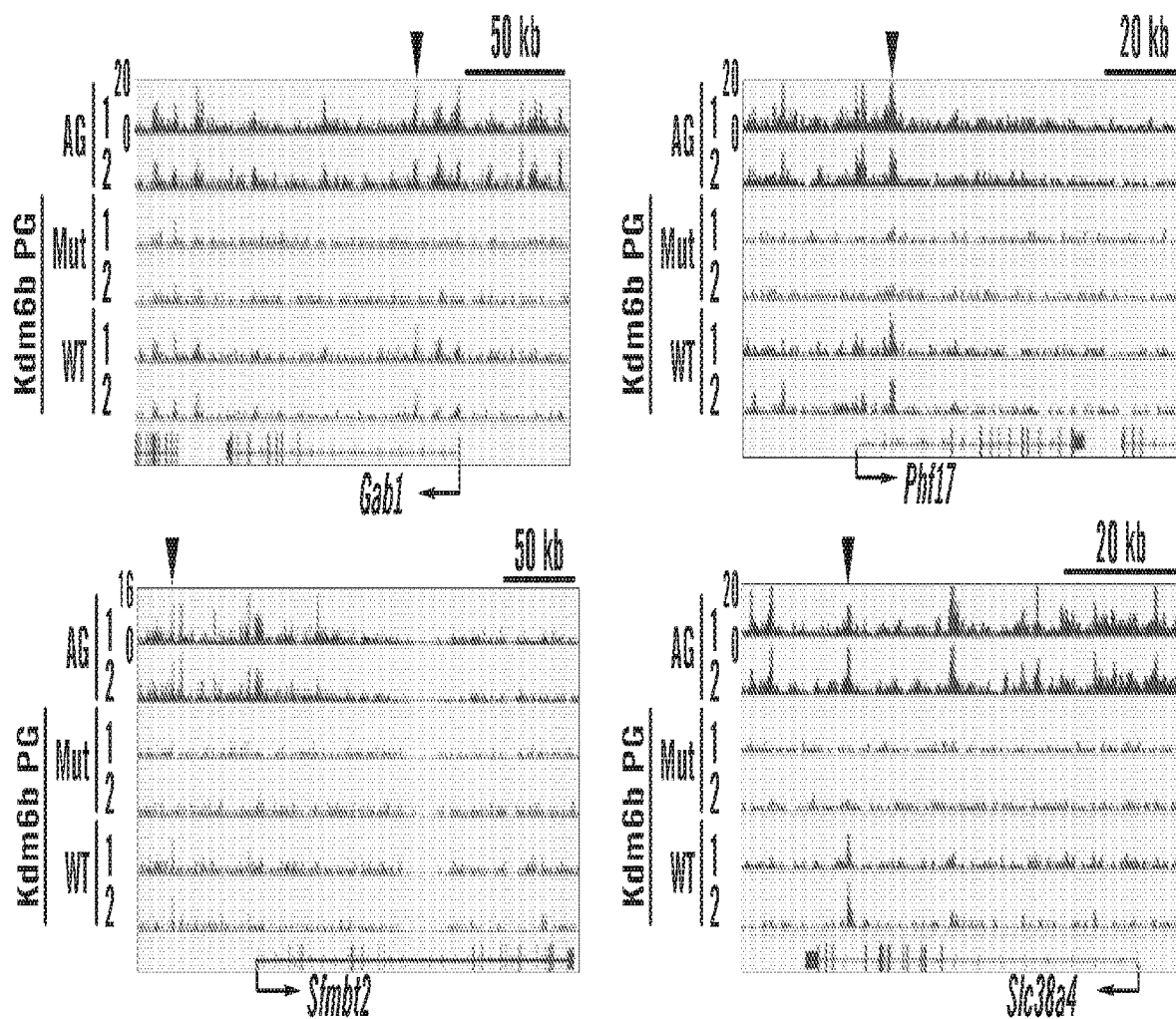
Figure 11F:
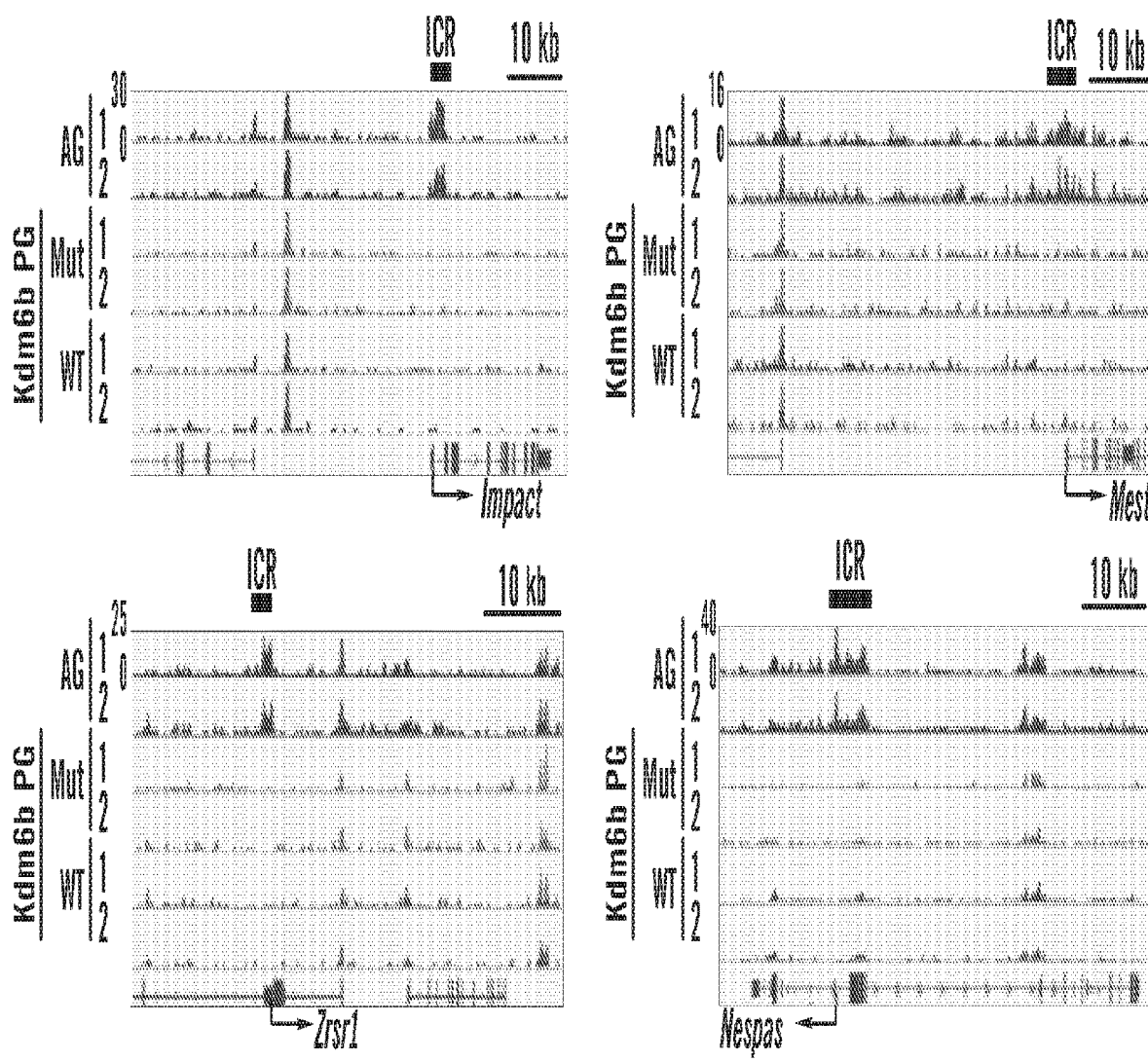
Figure 11G:
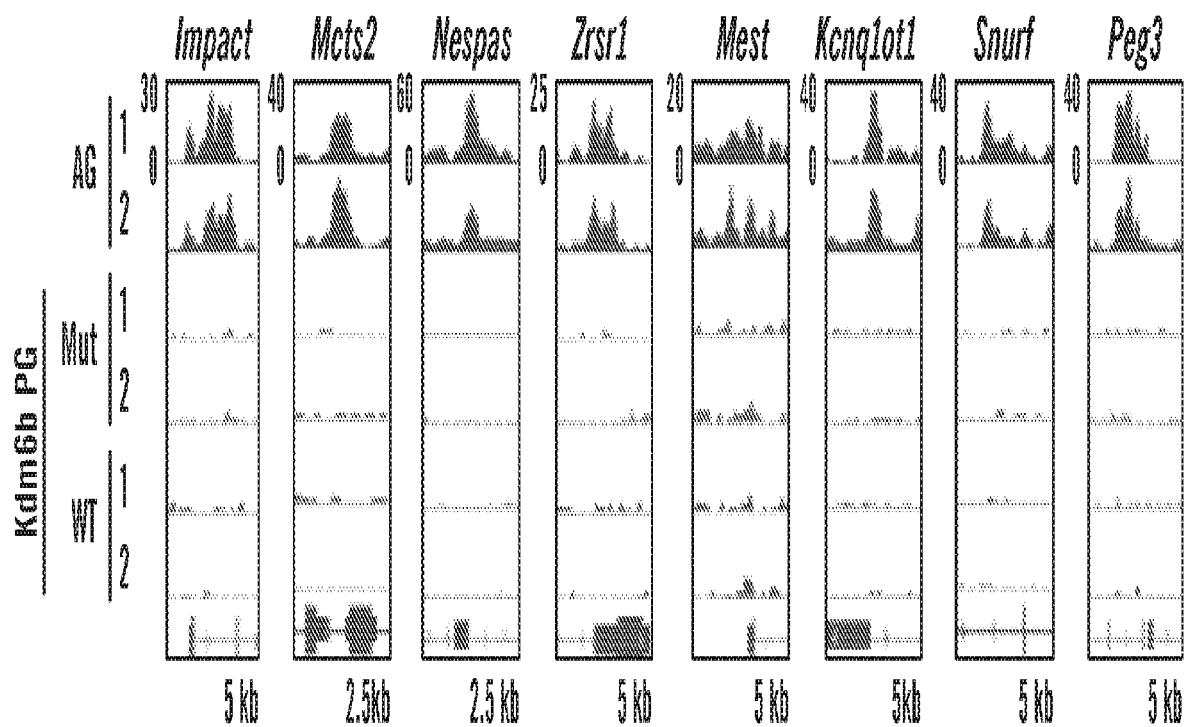

To determine whether maternal allele derepression couples with gain of maternal chromatin accessibility, liD-Nase-seq was performed for Kdm6b$^{WT}$- and Kdm6b$^{MUT}$-injected PG morula embryos (FIG. 7D). We found that Kdm6b$^{WT}$, but not Kdm6b$^{MUT}$, markedly increased chromatin accessibility in AG-DHSs of putative H3K27me3-dependent imprinted genes, including all 4 non-canonical imprinted genes (FIG. 10D, FIG. 10E and FIG. 11E). In contrast, ICRs of canonical imprinted genes were not affected (FIG. 10D and FIG. 11F, FIG. 11G). These results indicated that maternal H3K27me3 restricts maternal allele accessibility to mediate H3K27me3-dependent genomic imprinting.

Example 5: Imprinting Status in Blastocysts

Figure 12A:
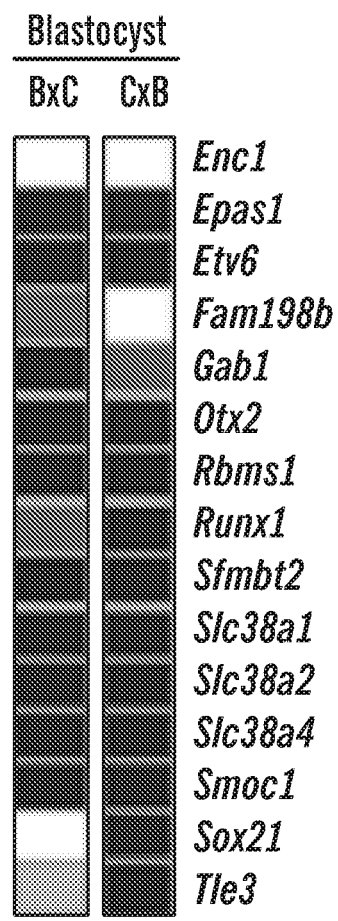
FIG. 12A-FIG. 12E shows cell lineage-specific dynamics of H3K27me3-dependent genomic imprinting.

The imprinting status of putative H3K27me3-dependent imprinted genes was then analyzed in blastocyst embryos by SNP tracking of recently published datasets. Of the 28 genes imprinted in morula embryos (FIG. 7D), 15 had sufficient SNP reads in both reciprocal crosses (FIG. 12A). Among them, 12 (80%) showed paternal allelic expression in both crosses (FIG. 12A), demonstrating that H3K27me3-dependent imprinting was largely maintained in blastocysts.

Figure 12B:
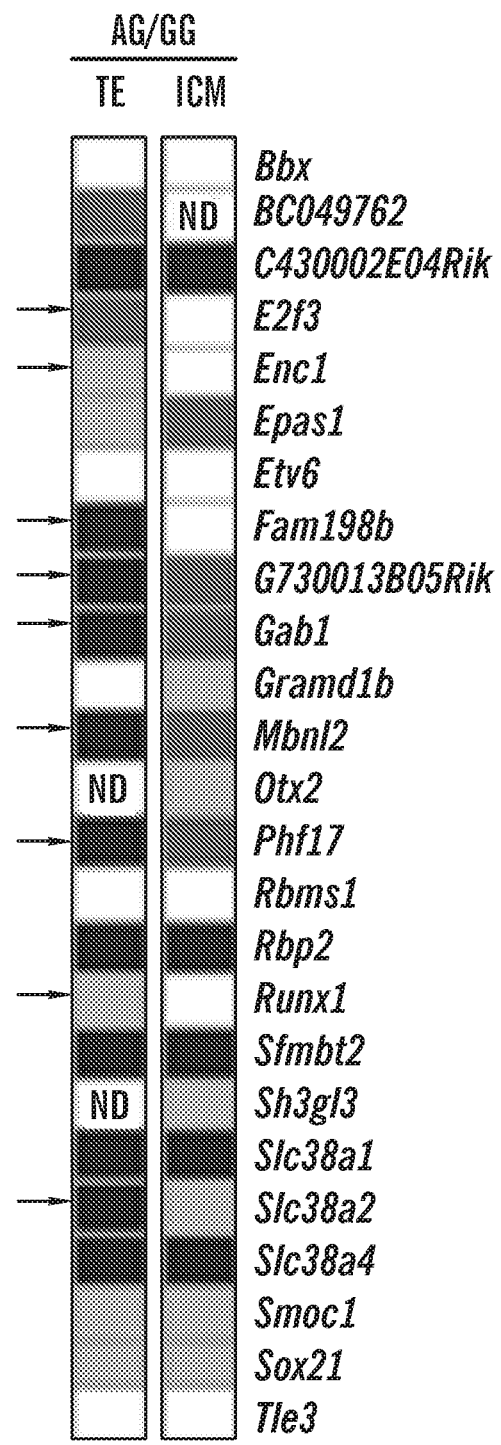
Figure 13A:
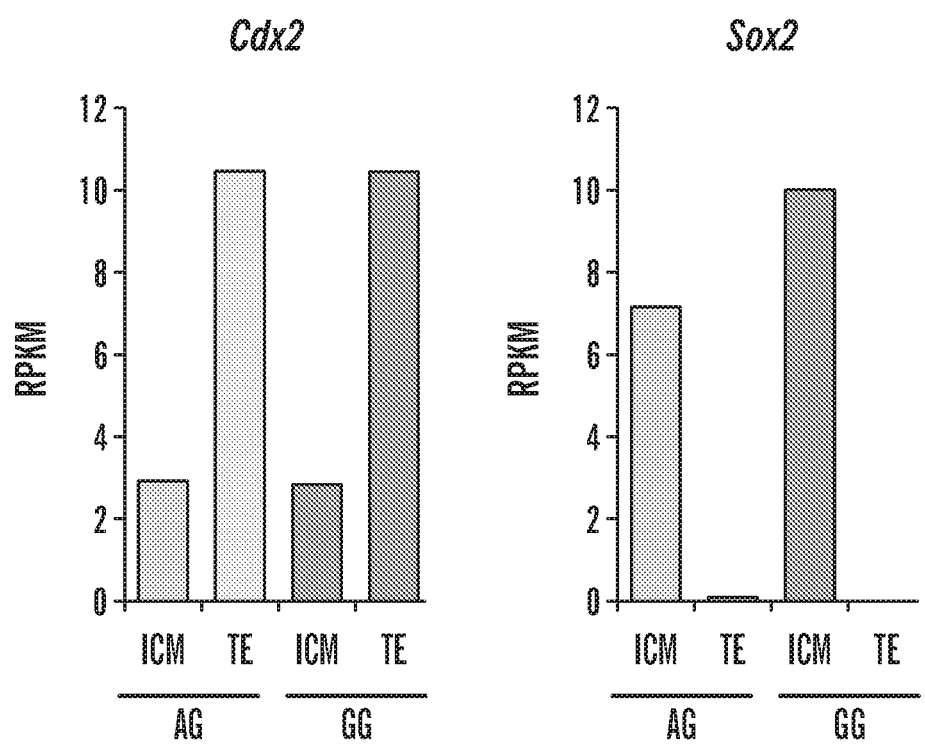
FIG. 13A-FIG. 13E shows genomic imprinting in E6.5 embryos, related to FIG. 12.

Since previous studies have indicated that Gab1, Sfmbt2, and Phf17 are imprinted only in extra-embryonic tissues, their imprinting status was examined in ICM. TE and ICM cells were isolated from AG and GG blastocysts and RNA-seq analysis was performed. Marker gene expression confirmed no cross-contamination (FIG. 13A). Of the 28 putative imprinted genes (FIG. 7D), 23 and 24 were expressed in TE and ICM, respectively (RPKM>0.5). Of these, 18 (78%) in TE and 16 (67%) in ICM showed AG-biased expression (FC>2) (FIG. 12B). Notably, 9 genes showed weaker AG-bias in ICM compared to TE (FIG. 12B, arrows), suggesting that H3K27me3-dependent imprinting might start to diminish in ICM.

Example 6: Post-Implantation Imprinting Dynamics

Figure 13B:
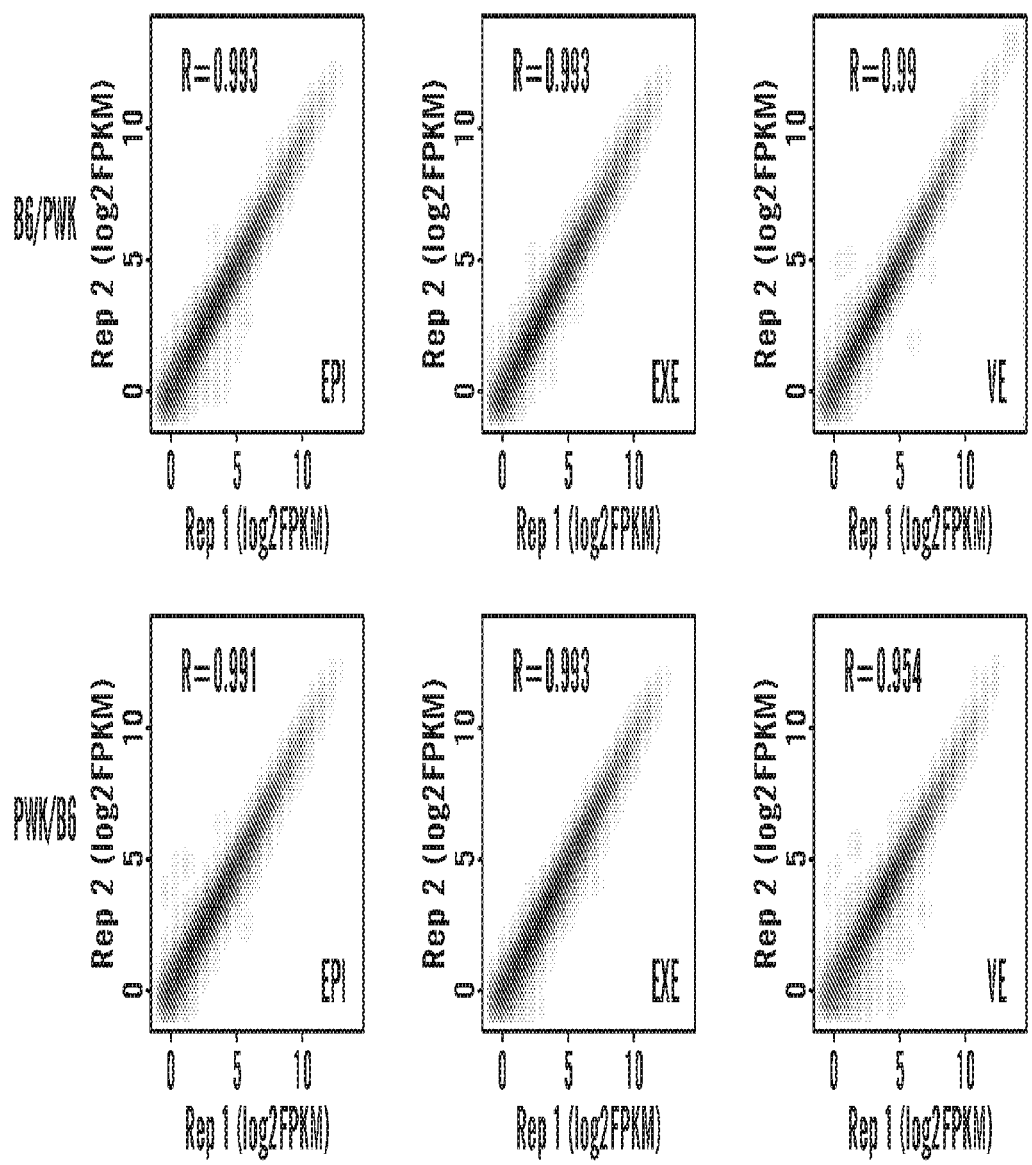
Figure 13C:
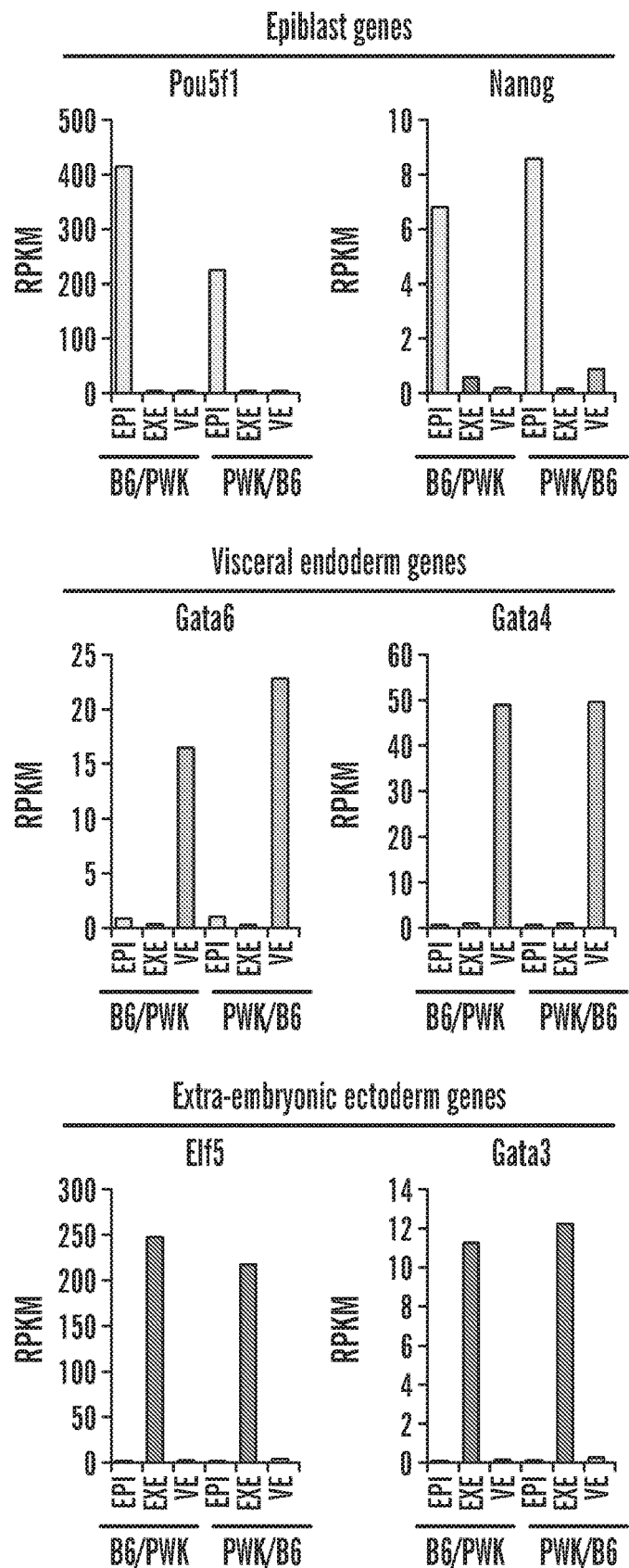
Figure 13D:
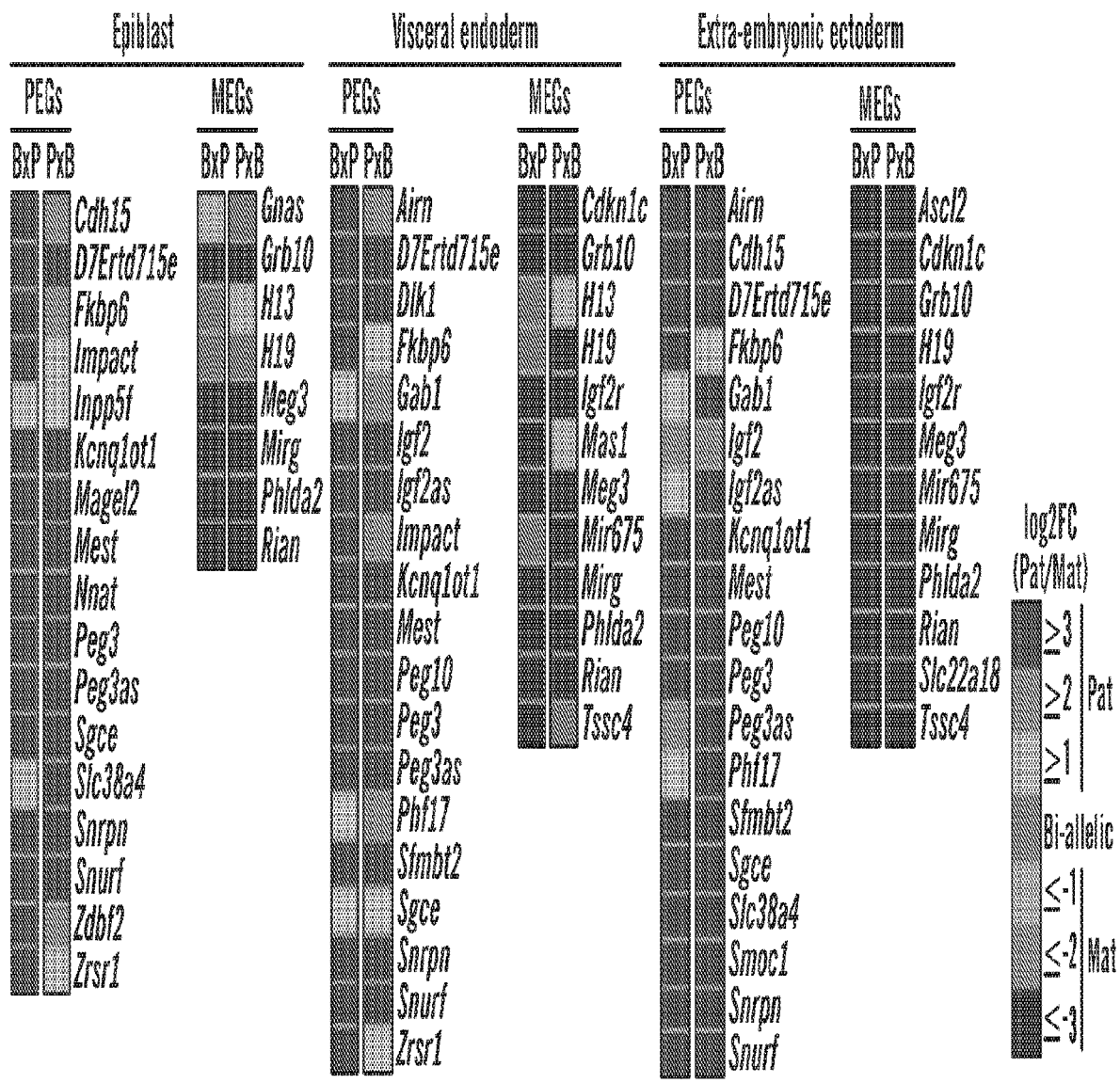
Figure 13E:
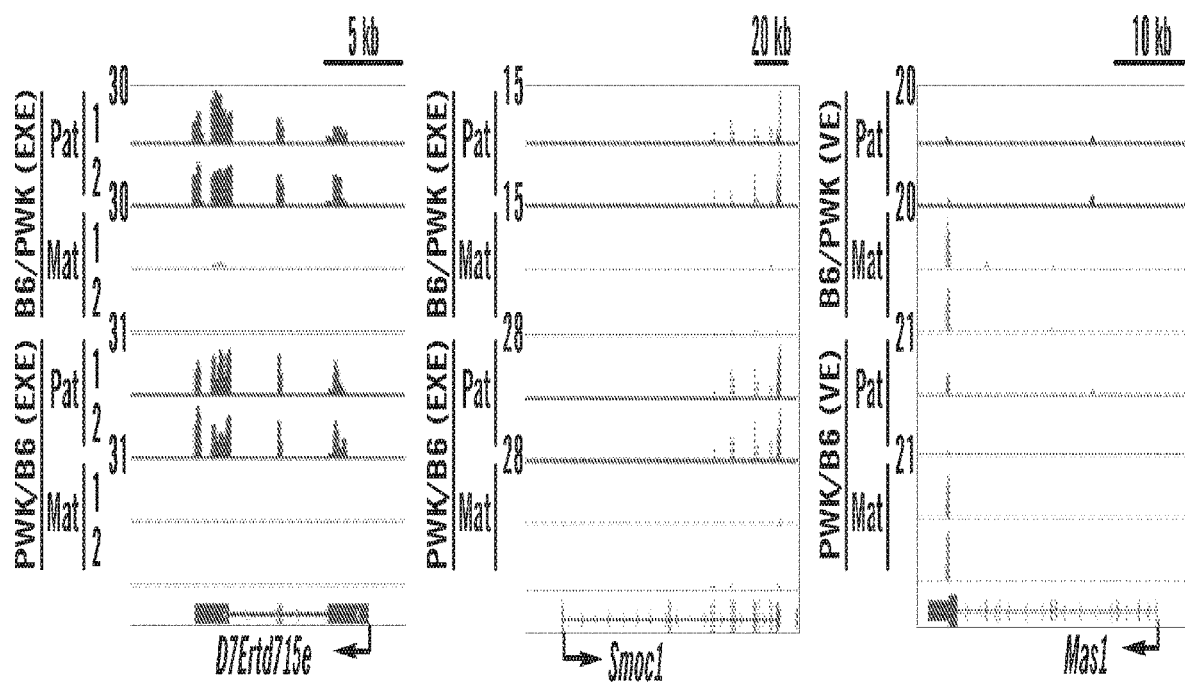

To determine the imprinting status in post-implantation embryos, hybrid E6.5 embryos were dissected into epiblast (EPI), visceral endoderm (VE), and extra-embryonic ectoderm (EXE), and RNA-seq analysis performed (FIG. 13B). Cell identity was confirmed by analyzing cell lineage-specific marker gene expression (FIG. 13C) and identified 17 paternally-expressed genes (PEGs) and 8 maternally-expressed genes (MEGs) in EPI, 19 PEGs and 12 MEGs in both VE and EXE, which included new imprinted genes, such as D7Ertd715e (also known as Snhg14), Smoc1, and Mas1 (FIG. 13D, FIG. 13E).

Figure 12C:
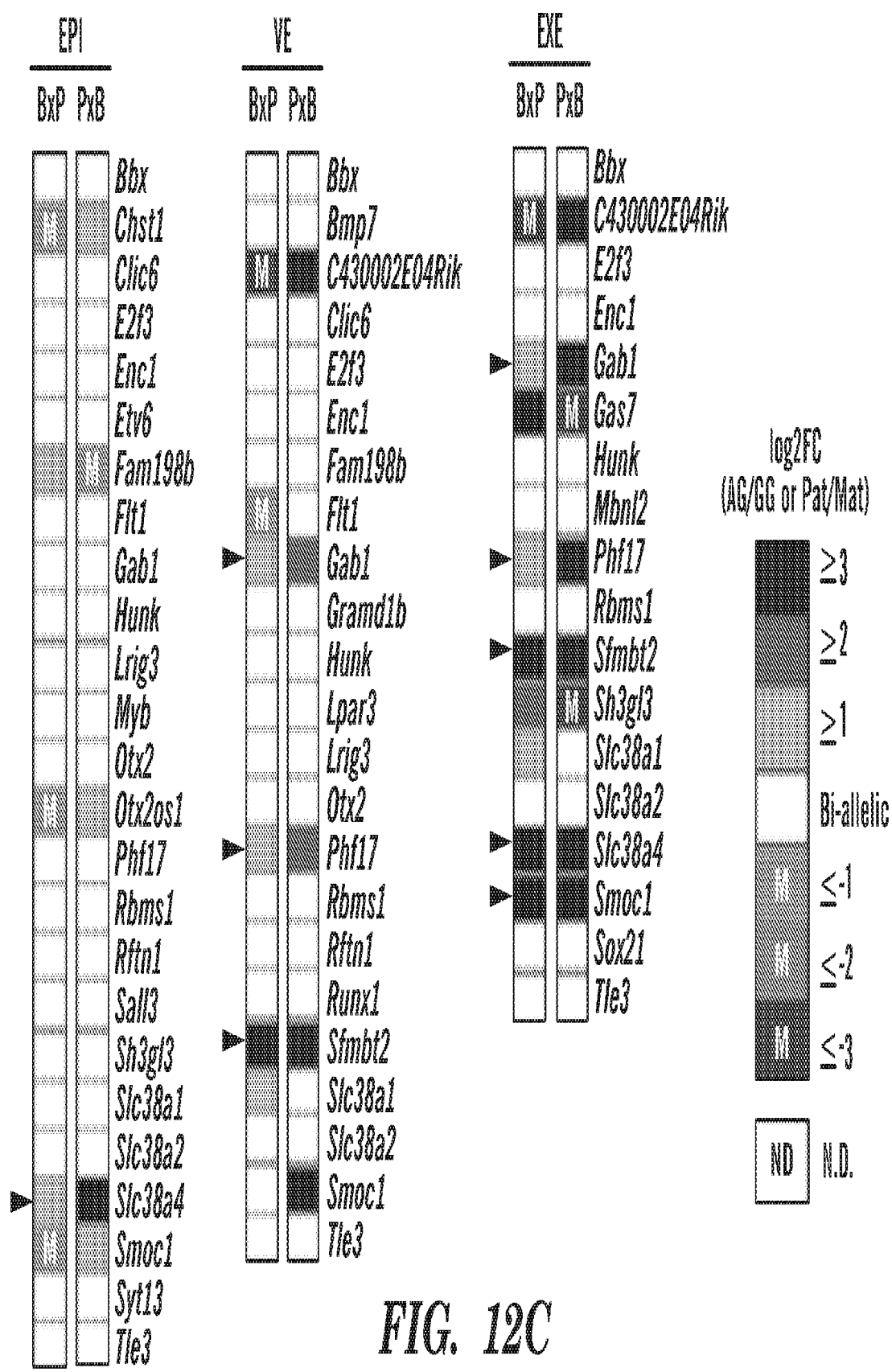

Among the 76 putative H3K27me3-dependent imprinted genes, 25, 23, and 17 genes had enough SNP reads in both reciprocal crosses in EPI, VE, and EXE, respectively (FIG. 12C). It was found that 1, 3, and 5 genes are paternally expressed in EPI, VE, and EXE, respectively (FIG. 12C, arrowheads). The genes imprinted in EXE included the 4 non-canonical imprinted genes, Gab1, Phf17, Sfinbt2, and Slc38a4, and a new imprinted gene, Smoc1 (FIG. 12C). These results suggested that H3K27me3-dependent imprinting was completely erased in the epiblast with the exception of Slc38a4, but some are maintained in the extra-embryonic cell lineages.

Figure 12D:
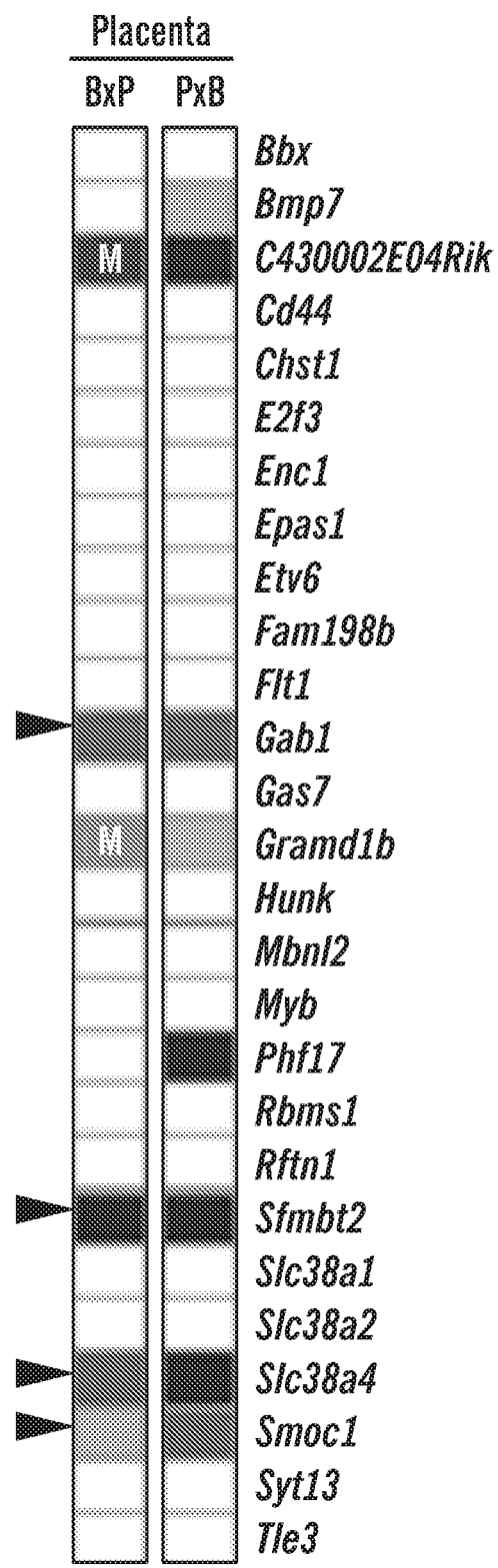
Figure 12E:
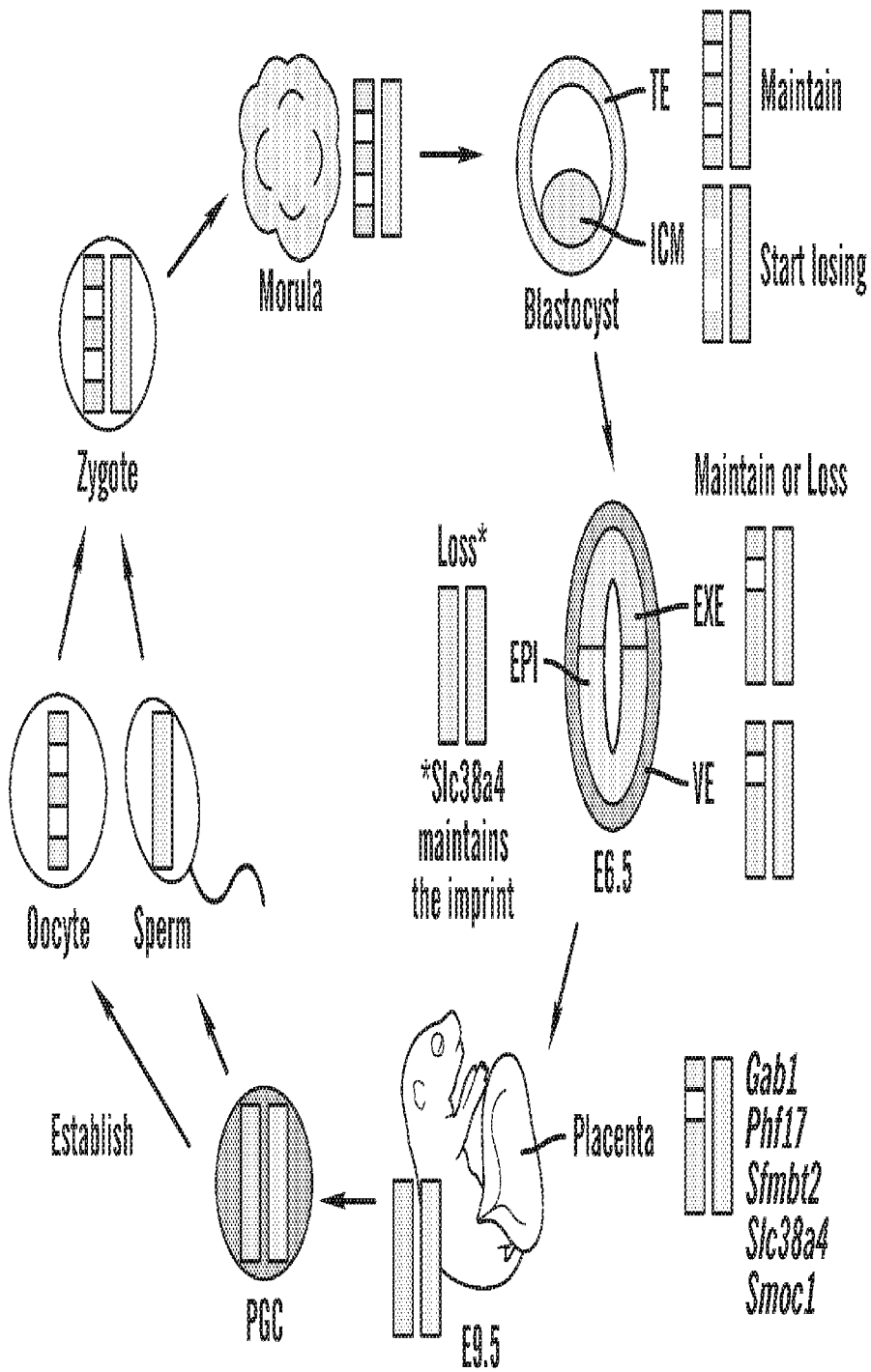
Figure 14A:
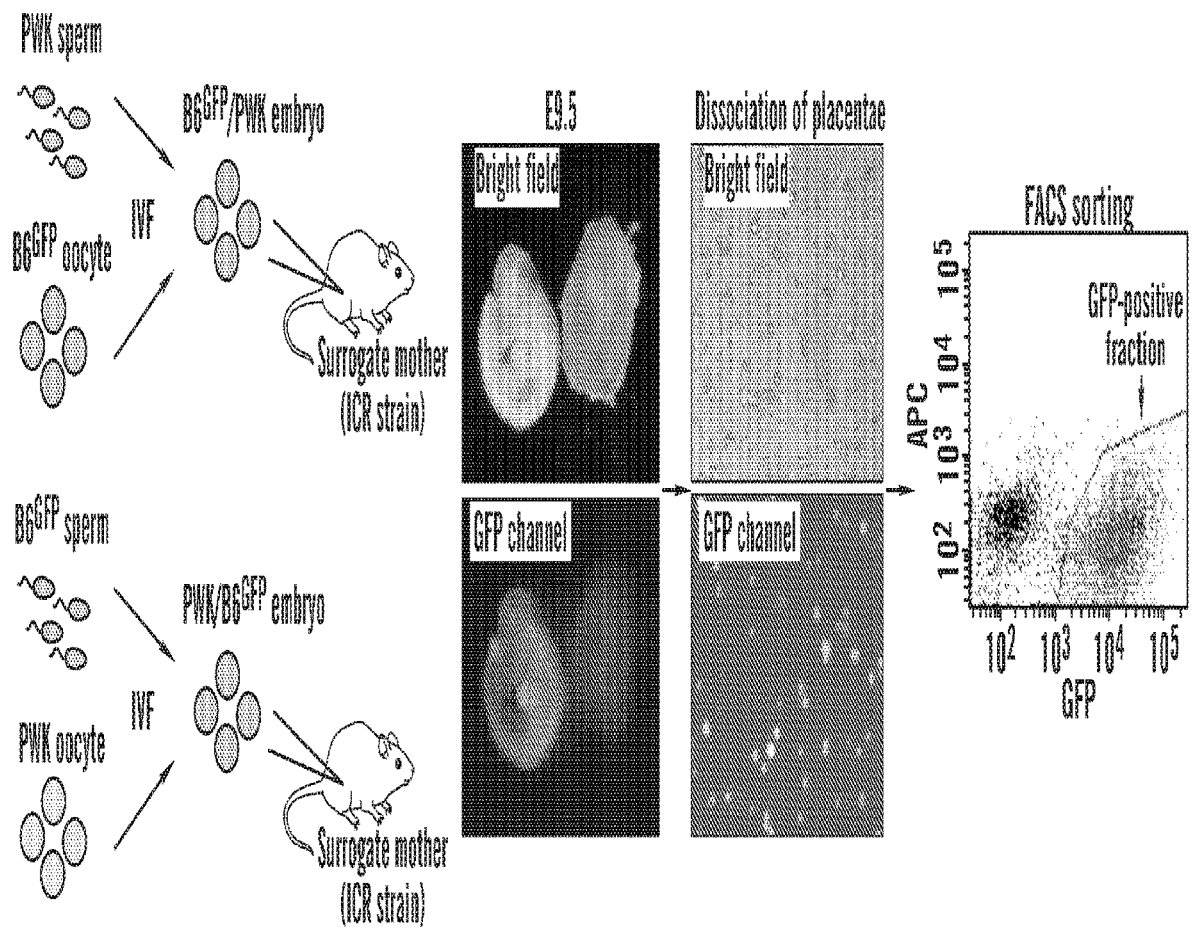
FIG. 14A-FIG. 14C shows sample preparation and quality verification, related to FIG. 12
Figure 14B:
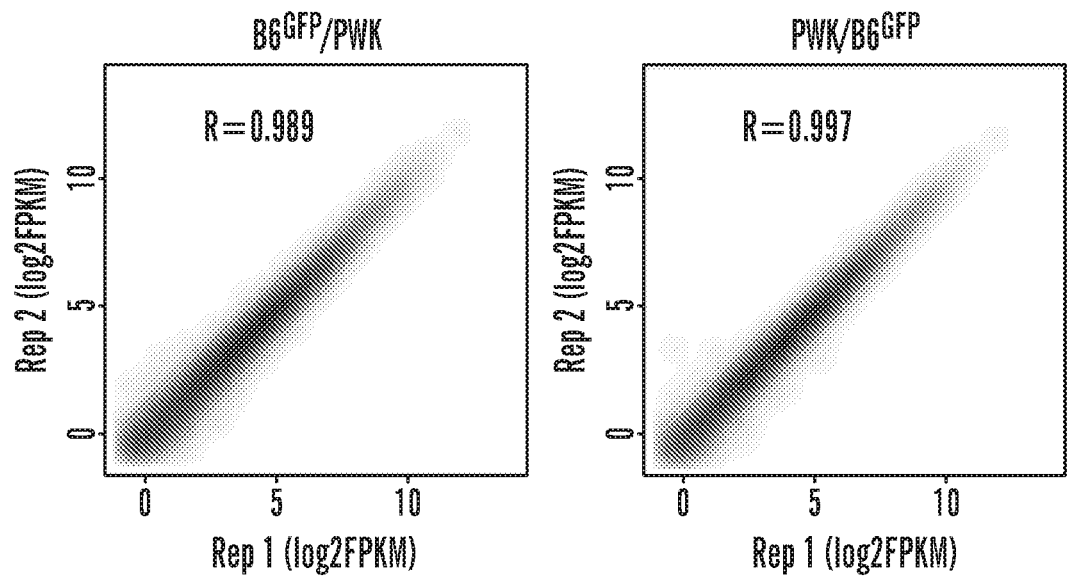
Figure 14C:
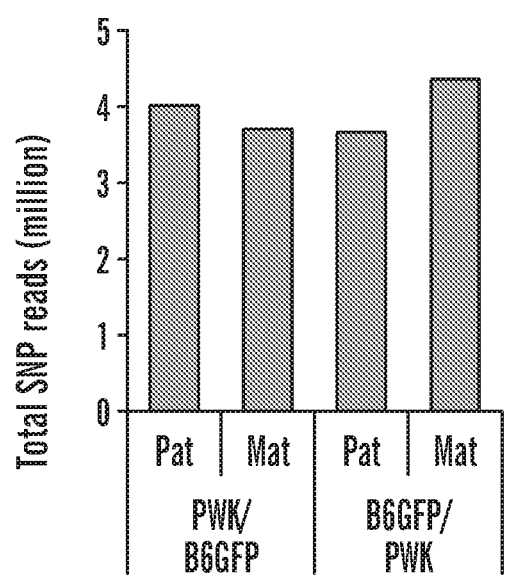
Figure 15A:
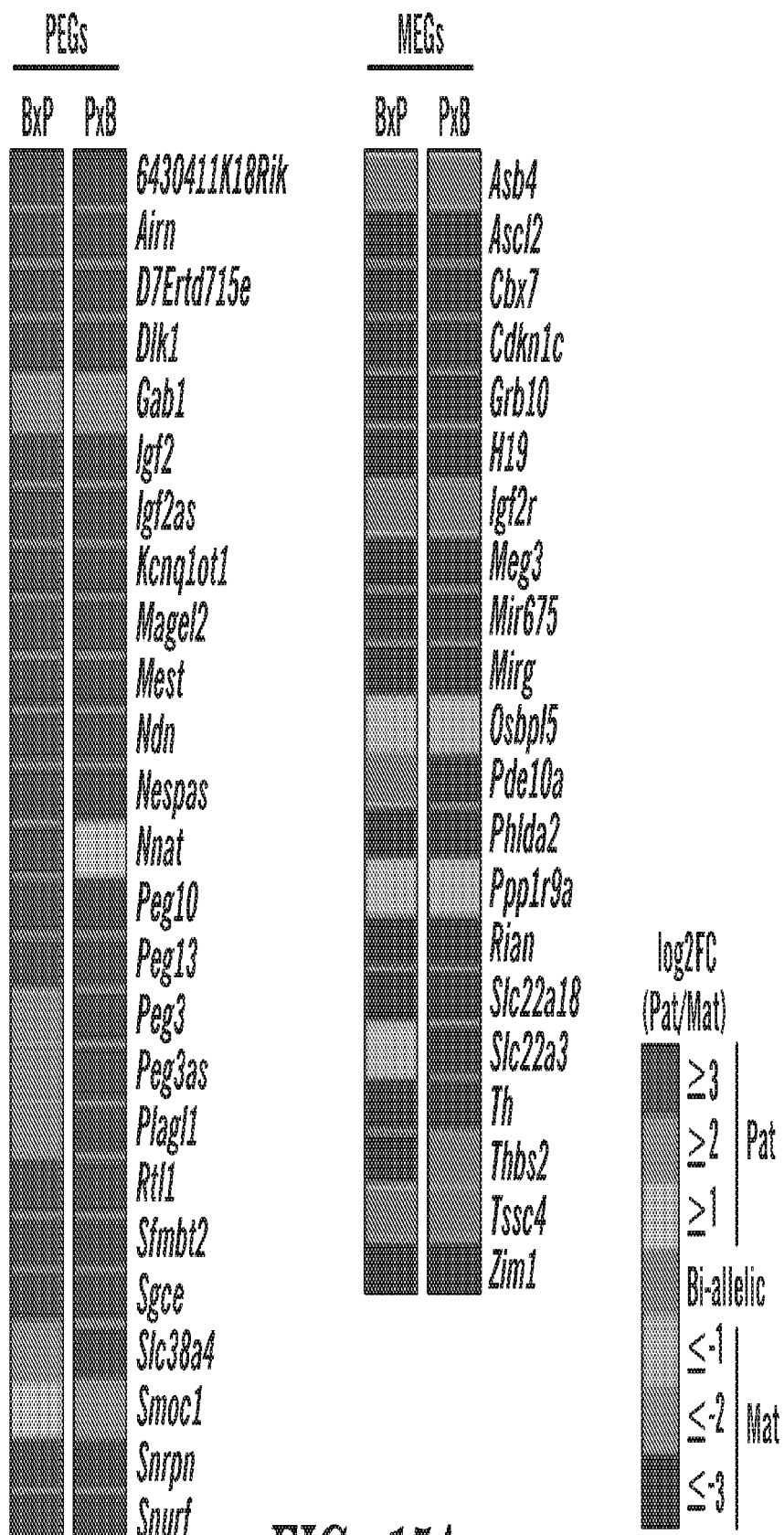
FIG. 15A and FIG. 15B show genomic imprinting in E9.5 placentae, related to FIG. 12.
Figure 15B:
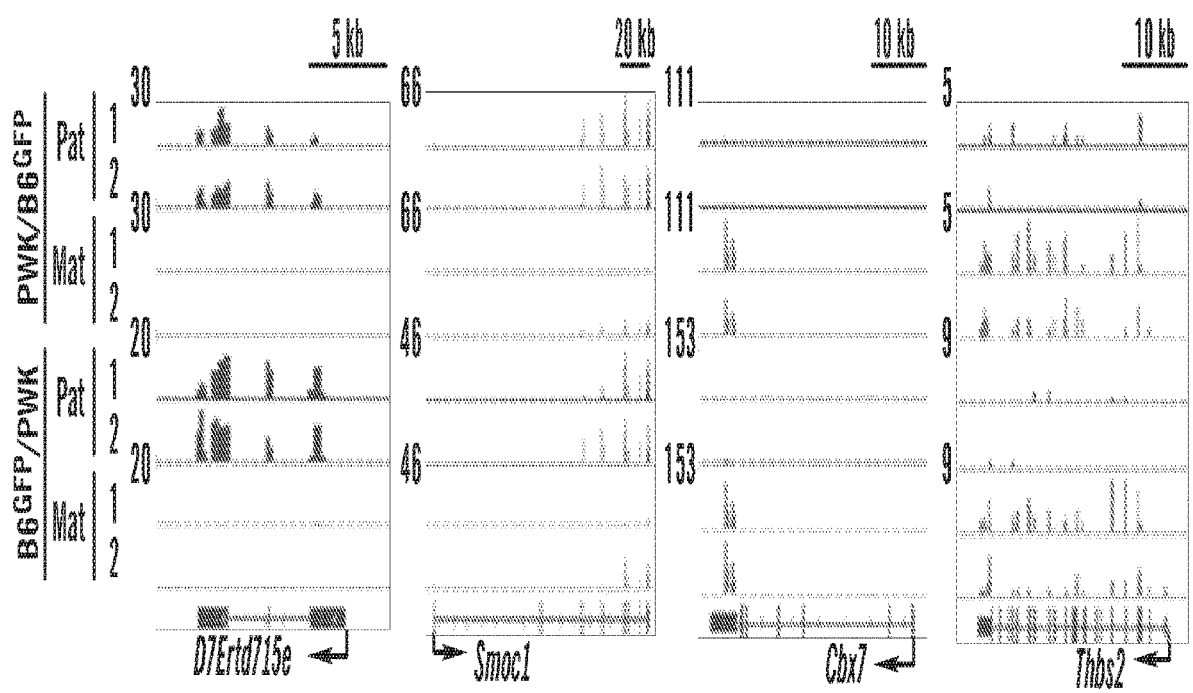

To analyze the imprinting status in E9.5 placentae avoiding possible maternal cell contamination, fetus-derived placental cells were purified from GFP transgenic embryos by FACS-sorting (FIG. 14A) and RNA-seq analysis performed (FIG. 14B). After confirming cell purity by demonstrating comparable total SNP reads from parental alleles (FIG. 14C), 25 PEGs and 21 MEGs were identified, which included new imprinted genes, such as D7Ertd715e, Smoc1, Cbx7 and Thbs2 (FIG. 15A, FIG. 15B). Among the 76 putative H3K27me3-dependent imprinted genes, 27 genes had sufficient SNP reads in both reciprocal crosses (FIG. 12D). Among them, Gab1, Sfinbt2, Slc38a4, and Smoc1 are paternally expressed (FIG. 12D). Imprinting of Phf17 in one cross was weak (FC=1.87) (FIG. 12D), which was consistent with a previous study. Taken together, the data not only identified Smoc1 as a new H3K27me3-dependent imprinted gene, but also suggested that most H3K27me3-dependent imprinted genes are transiently imprinted in preimplantation embryos, while some remain imprinted in the extra-embryonic cell lineage (FIG. 12E).

Since the identification of DNA methylation as a genomic imprinting mark more than 20 years ago, it has been the only known mammalian germline imprinting mark. However, recent studies have identified several imprinted genes capable of maintaining paternal allele-specific expression in the absence of oocyte DNA methylation, suggesting the existence of a DNA methylation-independent imprinting mechanism. As reported herein, these non-canonical imprinted genes harbor high level of oocyte-specific H3K27me3, and loss of H3K27me3 results in loss-of-imprinting. Although previous studies have revealed a link between a repressed allele and repressive histone modifications, including H3K27me3, at certain imprinted loci, the imprinting status of these loci originally depends on gDMRs. Consistently, ectopic removal of H3K27me3 specifically affected non-canonical imprinted genes, indicating that the regulatory mechanism of H3K27me3-dependent imprinting is fundamentally different from that of gDMR-mediated canonical imprinting.

The dynamics of H3K27me3-dependent imprinting is strikingly different from DNA methylation-dependent imprinting which is largely maintained in both embryonic and extra-embryonic lineages. The H3K27me3 imprint mark is likely established during oogenesis and maintained in preimplantation embryos (FIG. 12e). While it begins to dilute in ICM and is almost completely lost in the epiblast of E6.5 embryos, it is maintained in some genes at least until E9.5 placenta. Further investigation is warranted to understand why and how these genes are selected to maintain imprinting and why they use H3K27me3, instead of DNA methylation, as an imprinting mark, as well as how cell lineage-specific imprinting is achieved. Furthermore, what other organisms may conserve H3K27me3-dependent genomic imprinting is a fascinating question given that flowering plants also adopt this mechanism.

Example 7: Maternal H3K27me3 Coats Xist

Figure 16A:
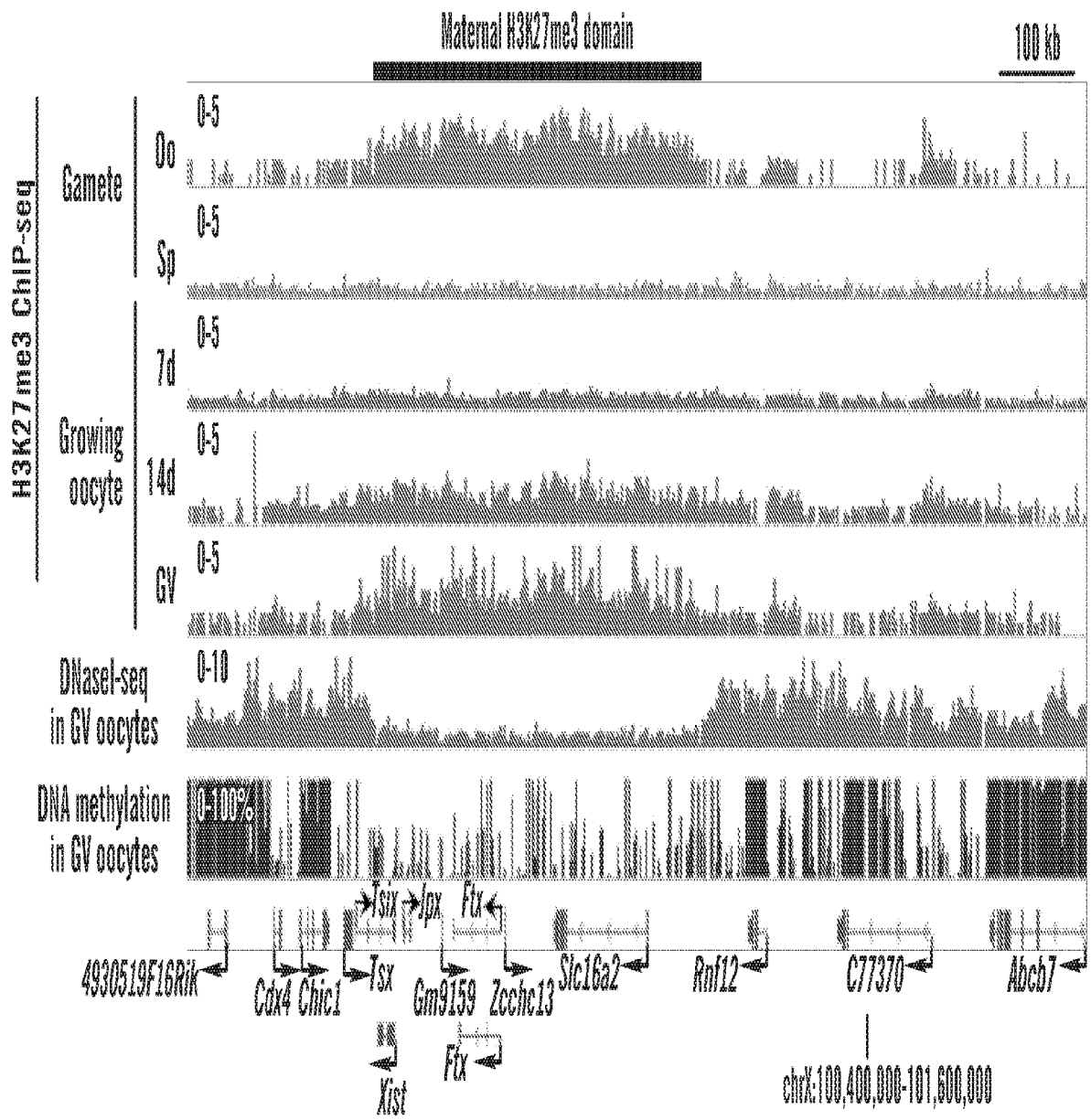
FIG. 16A and FIG. 16B show maternal H3K27me3 coats Xist and persists through preimplantation development.

If H3K27me3 serves as the imprinting mark of Xist, it would be present in oocytes, but not sperm. To test this notion, public H3K27me3 ChIP-seq datasets were analyzed, which revealed that the Xist locus was coated with a broad H3K27me3 domain that spans to ~450 kb including the Xist gene body in oocytes (FIG. 16A). Consistent with previous studies showing that Xist imprinting was established during oocyte growth, the H3K27me3 domain was gradually gained during this period (FIG. 16A). Furthermore, analyses of the oocyte DNaseI-sequencing dataset revealed that the chromatin accessibility of this entire H3K27me3 domain was markedly lower than the surrounding regions (FIG. 16A), suggesting formation of a heterochromatin domain. Analyses of the oocyte DNA methylome revealed that this domain was largely hypomethylated in oocytes (FIG. 16A), which is consistent with a previous report showing that Xist imprinting is independent of oocyte DNA methylation.

Figure 16B:
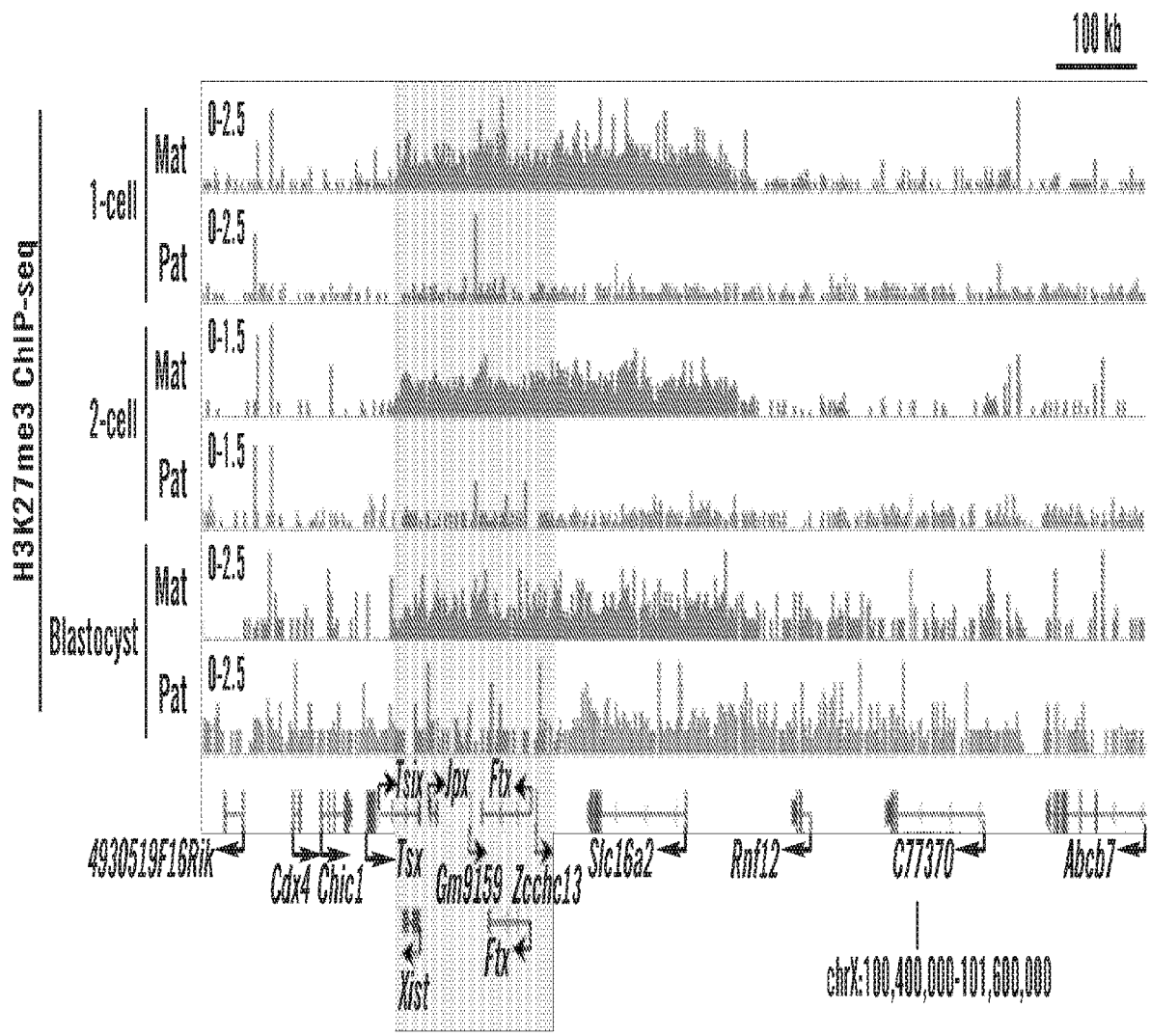

To determine whether the maternal allele-specific H3K27me3 observed in oocytes was maintained during preimplantation development, the ChIP-seq datasets of 1-cell, 2-cell, and blastocyst embryos was analyzed. The maternal H3K27me3 domain was found to be maintained throughout preimplantation development (FIG. 16B), and the upstream ~200 kb region of the H3K27me3 domain, including Xist, maintained the maternal allele-bias of H3K27me3 enrichment in blastocyst embryos (FIG. 16B). In contrast, the downstream ~250 kb region of the H3K27me3 domain almost loses the allelic difference in blastocysts due to gain of paternal H3K27me3 (FIG. 16B). These data supported a potential role of maternal H3K27me3 in maternal Xist silencing.

Example 8: Maternal H3K27Me3 is Responsible for Maternal Xist Silencing

Figure 17A:
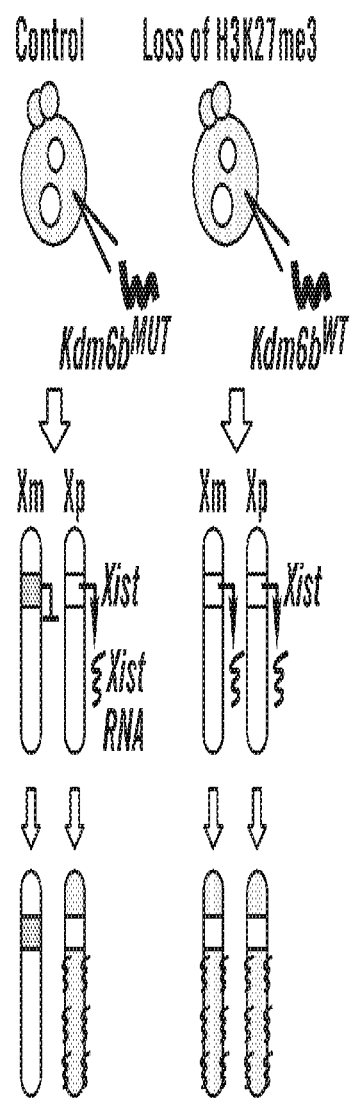
FIG. 17A-FIG. 17D shows ectopic removal of H3K27me3 induces maternal Xist expression.
Figure 17B:
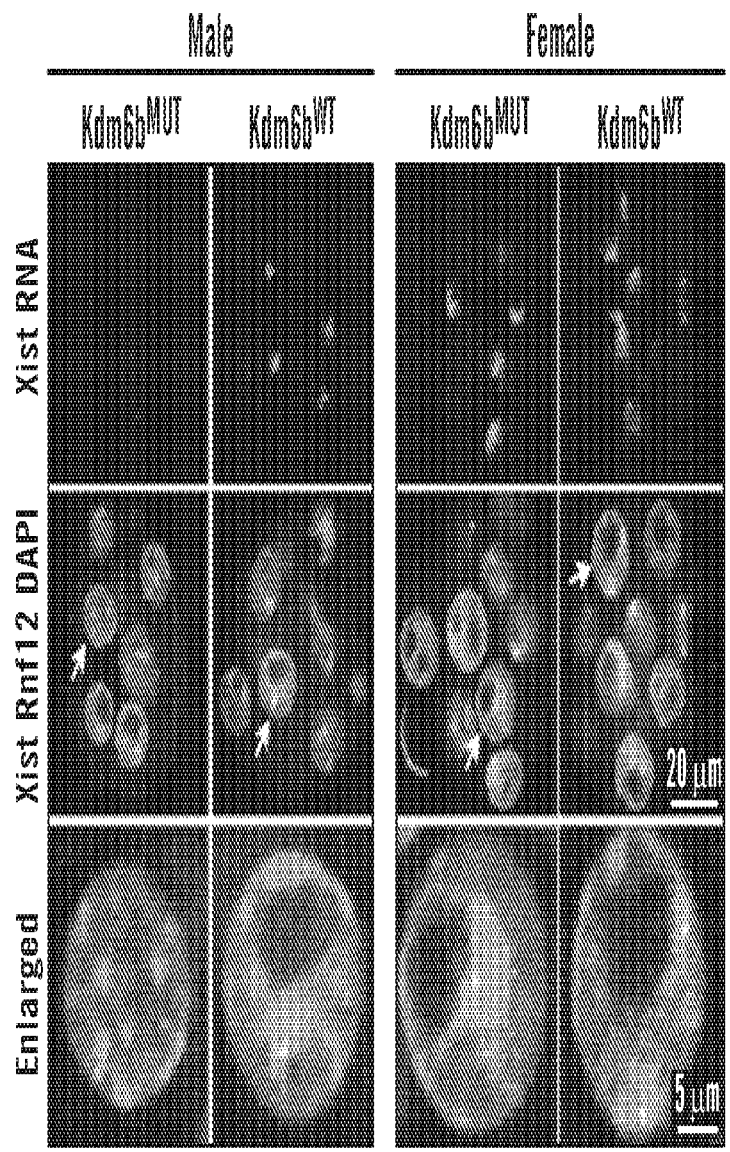
Figure 17C:
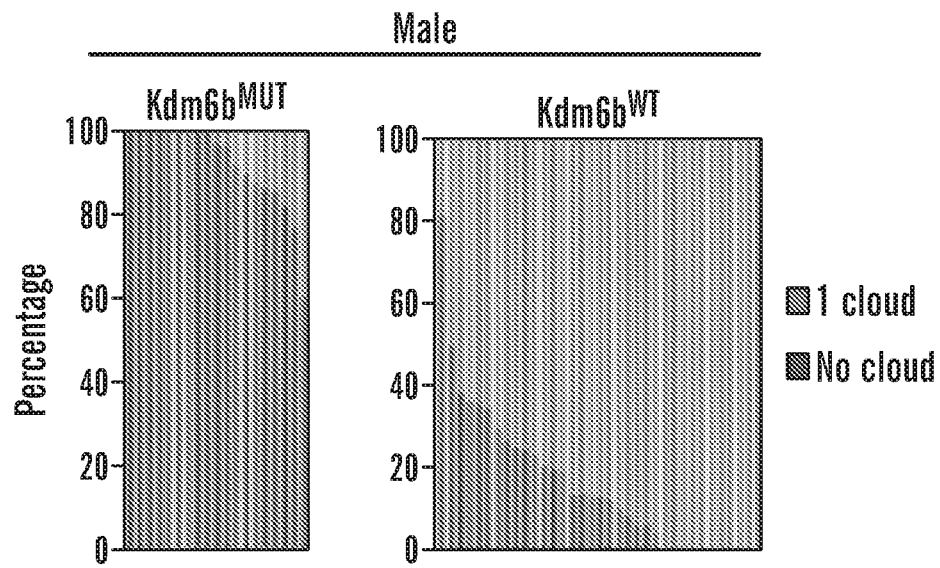
Figure 17D:
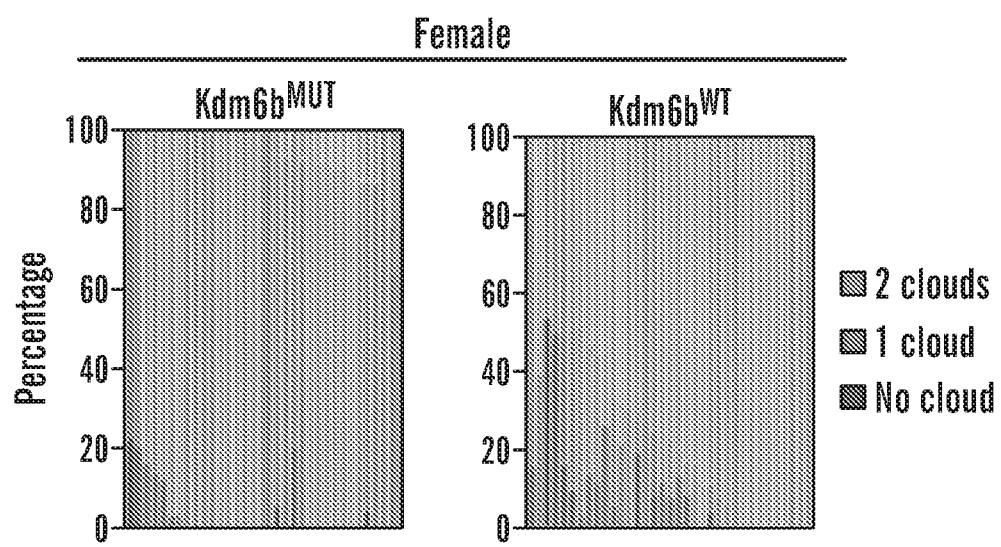
Figure 19A:
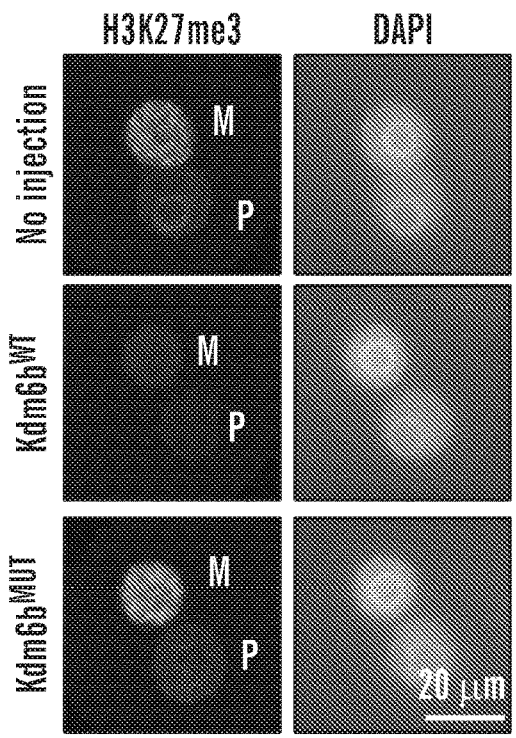
FIG. 19A and FIG. 19B show Kdm6b mRNA injection results in loss of H3K27me3 in a catalytic activity-dependent manner, related to FIG. 17.
Figure 19B:
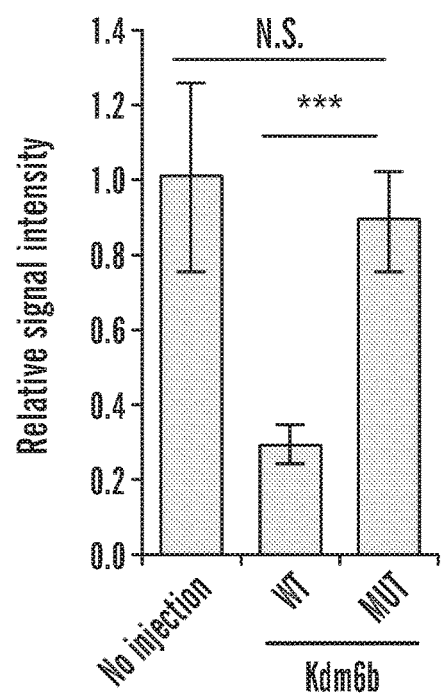

To examine whether H3K27me3 was responsible for maternal Xist silencing, H3K27me3 in zygotes were depleted by injecting mRNA coding an H3K27me3-specific demethylase, Kdm6b$^{WT}$, (FIG. 17A). As a negative control, zygotes injected with its catalytic mutant, Kdm6b$^{MUT}$, harboring a point mutation at the catalytic domain were prepared. This approach allowed efficient reduction of H3K27me3 in zygotes in a catalytic activity-dependent manner (FIG. 19A, FIG. 19B). To visualize Xist RNA expression, RNA fluorescent in situ hybridization (FISH) analysis was performed at the morula stage. To distinguish between male and female embryos, X chromosomes were simultaneously labeled by performing DNA FISH with a probe for an X chromosome locus harboring Rnf12. As such, one and two DNA FISH signals in a blastomere can distinguish male and female embryos, respectively. As expected, RNA/DNA FISH analysis revealed that the majority of Kdm6b$^{MUT}$-injected females showed one RNA cloud, whereas males showed no RNA cloud signal (FIG. 17B, FIG. 17C). In contrast, the majority of Kdm6b$^{WT}$-injected males and females showed one and two Xist RNA clouds, respectively (FIG. 17B, FIG. 17C, FIG. 17D), demonstrating that H3K27me3 is responsible for repression of the maternal Xist in preimplantation embryos.

Figure 20A:
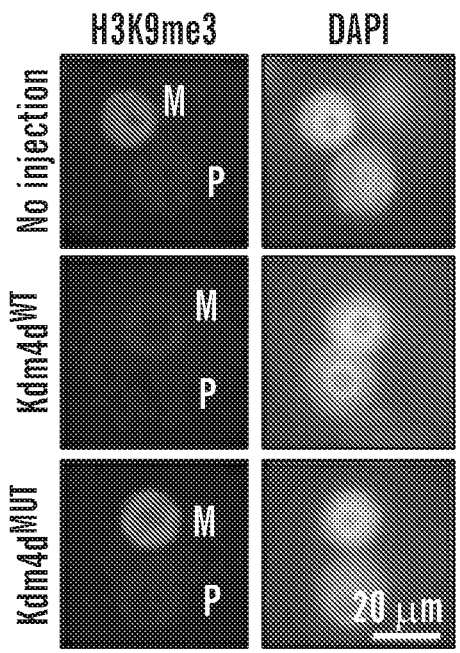
FIG. 20A-FIG. 20E shows ectopic removal of H3K9me3 does not induce maternal Xist expression, related to FIG. 17.
Figure 20B:
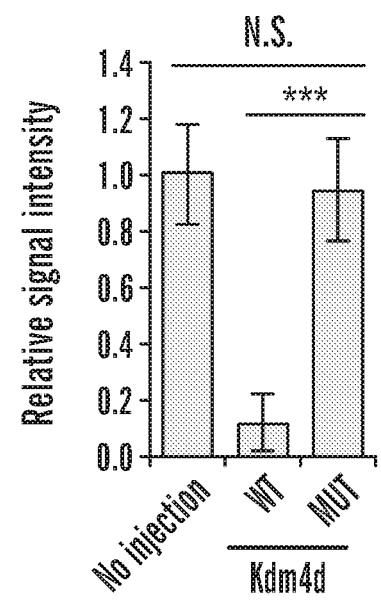
Figure 20C:
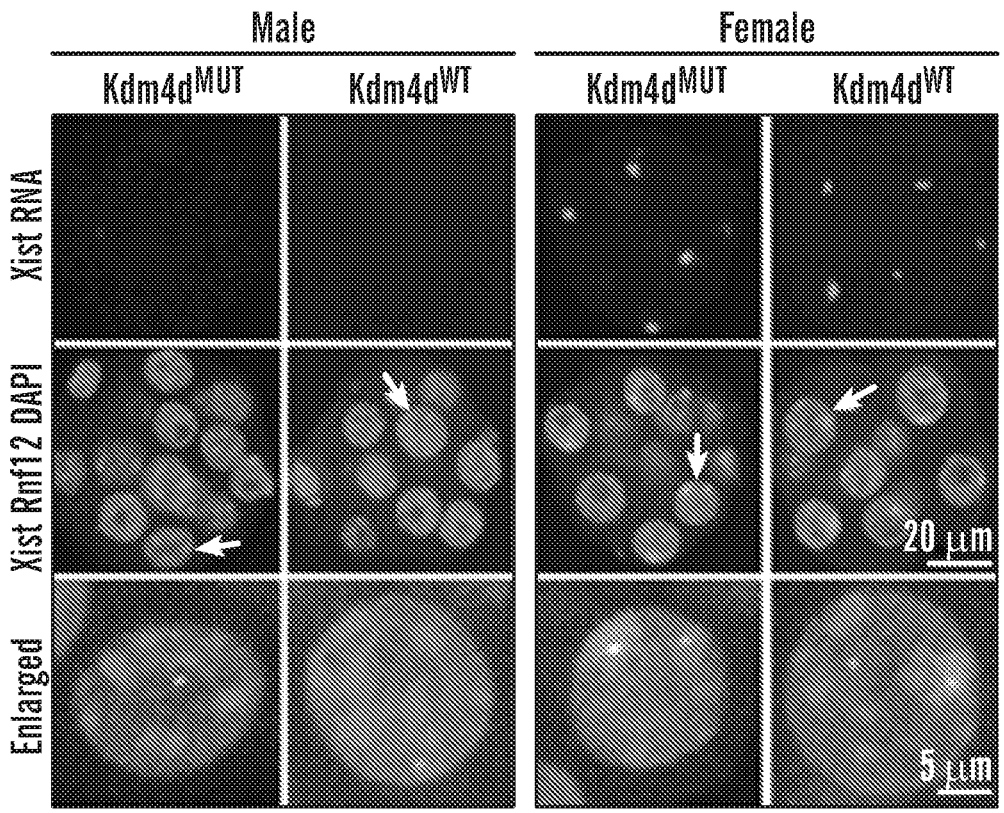
Figure 20D:
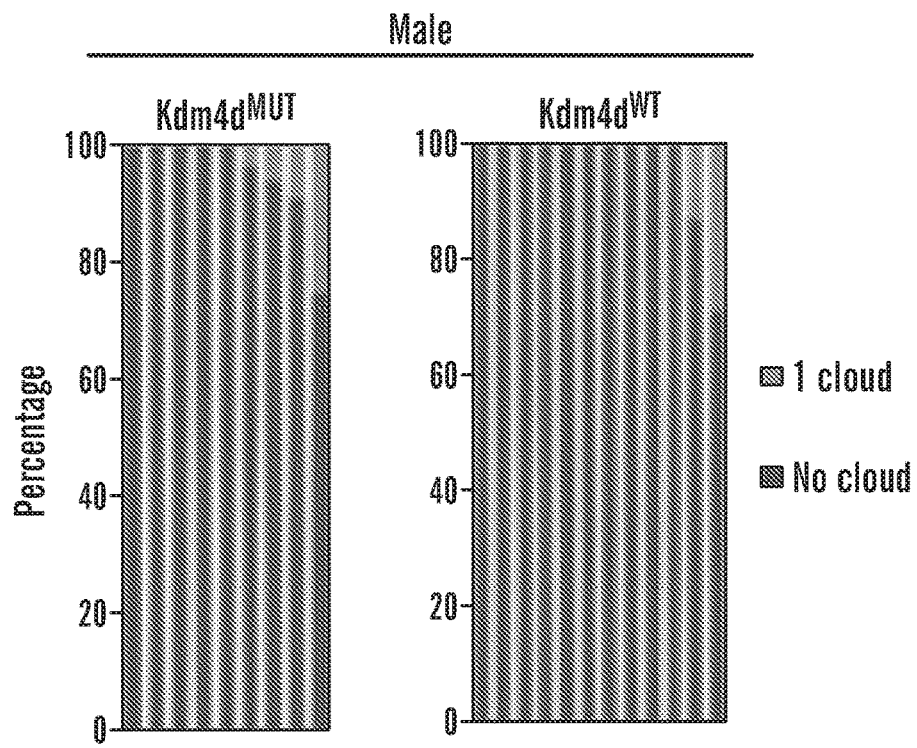
Figure 20E:
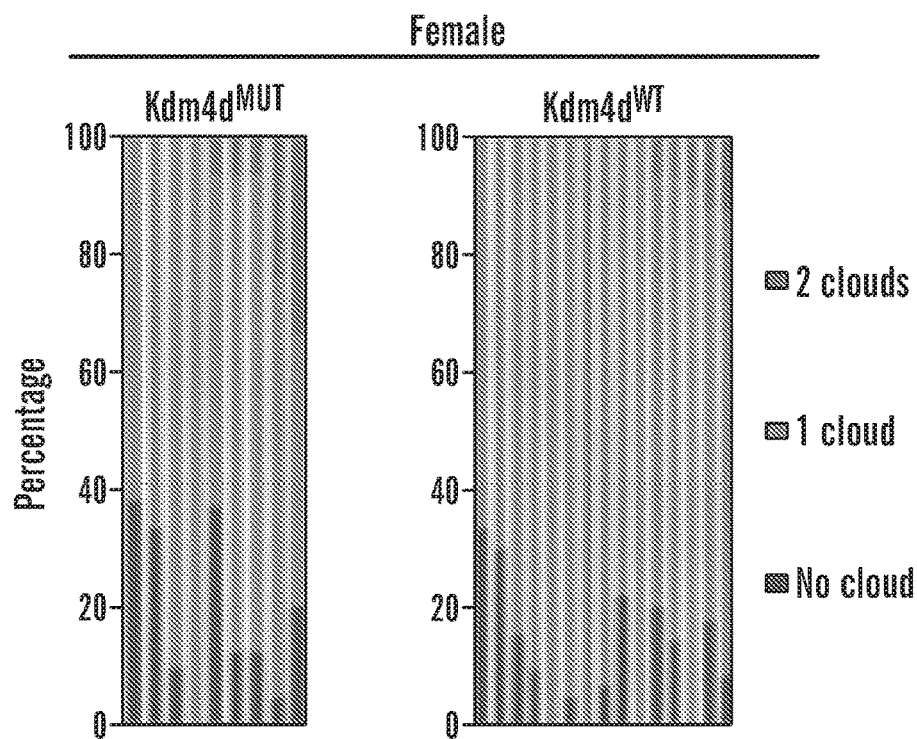

Next, it was whether ectopic loss of H3K9me3 in normal, bi-parental, embryos leads to maternal Xist derepression, as in the case of PG embryos. To this end, mRNA coding Kdm4d in zygotes was injected, which efficiently reduced H3K9me3 in a catalytic activity-dependent manner (FIG. 20A, FIG. 20B). RNA/DNA FISH analysis at the morula stage embryos revealed that expression of Kdm4d$^{WT}$ did not induce maternal Xist expression in either male or female embryos (FIG. 20C, FIG. 20D, FIG. 20E), suggesting that H3K9me3 did not play a major role in maternal Xist repression under physiological conditions.

Example 9: Loss of H3K27Me3 Induces Maternal XCI

Figure 18A:
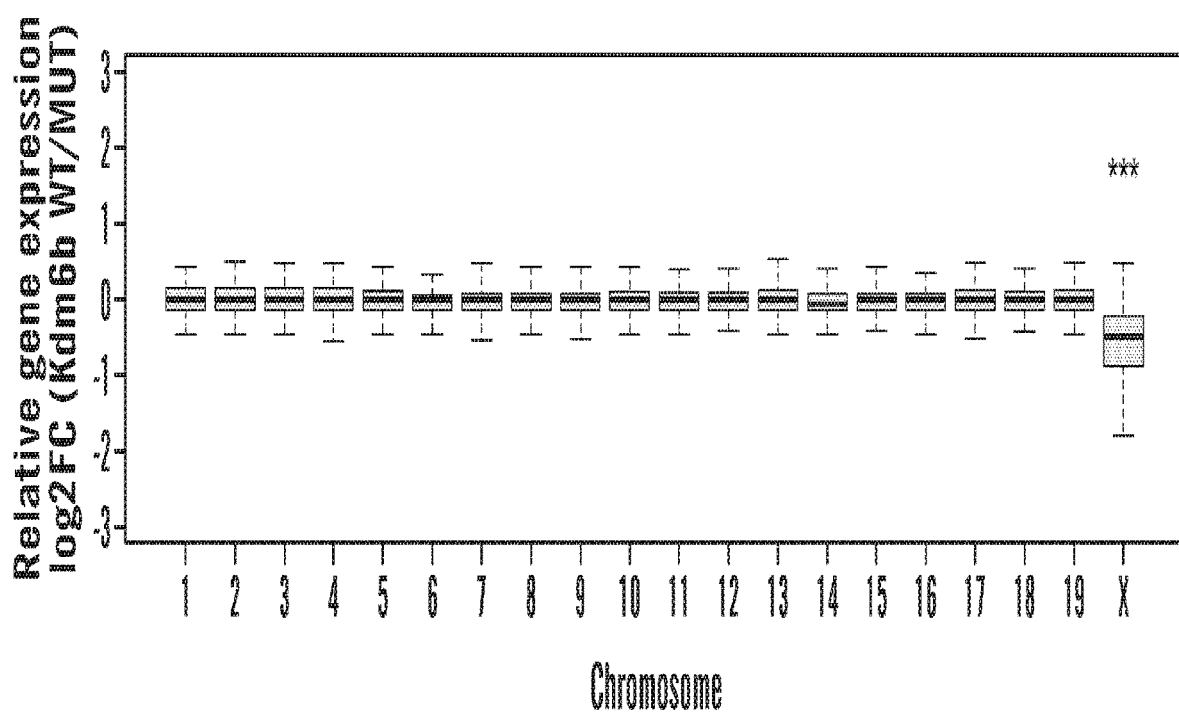
FIG. 18A-FIG. 18C shows ectopic removal of H3K27me3 induces maternal XCI.
Figure 18B:
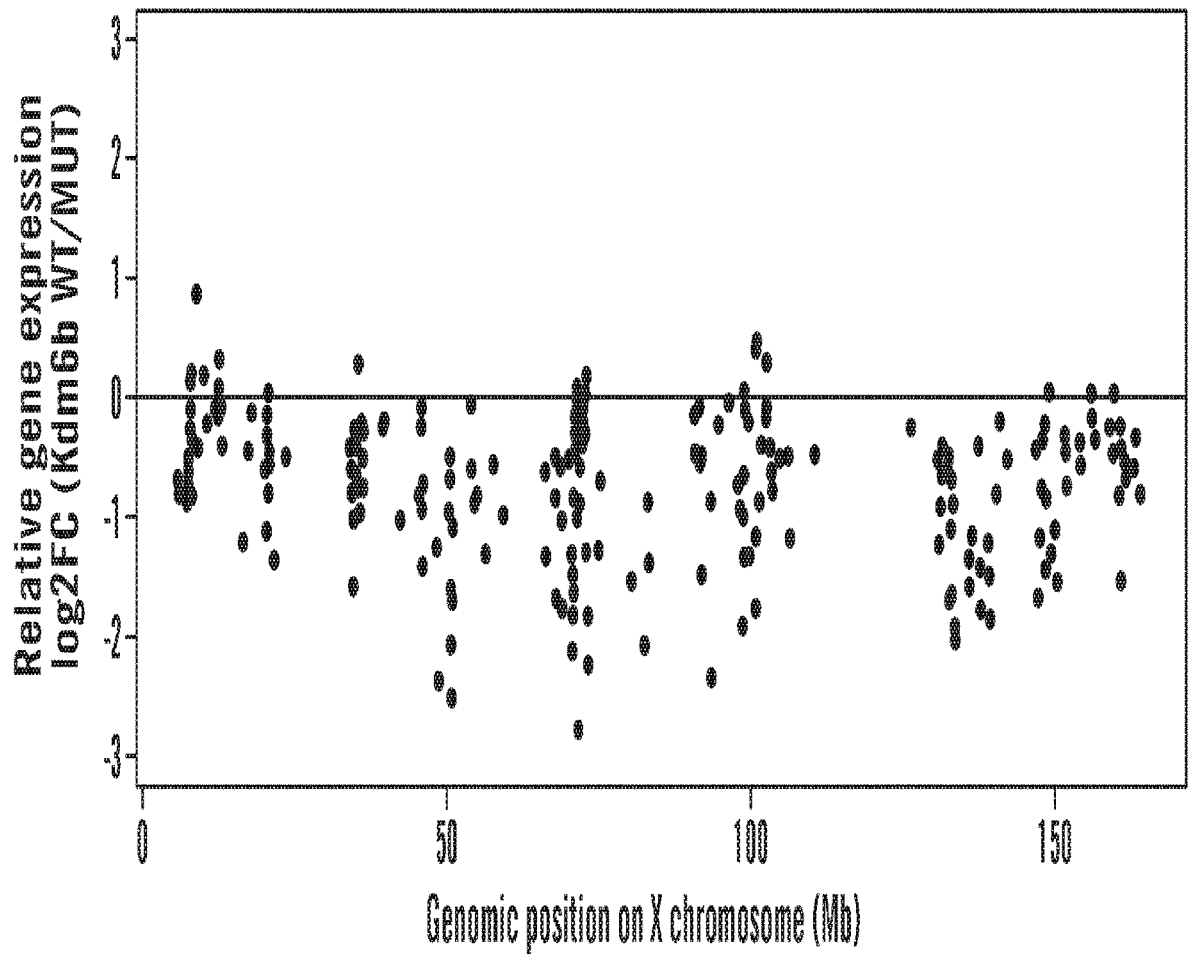
Figure 18C:
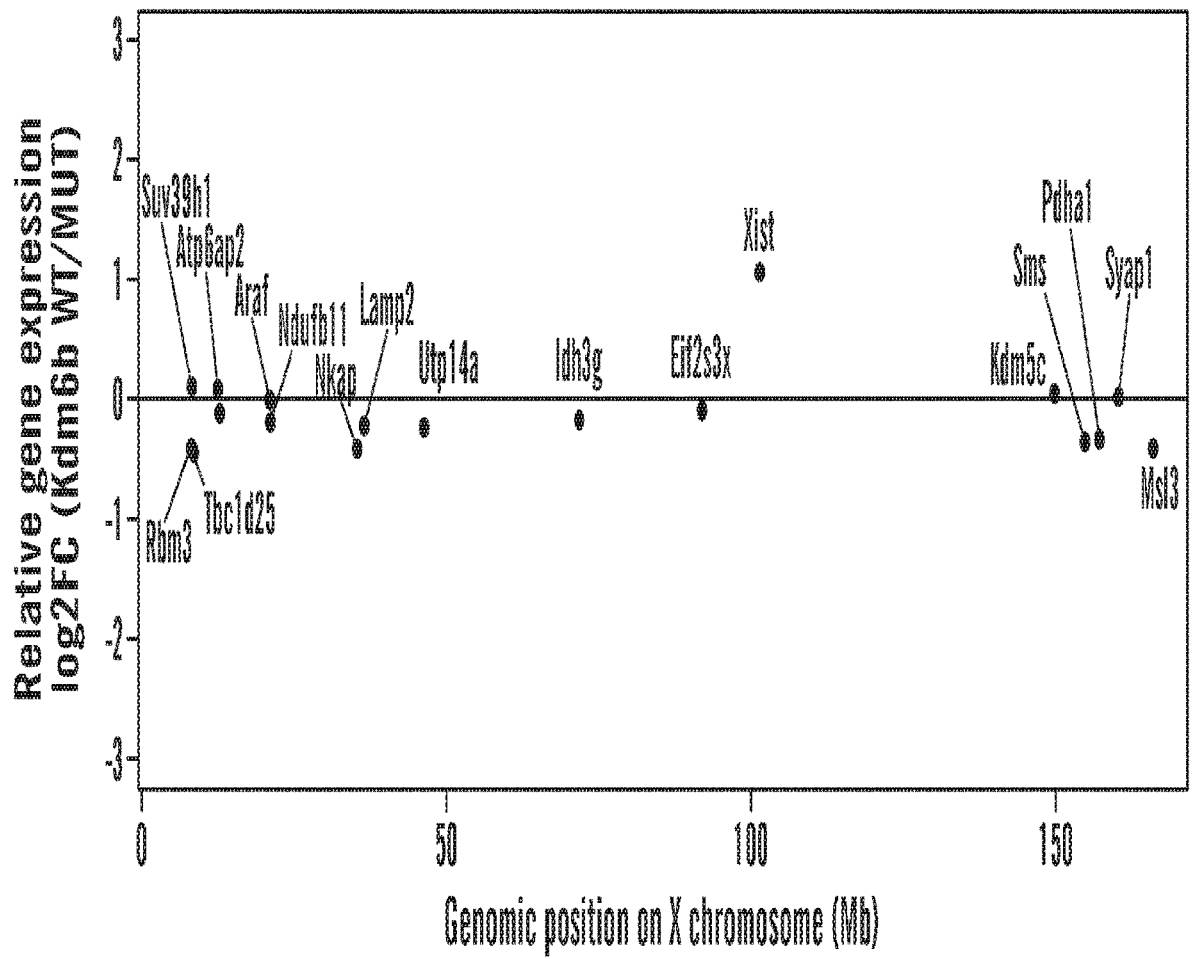
Figure 21:
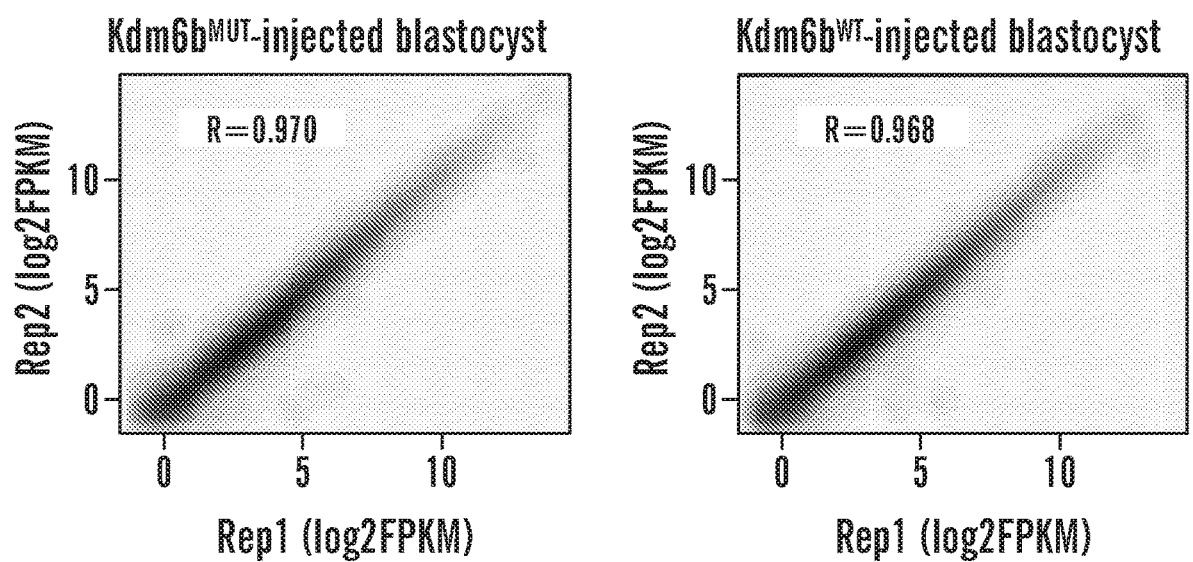
FIG. 21 provides a scatter plot showing the correlation between biological duplicate of RNA-seq samples, related to FIG. 18.

To determine whether maternal Xist expression led to maternal XCI in Kdm6b$^{WT}$-injected embryos, RNA-seq analysis was performed on early blastocyst embryos. To distinguish between parental alleles, hybrid strain embryos derived from BDF1 oocytes fertilized with PWK sperm were prepared. The biological duplicates of RNA-seq datasets were highly reproducible (FIG. 21). Analysis of single nucleotide polymorphism (SNP) information revealed that the expression level of the maternal allele of X-linked genes, but not those of autosomal genes, was significantly downregulated in Kdm6b$^{WT}$-injected embryos (FIG. 18A). A closer examination of individual SNP-tracked X-linked genes confirmed that most genes were downregulated (FIG. 18B). Furthermore, genes known to escape imprinted XCI (called 'escapees') escaped from the maternal XCI (FIG. 18C). These data further support the responsibility of H3K27me3 for maternal Xist silencing to prevent maternal XCI.

The results described herein above, were obtained using the following methods and materials.

Isolation of Maternal and Paternal Pronuclei from PN5 Stage Zygotes

All animal studies were performed in accordance with guidelines of the Institutional Animal Care and Use Committee at Harvard Medical School. MII-stage oocytes were collected from 8 week-old B6D2F1/J (BDF1) females superovulated by injecting 7.5 I.U. of PMSG (Millipore) and hCG (Millipore). For in vitro fertilization (IVF), MII oocytes were inseminated with activated spermatozoa obtained from the caudal epididymis of adult BDF1 male mice in HTF medium supplemented with 10 mg/ml bovine serum albumin (BSA; Sigma-Aldrich). Spermatozoa capacitation was attained by 1 h incubation in the HTF medium. Zygotes were cultured in a humidified atmosphere with 5% $CO_2$/95% air at 37.8° C. At 10 hours post-fertilization (hpf), zygotes were transferred into M2 media containing 10 μg/ml cytochalasin B (Sigma-Aldrich). Zona pellucidae were cut by a Piezo impact-driven micromanipulator (Prime Tech Ltd., Ibaraki, Japan) and the pronuclei were isolated from the zygotes. At 12 hpf (PN5-stage), isolated pronuclei were washed with 0.2% BSA/PBS, transferred into Eppendorf LoBind 1.5 ml tubes, and placed on ice until DNase I treatment. For each experiment, 150-200 pronuclei were collected and prepared for liDNase-seq. The parental pronuclei were distinguished by (1) the distance from the second polar body and (2) the size of the pronucleus.

Preparation of Androgenetic (AG) and Gynogenetic (GG) Embryos

MII oocytes were collected from 8 week-old superovulated BDF1 females and inseminated with BDF1 sperm. At 7 hpf, zygotes were transferred into M2 media containing g/ml cytochalasin B, and parental pronuclei were exchanged by using a Piezo impact-driven micromanipulator. The sendai virus (HVJ, Cosmo-bio) was used for fusing karyoplasts with cytoplasms as previously described. After reconstruction, embryos were cultured in KSOM.

When collecting embryos for RNA-seq or/and liDNase-seq, we removed zona pellucida (ZP) by a brief exposure to Acid tyrode's solution (Sigma-Aldrich), then the embryos were washed with M2 media, and then 0.2% BSA/PBS. For liDNase-seq, 10 morula embryos were transferred into an Eppendorf LoBind 1.5 ml tube, and placed on ice until DNase I treatment. For RNA-seq, seven to ten embryos were transferred into a thin-walled RNase-free PCR tubes (Ambion). The 2-cell and morula embryos were collected at 30 and 78 hpf, respectively. When preparing α-amanitin treated 2-cell embryos, 5 hpf zygotes were transferred into KSOM containing 25 μg/ml α-amanitin (Sigma-Aldrich) and cultured in the presence of α-amanitin until collection (30 hpf).

ICM and TE were isolated. Briefly, AG and GG embryos at 120 hpi were treated with Acid tyrode's solution to remove ZP. After being washed in M2 media, the embryos were incubated in KSOM containing rabbit anti-mouse lymphocyte serum (Cedarlane, 1:8 dilution) for 45 min at 37° C. After being washed in M2 media, they were transferred into KSOM containing guinea pig complement (MP Biomedicals, 1:3.3 dilution). After incubation for 30 min at 37° C., lysed TE cells were removed by pipetting with a glass capillary. The remaining ICM clumps were incubated in 0.25% Trypsin/EDTA (Thermo Fisher, 25200) for 10 min at 37° C., and then dissociated into single cells to avoid contamination of lysed TE cells. 100-200 cells were collected for RNA-seq.

Isolation of GV Nuclei from Fully-Grown Oocytes

Fully-grown GV-stage oocytes were obtained from 3-week-old BDF1 mice 44-48 h after injection with 5 I.U. PMSG. The ovaries were transferred to M2 media. The ovarian follicles were punctured with a 30-gauge needle, and the cumulus cells were gently removed from the cumulus-oocyte complexes using a narrow-bore glass pipette. The oocytes were then transferred into α-MEM (Life technologies, 12571-063) supplemented with 5% Fetal Bovine Serum (FBS) (Sigma-Aldrich, F0926), 10 ng/ml Epidermal Growth Factor (Sigma-Aldrich, E4127), and 0.2 mM 3-isobutyl-1-methylxanthine (IBMX; Sigma-Aldrich). One hour after collection, GV oocytes exhibiting visible perivitelline spaces, which have the surrounding-nucleolus (SN)-type chromatin, were culled. They were then incubated in M2 media containing 10 µg/ml cytochalasin B, 0.1 µg/ml colcemid (Sigma-Aldrich), and 0.2 mM IBMX for 15 min. Then, GV nuclei were isolated by using a Piezo-driven micromanipulator. After washing with 0.2% BSA/PBS, the GV nuclei were transferred into an Eppendorf LoBind 1.5 ml tube. For each experiment, 115-150 GV nuclei were collected for liDNase-seq.

Dissection of E6.5 Embryos and FACS Sorting of GFP-Positive E9.5 Placental Cells To obtain C57BL6(B6)/PWK hybrid embryos, a natural mating scheme was used. To obtain PWK/B6 hybrid embryos, in vitro fertilization of PWK oocytes with B6 sperm was used, and the 2-cell embryos were transferred into surrogate ICR strain mothers. Dissection of E6.5 embryos into EPI, EXE, and VE was performed. To collect E9.5 placental cells, the B6$^{GFP}$ mice from Jackson laboratory were purchased [C57BL/6-Tg(CAG-EGFP)131Osb/LeySopJ, Stock number 006567]. MII oocytes and sperms were collected from superovulated 8-week old B6$^{GFP}$ or PWK mice. After in vitro fertilization, the 2-cell embryos were transferred into surrogate ICR strain mothers. At E9.5, placentae were harvested, cut into ~0.5 mm pieces, transferred into 50 ml tubes, and treated with 2 ml of 0.25% Trypsin-EDTA (Thermo Fisher Scientific, 25200) at 30° C. for 15 min in a shaker at 200 rpm to dissociate placental cells. Trypsin treatment was stopped by the addition of 2 ml DMEM containing 10% FBS. After pipetting, the tubes were centrifuged and the pelleted cells were washed with 0.2% BSA/PBS three times. DAPI was added at the final concentration of 1 M in the final cell suspension. The GFP-positive cells were sorted using a BD FACSaria machine (BD Biosciences) with DAPI positive cells excluded as dead cells. Approximately 10,000-20,000 GFP-positive cells were collected from each placenta, which corresponded to 40-60% of total placental cells.

Plasmid Construction and mRNA Preparation

To generate the Kdm6b$^{WT}$ construct, the cDNA encoding the carboxyl-terminal part containing the catalytic domain (amino acid 1025-End) was amplified. The PCR amplicon was cloned between a Flag tag and poly(A) of the pcDNA3.1-Flag-poly(A)83 plasmid. The H1390A Kdm6b$^{MUT}$ construct were generated by using PrimeSTAR mutagenesis (TAKARA). Primers used for the mutagenesis are 5'-CCAGGCgctCAAGAGAATAACAAT-TTCTGCTCAGTCAACATCAAC-3' and 5'-CTCTT-GagcGCCTGGCGTTCGGCTGCCAGGGACCTTCATG-3'. All constructs were verified by DNA sequencing. The plasmids for wild-type and H189A mutant Kdm4d were previously described.

After linearization by a restriction enzyme, the construct was purified with phenol-chloroform extraction. mRNA was synthesized by in vitro transcription using a mMESSAGE mMACHINE T7 Ultra Kit (Life technologies) according to manufacturer's instructions. The synthesized mRNA was purified by lithium chloride precipitation and diluted with nuclease-free water. mRNA aliquots were stored in −80° C. until use.

mRNA Injection

MII oocytes were collected from superovulated 8 week-old BDF1 females and inseminated with BDF1 sperm. At 2.5 hpf, fertilized oocytes were transferred into M2 media and mRNA was injected using a Piezo impact-driven micromanipulator. mRNA injection was completed by 4 hpf. The mRNA concentrations of Kdm6b$^{WT}$ and Kdm6b$^{MUT}$ were 1.8 µg/µl, and those of Kdm4d$^{WT}$ and Kdm4d$^{MUT}$ were 1.5 µg/µl. When preparing Kdm6b-injected PG embryos, MII oocytes were chemically activated by treating with 3 mM SrCl$_2$ in Ca$^{2+}$-free KSOM containing 5 µg/ml cytochalasin B. At 4 hrs post-activation (hpa), the embryos were washed with KSOM. At 5 hpa, they were injected with mRNA.

Whole Mount Immunostaining

Zygotes were fixed in 3.7% paraformaldehyde (PFA) in PBS containing 0.2% Triton for 20 min. After 4× washes with PBS containing 10 mg/ml BSA (PBS/BSA), zygotes were treated with primary antibodies at 4° C. overnight. The primary antibodies used in this study were mouse-anti-H3K27me3 (1/500, Active Motif, 61017), rabbit anti-H3K9me3 (1/500, Millipore, 07-442), and rabbit anti-FLAG (1/2000, Sigma-Aldrich, F7524). After 3× washes with PBS/BSA, samples were incubated with a 1:250 dilution of fluorescein isothiocyanate-conjugated anti-mouse IgG (Jackson Immuno-Research) or Alexa Flour 568 donkey anti-rabbit IgG (Life technologies) for 1 h. The zygotes were then mounted on a glass slide in Vectashield anti-bleaching solution with 4',6-diamidino-2-phenylindole (DAPI) (Vector Laboratories, Burlingame, CA.). Fluorescence was detected under a laser-scanning confocal microscope with a spinning disk (CSU-10, Yokogawa) and an EM-CCD camera (ImagEM, Hamamatsu) or Zeiss LSM800.

All images were acquired and analyzed using the Axio-vision software (Carl Zeiss). The fluorescent signal intensity was quantified with the Axiovision software. Briefly, the signal intensity within the maternal pronuclei was determined, and the cytoplasmic signal was subtracted as background. Then, the averaged signal intensity of the no-injection control zygotes was set as 1.0.

Low-Input DNase-Seq

Low-input DNase-seq libraries were prepared as previously described with minor modifications. Embryos or nuclei collected in 1.5 ml tubes were resuspended in 36 µl lysis buffer (10 mM Tris-HCl, pH 7.5, 10 mM NaCl, 3 mM MgCl2, 0.1% Triton X-100) and incubated on ice for 5 min. DNase I (10 U/µl, Roche) was added to the final concentration of 80 U/ml (for the GV nucleus sample) or 40 U/ml (for all the other samples) and incubated at 37° C. for exactly 5 min. The reaction was stopped by adding 80 µl Stop Buffer (10 mM Tris-HCl, pH 7.5, 10 mM NaCl, 0.15% SDS, 10 mM EDTA) containing 2 µl Proteinase K (20 mg/ml, Life technologies). Then 20 ng of a circular carrier DNA [a pure plasmid DNA without any mammalian genes purified with 0.5× Beckman SPRIselect beads (Beckman Coulter) to remove small DNA fragments] was added. The mixture was incubated at 50° C. for 1 hr, then DNA was purified by extraction with phenol-chloroform and precipitated by ethanol in the presence of linear acrylamide (Life technologies) overnight at −20° C. Precipitated DNA was resuspended in 50 µl TE (2.5 mM Tris, pH 7.6, 0.05 mM EDTA), and the entire volume was used for sequencing library construction.

Sequencing library was prepared using NEBNext Ultra II DNA Library Prep Kit for Illumina (New England Biolabs) according to the manufactures' instruction with the exception that the adaptor ligation was performed with 0.03 µM adaptor in the ligation reaction for 30 minutes at 20° C. and that PCR amplification was performed using Kapa Hifi hotstart readymix (Kapa Biosystems) for 8-cycles. The PCR products were purified with ×1.3 volume of SPRIselect beads (Beckman Coulter) and then size selected with ×0.65 volume followed by ×0.7 volume of SPRIselect beads. The sample was eluted in 24 µl TE. The number of cycles needed for the second PCR amplification was determined by qPCR using 1 µl of the 1:1,000 diluted samples. The remaining 23 µl of the samples was then amplified with Kapa Hifi hotstart readymix (we used 7 cycles for all samples in this study). The PCR product was purified with ×1.3 volume of SPRIselect beads and then size selected with ×0.65 volume followed by ×0.7 volume of SPRIselect beads. The DNA was eluted in 30 µl of TE and quantified by Qubit dsDNA HS assay kit (Thermo Fisher Scientific, Q32854) and Agilent high sensitivity assay kit (Agilent Technologies). The libraries were sequenced on a Hiseq2500 with single-end 100 bp reads (Illumina).

RNA-Sequencing

RNA-seq libraries were prepared as previously described. Briefly, reverse transcription and cDNA amplification were performed using whole embryo lysates with SMARTer Ultra Low Input RNA cDNA preparation kit (Clontech, 634890). When processing 2-cell AG, GG and α-amanitin-treated IVF embryo samples, 1 µl of 1:40,000 diluted ERCC (External RNA Controls Consortium) standard RNA (Life technologies) was added to each of the tubes at the step of cell lysis. cDNAs were then fragmented using the Covaris M220 sonicator (Covaris) with microTUBE-50 (Covaris) into average 150-160 bp fragments. The fragmented cDNAs were end-repaired, adaptor ligated and amplified using NEBNext Ultra DNA Library Prep Kit for Illumina according to the manufacturer's instruction (New England Biolabs). Single end 100 bp sequencing was performed on a HiSeq2500 sequencer (Illumina).

liDNase-Seq Data Analysis

Reads of liDNase-seq data were firstly trimmed of low quality and adapter with trim_galore, and then mapped to the mouse genome (mm9) using Bowtie v0.12.9. '-m 1' parameter to keep unique mapping hits. The reads with mapping quality (MAPQ)≤10 or redundant reads that mapped to the same location with the same orientation were removed with SAMtools. The DHS peaks in liDNase-seq data were identified by Hotspot program with FDR<=0.01. The DHS peaks from all 33 libraries were merged using 'bedtools merge' from bedtools. The number of reads in each DHS for each library was calculated using 'multiBamSummary' from deepTools and normalized to the total number of mapped reads and to the length of DHS (possibility of a tag located on a position per 1 kb per million mapped reads). Reads of sex chromosomes were removed because the number of sex chromosomes is different between the parental pronuclei and between androgenetic and gynogenetic embryos. The Pearson correlation coefficient (r) of tag densities at genome-wide DHSs was calculated to measure the correlation between replicates. For identification of parental allele-specific DHSs in zygotes and morula embryos, we used a stringent cutoff (RPKM mean>2, RPKM>1 in all replicates in a biased allele, and mean value fold change larger than 4 between the two alleles). The 431 most reliable Ps-DHSs were identified by applying an additional criterion 'RPKM>1 in all replicates of paternal PNs of microinjected zygotes' to Ps-DHSs. The RefSeq gene assembly (mm9) from the UCSC Genome Browser database and CGIs previously defined were used as genomic feature distribution analysis in FIGS. 2d and 2e.

RNA-Seq Data Analysis

We constructed a custom reference sequence combining mouse genome (mm9) with the ERCC control. Reads of RNA-seq were mapped to the reference genome with TopHat v2.0.6 or STAR (github.com/alexdobin/STAR). All programs were run with default parameters unless otherwise specified. Uniquely mapped reads were subsequently assembled into transcripts guided by the reference annotation (UCSC gene models) with featureCounts from subread-v1.5.1. For all 2-cell RNA-seq libraries, library size factors were estimated with 'estimateSizeFactors' function form R package DESeq only using ERCC read counts. After the library size was normalized, the expression level of each gene was quantified with normalized FPKM (fragments per kilobase of exon per million mapped fragments). The Pearson correlation coefficient (r) of gene expression level was calculated to indicate the correlation between duplicates. For identification of newly synthesized transcripts at the 2-cell stage, we firstly filtered out statistically non-significant genes between AG or GG and α-amanitin treated 2-cell embryo. To this end, adjusted P value was calculated with 'nbinomTest' function form R pakage DESeq using a negative binomial model, and only genes with FDR<0.05 were selected. We then applied additional cutoffs [Mean FPKM (AG or GG)>2 and fold-change (FC) (AG/Ama or GG/Ama) >2]. As a result, 4,381 and 3,916 genes were identified as newly synthesized genes in AG and GG 2-cell embryos, respectively. For identifying AG- and GG-specific DEGs in 2-cell embryos, the gene expression level (FPKM) of each gene in ca-amanitin 2-cell embryos was subtracted from that of AG and GG embryos. Genes showing FC (AG/GG or GG/AG)>10 were identified as DEGs.

WGBS and H3K27Me3 ChIP-Seq Data Analyses

The DNA methylation level at DHSs was calculated using methpipe v3.4.2. When calculating the DNA methylation level at each DHS, to get enough coverage of WGBS reads, we extended each DHS to both up and downstream 2 kb to include more nearby CpG sites. The oocyte-methylated gDMR was defined by >80% methylation in oocytes and <20% in sperm. For FIG. 5a, "bedtools makewindows" were used to generate a set of non-overlapped 1 kb bins for the ±100 kb flanking region of Ps-DHSs. For H3K27me3 ChIP-seq analysis, Bed files were downloaded from Zheng et al., 2016 and converted to the bigWig format using 'bedClip' and 'bedGraphToBigWig' from UCSC Genome Browser database. 'multiBigwigSummary' from deepTools was used to compute H3K27me3 signal over the DHS and surrounding region.

Statistical Analyses and Data Visualization

Statistical analyses were implemented with R (www.r-project.org/). Pearson's r coefficient was calculated using the 'cor' function with default parameters. FIG. 6b and FIG. 10d were generated with R function 'heatmap.2'. FIG. 7d, FIG. 10c, FIG. 12a-d were generated with R function 'pheatmap'. FIG. 1b and FIG. 7b were generated using 'computeMatrix' and 'plotHeatmap' function in deepTools. Position-wise coverage of the genome by sequencing reads was determined by normalizing to the total unique mapped reads in the library using macs2 v2.1.0 and visualized as custom tracks in the IGV genome browser.

Known Imprinting Gene Information

Known imprinting information was downloaded from www.geneimprint.com/site/genes-by-species.Mus+musculus.

Code Availability

A customized pipeline was used to split the hybrid RNA-seq data to their parental origin based on SNP information. The code can be found at github.com/lanjiangboston/UniversalSNPsplit.

Data Availability Statement

All the liDNase-seq and RNA-seq datasets generated in this study were deposited at GEO database under accession number GSE92605. Sperm liDNase-seq datasets were from a previously publication (GSE76642). WGBS datasets for sperm and GV oocytes were downloaded from www.nodai-genome.org/mouse.html?lang=en. H3K27me3 ChIP-seq datasets of sperm, MII oocytes, and SNP-tracked maternal and paternal alleles of 1-cell embryos were downloaded from a previous publication (GSE76687).

Collection of Mouse Preimplantation Embryos

All animal studies were performed in accordance with guidelines of the Institutional Animal Care and Use Committee at Harvard Medical School. MII-stage oocytes were collected from 8 week-old B6D2F1/J (BDF1) females superovulated by injecting 7.5 I.U. of PMSG (Millipore) and hCG (Millipore). For in vitro fertilization (IVF), MII oocytes were inseminated with activated spermatozoa obtained from the caudal epididymis of adult BDF1 or PWK (Jackson Laboratory, 003715) males in HTF medium supplemented with 10 mg/ml bovine serum albumin (BSA; Sigma-Aldrich). Spermatozoa capacitation was attained by 1 h incubation in the HTF medium. Zygotes were transferred to KSOM and cultured in a humidified atmosphere with 5% $CO_2$/95% air at 37.8° C.

mRNA Injection

At 4 hrs post-fertilization (hpf), zygotes were transferred into M2 media and mRNA was injected using a Piezo impact-driven micromanipulator (Prime Tech Ltd., Ibaraki, Japan). The construction and preparation of mRNA were described above. The concentrations of injected mRNA of $Kdm6b^{WT}$ and $Kdm6b^{MUT}$ were 1.8 µg/µl, and those of $Kdm4d^{WT}$ and $Kdm4d^{MUT}$ were 1.5 µg/µl.

Probe for Fluorescent In Situ Hybridization

A probe for Xist RNA was prepared by using Nick translation reagent kit (Abbott Molecular, 07J00-001) with Cy3-dCTP (GE healthcare, PA53021), according to the manufacturer's instruction. The template DNA used for the probe preparation was a plasmid coding the full-length mouse Xist gene, a gift from Rudolf Jaenisch (pCMV-Xist-PA, 26760) (Wutz and Jaenisch, 2000). A probe for DNA FISH was prepared using the same kit with Green-dUTP (Abbott Molecular, 02N32-050). The template DNA was a BAC clone containing the Rnf12 locus (RP23-36C20). The fluorescent probes were ethanol precipitated with 5 µg Cot-1 DNA (Life technologies), 5 µg herring sperm DNA (Thermo Fisher Scientific), and 2.5 µg yeast tRNA (Thermo Fisher Scientific, AM7119), and then dissolved with 20 µl formamide (Thermo Fisher Scientific, 17899). The probes were stored at 4° C. Before being used, the probes (0.75 µl each) were mixed with 0.75 µl Cot-1 DNA, which had been ethanol precipitated and dissolved in formamide, and 2.25 µl of 4×SSC/20% Dextran (Millipore S4030). The probe mixtures were heated at 80° C. for 30 min and then transferred to a 37° C. incubator ('pre-annealed probes').

Whole Mount RNA/DNA Fluorescent In Situ Hybridization

Morula embryos were fixed at 78 hpf in 2% paraformaldehyde (PFA) in PBS containing 0.5% Triton X-100 for 20 min at room temperature. After 3× washes with PBS containing 1 mg/ml BSA (PBS/BSA), embryos were treated with 0.1 N HCl containing 0.02% Triton X-100 for 15 min at 4° C. After 3× washes with 2×SSC containing 0.1% BSA, embryos were incubated in 15 µl of 10% formamide/2×SSC in a glass dish (Electron Microscopy Science, 705430-30). All embryos were sunk and attached to the bottom of the glass dish by gentle pipetting. After 5 min, 15 µl of 30% formamide/2×SSC was added. After 5 min, 90 µl of 60% formamide/2×SSC was added to make the final formamide concentration 50%, and embryos were incubated for additional 30 min at room temperature. The formamide solution containing embryos were covered with mineral oil. The samples were heated at 80° C. for 30 min, and then transferred to a 37° C. incubator for at least 30 min. The embryos were picked in a glass pipette, transferred into 4.5 µl of 'pre-annealed probes' covered with mineral oil on another glass dish, and incubated in 37° C. for at least 24 hrs. Embryos were washed with pre-warmed (42° C.) 2×SSC containing 0.1% BSA and left in the last drop for 30 min. After 3× wash with 1% BSA/PBS, they were mounted on a glass slide in Vectashield anti-bleaching solution with 4',6-diamidino-2-phenylindole (DAPI) (Vector Laboratories, Burlingame, CA.). Fluorescence was detected under a laser-scanning confocal microscope Zeiss LSM800.

Whole Mount Immunostaining

The procedure of immunostaining and quantification was described above.

Computational Identification of Maternal Allele-Biased H3K27Me3

The bed files including RPKM values in 100 bp bins for H3K27me3 ChIP-seq in inner cell mass (ICM) were downloaded from GEO under the number GSE76687. Bed files labeled maternal or paternal containing RPKM values for two parental alleles and allelic reads were normalized to total reads number. 'bedtools makewindows' was used to generate 1000 bp bins for mm9 genome, then RPKM value for each bin was calculated by 'bedtools map'. All the bins are classified to three categories of no signal, biallelic, maternal bias using a signal cutoff of 1 and a fold change cutoff of 4. A sliding window approach was used to identify windows containing maternal biased H3K27me3 bins with criteria of the window size of 20 kb, the minimum bin number of 3 and the percentage of maternal biased H3K27me3 bins larger than 50%. Overlapped windows were merged with "bedtools merge". A total of 5986 windows were identified in the genome.

RNA-Sequencing

RNA-seq libraries were prepared as described above with minor modifications. Briefly, reverse transcription and cDNA amplification were performed using whole embryo lysates with SMARTer Ultra Low Input RNA cDNA preparation kit (Clontech, 634890). cDNAs were then fragmented using Tagmentation with Nextera XT DNA library prep kit (Illumina). The fragmented cDNAs were amplified using Nextera PCR master mix according to the manufacturer's instruction. Single end 100 bp sequencing was performed on a HiSeq2500 sequencer (Illumina).

RNA-Seq Data Analysis

Reads of RNA-seq were mapped to the reference genome with STAR (github.com/alexdobin/STAR). All programs were run with default parameters unless otherwise specified. Uniquely mapped reads were subsequently assembled into transcripts guided by the reference annotation (UCSC gene models) with featureCounts from subread-v1.5.1. After the library size was normalized, the expression level of each gene was quantified with normalized FPKM (fragments per kilobase of exon per million mapped fragments). The Pearson correlation coefficient (r) of gene expression level was calculated to indicate the correlation between duplicates.

Statistical analyses were implemented with R (www.r-project.org/). Pearson's r coefficient was calculated using the 'cor' function with default parameters. FIG. 18A was generated with R function 'boxplot'. FIG. 18B was generated with R function 'plot'.

Code Availability

A customized pipeline was used to split the hybrid RNA-seq data to their parental origin based on SNP information. The code can be found at github.com/lanjiangboston/Universal SNP split.

Data Availability

RNA-seq datasets generated in this study were deposited at GEO database under accession number GSEXXXXX.

The WGBS dataset for GV oocytes was downloaded from www.nodai-genome.org/mouse.html?lang=en. WGBS reads from same 100 bp bins were pooled together to calculate the average methylation level and minimal coverage of 10 reads was required. H3K27me3 ChIP-seq datasets of sperm, MII oocytes, and SNP-tracked maternal and paternal alleles of 1-cell, 2-cell, and inner cell mass of blastocyst embryos were downloaded from a previous study (GSE76687). The oocyte DNaseI-seq datasets were from above (GSE92605).

OTHER EMBODIMENTS

From the foregoing description, it will be apparent that variations and modifications may be made to the invention described herein to adopt it to various usages and conditions. Such embodiments are also within the scope of the following claims.

The recitation of a listing of elements in any definition of a variable herein includes definitions of that variable as any single element or combination (or subcombination) of listed elements. The recitation of an embodiment herein includes that embodiment as any single embodiment or in combination with any other embodiments or portions thereof.

All patents and publications mentioned in this specification are herein incorporated by reference to the same extent as if each independent patent and publication was specifically and individually indicated to be incorporated by reference.

What is claimed is:

1. A method of activating a histone H3 lysine 27 trimethylation (H3K27me3) repressed allele within an imprinting control region of a H3K27me3-dependent, paternally- or maternally-expressed imprinted gene in a non-human mammalian zygote or preimplantation embryo, the method comprising contacting the non-human, mammalian zygote or preimplantation embryo with a small molecule inhibitor of H3K27 methyltransferase to inhibit histone H3 lysine 27 trimethylation; wherein the H3 lysine 27 trimethylation mediates imprinting of the gene and the inhibitor relieves H3K27me3-dependent imprinting within the imprinting control region of the gene.

2. The method of claim 1, wherein the H3K27 methyltransferase is selected from the group consisting of EZH1, EZH2, PRC2, PRC2-Ezh1, or PRC2-Ezh2 H3K27 methyltransferase.

3. The method of claim 2, wherein the inhibitor of the H3K27 methyltransferase is selected from the group consisting of tazemetostat, DZNep, GSK373, GSK126, El1, Epz005687, and CPI-169.

4. The method of claim 1, wherein the contacting occurs in vitro or ex vivo.

5. The method of claim 1, wherein the non-human mammalian zygote or preimplantation embryo is a mouse zygote or preimplantation embryo.

6. The method of claim 1, wherein the non-human mammalian zygote or preimplantation embryo is a zygote or preimplantation embryo of an agriculturally significant non-human mammal, a non-human mammal pet, a rare non-human mammal, or an endangered non-human mammal.

* * * * *

UNITED STATES PATENT AND TRADEMARK OFFICE
CERTIFICATE OF CORRECTION

| | | |
|---|---|---|
| PATENT NO. | : 12,178,854 B2 | Page 1 of 2 |
| APPLICATION NO. | : 16/631762 | |
| DATED | : December 31, 2024 | |
| INVENTOR(S) | : Yi Zhang and Azusa Inoue | |

It is certified that error appears in the above-identified patent and that said Letters Patent is hereby corrected as shown below:

In the Specification

Delete "BCO49762" at Column 2, Line 22, and replace it with -- BC049762 --.
Delete "Sfinbt2" at Column 2, Lines 25, 29, 33, 39, and 45, and replace it with -- Sfmbt2 --.
Delete "Sfinbt2" at Column 3, Lines 1, 4, and 8, and replace it with -- Sfmbt2 --.
Delete "svgreqsihs" at Column 8, Line 241 in the amino acid sequence, and replace it with -- svqreqsihs --.
Delete "Sequence: 015550.2" at Column 11, Line 26, and replace it with -- Sequence: O15550.2 --.
Delete "rtnitssaee" at Column 11, Line 601 in the amino acid sequence, and replace it with -- rtnltssaee --.
Delete "gglhkgqssh" at Column 11, Line 601 in the amino acid sequence, and replace it with -- qglhkgqssh --.
Delete "esqspmktd1" at Column 11, Line 841 in the amino acid sequence, and replace it with -- esqspmktdl --.
Delete "Sequence: 015054.4" at Column 14, Line 10, and replace it with -- Sequence: O15054.4 --.
Delete "dssyspaatt" at Column 14, Line 361 in the amino acid sequence, and replace it with -- dssvspaatt --.
Delete "tgaaystrpg" at Column 14, Line 781 in the amino acid sequence, and replace it with -- tgaavstrpg --.
Delete "eaggvaaysg" at Column 14, Line 961 in the amino acid sequence, and replace it with -- eaggvaavsg --.
Delete "tktiveasge" at Column 14, Line 1201 in the amino acid sequence, and replace it with -- tktlveasge --.
Delete "seeesysltv" at Column 22, Line 1 in the amino acid sequence, and replace it with -- seeesvsity --.
Delete "gkavroyesl" at Column 22, Line 61 in the amino acid sequence, and replace it with -- gkavrcyesl --.
Delete "sqfvimggmr" at Column 22, Line 421 in the amino acid sequence, and replace it with -- sqfvlmqqmr --.

Signed and Sealed this
Sixth Day of May, 2025

Coke Morgan Stewart
*Acting Director of the United States Patent and Trademark Office*

CERTIFICATE OF CORRECTION (continued)
U.S. Pat. No. 12,178,854 B2

Delete "hkevaqyrtt" at Column 22, Line 421 in the amino acid sequence, and replace it with -- hkevaqvrtt --.
Delete "siptnsysnr" at Column 22, Line 481 in the amino acid sequence, and replace it with -- siptnsvsnr --.
Delete "sysqpgvipa" at Column 22, Line 481 in the amino acid sequence, and replace it with -- svsqpgvrpa --.
Delete "fstktivean" at Column 22, Line 901 in the amino acid sequence, and replace it with -- fstktlvean --.
Delete "wgvindfcek" at Column 22, Line 1081 in the amino acid sequence, and replace it with -- wgvlndfcek --.
Delete "andrspvetc" at Column 27, Line 301 in the amino acid sequence, and replace it with -- ahdrspvetc --.
Delete "nvltvgsyss" at Column 27, Line 421 in the amino acid sequence, and replace it with -- nvitvgsvss --.
Delete "rpvgwcgenk" at Column 35, Line 241 in the amino acid sequence, and replace it with -- rpvgwcqenk --.
Delete "ggaagaqaca" at Column 37, Line 241 in the nucleic acid sequence, and replace it with -- ggaagagaca --.
Delete "Sfinbt2" at Column 67, Line 62, and replace it with -- Sfmbt2 --.
Delete "Sfinbt2" at Column 68, Line 12, and replace it with -- Sfmbt2 --.
Delete "containing g/ml" at Column 70, Line 50, and replace it with -- containing 5 μg/ml --.
Delete "concentration of 1 M" at Column 71, Line 59, and replace it with -- concentration of 1 μM --.
Delete "ca-amanitin 2-cell" at Column 74, Line 49, and replace it with -- α-amanitin 2-cell --.